United States Patent
Gray

(10) Patent No.: US 11,008,583 B2
(45) Date of Patent: May 18, 2021

(54) INCREASING PLANT GROWTH AND YIELD BY USING AN ADP-GLUCOSE PYROPHOSPHORYLASE SEQUENCE

(71) Applicant: BENSON HILL BIOSYSTEMS, INC., Research Triangle Park, NC (US)

(72) Inventor: Benjamin Neil Gray, Chapel Hill, NC (US)

(73) Assignee: Benson Hill, Inc., St. Louis, MO (US)

(*) Notice: Subject to any disclaimer, the term of this patent is extended or adjusted under 35 U.S.C. 154(b) by 191 days.

(21) Appl. No.: 16/311,377

(22) PCT Filed: Jun. 14, 2017

(86) PCT No.: PCT/IB2017/053534
§ 371 (c)(1),
(2) Date: Dec. 19, 2018

(87) PCT Pub. No.: WO2017/221112
PCT Pub. Date: Dec. 28, 2017

(65) Prior Publication Data
US 2020/0308597 A1 Oct. 1, 2020

Related U.S. Application Data

(60) Provisional application No. 62/353,399, filed on Jun. 22, 2016.

(51) Int. Cl.
*C12N 15/82* (2006.01)
*C12N 9/12* (2006.01)

(52) U.S. Cl.
CPC ....... *C12N 15/8261* (2013.01); *C12N 9/1241* (2013.01); *C12Y 207/07027* (2013.01)

(58) Field of Classification Search
CPC .................................................. C12N 9/1241
See application file for complete search history.

(56) References Cited

U.S. PATENT DOCUMENTS 8,710,298 B2 * 4/2014 Hannah .............. C12N 15/8271
800/289

FOREIGN PATENT DOCUMENTS

| CN | 103173485 A | | 6/2013 |
|----|---|---|---|
| CN | 103740718 A | * | 4/2014 |
| CN | 105087516 A | | 11/2015 |
| KR | 100 780 485 B1 | | 11/2007 |
| WO | WO 03/047527 A2 | | 6/2003 |
| WO | WO 2005/019425 A2 | | 3/2005 |
| WO | WO 2009/126208 A2 | | 10/2009 |
| WO | WO 2016/014809 A1 | | 1/2016 |
| WO | WO 2016/094362 A1 | | 6/2016 |
| WO | WO 2016/182847 A1 | | 11/2016 |

OTHER PUBLICATIONS

Tuncel, Aytug, and Thomas W. Okita. "Improving starch yield in cereals by over-expression of ADPglucose pyrophosphorylase: expectations and unanticipated outcomes." Plant science 211 (2013): 52-60. (Year: 2013).*
Schäffner, Anton R., and Jen Sheen. "Maize rbcS promoter activity depends on sequence elements not found in dicot rbcS promoters." The Plant Cell 3.9 (1991): 997-1012. (Year: 1991).*
Schlosser, A., et al., "Enhanced Rice Growth is Conferred by Increased Leaf ADP-Glucose Pyrophosphyorylase Activity," *J Plant Physiol Path Pathol*, 2014, vol. 2(4), pp. 1-10.

* cited by examiner

*Primary Examiner* — Lee A Visone
(74) *Attorney, Agent, or Firm* — Womble Bond Dickinson (US) LLP

(57) ABSTRACT

Compositions and methods for improving plant growth are provided herein. Polynucleotides encoding ADP-glucose pyrophosphorylase small subunit (AGPaseSS) proteins, polypeptides encompassing AGPaseSS proteins, and expression constructs for expressing genes of interest whose expression may improve agronomic properties including but not limited to crop yield, biotic and abiotic stress tolerance, and early vigor, plants comprising the polynucleotides, polypeptides, and expression constructs, and methods of producing transgenic plants are also provided.

14 Claims, 8 Drawing Sheets

Specification includes a Sequence Listing.

| | | |
|---|---|---|
| | **:*.*******:* | |
| Seq3 | VPFGANYRLIDIPIS | 15 |
| Seq55 | VPLGANYRLIDIPVS | 15 |
| Seq56 | VPLGANYRLIDIPVS | 15 |
| Seq57 | VPLGANYRLIDIPVS | 15 |
| Seq58 | VPLGANYRLIDIPVS | 15 |
| Seq59 | VPLGANYRLIDIPVS | 15 |
| Seq60 | VPLGANYRLIDIPVS | 15 |
| Seq61 | VPLGANYRLIDIPVS | 15 |
| Seq62 | VPLGANYRLIDIPVS | 15 |
| Seq63 | VPLGANYRLIDIPVS | 15 |
| Seq64 | VPLGANYRLIDIPVS | 15 |
| Seq65 | VPLGANYRLIDIPVS | 15 |
| Seq66 | VPFGANYRLIDIPVS | 15 |
| Seq67 | VPLGANYRLIDIPVS | 15 |
| Seq68 | VPLGANYRLIDIPVS | 15 |
| Seq69 | VPLGANYRLIDIPVS | 15 |
| Seq70 | VPLGANYRLIDIPVS | 15 |
| Seq71 | VPLGANYRLIDIPVS | 15 |
| Seq72 | VPLGANYRLIDIPVS | 15 |
| Seq73 | VPLGANYRLIDIPVS | 15 |
| Seq74 | VPLGANYRLIDIPVS | 15 |
| Seq75 | VPLGANYRLIDIPVS | 15 |
| Seq76 | VPLGANYRLIDIPVS | 15 |
| Seq77 | VPLGANYRLIDIPVS | 15 |
| Seq78 | VPLGANYRLIDIPVS | 15 |
| Seq79 | VPLGANYRLIDIPVS | 15 |
| Seq80 | VPLGANYRLIDIPVS | 15 |
| Seq81 | VPLGANYRLIDIPVS | 15 |
| Seq82 | VPLGANYRLIDIPVS | 15 |
| Seq83 | VPLGANYRLIDIPVS | 15 |
| Seq84 | VPLGANYRLIDIPVS | 15 |
| Seq85 | VPLGANYRLIDIPVS | 15 |
| Seq86 | VPLGANYRLIDIPVS | 15 |
| Seq87 | VPLGANYRLIDIPVS | 15 |
| Seq88 | VPLGANYRLIDIPVS | 15 |
| Seq89 | VPLGANYRLIDIPVS | 15 |
| Seq90 | VPLGANYRLIDIPVS | 15 |
| Seq91 | VPLGANYRLIDIPVS | 15 |
| Seq92 | VPLGANYRLIDIPVS | 15 |
| Seq93 | VPLGANYRLIDIPVS | 15 |
| Seq94 | VPLGANYRLIDIPVS | 15 |
| Seq95 | VPLGANYRLIDIPVS | 15 |
| Seq96 | VPLGANYRLIDIPVS | 15 |
| Seq97 | VPLGANYRLIDIPVS | 15 |
| Seq98 | VPLGANYRLIDIPVS | 15 |
| Seq99 | VPLGANYRLIDIPVS | 15 |
| Seq100 | VPLGANYRLIDIPVS | 15 |
| Seq101 | VPLGANYRLIDIPVS | 15 |
| Seq102 | VPLGANYRLIDIPVS | 15 |
| Seq103 | VPLGANYRLIDIPVS | 15 |
| Seq104 | VPLGANYRLIDIPVS | 15 |
| Seq105 | VPLGANYRLIDIPVS | 15 |
| Seq106 | VPLGANYRLIDIPVS | 15 |

| | | |
|---|---|---|
| | **:*.**********:* | |
| Seq107 | VPLGGNYRLIDIPVS | 15 |
| Seq108 | VPLGANYRLIDIPVS | 15 |
| Seq109 | VPLGANYRLIDIPVS | 15 |
| Seq110 | VPLGANYRLIDIPVS | 15 |
| Seq111 | VPLGANYRLIDIPVS | 15 |
| Seq112 | VPLGANYRLIDIPVS | 15 |
| Seq113 | VPLGGNYRLIDIPVS | 15 |
| Seq114 | VPLGANYRLIDIPVS | 15 |
| Seq115 | VPLGANYRLIDIPVS | 15 |
| Seq116 | VPLGANYRLIDIPVS | 15 |
| Seq117 | VPLGANYRLIDIPVS | 15 |
| Seq118 | VPLGANYRLIDIPVS | 15 |
| Seq119 | VPFGANYRLIDIPVS | 15 |
| Seq120 | VPLGANYRLIDIPVS | 15 |
| Seq121 | VPLGANYRLIDIPVS | 15 |
| Seq122 | VPLGANYRLIDIPVS | 15 |
| Seq123 | VPLGANYRLIDIPVS | 15 |
| Seq124 | VPLGANYRLIDIPVS | 15 |
| Seq125 | VPLGANYRLIDIPVS | 15 |
| Seq126 | VPLGANYRLIDIPVS | 15 |
| Seq127 | VPLGANYRLIDIPVS | 15 |
| Seq128 | VPLGANYRLIDIPVS | 15 |
| Seq129 | VPLGANYRLIDIPVS | 15 |
| Seq130 | VPLGANYRLIDIPVS | 15 |
| Seq131 | VPLGANYRLIDIPVS | 15 |
| Seq132 | VPLGANYRLIDIPVS | 15 |

FIG. 2

| | | |
|---|---|---|
| Seq3 | : *:****  FSLYDRSAPIYTQPRCLP | 18 |
| Seq55 | FSFYDRSAPIYTQPRYLP | 18 |
| Seq56 | FSFYDRSAPIYTQPRYLP | 18 |
| Seq57 | FSFYDRSAPIYTQPRYLP | 18 |
| Seq58 | FSFYDRSAPIYTQPRYLP | 18 |
| Seq59 | FSFYDRSAPIYTQPRYLP | 18 |
| Seq60 | FSFYDRSAPIYTQPRYLP | 18 |
| Seq61 | FSFYDRSAPIYTQPRYLP | 18 |
| Seq62 | FSFYDRSAPIYTQPRYLP | 18 |
| Seq63 | FSFYDRSAPIYTQPRYLP | 18 |
| Seq64 | FSFYDRSAPIYTQPRYLP | 18 |
| Seq65 | FSFYDRSAPIYTQPRYLP | 18 |
| Seq66 | FSFYDRSAPIYTQPRYLP | 18 |
| Seq67 | FSFYDRSAPIYTQPRYLP | 18 |
| Seq68 | FSFYDRSAPIYTQPRYLP | 18 |
| Seq69 | FSFYDRSAPIYTQPRYLP | 18 |
| Seq70 | FSFYDRSAPIYTQPRYLP | 18 |
| Seq71 | FSFYDRSSPIYTQPRYLP | 18 |
| Seq72 | FSFYDRSSPIYTQPRYLP | 18 |
| Seq73 | FSFYDRSAPIYTQPRYLP | 18 |
| Seq74 | FSFYDRSAPIYTQPRYLP | 18 |
| Seq75 | FSFYDRSSPIYTQPRYLP | 18 |
| Seq76 | FSFYDRSAPIYTQPRYLP | 18 |
| Seq77 | FSFYDRSSPIYTQPRYLP | 18 |
| Seq78 | FSFYDRSAPIYTQPRYLP | 18 |
| Seq79 | FSFYDRSSPIYTQPRYLP | 18 |
| Seq80 | FSFYDRSAPIYTQPRYLP | 18 |
| Seq81 | FSFYDRSSPIYTQPRYLP | 18 |
| Seq82 | FSFYDRSSPIYTQPRYLP | 18 |
| Seq83 | FSFYDRSSPIYTQPRYLP | 18 |
| Seq84 | FSFYDRSAPIYTQPRYLP | 18 |
| Seq85 | FSFYDRSSPIYTQPRYLP | 18 |
| Seq86 | FSFYDRSAPIYTQPRYLP | 18 |
| Seq87 | FSFYDRSAPIYTQPRYLP | 18 |
| Seq88 | FSFYDRSAPIYTQPRYLP | 18 |
| Seq89 | FSFYDRSSPIYTQPRYLP | 18 |
| Seq90 | FSFYDRSAPIYTQPRYLP | 18 |
| Seq91 | FSFYDRSSPIYTQPRYLP | 18 |
| Seq92 | FSFYDRSSPIYTQPRYLP | 18 |
| Seq93 | FSFYDRSAPIYTQPRYLP | 18 |
| Seq94 | FSFYDRSSPIYTQPRYLP | 18 |
| Seq95 | FSFYDRSAPIYTQPRYLP | 18 |
| Seq96 | FSFYDRSAPIYTQPRYLP | 18 |
| Seq97 | FSFYDRSAPIYTQPRYLP | 18 |
| Seq98 | FSFYDRSAPIYTQPRYLP | 18 |
| Seq99 | FSFYDRSAPIYTQPRYLP | 18 |
| Seq100 | FSFYDRSSPIYTQPRYLP | 18 |
| Seq101 | FSFYDRSSPIYTQPRYLP | 18 |
| Seq102 | FSFYDRSAPIYTQPRYLP | 18 |
| Seq103 | FSFYDRSAPIYTQPRYLP | 18 |
| Seq104 | FSFYDRSAPIYTQPRYLP | 18 |
| Seq105 | FSFYDRSAPIYTQPRYLP | 18 |
| Seq106 | FSFYDRSAPIYTQPRYLP | 18 |
| Seq107 | : *:****  FSFYDRSSPIYTQPRYLP | 18 |
| Seq108 | FSFYDRSAPIYTQPRYLP | 18 |
| Seq109 | FSFYDRSSPIYTQPRYLP | 18 |
| Seq110 | FSFYDRSSPIYTQPRYLP | 18 |
| Seq111 | FSFYDRSSPIYTQPRYLP | 18 |
| Seq112 | FSFYDRSSPIYTQPRYLP | 18 |
| Seq113 | FSFYDRSSPIYTQPRYLP | 18 |
| Seq114 | FSFYDRSSPIYTQPRYLP | 18 |
| Seq115 | FSFYDRSSPIYTQPRYLP | 18 |
| Seq116 | FSFYDRSSPIYTQPRYLP | 18 |
| Seq117 | FSFYDRSSPIYTQPRYLP | 18 |
| Seq118 | FSFYDRSSPIYTQPRYLP | 18 |
| Seq119 | FSFYDRSSPIYTQPRYLP | 18 |
| Seq120 | FSFYDRSAPIYTQPRYLP | 18 |
| Seq121 | FSFYDRSSPIYTQPRYLP | 18 |
| Seq122 | FSFYDRSAPIYTQPRYLP | 18 |
| Seq123 | FSFYDRSAPIYTQPRYLP | 18 |
| Seq124 | FSFYDRSAPIYTQPRYLP | 18 |
| Seq125 | FSFYDRSSPIYTQPRYLP | 18 |
| Seq126 | FSFYDRSAPIYTQPRYLP | 18 |
| Seq127 | FSFYDRSAPIYTQPRHLP | 18 |
| Seq128 | FSFYDRSAPIYTQPRHLP | 18 |
| Seq129 | FSFYDRSAPIYTQPRHLP | 18 |
| Seq130 | FSFYDRSAPIYTQPRHLP | 18 |
| Seq131 | FSFYDRSAPIYTQPRHLP | 18 |
| Seq132 | FSFYDRSAPIYTQPRHLP | 18 |

FIG. 3

| | | | | | |
|---|---|---|---|---|---|
| Seq3 | : | 8 | Seq107 | DKRFLAAK | 8 |
| Seq55 | DRKSLAAK | 8 | Seq108 | DRRFLAAK | 8 |
| Seq56 | DRKLLAAK | 8 | Seq109 | DRRFLAAK | 8 |
| Seq57 | DRKLLAAK | 8 | Seq110 | DKRFLAAK | 8 |
| Seq58 | DRKLLAAK | 8 | Seq111 | DRRFLAAK | 8 |
| Seq59 | ERKLLAAK | 8 | Seq112 | DRRLLAAK | 8 |
| Seq60 | DRRFLAAK | 8 | Seq113 | DKRFLAAK | 8 |
| Seq61 | DRRFLAAK | 8 | Seq114 | DKRFLAAK | 8 |
| Seq62 | DRRFLAAK | 8 | Seq115 | DRRFLAAK | 8 |
| Seq63 | DRKLLASK | 8 | Seq116 | DRRLMAKK | 8 |
| Seq64 | DRKLLAAK | 8 | Seq117 | DRRFLAAK | 8 |
| Seq65 | DRRFLAAK | 8 | Seq118 | DRRFLAAK | 8 |
| Seq66 | DRRLLAAK | 8 | Seq119 | DKRFLAAK | 8 |
| Seq67 | DRRLLAAK | 8 | Seq120 | EKSLLTAK | 8 |
| Seq68 | DRTLLAAK | 8 | Seq121 | DRRFLAAK | 8 |
| Seq69 | DRRLMAKK | 8 | Seq122 | DRRFLAAK | 8 |
| Seq70 | DRRFLAAK | 8 | Seq123 | EKSLLSAK | 8 |
| Seq71 | DRRSLAAK | 8 | Seq124 | EKSILSAK | 8 |
| Seq72 | DRRFLAAK | 8 | Seq125 | DRRFLAAK | 8 |
| Seq73 | DRRFLAAK | 8 | Seq126 | DKKLLAEN | 8 |
| Seq74 | DRRFLAAK | 8 | Seq127 | DKKLLAEN | 8 |
| Seq75 | DRRFLAAK | 8 | Seq128 | DKKLLAEN | 8 |
| Seq76 | DRRFLAAK | 8 | Seq129 | DKQLLAEK | 8 |
| Seq77 | DRRLMAKK | 8 | Seq130 | DKKLLAEK | 8 |
| Seq78 | DRTLLAAK | 8 | Seq131 | DKKLLGEK | 8 |
| Seq79 | DRRFLAAK | 8 | Seq132 | DKKLLAEK | 8 |
| Seq80 | DRRFLAAK | 8 | | | |
| Seq81 | DRRFLAAK | 8 | | | |
| Seq82 | DKRFLAAK | 8 | | | |
| Seq83 | DKRFLAAK | 8 | | | |
| Seq84 | DRRFLAAK | 8 | | | |
| Seq85 | DRRFLAAK | 8 | | | |
| Seq86 | DRTLLAAK | 8 | | | |
| Seq87 | DKRFLMAK | 8 | | | |
| Seq88 | DRRFLMAK | 8 | | | |
| Seq89 | DRRFLAAK | 8 | | | |
| Seq90 | DKRFLAAK | 8 | | | |
| Seq91 | DKRFLAAK | 8 | | | |
| Seq92 | EKSLLTAK | 8 | | | |
| Seq93 | DKRFLAAK | 8 | | | |
| Seq94 | DRRFLAAK | 8 | | | |
| Seq95 | DRTLLAAK | 8 | | | |
| Seq96 | DRRLLAAK | 8 | | | |
| Seq97 | EKSLLSAK | 8 | | | |
| Seq98 | DRRFLMAK | 8 | | | |
| Seq99 | DRRFLAAK | 8 | | | |
| Seq100 | DRRFLAAK | 8 | | | |
| Seq101 | DKRFLAAK | 8 | | | |
| Seq102 | DRRFLAAK | 8 | | | |
| Seq103 | DKRFLAAK | 8 | | | |
| Seq104 | DRRFLAAK | 8 | | | |
| Seq105 | DRRLLAAK | 8 | | | |
| Seq106 | DRRFLAAK | 8 | | | |

INCREASING PLANT GROWTH AND YIELD BY USING AN ADP-GLUCOSE PYROPHOSPHORYLASE SEQUENCE

CROSS-REFERENCE TO RELATED APPLICATIONS

This application is a national stage filing under 35 U.S.C. 371 of PCT/I132017/053534 filed Jun. 14, 2017, which International Application was published by the International Bureau in English on Dec. 28, 2017, and claims priority from U.S. Provisional Application No. 62/353,399, filed Jun. 22, 2016 which applications are hereby incorporated by reference in their entirety in this application.

FIELD OF THE INVENTION

The invention is drawn to compositions and methods for increasing plant growth and yield through expression of an ADP-glucose pyrophosphorylase small subunit gene in a plant.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in plant growth and development. Modulating the expression of one or more such genes in a plant can produce a plant with improved growth and development relative to a control plant, but often can produce a plant with impaired growth and development relative to a control plant. Therefore, methods to improve plant growth and development are needed.

SUMMARY OF THE INVENTION

Compositions and methods for regulating gene expression in a plant are provided. The methods increase plant growth resulting in higher crop yield. Such methods include increasing the expression of at least one ADP-glucose pyrophosphorylase small subunit (AGPaseSS) gene in a plant of interest. The invention also encompasses constructs comprising a promoter that drives expression in a plant cell operably linked to an ACGPaseSS coding sequence. Compositions further comprise plants, plant seeds, plant organs, plant cells, and other plant parts that have increased expression of an AGPaseSS sequence. The invention includes methods that can be utilized to increase expression of an AGPaseSS gene in a plant. Such AGPaseSS gene may be a native sequence or alternatively, may be a sequence that is heterologous to the plant of interest.

Embodiments of the Invention Include:

1. A method for increasing crop yield comprising transforming a plant with at least one AGPaseSS protein-encoding sequence.
2. The method of embodiment 1, wherein said AGPaseSS protein-encoding sequence comprises SEQ ID NO:1 or 2, or encodes a protein selected from the group consisting of SEQ ID NOs: 3 and 55-132.
3. The method of embodiment 1, wherein said AGPaseSS protein-encoding sequence encodes a protein with at least 80%, 90%, 95%, 96%, 97%, 98%, or 99% sequence identity to a sequence selected from the group consisting of SEQ ID NOs: 3 and 55-132, and that has AGPase enzyme activity.
4. The method of embodiment 1, wherein said AGPaseSS protein-encoding sequence encodes a protein with at least 80%, 85%, 90%, 95%, 96%, 97%, 98%, or 99% sequence positives relative to a sequence selected from the group consisting of SEQ II) NOs: 3 and 55-132, and that has AGPase enzyme activity.
5. A plant having stably incorporated into its genome a promoter that drives expression in a plant operably linked to an AGPaseSS protein-encoding sequence, wherein said promoter is heterologous to said AGPaseSS protein-encoding sequence.
6. The plant of embodiment 5, wherein said AGPaseSS protein-encoding sequence comprises SEQ ID NO:1 or 2, or encodes a protein selected from the group consisting of SEQ ID NOs: 3 and 55-132.
7. The plant of embodiment 5, wherein said AGPaseSS protein-encoding sequence encodes a protein with at least 80%, 85%, 90%, 95%, 96%, 97%, 98%, or 99% sequence identity to a sequence selected from the group consisting of SEQ ID NOs: 3 and 55-132, and that has AGPase enzyme activity.
8. The plant of embodiment 5, wherein said AGPaseSS protein-encoding sequence encodes a protein with at least 80%, 85%, 90%, 95%, 96%, 97%, 98%, or 99% sequence positives relative to a sequence selected from the group consisting of SEQ ID NOs: 3 and 55-132, and that has AGPase enzyme activity.

9. Transformed seed of any one of the plants of embodiments 5-8.

10. The plant of any one of embodiments 5-8 wherein said plant is a monocot.

11. The plant of embodiment 10 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena,* or *Hordeum.*

12. The plant of any one of embodiments 5-8 wherein said plant is a dicot.

13. The plant of embodiment 12 wherein said plant is from the genus *Glycine, Brassica, Medicago, Helianthus, Carthamus, Nicotiana, Solanum, Gossypium, Ipomoea, Manihot, Coffea, Citrus, Theobroma, Camellia, Persea, Ficus, Psidium, Mangifera, Olea, Carica, Anacardium, Macadamia, Prumus, Beta, Populus,* or *Eucalyptus.*

14. The plant of any one of embodiments 5-8 wherein said plant exhibits increased growth relative to a control plant.

15. The plant of any one of embodiments 5-8 wherein said plant exhibits increased biomass yield relative to a control plant.

16. The plant of any one of embodiments 5-8 wherein said plant exhibits increased seed yield relative to a control plant.

17. The method of any one of embodiments 1-4, wherein said AGPaseSS protein-encoding sequence is expressed from a constitutive promoter.

18. The method of embodiment 17, wherein said constitutive promoter is selected from the group of SEQ NOs: 4 and 11.

19. The method of any one of embodiments 1-4, wherein said AGPaseSS protein-encoding sequence is expressed from a bundle sheath-preferred promoter.

20. The method of embodiment 19, wherein said bundle sheath-preferred promoter is selected from the group of SEQ ID NOs: 6, 8, and 10.

21. The method of any one of embodiments 19-20, wherein said bundle sheath-preferred promoter comprises SEQ ID NO:8.

22. The plant of any one of embodiments 5-8, wherein said promoter that drives expression in a plant is a constitutive promoter.

23. The plant of embodiment 22, wherein said constitutive promoter is selected from the group of SEQ NOs: 4 and 11.

24. The plant of any one of embodiments 5-8, wherein said promoter that drives expression in a plant is a bundle sheath-preferred promoter.

25. The plant of embodiment 24, wherein said bundle sheath-preferred promoter is selected from the group of SEQ ID NOs: 6, 8, and 10.

26. The plant of any one of embodiments 24-25, wherein said bundle sheath-preferred promoter comprises SEQ ID NO:8.

27. A DNA construct comprising, in operable linkage,
a. A promoter that is functional in a plant cell and,
b. A nucleic acid sequence encoding an AGPaseSS protein.

28. The DNA construct of embodiment 27, wherein said nucleic acid sequence encoding an AGPaseSS protein comprises SEQ ID NO: 1 or 2, or encodes a protein selected from the group consisting of SEQ ID NOs: 3 and 55-132.

29. The DNA construct of embodiment 27 or 28, wherein said nucleic acid sequence encoding an AGPaseSS protein encodes a protein with at least 80%, 85%, 90%, 95%, 96%, 97%, 98%, or 99% sequence identity to a sequence selected from the group consisting of SEQ ID NOs: 3 and 55-132, and that has AGPase enzyme activity.

30. The DNA construct of embodiment 27 or 28, wherein said nucleic acid sequence encoding an AGPaseSS protein encodes a protein with at least 80%, 85%, 90%, 95%, 96%, 97%, 98%, or 99% sequence positives relative to a sequence selected from the group consisting of SEQ ID NOs: 3 and 55-132, and that has AGPase enzyme activity.

31. The DNA construct of embodiment 27 or 28, wherein said promoter that is functional in a plant cell is selected from the group of SEQ ID NOs: 4, 6, 8, 10, and 11.

32. The DNA construct of any one of embodiments 27-31, wherein said promoter that is functional in a plant cell comprises SEQ ID NO:8.

33. A method for increasing crop yield comprising modulating the expression of at least one AGPaseSS protein-encoding sequence in a plant.

34. The method of embodiment 33 wherein said modulating the expression comprises increasing the expression of at least one AGPaseSS protein-encoding sequence in a plant.

35. The method of embodiment 34, wherein said increasing the expression comprises increasing the activity of a native AGPaseSS sequence in said plant or increasing activity of a native AGPaseSS protein-encoding sequence in said plant.

36. The method of any one of embodiments 1-4, wherein said AGPaseSS protein-encoding sequence is expressed from a promoter that is active in leaf tissue.

37. The method of any one of embodiments 1, 2, 3, 4, and 36 wherein said promoter that is active in leaf tissue is selected from the group of SEQ NOs:4, 6, 8, 10, and 11.

38. The plant of any one of embodiments 5-8, wherein said promoter that drives expression in a plant is a promoter that is active in leaf tissue.

39. The plant of any one of embodiments 5, 6, 7, and 38 wherein said promoter that is active in leaf tissue is selected from the group of SEQ ID NOs:4, 6, 8, 10, and 11.

40. The DNA construct of embodiment 27 or 28, wherein said promoter that is functional in a plant cell is a promoter that is active in leaf tissue.

41. The DNA construct of any one of embodiments 27, 28, and 40 wherein said promoter that is active in leaf tissue is selected from the group of SEQ ID NOs:4, 6, 8, 10, and 11.

42. The method of any one of embodiments 1-4, wherein said AGPaseSS protein-encoding sequence encodes a protein that comprises at least one of:
a. A Phe residue at a position corresponding to amino acid residue 118 in SEQ NO:3,
b. An Ile residue at a position corresponding to amino acid residue 129 in SEQ ID NO:3;
c. A Leu residue at a position corresponding to amino acid residue 374 in SEQ ID NO:3;
d. A Cys residue at a position corresponding to amino acid residue 387 in SEQ ID NO:3; or e. A Ser residue at a position corresponding to amino acid residue 450 in SEQ ID NO:3.
43. The plant of any one of embodiments 5-8, wherein said AGPaseSS protein-encoding sequence encodes a protein that comprises at least one of:
    a. A Phe residue at a position corresponding to amino acid residue 118 in SEQ ID NO:3;
    b. An Ile residue at a position corresponding to amino acid residue 129 in SEQ ID NO:3;
    c. A Leu residue at a position corresponding to amino acid residue 374 in SEQ ID NO:3;
    d. A Cys residue at a position corresponding to amino acid residue 387 in SEQ ID NO:3; or
    e. A Ser residue at a position corresponding to amino acid residue 450 in SEQ ID NO:3.
44. The DNA construct of embodiment 27 or 28, wherein said nucleic acid sequence encoding an AGPaseSS protein encodes a protein that comprises at least one of:
    a. A Phe residue at a position corresponding to amino acid residue 118 in SEQ ID NO:3;
    b. An Ile residue at a position corresponding to amino acid residue 129 in SEQ ID NO:3;
    c. A Leu residue at a position corresponding to amino acid residue 374 in SEQ ID NO:3;
    d. A Cys residue at a position corresponding to amino acid residue 387 in SEQ ID NO:3; or
    e. A Ser residue at a position corresponding to amino acid residue 450 in SEQ ID NO:3.
45. The DNA construct of any one of embodiments 27, 28, 29, 30, 31, 32, 40, 41, or 44, wherein said promoter is heterologous to said nucleic acid sequence encoding an AGPaseSS protein.
46. The method of any one of embodiments 1-4, further comprising transforming a plant with at least one additional protein-encoding sequence.
47. The method of embodiment 46 wherein said additional protein-encoding sequence shares at least 70% identity with a sequence selected from the group of SEQ ID NOs:28, 30, 32, 34, 36, 38, 39, 42, 46, 47, 49, 51, 53, and 134, or encodes a protein that shares at least 80% identity with a sequence selected from the group of SEQ ID NOs:29, 31, 33, 35, 37, 40, 43, 48, 50, 52, 54, and 135.
48. The method of embodiment 47 wherein said additional protein-encoding sequence comprises a sequence selected from the group of SEQ ID NOs:28, 30, 32, 34, 36, 38, 39, 42, 46, 47, 49, 51, 53, and 134, or encodes a protein that comprises a sequence selected from the group of SEQ ID NOs:29, 31, 33, 35, 37, 40, 43, 48, 50, 52, 54, and 135.
49. The plant of any one of embodiments 5-8, wherein said plant has stably incorporated into its genome a second promoter that drives expression of at least one additional coding sequence, wherein said second promoter is heterologous to said additional coding sequence.
50. The plant of embodiment 49, wherein said additional coding sequence shares at least 70% identity with a sequence selected from the group of SEQ ID NOs:28, 30, 32, 34, 36, 38, 39, 42, 46, 47, 49, 51, 53, and 134, or encodes a protein that shares at least 80% identity with a sequence selected from the group of SEQ ID NOs:29, 31, 33, 35, 37, 40, 43, 48, 50, 52, 54, and 135.
51. The plant of embodiment 50, wherein said additional coding sequence comprises a sequence selected from the group of SEQ ID NOs:28, 30, 32, 34, 36, 38, 39, 42, 46, 47, 49, 51, 53, and 134, or encodes a protein that comprises a sequence selected from the group of SEQ ID NOs:29, 31, 33, 35, 37, 40, 43, 48, 50, 52, 54, and 135.
52. The DNA construct of any one of embodiments 27-32, further comprising, in operable linkage,
    a. A second promoter that is functional in a plant cell and,
    b. A nucleic acid sequence encoding an additional protein, wherein said second promoter is heterologous to said nucleic acid sequence encoding an additional protein.
53. The DNA construct of embodiment 52, wherein said nucleic acid sequence encoding an additional protein shares at least 70% identity with a sequence selected from the group of SEQ ID NOs:28, 30, 32, 34, 36, 38, 39, 42, 46, 47, 49, 51, 53, and 134, or encodes a protein that shares at least 80% identity with a sequence selected from the group of SEQ ID NOs:29, 31, 33, 35, 37, 40, 43, 48, 50, 52, 54, and 135.
54. The DNA construct of embodiment 53, wherein said nucleic acid sequence encoding an additional protein comprises a sequence selected from the group of SEQ ID NOs:28, 30, 32, 34, 36, 38, 39, 42, 46, 47, 49, 51, 53, and 134, or encodes a protein that comprises a sequence selected from the group of SEQ NOs:29, 31, 33, 35, 37, 40, 43, 48, 50, 52, 54, and 135.

BRIEF DESCRIPTION OF THE DRAWINGS

Figure 1:
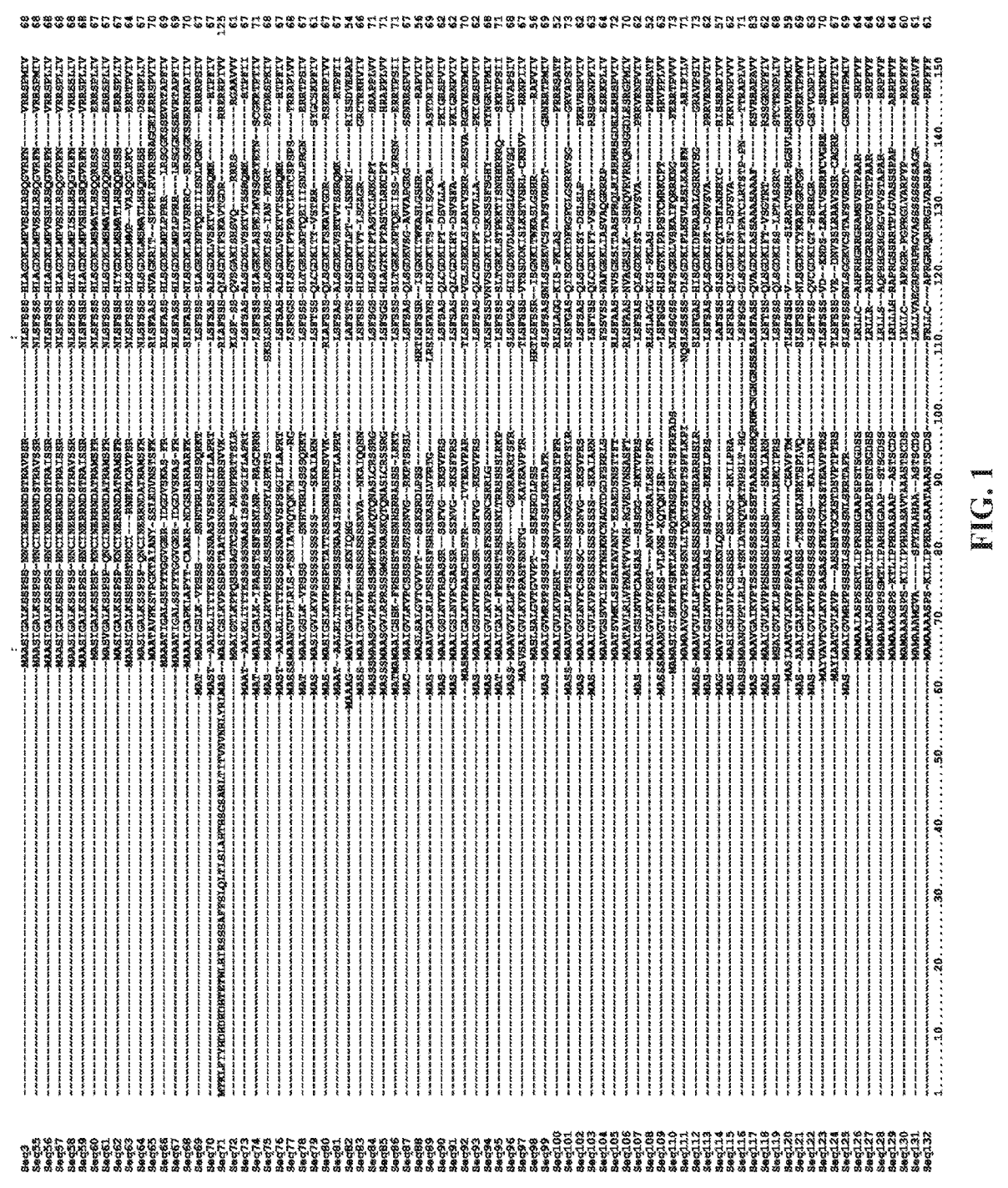
Figure 1:
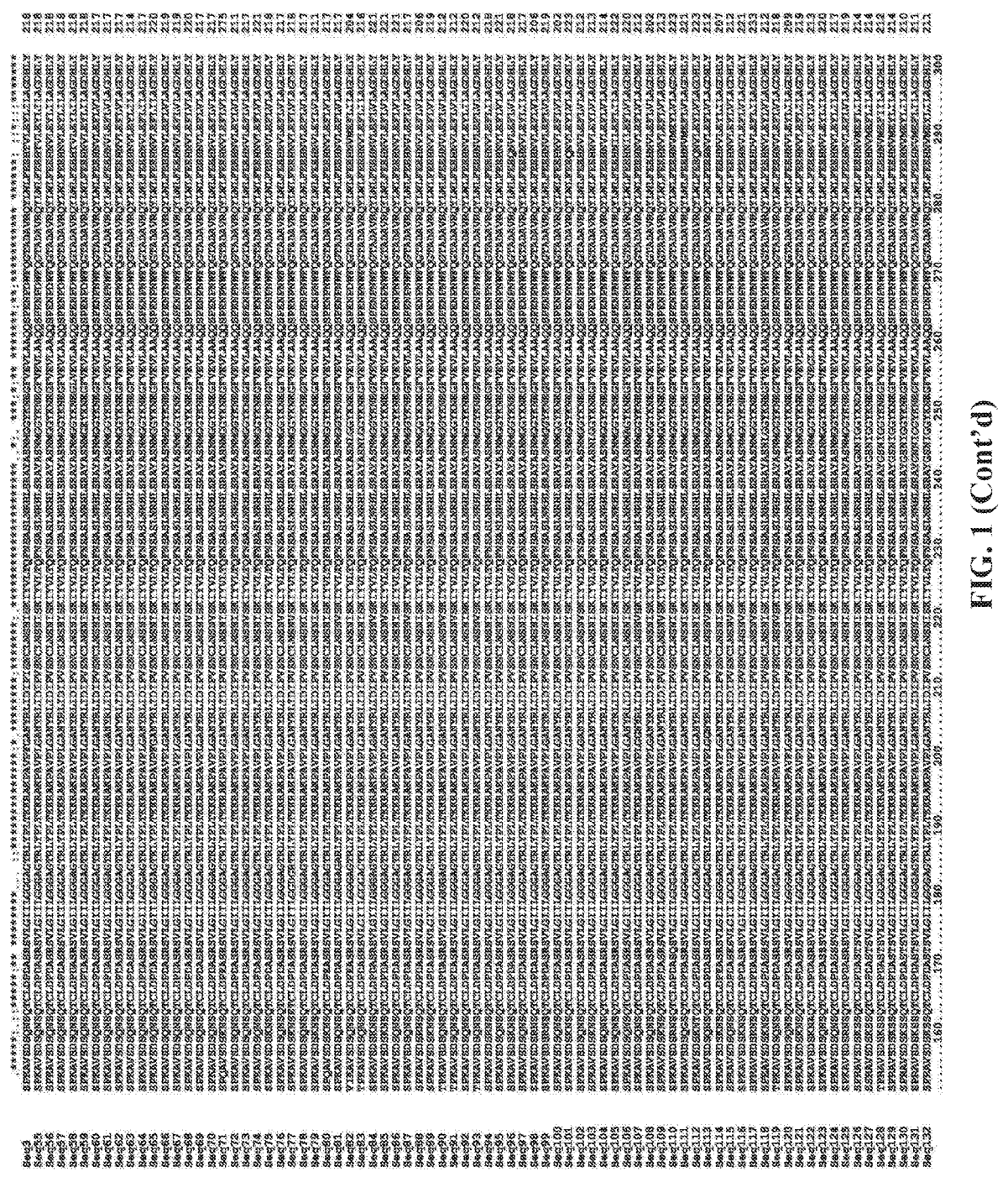
Figure 1:
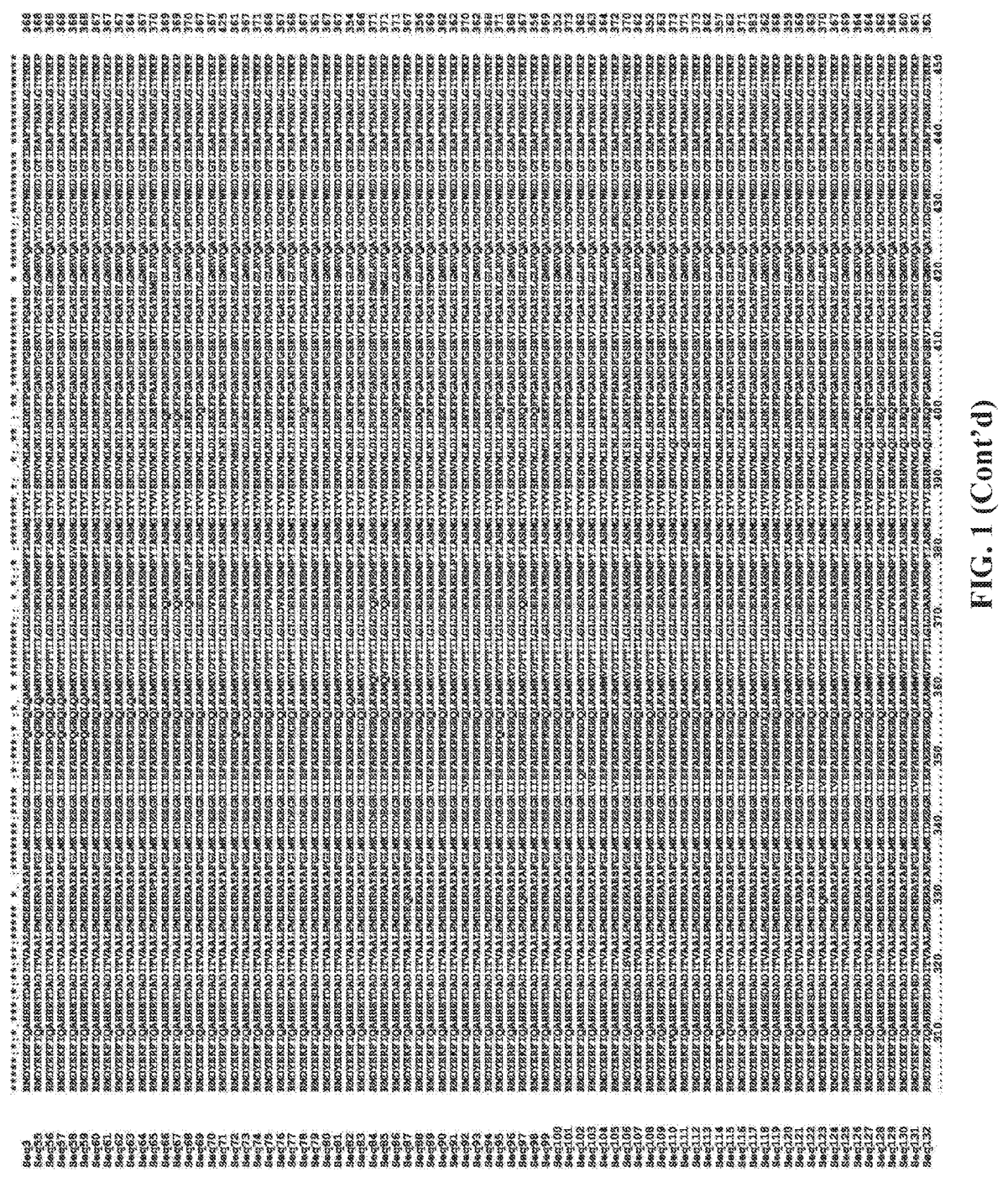
Figure 1:
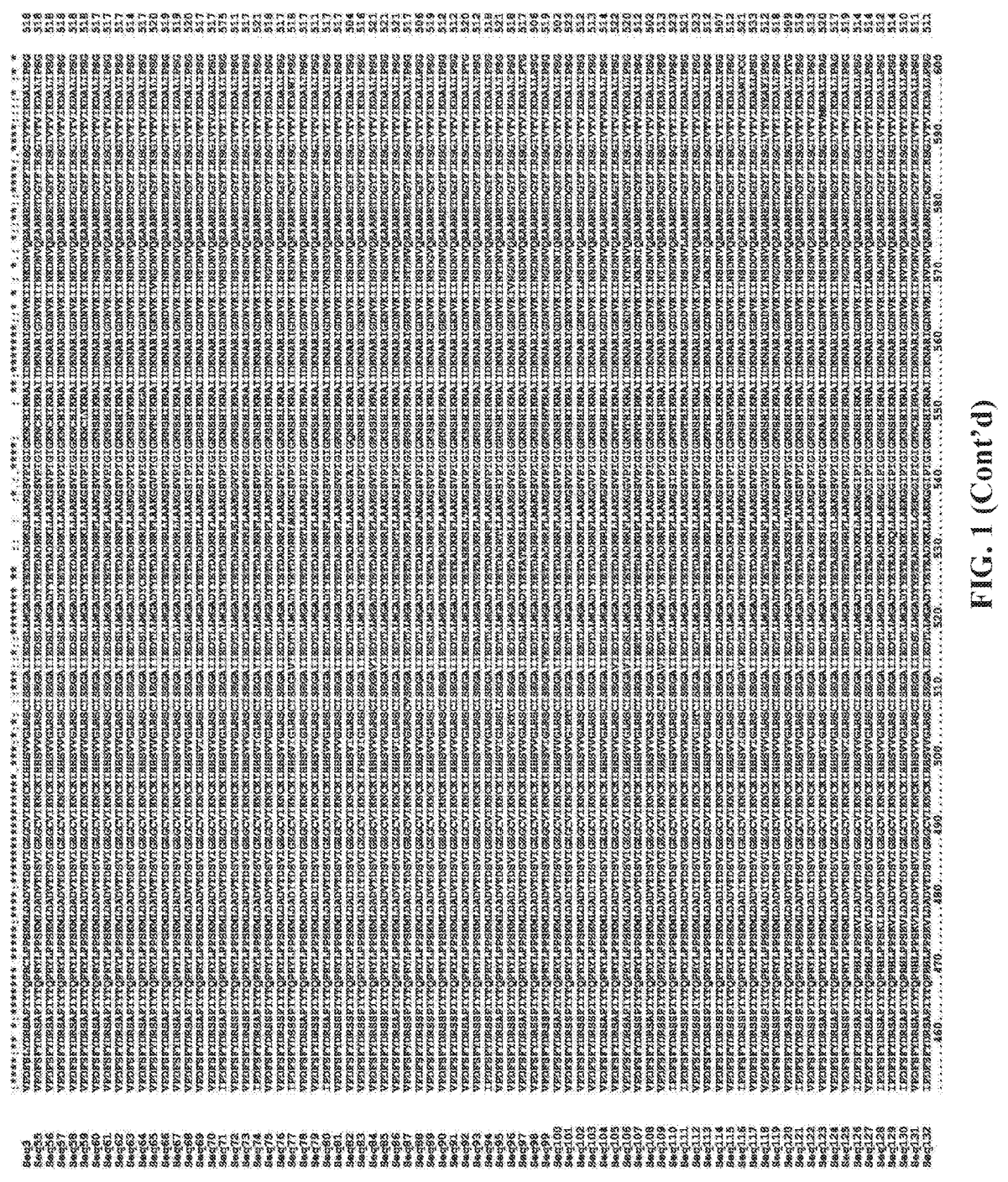
Figure 1:
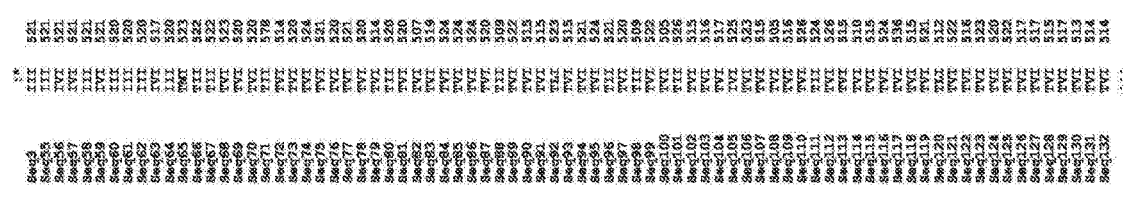

FIG. 1: Amino acid alignment of SEQ NOs:3 and 55-132.
FIG. 2: Amino acid alignment of a selected region of SEQ ID NOs:3 and 55-132, highlighting two mutations of interest.
FIG. 3: Amino acid alignment of a selected region of SEQ NOs:3 and 55-132, highlighting two mutations of interest.
FIG. 4: Amino acid alignment of a selected region of SEQ ID NOs:3 and 55-132, highlighting a mutation of interest.

DETAILED DESCRIPTION OF THE INVENTION

Compositions and methods for increasing crop biomass and yield are provided. The methods include increasing the expression of at least one ADP-glucose pyrophosphorylase small subunit (AGPaseSS) gene in a plant of interest. Crop yield is an extremely complex trait that results from the growth of a crop plant through all stages of its development and allocation of plant resources to the harvestable portions of the plant. In some crops including but not limited to maize and soybean, the primary harvestable portions may include seeds, with secondary applications from the remainder of the biomass (e.g., leaves and stems). In other crops including but not limited to sugarcane and alfalfa, the primary harvestable portions of the plant consist of the stems or entire above-ground portion of the plant. In other crops including but not limited to potato and carrot, the primary harvestable portions of the plant are found below-ground. Regardless of the harvested portion(s) of the crop plant, the accumulation of harvestable biomass results from plant growth and allocation of photosynthetically fixed carbon to the harvested portion(s) of the plant. Plant growth may be manipulated by modulating the expression of one or more plant genes. This modulation can alter the function of one or more metabolic pathways that contributes to plant growth and accumulation of harvestable biomass.

One important metabolic pathway that contributes to plant growth and yield is the starch biosynthesis pathway. In many plants, carbon dioxide (CO$_2$) diffuses into photosynthetically active tissues, where it is chemically fixed by the reactions of photosynthesis to form carbon-containing molecules that the plant uses for growth. In many plants, CO$_2$ is converted into starch in chloroplasts during the day, and this starch is then remobilized at night, with the starch being metabolized to produce sucrose that can be transported to growing tissues within the plant. Because starch is produced in this way with a diurnal rhythm such that starch levels increase during the day and then return to low levels again at the end of the night period, such starch is often termed 'transitory' starch. This transitory starch serves an important function in plant photosynthesis and growth. Mutant plant lines deficient in transitory starch biosynthesis often display impaired growth (Caspar et al. (1985) *Plant Physiol* 79:11-17; Lin et al. (1988) *Plant Physiol* 86:1131-1135). It has been proposed that this impaired growth results from feedback inhibition of photosynthesis, thus slowing the rate of photosynthetic carbon fixation (Tuncel and Okita (2013) *Plant Sci* 211:52-60). Without being limited by theory, it is possible that improving the rate of transitory starch biosynthesis may improve whole-plant growth and yield. Increasing the flux through a metabolic pathway can be effected by improving the rate of the rate-limiting reaction in that pathway. In the transitory starch biosynthesis pathway, the reaction catalyzed by AGPase, in which glucose-1-phosphate (G-1-P) is converted to ADP-glucose, has been identified as a rate-limiting reaction (Zhu et al. (2007) *Plant Physiol* 145:513-526; Salamone et al. (2002) *Proc Natl Acad Sci USA*. 99:1070-1075). Thus, without being limited by theory, improving the AGPase-catalyzed reaction may improve transitory starch biosynthesis.

AGPase enzymes in higher plants convert G-1-P to ADP-glucose, utilizing ATP and producing diphosphate in the process. AGPase enzyme activity is regulated in part by the concentration of 3-phosphoglycerate (3-PGA), which is required for the enzyme's activation, and by the concentration of phosphate, which tends to inhibit the enzyme. Mutant forms of higher plant AGPase subunits have been developed that exhibit improved biochemical properties relative to their wild-type counterparts (Salamone et al. (2002) *Proc Natl Acad Sci USA* 99:1070-1075; Greene et al. (1998) *Proc Natl Acad Sci USA* 95:10322-10327). These mutant higher plant AGPase subunit enzymes typically require lower concentrations of 3-PGA for activation and exhibit decreased sensitivity to inhibition by phosphate. Without being limited by theory, the improved biochemical properties of such mutant AGPase subunit enzymes could provide benefits if expressed in plants. Now that valuable mutant forms of AGPase subunit enzymes have been identified, amino acid alignments can be performed to identify amino acid residues in other AGPase subunit enzymes that may be mutated to produce AGPase subunit enzymes with improved biochemical properties similar to those that have been reported previously.

Methods of the invention include the manipulation of plant growth for increased yield through modulation of the expression of one or more genes encoding an AGPaseSS protein. In a preferred embodiment, the expression of an AGPaseSS-encoding gene is upregulated relative to AGPaseSS expression levels in a control plant, resulting in increased harvestable biomass in plants with increased AGPaseSS expression relative to control plants. Any methods for increasing the activity or expression of an AGPaseSS-encoding sequence in a plant are encompassed by the present invention.

The compositions of the invention include constructs comprising the coding sequences set forth in SEQ ID NOs:1-2 or encoding a protein selected from the group of SEQ ID NOs: 3 and 55-132 or variants thereof, operably linked to a promoter that is functional in a plant cell. By "promoter" is intended to mean a regulatory region of DNA that is capable of driving expression of a sequence in a plant or plant cell. It is recognized that having identified the AGPaseSS protein sequences disclosed herein, it is within the state of the art to isolate and identify additional AGPaseSS protein sequences and nucleotide sequences encoding AGPaseSS protein sequences, for instance through BLAST searches, PCR assays, and the like.

The coding sequences of the present invention, when assembled within a DNA construct such that a promoter is operably linked to the coding sequence of interest, enable expression and accumulation of AGPaseSS protein in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be co-transformed into the plant. Alternatively, the additional gene(s) can be provided on multiple expression cassettes or DNA constructs. The expression cassette may additionally contain selectable marker genes.

In this manner, the nucleotide sequences encoding the AGPaseSS proteins of the invention are provided in expression cassettes or expression constructs along with a promoter sequence of interest, typically a heterologous promoter sequence, for expression in the plant of interest. By "heterologous promoter sequence" is intended to mean a sequence that is not naturally operably linked with the AGPaseSS protein-encoding nucleotide sequence. While the AGPaseSS-encoding nucleotide sequence and the promoter sequence are heterologous to each other, either the AGPaseSS-encoding nucleotide sequence or the heterologous promoter sequence may be homologous, or native, or heterologous, or foreign, to the plant host. It is recognized that the promoter may also drive expression of its homologous or native nucleotide sequence. In this case, the transformed plant will have a change in phenotype.

Fragments and variants of the polynucleotides and amino acid sequences of the present invention may also be expressed by promoters that are operable in plant cells. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95, 96%, 97%, 98%, 99% or more sequence identity to that particular polynucleotide as determined by sequence alignment programs and parameters as described elsewhere herein. Fragments and variants of the polynucleotides disclosed herein can encode proteins with AGPase activity.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, such as AGPase activity. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. In some embodiments, the variant polypeptide sequences will comprise conservative amino acid substitutions. The number of such conservative amino acid substitutions, summed with the number of amino acid identities, can be used to calculate the sequence positives when this sum is divided by the total number of ammo acids in the sequence of interest. Sequence positive calculations are performed on the NCBI BLAST server that can be accessed on the the NCBI website. A biologically active variant of a protein of the invention may differ from that protein by as few as 1-15 amino acid residues, as few as 1-10, such as 6-10, as few as 5, as few as 4, 3, 2, or even 1 amino acid residue.

Amino acids can be generally categorized as aliphatic, hydroxyl or sulfur/selenium-containing, cyclic, aromatic, basic, or acidic and their amide. Without being limited by theory, conservative amino acid substitutions may be preferable in some cases to non-conservative amino acid substitutions for the generation of variant protein sequences, as conservative substitutions may be more likely than non-conservative substitutions to allow the variant protein to retain its biological activity. Polynucleotides encoding a polypeptide having one or more amino acid substitutions in the sequence are contemplated within the scope of the present invention. Table 1 below provides a listing of examples of amino acids belong to each class.

TABLE 1

Classes of Amino Acids

| Amino Acid Class | Example Amino Acids |
|---|---|
| Aliphatic | Gly, Ala, Val, Leu, Ile |
| Hydroxyl or sulfur/selenium-containing | Ser, Cys, Thr, Met, Sec |
| Cyclic | Pro |
| Aromatic | Phe, Tyr, Trp |
| Basic | His, Lys, Arg |
| Acidic and their Amide | Asp, Glu, Asn, Gln |

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) CABIOS 4:11-17; the local alignment algorithm of Smith et al. (1981) Adv. Appl. Math. 2:482; the global alignment algorithm of Needleman and Wunsch (1970) J. Mol. Biol. 48:443-453; the search-for-local alignment method of Pearson and Lipman (1988) Proc. Natl. Acad. Sci. 85:2444-2448; the algorithm of Karlin and Altschul (1990) Proc. Natl. Acad. Sci. USA 87:2264-2268, modified as in Karlin and Altschul (1993) Proc. Natl. Acad. Sci. USA 90:5873-5877.

Computer implementations of these mathematical algorithms can be utilized for comparison of sequences to determine sequence identity. Such implementations include, but are not limited to: CLUST AL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) Gene 73:237-244 (1988); Higgins et al. (1989) CABIOS 5: 151-153, Corpet et al. (1988) Nucleic Acids Res. 16: 10881-90; Huang et al. (1992) CABIOS 8: 155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2. 0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLAS TX for proteins) can be used. See the NCBI website. Alignment may also be performed manually by inspection.

Such genes and coding regions can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) Gene 105:61-72; Murray et al. (1989) Nucl. Acids Res. 17:477-508). Methodology for optimizing a nucleotide sequence for expression in a plant is provided, for example, in U.S. Pat.

No. 6,015,891, and the references cited therein, as well as in WO 2012/142,371, and the references cited therein.

The nucleotide sequences of the invention may be used in recombinant polynucleotides. A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

By "altering" or "modulating" the expression level of a gene is intended that the expression of the gene is upregulated or downregulated. It is recognized that in some instances, plant growth and yield are increased by increasing the expression levels of one or more genes encoding AGPaseSS proteins, i.e. upregulating expression. Likewise, in some instances, plant growth and yield may be increased by decreasing the expression levels of one or more genes encoding AGPaseSS proteins, i.e. downregulating expression. Thus, the invention encompasses the upregulation or downregulation of one or more genes encoding AGPaseSS proteins. Further, the methods include the upregulation of at least one gene encoding a AGPaseSS protein and the downregulation of at least one gene encoding a second AGPaseSS protein in a plant of interest. By modulating the concentration and/or activity of at leak one of the genes encoding an AGPaseSS protein in a transgenic plant is intended that the concentration and/or activity is increased or decreased by at least about 1%, about 5%, about 10%, about 20%, about 30%, about 40%, about 50%, about 60%, about 70%, about 80%, or about 90% or greater relative to a native control plant, plant part, or cell which did not have the sequence of the invention introduced.

It is recognized that the expression levels of the genes encoding AGPaseSS proteins of the present invention can be controlled by the use of one or more promoters that are functional in a plant cell. The expression level of the AGPaseSS protein-encoding gene of interest may be measured directly, for example, by assaying for the level of the photosynthetic gene transcript or of the encoded protein in the plant. Methods for such assays are well-known in the art. For example, Northern blotting or quantitative reverse transcriptase-PCR (qRT-PCR) may be used to assess transcript levels, while western blotting, ELISA assays, or enzyme assays may be used to assess protein levels. AGPase activity can be measured by monitoring the formation of ADP-glucose from glucose-1-phosphate as described elsewhere herein.

A "subject plant or plant cell" is one in which genetic alteration, such as transformation, has been effected as to an AGPaseSS protein-encoding gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels of an AGPaseSS protein-encoding gene of interest are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

To downregulate expression of an AGPaseSS protein-encoding gene of interest, antisense constructions, complementary to at least a portion of the messenger RNA (mRNA) for the sequences of a gene of interest, particularly a gene encoding an AGPaseSS protein of interest can be constructed. Antisense nucleotides are designed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85%, 90%, 95% or greater sequence identity to the corresponding sequences to be silenced may be used. Furthermore, portions of the antisense nucleotides may be used to disrupt the expression of the target gene.

The polynucleotides of the invention can be used to isolate corresponding sequences from other plants. In this manner, methods such as PCR, hybridization, and the like can be used to identify such sequences based on their sequence homology or identity to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity: Functions of orthologs are often highly conserved among species. Thus, isolated polynucleotides that have transcription activation or enhancer activities and which share at least 75% sequence identity to the sequences disclosed herein, or to variants or fragments thereof are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding sequences encoding AGPaseSS proteins can be identified and used in the methods of the invention. The variant sequences will retain the biological activity of an AGPaseSS protein (i.e., AGPase activity). In higher plants, two AGPaseSS proteins join with two AGPase large subunit (AGPaseLS) proteins to form a heterotetramer that is acts as the functional holoenzyme. This AGPase holoenzyme (sometimes also referred to as glucose-1-phosphate adenylyltransferase) catalyzes the conversion of Glucose-1-phosphate (G1P) to ADP-glucose. One important function of ADP-glucose and hence of the AGPase-catalyzed reaction is the production of starch. Starch production is catalyzed by starch synthase, using ADP-glucose as its substrate. AGPase enzyme activity has been identified as the rate-limiting step in the starch production pathway in plant leaves (Kavakli et al. (2002) Planta 215:430-439), where one important function of starch is as a temporary storage for carbon fixed by photosynthesis. The amount of this so-called transitory starch, which accumulates in chloroplasts, typically increases in plant leaves throughout the daylight, and then the transitory starch is metabolized and remobilized, often in the form of sucrose, to other tissues in the plant to provide carbon for plant growth. In a number of plant species, starch formation is also an important part of seed development, with starch forming a large portion of seed endosperm. Assaying for AGPase activity in plant tissue can thus be performed indirectly by measuring starch content in the plant tissue. Such starch content measurements can be performed semi-quantitatively through the use of an iodine staining procedure (Hostettler et al. (2011) *Methods in Molecular Biology* 775:387-410), or can be performed quantitatively by measuring glucose production following treatment of plant tissue extracts with alpha-amylase and amyloglucosidase (Smith and Zeeman (2006) *Nature Protocols* 1:1342-1345). AGPase enzyme activity can also be assayed directly through the use of previously published protocols (e.g., Salamone et al. (2002) *Proc Natl. Acad. Sci. USA* 99:1070-1075).

The expression cassette will include in the 5'-3' direction of transcription, a transcriptional and translational initiation region, a polynucleotide encoding an AGPaseSS protein of the present invention, and a transcriptional and translational termination region (i.e., termination region) functional in plants.

A number of promoters may be used in the practice of the invention. The polynucleotides encoding an AGPaseSS protein of the invention may be expressed from a promoter with a constitutive expression profile. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Polynucleotides of the invention encoding AGPaseSS proteins of the invention may be expressed from tissue-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3):1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23 (6): 1129-1138; Matsuoka et al. (1993) *Proc Natl. Acad. Sci. USA* 90(20):9586-9590; and Guevara-Garcia et al. (1993) *Plant J.* 4(3):495-505. Leaf-preferred promoters are also known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6): 1129-1138; and Matsuoka et al. (1993) *Proc. Natl. Acad. Sci. USA* 90(20):9586-9590.

Developmentally-regulated promoters may be desirable for the expression of a polynucleotide encoding an AGPaseSS protein. Such promoters may show a peak in expression at a particular developmental stage. Such promoters have been described in the art, e.g., US 62/029,068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of a polynucleotide encoding an AGPaseSS protein. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 201:3: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of a polynucleotide encoding an AGPaseSS protein. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol* 8: 112-125; Engelmann et al. (2008) *Plant Physiol* 146: 1773-1785; Matsuoka et al. (1994) Plant J 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta have been described in the scientific literature (Vandepoele et al. (2009) *Plant Physiol* 150: 535-546; Rushton et al. (2002) *Plant Cell* 14: 749-762). Cis-regulatory elements may also be used to alter promoter expression profiles, as described in Venter (2007) *Trends Plant Sci.* 12: 118-124.

Plant terminators are known in the art and include those available from the Ti-plasmid of *A. tumelaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the nucleotides encoding AGPaseSS proteins of the present invention can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. The term "transform" or "transformation" refers to any method used to introduce polypeptides or polynucleotides into plant cells. Suitable methods of introducing polypeptides and polynucleotides into plant cells include microinjection (Crossway et al. (1986) *Biotechniques:* 4:320-334), electroporation (Riggs et al. (1986) *Proc. Natl. Acad. Sci. USA* 83:5602-5606, Agrobacterium-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lev1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), Brassica sp. (e.g., *B. napes, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

In one embodiment, a construct containing a promoter that is operable in a plant cell, operably linked to a coding sequence encoding an AGPaseSS protein of the present invention is used to transform a plant cell or cells. The transformed plant cell or cells are regenerated to produce transformed plants. These plants transformed with a construct comprising a functional promoter driving expression of an AGPaseSS protein-encoding polynucleotide of the invention demonstrated increased plant yield, i.e., increased above-ground biomass and increased seed yield.

Now that it has been demonstrated that upregulation of AGPaseSS increases plant yield, other methods for increasing expression of an endogenous AGPaseSS sequence in a plant of interest can be used. The expression of an AGPaseSS gene present in a plant's genome can be altered by inserting a transcriptional enhancer upstream of the AGPaseSS gene present in the plant's genome. This strategy will allow the AGPaseSS gene's expression to retain its normal developmental profile, while showing elevated transcript levels. This strategy will occur through the insertion of an enhancer element upstream of an AGPaseSS gene of interest using a meganuclease designed against the genomic sequence of interest. Alternatively, a Cas9 endonuclease coupled with a guide RNA (gRNA) designed against the genomic sequence of interest, or a Cpf1 or Csm1 endonuclease coupled with a gRNA designed against the genomic sequence of interest, is used to effect the insertion of an enhancer element upstream of an AGPaseSS gene of interest. Alternatively, a deactivated Cas9 endonuclease fused to a transcriptional enhancer element is targeted to a genomic location near the transcription start site for an AGPaseSS gene of interest, thereby modulating the expression of said AGPaseSS gene of interest (Piatek et al. (2015) *Plant Biotechnol J* 13:578-589).

Alteration of the expression of an AGPaseSS protein-encoding gene may be achieved through the use of precise genome-editing technologies to modulate the expression of the endogenous sequence. In this manner, a nucleic acid sequence will be inserted proximal to a native plant sequence encoding the AGPaseSS through the use of methods available in the art. Such methods include, but are not limited to, meganucleases designed against the plant genomic sequence of interest (D'Halluin et al (2013) *Plant Biotechnol J* 11: 933-941); CRISPR-Cas9, CRTSPR-Cpf1, CRISPR-Csm1, TALENs, and other technologies for precise editing of genomes (Feng et al. (2013) Cell Research 23:1229-1232, Podevin et al. (2013) *Trends Biotechnology* 31: 375-383. Wei et al. (2013) *J Gen Genomics* 40: 281-289, Zhang et al (2013) WO 2013/026740, Zetsche et al. (2015) *Cell* 163:759-771, US Provisional Patent Application 62/295,325); *N. gregoryi* Argonaute-mediated DNA insertion (Gao et al. (2016) *Nat Biotechnol* doi:10.1038/nbt.3547); Cre-lox site-specific recombination (Dale et al. (1995) *Plant J* 7:649-659; Lyznik, et al. (2007) Transgenic Plant J 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J.* 44:693-705); Cai et al. (2009) *Plant Mol Biol* 69:699-709); and homologous recombination (Lieberman-Lazarovich and Levy (2011) *Methods Mol Biol* 701: 51-65; Puchta (2002) *Plant Mol Biol* 48:173-182). The insertion of said nucleic acid sequences will be used to achieve the desired result of overexpression and/or altered expression profile of an AGPaseSS gene.

Enhancers include any molecule capable of enhancing gene expression when inserted into the genome of a plant. Thus, an enhancer can be inserted in a region of the genome upstream or downstream of an AGPaseSS sequence of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene encoding an AGPaseSS protein or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi (2011) *Methods Mol. Biol.* 701:285-300). In some embodiments, the present invention comprises a subdomain, fragment, or duplicated enhancer element (Benfrey et al. (1990) *EMBO J* 9:1677-1684).

Alteration of AGPaseSS gene expression may also be achieved through the modification of DNA in a way that does not alter the sequence of the DNA. Such changes could include modifying the chromatin content or structure of the AGPaseSS gene of interest and/or of the DNA surrounding the AGPaseSS gene. It is well known that such changes in chromatin content or structure can affect gene transcription (Hirschhorn et al. (1992) *Genes and Dev* 6:2288-2298; Narlikar et al. (2002) Cell 108: 475-487). Such changes could also include altering the methylation status of the AGPaseSS gene of interest and/or of the DNA surrounding the AGPaseSS gene of interest. It is well known that such changes in DNA methylation can alter transcription (Hsieh (1994) *Mol Cell Biol* 14: 5487-5494). Targeted epigenotne editing has been shown to affect the transcription of a gene in a predictable manner (Hilton et al. (2015) 33: 510-517). It will be obvious to those skilled in the art that other similar alterations (collectively termed "epigenetic alterations") to the DNA that regulates transcription of the AGPaseSS gene of interest may be applied in order to achieve the desired result of an altered AGPaseSS gene expression profile.

Alteration of AGPaseSS gene expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding AGPaseSS may be achieved by inserting a transposable element upstream of the AGPaseSS gene of interest, causing the expression of said gene to be altered.

Alteration of AGPaseSS gene expression may also be achieved through expression of a transcription factor or transcription factors that regulate the expression of the AGPaseSS gene of interest. It is well understood that alteration of transcription factor expression can in turn alter the expression of the target gene(s) of said transcription factor (Hiratsu et al. (2003) *Plant J* 34:733-739). Alteration of AGPaseSS gene expression may be achieved by altering the expression of transcription factor(s) that are known to interact with the AGPaseSS gene of interest (e.g., the AtWRKY20 TF (Nagata et al. (2012) *Plant Production Science* 15:10-18) or the OsbZIP58 TF (Wang et al. (2013) *J Exp Bat* 64:3453-3466)).

Alteration of AGPaseSS gene expression may also be achieved through the insertion of a promoter upstream of the open reading frame encoding a native AGPaseSS in the plant species of interest. This will occur through the insertion of a promoter of interest upstream of an AGPaseSS protein-encoding open reading frame using a meganuclease designed against the genomic sequence of interest. This strategy is well-understood and has been demonstrated previously to insert a transgene at a predefined location in the cotton genome (D'Halluin et al. (2013) *Plant Biotechnol J* 11: 933-941). A similar strategy was undertaken to insert a promoter at a predefined location in the tomato genome, using the CRISPR-Cas9 system to induce a double-strand break (Čermák et al. (2015) *Genome Biol* 16:232). It will be obvious to those skilled in the art that other technologies can be used to achieve a similar result of insertion of genetic elements at a predefined genomic locus by causing a double-strand break at said predefined genomic locus and providing an appropriate DNA template for insertion (e.g., CRISPR-Cas9, CRISPR-Cpf1, CRISPR-Csm1, TALENs, and other technologies for precise editing of genomes).

Alteration of a native AGPaseSS-encoding gene may be performed through genome editing techniques including TALENs, CRISPR-based technologies, zinc-finger nucleases, meganucleases, and other methods known in the art. Using these technologies, one or more double-stranded break(s) is induced at a predetermined genomic locus/loci, and a suitable DNA repair template is provided to induce a desired mutation. In this way, precise mutations in native AGPaseSS protein-encoding sequences may be provided such that one or more amino acid changes is caused relative to the native AGPaseSS amino acid sequence. Desirable amino acid changes including the amino acid changes described in Table 7, herein, may be induced. Such targeted editing of native plant DNA sequences has been demonstrated previously (Li et al. (2013) *Nat Biotechnol* 31:688-691; Li et al. (2015) *Plant Physiol* 169:960-970; Svitashev et al. (2015) *Plant Physiol* 169:931-945), and it would be obvious to one skilled in the art to use a genome editing approach to alter a plant AGPaseSS coding sequence so that a mutant AGPaseSS comprising valuable mutations is encoded. Alternatively, genome editing without the induction of a double-stranded break has been demonstrated through expression of a Cas9 protein fused to a cytidine deaminase domain along with suitable guide RNAs (Komor et al. (2016) *Nature* 533:420-424). It would be obvious to one skilled in the art to use an approach similar to that described by Komor et al. to edit a native AGPaseSS coding sequence in a plant genome such that the AGPaseSS coding sequence would encode an AGPaseSS protein comprising one or more mutations relative to the native AGPaseSS protein that would provide improved properties to the AGPaseSS protein. Without being limited by theory, one or more of the mutations described in Table 7, herein, may be of particular interest.

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1—Construction of AGPaseSS Plant Transformation Vectors

An open reading frame encoding an AGPaseSS protein was synthesized. This open reading frame comprised SEQ ID NO:1 or SEQ ID NO:2, encoding the protein sequence of SEQ ID NO: 3. Appropriate restriction sites were included at the 5' and 3' ends of the coding sequence to allow this DNA to be cloned into plant transformation vectors that contained genetic elements suitable for controlling gene expression. In each plant transformation construct, the AGPaseSS open reading frame was located downstream of a plant promoter and 5' untranslated region (5'UTR) and upstream of a 3'UTR Table 2. summarizes the plant transformation constructs that were built containing an AGPaseSS open reading frame. The AGPaseSS protein encoded by each of the ORFs in Table 2 is the protein sequence of SEQ ID NO:3.

TABLE 2

AGPaseSS plant transformation constructs

| Construct ID | Promoter + 5'UTR | ORF | 3'UTR |
| --- | --- | --- | --- |
| 130101 | ZmUbi (SEQ ID NO: 4) | AGPaseSS (SEQ ID NO: 1) | ZmUbi (SEQ ID NO: 5) |
| 130511 | ZmUbi (SEQ ID NO: 4) | AGPaseSS (SEQ ID NO: 1) | ZmUbi (SEQ ID NO: 5) |
| 130514 | ZjPCK (SEQ ID NO: 6) | AGPaseSS (SEQ ID NO: 1) | ZjPCK (SEQ ID NO: 7) |
| 130563 | ZmUbi (SEQ ID NO: 4) | AGPaseSS (SEQ ID NO: 1) | ZmUbi (SEQ ID NO: 5) |
| 130566 | ZjPCK (SEQ ID NO: 6) | AGPaseSS (SEQ ID NO: 1) | ZjPCK (SEQ ID NO: 7) |
| 130631 | ZjPCK (SEQ ID NO: 6) | AGPaseSS (SEQ ID NO: 1) | ZjPCK (SEQ ID NO: 7) |
| 130653 | CsVMV (SEQ ID NO: 11) | AGPaseSS (SEQ ID NO: 2) | AtRbcS (SEQ ID NO: 12) |
| 130816 | ZmRbcS (SEQ ID NO: 8) | AGPaseSS (SEQ ID NO: 1) | ZmRbcS (SEQ ID NO: 9) |
| 130827 | ZmUbi (SEQ ID NO: 4) | AGPaseSS (SEQ ID NO: 1) | ZmUbi (SEQ ID NO: 5) |
| 131170 | FbGLDC (SEQ ID NO: 10) | AGPaseSS (SEQ ID NO: 1) | ZmRbcS (SEQ ID NO: 9) |
| 131898 | ZmRbcS (SEQ ID NO: 8) | AGPaseSS (SEQ ID NO: 1) | ZmRbcS (SEQ ID NO: 9) |

In addition to the single-genic AGPaseSS plant transformation constructs listed in Table 2, multigenic plant transformation constructs containing an AGPaseSS gene cassette and a second linked cassette were also built. Table 3 summarizes the multigenic AGPaseSS plant transformation constructs. In Table 3, the SEQ m NO for each promoter and 3'UTR is shown. For the ORFs in this table, the numbers in parentheses indicate the SEQ ID NO of the DNA sequence for the ORF, followed by a slash, followed by the SEQ ID NO of the encoded protein.

TABLE 3

AGPaseSS multigenic plant transformation constructs

| Construct ID | AGPaseSS Promoter | AGPaseSS ORF | AGPaseSS 3'UTR | GOI2 Promoter | GOI2 ORF | GOI2 3'UTR | GOI3 Promoter |
|---|---|---|---|---|---|---|---|
| 130235 | ZmRbcS (SEQ ID NO: 13) | AGPaseSS (1/3) | ZmRbcS (SEQ ID NO: 9) | ZmRbcS (SEQ ID NO: 13) | RbcS-ictB (38/33) | ZmRbcS (SEQ ID NO: 9) | ZmRbcS (SEQ ID NO: 13) |
| 130417 | ZmRbcS (SEQ ID NO: 13) | AGPaseSS (1/3) | ZmRbcS (SEQ ID NO: 9) | ZmRbcS (SEQ ID NO: 13) | RbcS-ictB (38/33) | ZmRbcS (SEQ ID NO: 9) | ZmRbcS (SEQ ID NO: 13) |
| 130881 | ZmRbcS (SEQ ID NO: 8) | AGPaseSS (1/3) | ZmRbcS (SEQ ID NO: 9) | LOC_Os01g45274 (SEQ ID NO: 24) | SBPase (28/29) | LOC_Os01g 45274 (SEQ ID NO: 25) | 2x35S (SEQ ID NO: 14) |
| 130966 | ZmRbcS (SEQ ID NO: 8) | AGPaseSS (1/3) | ZmRbcS (SEQ ID NO: 9) | 2x35S (SEQ ID NO: 14) | RbcS-ictB (41/33) | 35S polyA (SEQ ID NO: 15) | 2x35S (SEQ ID NO: 14) |
| 131009 | ZmRbcS (SEQ ID NO: 8) | AGPaseSS (1/3) | ZmRbcS (SEQ ID NO: 9) | LOC_Os12g17600 (SEQ ID NO: 26) | SBPase (28/29) | LOC_Os12g17600 (SEQ ID NO: 27) | 2x35S (SEQ ID NO: 14) |
| 131011 | ZmRbcS (SEQ ID NO: 8) | AGPaseSS (1/3) | ZmRbcS (SEQ ID NO: 9) | LOC_Os01g45274 (SEQ ID NO: 24) | SBPase (28/29) | LOC_Os01g45274 (SEQ ID NO: 25) | 2x35S (SEQ ID NO: 14) |
| 131013 | ZmRbcS (SEQ ID NO: 8) | AGPaseSS (1/3) | ZmRbcS (SEQ ID NO: 9) | 4xRGCGR (SEQ ID NO: 16) | SBPase (28/29) | ZmCA (SEQ ID NO: 17) | 2x35S (SEQ ID NO: 14) |
| 130445 | ZmRbcS (SEQ ID NO: 8) | AGPaseSS (1/3) | ZmRbcS (SEQ ID NO: 9) | ZmRbcS (SEQ ID NO: 8) | RbcS-ictB (38/33) | ZmRbcS (SEQ ID NO: 9) | ZmRbcS (SEQ ID NO: 8) |
| 130594 | ZmRbcS (SEQ ID NO: 8) | AGPaseSS (1/3) | ZmRbcS (SEQ ID NO: 9) | ZmUbi (SEQ ID NO: 4) | hc1 (42/43) | ZmUbi (SEQ ID NO: 5) | LOC_Os01g45274 (SEQ ID NO: 24) |
| 130629 | ZjPCK (SEQ ID NO: 6) | AGPaseSS (1/3) | ZjPCK (SEQ ID NO: 7) | LOC_Os01g45274 (SEQ ID NO: 24) | SBPase (28/29) | LOC_Os01g45274 (SEQ ID NO: 25) | 4xRGCGR (SEQ ID NO: 16) |
| 130636 | ZjPCK (SEQ ID NO: 6) | AGPaseSS (1/3) | ZjPCK (SEQ ID NO: 7) | ZmUbi (SEQ ID NO: 4) | hc1 (42/43) | ZmUbi (SEQ ID NO: 5) | ZmRbcS (SEQ ID NO: 8) |
| 130884 | ZmRbcS (SEQ ID NO: 8) | AGPaseSS (1/3) | ZmRbcS (SEQ ID NO: 9) | LOC_Os01g45274 (SEQ ID NO: 24) | SBPase (28/29) | LOC_Os01g45274 (SEQ ID NO: 25) | GluB-2 (SEQ ID NO: 19) |
| 130064 | ZmUbi (SEQ ID NO: 4) | AGPaseSS (1/3) | ZmUbi (SEQ ID NO: 5) | ZmUbi (SEQ ID NO: 4) | SBPase (28/29) | ZmUbi (SEQ ID NO: 5) | ZmUbi (SEQ ID NO: 4) |
| 130065 | ZjPCK (SEQ ID NO: 6) | AGPaseSS (1/3) | ZjPCK (SEQ ID NO: 7) | ZjPCK (SEQ ID NO: 6) | SBPase (28/29) | ZjPCK (SEQ ID NO: 7) | ZjPCK (SEQ ID NO: 6) |
| 130243 | ZmRbcS (SEQ ID NO: 13) | AGPaseSS (1/3) | ZmRbcS (SEQ ID NO: 9) | ZmRbcS (SEQ ID NO: 13) | RbcS-ictB (38/33) | ZmRbcS (SEQ ID NO: 9) | ZmPepC (SEQ ID NO: 22) |
| 130401 | ZmUbi (SEQ ID NO: 4) | AGPaseSS (1/3) | ZmUbi (SEQ ID NO: 5) | ZmUbi (SEQ ID NO: 4) | SBPase (28/29) | ZmUbi (SEQ ID NO: 5) | ZmUbi (SEQ ID NO: 4) |
| 130402 | ZjPCK (SEQ ID NO: 6) | AGPaseSS (1/3) | ZjPCK (SEQ ID NO: 7) | ZjPCK (SEQ ID NO: 6) | SBPase (28/29) | ZjPCK (SEQ ID NO: 7) | ZjPCK (SEQ ID NO: 6) |
| 130420 | ZmRbcS (SEQ ID NO: 13) | AGPaseSS (1/3) | ZmRbcS (SEQ ID NO: 9) | ZmRbcS (SEQ ID NO: 13) | SBPase (28/29) | ZmRbcS (SEQ ID NO: 9) | ZmRbcS (SEQ ID NO: 13) |
| 130438 | ZmRbcS (SEQ ID NO: 13) | AGPaseSS (1/3) | ZmRbcS (SEQ ID NO: 9) | ZmRbcS (SEQ ID NO: 13) | RbcS-ictB (38/33) | ZmRbcS (SEQ ID NO: 9) | ZmRbcS (SEQ ID NO: 13) |
| 130471 | CsVMV (SEQ ID NO: 11) | AGPaseSS (2/3) | AtRbcS (SEQ ID NO: 12) | 2X 35S + AtRbcS 5'UTR (SEQ ID NO: 18) | AGPaseLS (34/35) | AtRbcS (SEQ ID NO: 12) | 2X 35S + AtRbcS 5'UTR (SEQ ID NO: 18) |
| 130474 | CsVMV (SEQ ID NO: 11) | AGPaseSS (2/3) | AtRbcS (SEQ ID NO: 12) | AtSBPase (SEQ ID NO: 20) | SBPase (30/31) | AtSBPase (SEQ ID NO: 21) | 2X 35S + AtRbcS 5'UTR (SEQ ID NO: 18) |

TABLE 3-continued

AGPaseSS multigenic plant transformation constructs

| ID | | | | | | | |
|---|---|---|---|---|---|---|---|
| 130627 | ZjPCK (SEQ ID NO: 6) | AGPaseSS (1/3) | ZjPCK (SEQ ID NO: 7) | ZmRbcS (SEQ ID NO: 13) | RbcS-ictB (38/33) | ZmRbcS (SEQ ID NO: 9) | ZmRbcS (SEQ ID NO: 13) |
| 130673 | ZjPCK (SEQ ID NO: 6) | AGPaseSS (1/3) | ZjPCK (SEQ ID NO: 7) | GluB-2 (SEQ ID NO: 19) | ism2 (39/40) | ZmUbi (SEQ ID NO: 5) | ZmRbcS (SEQ ID NO: 13) |
| 130869 | ZmRbcS (SEQ ID NO: 8) | AGPaseSS (1/3) | ZmRbcS (SEQ ID NO: 9) | ZmUbi (SEQ ID NO: 4) | hc1 (42/43) | ZmUbi (SEQ ID NO: 5) | ZmUbi (SEQ ID NO: 4) |
| 130870 | ZmRbcS (SEQ ID NO: 8) | AGPaseSS (1/3) | ZmRbcS (SEQ ID NO: 9) | ZmUbi (SEQ ID NO: 4) | hc1 (44/45) | ZmUbi (SEQ ID NO: 5) | ZmUbi (SEQ ID NO: 4) |
| 130880 | ZmRbcS (SEQ ID NO: 8) | AGPaseSS (1/3) | ZmRbcS (SEQ ID NO: 9) | LOC_Os01g45274 (SEQ ID NO: 24) | SBPase (28/29) | LOC_Os01g45274 (SEQ ID NO: 25) | 2x35S (SEQ ID NO: 14) |
| 130965 | ZmRbcS (SEQ ID NO: 8) | AGPaseSS (1/3) | ZmRbcS (SEQ ID NO: 9) | 2x35S (SEQ ID NO: 14) | RbcS-ictB (41/33) | 35S polyA (SEQ ID NO: 15) | 2x35S (SEQ ID NO: 14) |
| 131002 | ZmRbcS (SEQ ID NO: 8) | AGPaseSS (1/3) | ZmRbcS (SEQ ID NO: 9) | 2x35S (SEQ ID NO: 14) | AGPaseLS (46/35) | 35S polyA (SEQ ID NO: 15) | FbGLDC (SEQ ID NO: 10) |
| 131008 | ZmRbcS (SEQ ID NO: 8) | AGPaseSS (1/3) | ZmRbcS (SEQ ID NO: 9) | LOC_Os12g17600 (SEQ ID NO: 26) | SBPase (28/29) | LOC_Os12g17600 (SEQ ID NO: 27) | 2x35S (SEQ ID NO: 14) |
| 131010 | ZmRbcS (SEQ ID NO: 8) | AGPaseSS (1/3) | ZmRbcS (SEQ ID NO: 9) | LOC_Os01g4S274 (SEQ ID NO: 24) | SBPase (28/29) | LOC_Os01g45274 (SEQ ID NO: 25) | 2x35S (SEQ ID NO: 14) |
| 131012 | ZmRbcS (SEQ ID NO: 8) | AGPaseSS (1/3) | ZmRbcS (SEQ ID NO: 9) | 4xRGCGR (SEQ ID NO: 16) | SBPase (28/29) | ZmCA (SEQ ID NO: 17) | 2x35S (SEQ ID NO: 14) |
| 130238 | ZmRbcS (SEQ ID NO: 8) | AGPaseSS (1/3) | ZmRbcS (SEQ ID NO: 9) | ZmRbcS (SEQ ID NO: 8) | SBPase (28/29) | ZmRbcS (SEQ ID NO: 9) | ZmRbcS (SEQ ID NO: 8) |
| 130437 | ZmRbcS (SEQ ID NO: 8) | AGPaseSS (1/3) | ZmRbcS (SEQ ID NO: 9) | ZmRbcS (SEQ ID NO: 8) | SBPase (28/29) | ZmRbcS (SEQ ID NO: 9) | ZmRbcS (SEQ ID NO: 8) |
| 130443 | ZmRbcS (SEQ ID NO: 8) | AGPaseSS (1/3) | ZmRbcS (SEQ ID NO: 9) | ZmRbcS (SEQ ID NO: 8) | SBPase (28/29) | ZmRbcS (SEQ ID NO: 9) | ZmUbi (SEQ ID NO: 4) |
| 130606 | ZjPCK (SEQ ID NO: 6) | AGPaseSS (1/3) | ZjPCK (SEQ ID NO: 7) | ZmUbi (SEQ ID NO: 4) | PHB8 (36/37) | ZmUbi (SEQ ID NO: 5) | ZmRbcS (SEQ ID NO: 8) |
| 130637 | ZjPCK (SEQ ID NO: 6) | AGPaseSS (1/3) | ZjPCK (SEQ ID NO: 7) | ZmRbcS (SEQ ID NO: 8) | AGPaseLS (46/35) | ZmRbcS (SEQ ID NO: 9) | GluB-2 (SEQ ID NO: 19) |
| 130710 | ZjPCK (SEQ ID NO: 6) | AGPaseSS (1/3) | ZjPCK (SEQ ID NO: 7) | ZmUbi (SEQ ID NO: 4) | hc1 (42/43) | ZmUbi (SEQ ID NO: 5) | ZmRbcS (SEQ ID NO: 8) |
| 130877 | ZmRbcS (SEQ ID NO: 8) | AGPaseSS (1/3) | ZmRbcS (SEQ ID NO: 9) | ZmUbi (SEQ ID NO: 4) | hc1 (42/43) | ZmUbi (SEQ ID NO: 5) | ZmUbi (SEQ ID NO: 4) |
| 130883 | ZmRbcS (SEQ ID NO: 8) | AGPaseSS (1/3) | ZmRbcS (SEQ ID NO: 9) | LOC_Os01g45274 (SEQ ID NO: 24) | SBPase (28/29) | LOC_Os01g45274 (SEQ ID NO: 25) | ZmUbi (SEQ ID NO: 4) |
| 131804 | FbGLDC (SEQ ID NO: 10) | AGPaseSS (1/3) | ZmRbcS (SEQ ID NO: 9) | ZmRbcS (SEQ ID NO: 8) | RbcS-ictB (38/33) | ZmRbcS (SEQ ID NO: 9) | LOC_OsO1g45274 (SEQ ID NO: 24) |
| 130247 | ZmRbcS (SEQ ID NO: 13) | AGPaseSS (1/3) | ZmRbcS (SEQ ID NO: 9) | ZmUbi (SEQ ID NO: 4) | PHB8 (53/54) | ZmUbi (SEQ ID NO: 5) | |
| 130262 | ZmRbcS (SEQ ID NO: 13) | AGPaseSS (1/3) | ZmRbcS (SEQ ID NO: 9) | ZmUbi (SEQ ID NO: 4) | RbcS-ictB (38/33) | ZmUbi (SEQ ID NO: 5) | |
| 130290 | ZmUbi (SEQ ID NO: 4) | AGPaseSS (1/3) | ZmUbi (SEQ ID NO: 5) | ZmRbcS (SEQ ID NO: 13) | RbcS-ictB (38/33) | ZmRbcS (SEQ ID NO: 9) | |
| 130355 | ZmUbi (SEQ ID NO: 4) | AGPaseSS (1/3) | ZmUbi (SEQ ID NO: 5) | ZmUbi (SEQ ID NO: 4) | hc1 (42/43) | ZmUbi (SEQ ID NO: 5) | |
| 130432 | ZmRbcS (SEQ ID NO: 13) | AGPaseSS (1/3) | ZmRbcS (SEQ ID NO: 9) | ZmUbi (SEQ ID NO: 4) | hc1 (42/43) | ZmUbi (SEQ ID NO: 5) | |
| 130434 | ZmRbcS (SEQ ID NO: 13) | AGPaseSS (1/3) | ZmRbcS (SEQ ID NO: 9) | ZmUbi (SEQ ID NO: 4) | hc1 (42/43) | ZmUbi (SEQ ID NO: 5) | |
| 130441 | ZmRbcS (SEQ ID NO: 13) | AGPaseSS (1/3) | ZmRbcS (SEQ ID NO: 9) | ZmRbcS (SEQ ID NO: 13) | SBPase (28/29) | ZmRbcS (SEQ ID NO: 9) | |

TABLE 3-continued

AGPaseSS multigenic plant transformation constructs

| | | | | | | |
|---|---|---|---|---|---|---|
| 130519 | ZjPCK (SEQ ID NO: 6) | AGPaseSS (1/3) | ZjPCK (SEQ ID NO: 7) | ZjPCK (SEQ ID NO: 6) | SBPase (28/29) | ZjPCK (SEQ ID NO: 7) |
| 130520 | ZjPCK (SEQ ID NO: 6) | AGPaseSS (1/3) | ZjPCK (SEQ ID NO: 7) | ZjPCK (SEQ ID NO: 6) | FBPase (47/48) | ZjPCK (SEQ ID NO: 7) |
| 130568 | CsVMV (SEQ ID NO: 11) | AGPaseSS (2/3) | AtRbcS (SEQ ID NO: 12) | 2X 35S + AtRbcS 5'UTR (SEQ ID NO: 18) | AGPaseLS (34/35) | AtRbcS (SEQ ID NO: 12) |
| 130630 | ZjPCK (SEQ ID NO: 6) | AGPaseSS (1/3) | ZjPCK (SEQ ID NO: 7) | ZmRbcS (SEQ ID NO: 13) | AGPaseLS (46/35) | ZmRbcS (SEQ ID NO: 9) |
| 130975 | ZmRbcS (SEQ ID NO: 8) | AGPaseSS (1/3) | ZmRbcS (SEQ ID NO: 9) | 2x35S (SEQ ID NO: 14) | AGPaseLS (46/35) | 35S polyA (SEQ ID NO: 15) |
| 130978 | ZmRbcS (SEQ ID NO: 8) | AGPaseSS (1/3) | ZmRbcS (SEQ ID NO: 9) | 2x35S (SEQ ID NO: 14) | RbcS-ictB (41/33) | 35S polyA (SEQ ID NO: 15) |
| 131063 | ZmRbcS (SEQ ID NO: 8) | AGPaseSS (1/3) | ZmRbcS (SEQ ID NO: 9) | LOC_Os01g45274 (SEQ ID NO: 24) | SBPase (28/29) | LOC_Os01g45274 (SEQ ID NO: 25) |
| 131064 | ZmRbcS (SEQ ID NO: 8) | AGPaseSS (1/3) | ZmRbcS (SEQ ID NO: 9) | LOC_Os12g17600 (SEQ ID NO: 26) | SBPase (28/29) | LOC_Os12g17600 (SEQ ID NO: 27) |
| 131581 | ZmRbcS (SEQ ID NO: 8) | AGPaseSS (1/3) | ZmRbcS (SEQ ID NO: 9) | ZmRbcS (SEQ ID NO: 8) | RbcS-ictB (41/33) | ZmRbcS (SEQ ID NO: 9) |
| 131582 | FbGLDC (SEQ ID NO: 10) | AGPaseSS (1/3) | ZmRbcS (SEQ ID NO: 9) | ZmRbcS (SEQ ID NO: 8) | RbcS-ictB (41/33) | ZmRbcS (SEQ ID NO: 9) |
| 130225 | ZmUbi (SEQ ID NO: 4) | AGPaseSS (1/3) | ZmUbi (SEQ ID NO: 5) | ZmRbcS (SEQ ID NO: 8) | RbcS-ictB (38/33) | ZmRbcS (SEQ ID NO: 9) |
| 130436 | ZmRbcS (SEQ ID NO: 8) | AGPaseSS (1/3) | ZmRbcS (SEQ ID NO: 9) | ZmRbcS (SEQ ID NO: 8) | AGPaseLS (46/35) | ZmRbcS (SEQ ID NO: 9) |
| 130516 | ZmUbi (SEQ ID NO: 4) | AGPaseSS (1/3) | ZmUbi (SEQ ID NO: 5) | ZmUbi (SEQ ID NO: 4) | SBPase (28/29) | ZmUbi (SEQ ID NO: 5) |
| 130517 | ZmUbi (SEQ ID NO: 4) | AGPaseSS (1/3) | ZmUbi (SEQ ID NO: 5) | ZmUbi (SEQ ID NO: 4) | FBPase (47/48) | ZmUbi (SEQ ID NO: 5) |
| 130670 | ZjPCK (SEQ ID NO: 6) | AGPaseSS (1/3) | ZjPCK (SEQ ID NO: 7) | ZmRbcS (SEQ ID NO: 8) | AGPaseLS (46/35) | ZmRbcS (SEQ ID NO: 9) |
| 130979 | ZmRbcS (SEQ ID NO: 8) | AGPaseSS (1/3) | ZmRbcS (SEQ ID NO: 9) | ZmRbcS (SEQ ID NO: 8) | RbcS-ictB (38/33) | ZmRbcS (SEQ ID NO: 9) |
| 131830 | ZmRbcS (SEQ ID NO: 8) | AGPaseSS (1/3) | ZmRbcS (SEQ ID NO: 9) | ZmCA1-5'Mod (SEQ ID NO: 133) | TF (134/135) | ZmCA (SEQ ID NO: 17) |
| 131841 | ZmRbcS (SEQ ID NO: 8) | AGPaseSS (1/3) | ZmRbcS (SEQ ID NO: 9) | FbGLDC (SEQ ID NO: 10) | AGPaseLS (46/35) | ZmRbcS (SEQ ID NO: 9) |

| Construct | GOI3 | | GOI4 | | |
|---|---|---|---|---|---|
| ID | ORF | 3'UTR | Promoter | ORF | 3'UTR |
| 130235 | SBPase (28/29) | ZmRbcS (SEQ ID NO: 9) | ZmRbcS (SEQ ID NO: 13) | FBPase (47/48) | ZmRbcS (SEQ ID NO: 9) |
| 130417 | SBPase (28/29) | ZmRbcS (SEQ ID NO: 9) | ZmRbcS (SEQ ID NO: 13) | FBP aldolase (49/50) | ZmRbcS (SEQ ID NO: 9) |
| 130881 | AGPaseLS (46/35) | 35S polyA (SEQ ID NO: 15) | GluB-2 (SEQ ID NO: 19) | ism2 (39/40) | ZmUbi (SEQ ID NO: 5) |
| 130966 | AGPaseLS (46/35) | 35S polyA (SEQ ID NO: 15) | FbGLDC (SEQ ID NO: 10) | FBP aldolase (49/50) | ZmRbcS (SEQ ID NO: 9) |
| 131009 | AGPaseLS (46/35) | 35S polyA (SEQ ID NO: 15) | FbGLDC (SEQ ID NO: 10) | FBP aldolase (49/50) | ZmRbcS (SEQ ID NO: 9) |

TABLE 3-continued

| AGPaseSS multigenic plant transformation constructs | | | | | | |
|---|---|---|---|---|---|---|
| 131011 | AGPaseLS (46/35) | 35S polyA (SEQ ID NO: 15) | FbGLDC (SEQ ID NO: 10) | FBP aldolase (49/50) | ZmRbcS (SEQ ID NO: 9) | |
| 131013 | AGPaseLS (46/35) | 35S polyA (SEQ ID NO: 15) | FbGLDC (SEQ ID NO: 10) | FBP aldolase (49/50) | ZmRbcS (SEQ ID NO: 9) | |
| 130445 | SBPase (28/29) | ZmRbcS (SEQ ID NO: 9) | ZmRbcS (SEQ ID NO: 8) | AGPaseLS (46/35) | ZmRbcS (SEQ ID NO: 9) | |
| 130594 | SBPase (23/29) | LOC_Os01g45274 (SEQ ID NO: 25) | ZmRbcS (SEQ ID NO: 8) | AGPaseLS (46/35) | ZmRbcS (SEQ ID NO: 9) | |
| 130629 | FBP aldolase (49/50) | ZmCA (SEQ ID NO: 17) | ZmRbcS (SEQ ID NO: 8) | AGPaseLS (46/35) | ZmRbcS (SEQ ID NO: 9) | |
| 130636 | AGPaseLS (46/35) | ZmRbcS (SEQ ID NO: 9) | GluB-2 (SEQ ID NO: 19) | ism2 (39/40) | ZmUbi (SEQ ID NO: 5) | |
| 130884 | ism2 (39/40) | ZmUbi (SEQ ID NO: 5) | ZmUbi (SEQ ID NO: 4) | AGPaseLS (46/35) | ZmUbi (SEQ ID NO: 5) | |
| 130064 | FBPase (47/48) | ZmUbi (SEQ ID NO: 5) | | | | |
| 130065 | FBPase (47/48) | ZjPCK (SEQ ID NO: 7) | | | | |
| 130243 | CA (51/52) | ZmPepC (SEQ ID NO: 23) | | | | |
| 130401 | FBPase (47/48) | ZmUbi (SEQ ID NO: 5) | | | | |
| 130402 | FBPase (47/48) | ZjPCK (SEQ ID NO: 7) | | | | |
| 130420 | FBP aldolase (49/50) | ZmRbcS (SEQ ID NO: 9) | | | | |
| 130438 | SBPase (28/29) | ZmRbcS (SEQ ID NO: 9) | | | | |
| 130471 | RbcS-ictB (32/33) | AtRbcS (SEQ ID NO: 12) | | | | |
| 130474 | PHB8 (36/37) | AtRbcS (SEQ ID NO: 12) | | | | |
| 130627 | AGPaseLS (46/35) | ZmRbcS (SEQ ID NO: 9) | | | | |
| 130673 | AGPaseLS (46/35) | ZmRbcS (SEQ ID NO: 9) | | | | |
| 130869 | AGPaseLS (46/35) | ZmUbi (SEQ ID NO: 5) | | | | |
| 130870 | AGPaseLS (46/35) | ZmUbi (SEQ ID NO: 5) | | | | |
| 130880 | AGPaseLS (46/35) | 35S polyA (SEQ ID NO: 15) | | | | |
| 130965 | AGPaseLS (46/35) | 35S polyA (SEQ ID NO: 15) | | | | |
| 131002 | FBP aldolase (49/50) | ZmRbcS (SEQ ID NO: 9) | | | | |
| 131008 | AGPaseLS (46/35) | 35S polyA (SEQ ID NO: 15) | | | | |
| 131010 | AGPaseLS (46/35) | 35S polyA (SEQ ID NO: 15) | | | | |
| 131012 | AGPaseLS (46/35) | 35S polyA (SEQ ID NO: 15) | | | | |

TABLE 3-continued

AGPaseSS multigenic plant transformation constructs

| | | |
|---|---|---|
| 130238 | FBPase (47/48) | ZmRbcS (SEQ ID NO: 9) |
| 130437 | FBPase (47/48) | ZmRbcS (SEQ ID NO: 9) |
| 130443 | hc1 (42/43) | ZmUbi (SEQ ID NO: 5) |
| 130606 | AGPaseLS (46/35) | ZmRbcS (SEQ ID NO: 9) |
| 130637 | ism2 (39/40) | ZmUbi (SEQ ID NO: 5) |
| 130710 | AGPaseLS (46/35) | ZmRbcS (SEQ ID NO: 9) |
| 130877 | AGPaseLS (46/35) | ZmUbi (SEQ ID NO: 5) |
| 130883 | AGPaseLS (46/35) | ZmUbi (SEQ ID NO: 5) |
| 131804 | SBPase (28/29) | LOC_Os01g45274 (SEQ ID NO: 25) |

In addition to the gene cassettes described in Tables 2 and 3, each plant transformation construct listed in Tables 2 and 3 also contained a selectable marker cassette suitable for the selection of transformed plant cells and regeneration of plants following the introduction of the plant transformation vector, as described below. Each transformation vector was built in a plasmid that contained sequences suitable for plasmid maintenance in *E. coli* and in *Agrobacterium tumefaciens*. Following verification that the plant transformation constructs listed in Tables 2 and 3 contained the desired sequences, they were transformed into *A. tumefaciens* cells for plant transformation.

Example 2—Transformation of *Setaria viridis*

*A. tumefaciens* cells harboring AGPaseSS plant transformation vectors were used to transform *S. viridis* cells according to a previously described method (PCT/US2015/43989, herein incorporated by reference). Following transformation of the *S. viridis* cells with the relevant plant transformation vectors and regeneration of *S. viridis* plants, the plants were transferred to soil and PCR analyses were performed to confirm the presence of the gene(s) of interest in the *S. viridis* genome. Table 4 summarizes the transformation constructs used to transform *S. viridis*, along with the number of plants that were transferred to soil following *S. viridis* transformation with each construct.

TABLE 4

Summary of *S. viridis* transformation with AGPaseSS plant transformation vectors

| Construct | # To Soil |
|---|---|
| 130816 | 27 |
| 131170 | 41 |
| 130966 | 3 |
| 131009 | 46 |
| 131011 | 25 |
| 130965 | 59 |

TABLE 4-continued

Summary of *S. viridis* transformation with AGPaseSS plant transformation vectors

| Construct | # To Soil |
|---|---|
| 131002 | 18 |
| 131008 | 28 |
| 131010 | 35 |
| 130630 | 1 |
| 130978 | 37 |
| 131063 | 62 |
| 131064 | 10 |

Example 3—Transformation of Maize (*Zea mays*)

*A. tumefaciens* cells harboring AGPaseSS plant transformation vectors were used to transform maize (*Zea mays* cv. B104) cells suitable for regeneration on tissue culture medium. Following transformation of the maize cells with the relevant plant transformation vectors and regeneration of maize plants, the plants are transferred to soil and PCR analyses are performed to confirm the presence of the gene(s) of interest in the maize genome. Constructs 130673 and 130880 were used to transform maize, resulting in two and six plants, respectively, that were transferred to soil.

Example 4—Transformation of Rice (*Oryza sativa*)

*A. tumefaciens* cells harboring AGPaseSS plant transformation vectors were used to transform rice (*Oryza sativa* cv. Kitaake) cells suitable for regeneration on tissue culture medium. Following transformation of the rice cells with the relevant plant transformation vectors and regeneration of rice plants, the plants were transferred to soil and PCR analyses were performed to confirm the presence of the gene(s) of interest in the rice genome. Table 5 summarizes the rice transformations that were performed with transformation vectors that contained an AGPaseSS gene cassette, along with the number of plants that were transferred to soil following transformation with the vectors indicated.

TABLE 5

Summary of Rice transformation with AGPaseSS plant transformation vectors

| Construct | # To Soil |
|---|---|
| 130631 | 21 |
| 130627 | 5 |
| 130965 | 3 |
| 131008 | 9 |
| 131010 | 4 |
| 130630 | 15 |
| 130975 | 1 |

Example 5—Characterization of Transgenic *S. viridis*

Following the transformation and regeneration of *S. viridis* plants transformed with an AGPaseSS plant transformation vector, the T0-generation plants were cultivated to maturity to produce T1-generation seeds. T1-generation *S. viridis* plants harboring the AGPaseSS gene cassette of interest were grown in a greenhouse setting to assess the effects of AGPaseSS gene expression on plant growth and terminal above-ground biomass and seed yield. A randomized block design was used with a wild-type *S. viridis* border row to eliminate edge effects from the analysis. Null segregant plants were grown alongside the transgenic *S. viridis* plants in identical environmental conditions. Table 6 summarizes the results of the biomass and seed yield determinations made from experiments with T1-generation *S. viridis* plants harboring an AGPaseSS gene cassette as a result of transformation. It should be noted that growth conditions (e.g., temperature and light conditions) likely changed between the experiment used to test the 130816 events and the experiment used to test the 131170 events, and thus there were differences in growth between these two experiments; comparisons were made between transgenic and null segregants grown under identical environmental conditions. This table indicates the construct used for transformation, as described in Tables 2 and 3, followed by the T0 event number from which the T1 seed was harvested.

TABLE 6

Summary of *S. viridis* greenhouse observations with T1-generation plants

| | DW (g) | Seed Yield (g) | DW Change (%) | Seed Yield Change (%) |
|---|---|---|---|---|
| 130816-11 | 4.62 ± 0.24 | 1.05 ± 0.10 | 6.5% | 2.9% |
| 130816-14 | 5.23 ± 0.24 | 1.33 ± 0.09 | 20.5% | 30.4% |
| 130816-17 | 4.42 ± 0.30 | 0.90 ± 0.13 | 1.8% | −11.8% |
| 130816-20 | 4.45 ± 0.29 | 1.09 ± 0.10 | 2.5% | 6.9% |
| 130816-5 | 4.78 ± 0.28 | 1.13 ± 0.08 | 10.1% | 10.8% |
| Null | 4.34 ± 0.32 | 1.02 ± 0.12 | N/A | N/A |
| 131170-2 | 3.11 ± 0.54 | 0.63 ± 0.11 | −8.0% | −19.2% |
| 131170-3A | 2.70 ± 0.52 | 0.59 ± 0.11 | −20.1% | −24.4% |
| 131170-3B | 3.29 ± 0.89 | 0.63 ± 0.17 | −2.7% | −19.2% |
| 131170-4A | 2.95 ± 0.44 | 0.59 ± 0.07 | −12.7% | −24.4% |
| 131170-5A | 3.54 ± 0.28 | 0.79 ± 0.05 | 4.7% | 1.3% |
| 131170-null | 3.38 ± 0.38 | 0.78 ± 0.09 | N/A | N/A |
| 131008-12 | 3.76 ± 0.57 | 1.18 ± 0.17 | 10.7% | −0.9% |
| 131008-25 | 3.81 ± 0.54 | 0.98 ± 0.15 | 12.2% | −17.7% |
| 131008-5 | 2.19 ± 0.31 | 0.45 ± 0.09 | −35.4% | −61.7% |
| 131008-8 | 3.72 ± 0.27 | 1.29 ± 0.10 | 9.5% | 8.5% |
| 131008-Null | 3.40 ± 0.28 | 1.19 ± 0.11 | n/a | n/a |
| 131010-1 | 4.53 ± 0.56 | 1.53 ± 0.17 | 72.3% | 73.5% |
| 131010-11 | 3.84 ± 0.38 | 1.23 ± 0.15 | 45.9% | 39.8% |
| 131010-13 | 3.51 ± 0.36 | 1.18 ± 0.11 | 33.6% | 34.2% |
| 131010-17 | 3.57 ± 0.50 | 1.19 ± 0.15 | 35.8% | 34.6% |
| 131010-Null | 2.63 ± 0.15 | 0.88 ± 0.08 | n/a | n/a |
| 131064-1A | 3.85 ± 0.46 | 1.23 ± 0.11 | −10.5% | −13.8% |
| 131064-3 | 3.74 ± 0.48 | 1.28 ± 0.15 | −13.1% | −10.5% |
| 131064-4 | 3.74 ± 0.51 | 1.13 ± 0.15 | −13.0% | −20.8% |
| 131064-6B | 4.33 ± 0.54 | 1.42 ± 0.17 | 0.7% | −0.1% |
| 131064-Null | 4.30 ± 0.65 | 1.43 ± 0.23 | n/a | n/a |
| 131011-21B | 2.88 ± 0.20 | 0.48 ± 0.11 | 2.1% | −30.1% |
| 131011-23 | 2.35 ± 0.32 | 0.37 ± 0.07 | −16.6% | −45.5% |
| 131011-3 | 1.69 ± 0.48 | 0.27 ± 0.10 | −40.0% | −59.5% |
| 131011-7 | 3.04 ± 0.30 | 0.69 ± 0.08 | 8.0% | 1.5% |
| 131011-null | 2.82 ± 0.21 | 0.68 ± 0.08 | n/a | n/a |

In Table 6, the dry weight of the above-ground biomass is indicated in the DW column in grams. Similarly, the dry weight of the harvested seeds is indicated in grams in the Seed Yield column. The DW Change and Seed Yield Change columns indicate the percent change in above-ground biomass and seed yield, respectively, relative to the null segregants from the appropriate experiment. As this table shows, five out of five events tested from the 130816 construct produced an increase in biomass yield, and four out of five events tested from the 130816 construct produced an increase in seed yield, relative to null segregant controls. One out of five events tested from the 131170 construct produced an increase in biomass yield and in seed yield relative to null segregant controls. Three out of four events tested from the 131008 construct produced an increase in biomass yield, with one out of four events tested from this construct also producing an increase in seed yield. Four out of four events tested from the 131010 construct produced an increase in both biomass and seed yield. Three out of four events tested from the 131064 construct produced a decrease in both biomass and seed yield, with the fourth event producing a slight increase in biomass yield and slight decrease in seed yield. Two out of four events tested from the 131011 construct produced an increase in biomass yield, while one out of four events tested from the 131011 construct produced an increase in seed yield.

Example 6—Characterization of Transgenic Maize

T0-generation maize plants transformed with the AGPaseSS plant transformation vector of interest and confirmed to contain the gene(s) of interest are grown to maturity in a greenhouse. When the T0 plants reach reproductive stages, they are pollinated by an appropriate inbred maize line to produce hybrid maize seeds. Alternatively, or in addition to pollination of the T0 transgenic maize plant, the pollen from the T0 is used to pollinate one or more inbred maize lines to produce hybrid maize seeds. The F1-generation hybrid seed resulting from these pollinations are planted in a field setting in two- or four-row plots and cultivated using standard agronomic practices. Plants are genotyped to determine which plants do and which do not contain the AGPaseSS gene cassette and any other relevant gene cassettes (e.g., a selectable marker gene cassette) that were included in the AGPaseSS plant transformation vector. Following the maturation of the maize plants, the seed is harvested. Seeds from the plants containing the AGPaseSS gene cassette are pooled, as are seeds from the null segregant plants lacking the AGPaseSS gene cassette. The seeds are weighed, and seed yields are calculated for the plants containing the AGPaseSS gene cassette as well as for the null segregant plants lacking the AGPaseSS gene cassette. Appropriate statistical analyses are performed to determine whether plants containing an AGPaseSS gene cassette produced higher yields than those plants that lacked an AGPaseSS gene cassette.

Alternatively, T0-generation maize plants transformed with the AGPaseSS plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. Pollen from homozygous T1 plants is used to pollinate one or more inbred maize lines to produce hybrid maize seeds. Pollen from null segregant plants is also used to pollinate one or more inbred maize lines to produce hybrid maize seeds. The resulting hybrid seeds are planted in a field setting in two- or four-row plots and cultivated using standard agronomic practices. Following the maturation of the maize plants, the seed is harvested. Seeds from the plants containing the AGPaseSS gene cassette are pooled, as are seeds from the null segregant plants lacking the AGPaseSS gene cassette. The seeds are weighed, and seed yields are calculated for the plants containing the AGPaseSS gene cassette as well as for the null segregant plants lacking the AGPaseSS gene cassette. Appropriate statistical analyses are performed to determine whether plants containing an AGPaseSS gene cassette produced higher yields than those plants that lacked an AGPaseSS gene cassette.

Example 7—Characterization of Transgenic Rice

T0-generation rice plants transformed with the AGPaseSS plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. The plants from each group are grown to maturity and allowed to self-pollinate to produce T2 seed. The T2 seed resulting from this self-pollination is harvested and weighed, and seed yields from homozygous, heterozygous, and null segregant plants are calculated. Appropriate statistical analyses are performed to determine whether plants containing an AGPaseSS gene cassette produced higher yields than those plants that lacked an AGPaseSS gene cassette.

T1-generation plants grown from seed that resulted from self-pollination of T0-generation plants, or T2-generation plants grown from seed that resulted from self-pollination of homozygous T1-generation plants, are grown in a field setting. In the case of T2-generation plants, null-segregant T1-generation plants are also self-pollinated to produce T2-generation null plants as negative controls. The plants are cultivated using standard agronomic practices and allowed to reach maturity. Upon reaching maturity, the plants are allowed to self-pollinate. The seed resulting from these self-pollinations is harvested and weighed, and seed yields from homozygous, heterozygous, and mill segregant plants are calculated. Appropriate statistical analyses are performed to determine whether plants containing an AGPaseSS gene cassette produced higher yields than those plants that lacked an AGPaseSS gene cassette.

Example 8—Identification of Amino Acid Residues Important for AGPase Regulatory Properties A mutant AGPaseSS gene (SEQ ID NO:1 or SEQ ID NO:2, encoding the amino acid sequence of SEQ ID NO:3) was expressed in plants, resulting in improved growth and yield. The mutant AGPaseSS amino acid sequence of SEQ ID NO:3 was developed by using a directed evolution approach with the native form of the potato-derived AGPaseSS sequence (SEQ ID NO:55) (Salamone et al. (2002) *Proc Natl Acad Sci USA* 99:1070-1075). Now that it has been shown that expression of this mutant AGPaseSS gene in plants can improve plant growth and yield, amino acid alignments of SEQ ID NOs: 3 and 55-132 were performed. The result of this alignment is shown in FIG. 1. In this figure, Seq3 refers to SEQ ID NO:3, Seq55 refers to SEQ ID NO:55, and so on. An asterisk (*) above an amino acid residue indicates that this amino acid residue is conserved among all of the amino acid sequences that were aligned. A colon (:) above an amino acid residue indicates that this amino acid residue is either conserved or that strongly similar properties are observed at that amino acid position. A period (.) above an amino acid residue indicates that this amino acid residue is either conserved or that weakly similar properties are observed at that amino acid position. The asterisk, colon, and period symbols are explained more fully elsewhere on the World Wide Web (http://www.ebi.ac.uk/Tools/msa/clustalo/help/faq.html).

The mutations in SEQ ID NO:3 relative to SEQ ID NO:55 are summarized in Table 7. In this table, the Mutation column indicates the mutation that exists in SEQ ID NO:3 (i.e., SEQ ID NO:3 contains a Phe residue at position 118, according to the amino acid numbering of SEQ ID NO:3, while SEQ ID NO:55 contains a Leu residue at this position)

TABLE 7

Summary of mutations found in SEQ ID NO: 3 relative to SEQ ID NO: 55

| Mutation | Location |
| --- | --- |
| Leu > Phe | 118 |
| Val > Ile | 129 |
| Phe > Leu | 374 |
| Tyr > Cys | 387 |
| Leu > Ser | 450 |

FIG. 2 shows an alignment of SEQ ID NOs:3 and 55-132 in the region surrounding the mutations at amino acid positions 118 and 129 according to the amino acid sequence of SEQ ID NO:3. These mutations correspond to amino acid positions number 3 and 14 in FIG. 2. FIG. 3 shows an alignment of SEQ ID NOs:3 and 55-132 in the region surrounding the mutations at amino acid positions 374 and 387 according to the amino acid sequence of SEQ ID NO:3. These mutations correspond to amino acid positions number 3 and 16 in FIG. 3. FIG. 4 shows an alignment of SEQ ID NOs:3 and 55-132 in the region surrounding the mutation at amino acid position 450 according to the amino acid sequence of SEQ ID NO:3. This mutation corresponds to amino acid position number 4 in FIG. 4. Visual inspection of the amino acid alignments in FIGS. 1-4 shows that most of the mutations summarized in Table 7 occur at locations in the AGPaseSS protein that are well-conserved among all of the aligned AGPaseSS amino acid sequences. At amino acid position 118 in SEQ ID NO:3, all of the aligned protein sequences contain a Leu residue at this position with the exception of SEQ ID NOs:3 and 65. At amino acid position 129 in SEQ ID NO:3, all of the aligned protein sequences contain a Val amino acid residue at this position with the exception of SEQ ID NO:3. At amino acid position 374 in SEQ ID NO:3, all of the aligned protein sequences contain a Phe amino acid residue at this position with the exception of SEQ NO:3. At amino acid position 387 in SEQ ID NO:3, SEQ ID NOs:55-125 contain a Tyr residue while SEQ ID NOs:126-132 contain a His residue at this position; only SEQ ID NO:3 contains a Cys residue at this position. Notably, SEQ ID NOs:55-125 are AGPaseSS sequences that originate from dicot plants while SEQ ID NOs:126-132 originate from monocot plants. At amino acid position 450 in SEQ ID NO:3, all of the aligned sequences contain either a Leu or Phe residue at this position with the exception of SEQ ID NO:124, which contains an Ile residue, and SEQ ID NOs: 3 and 72, which contain a Ser at this position.

Visual inspection of the amino acid alignment shown in FIG. 1 and of the number of asterisks (*), colons (:), and periods (.) at the top of the alignment shows a high degree of sequence conservation among the aligned AGPaseSS proteins, including at the amino acid residue positions indicated in Table 7. Now that it has been demonstrated that the mutant form of the *S. tuberosum* AGPaseSS protein (SEQ ID NO:3) has improved biochemical properties relative to the native sequence (SEQ ID NO:55) (Salamone et al. (2002) *Proc Natl Acad Sci USA* 99:1070-1075), and that expression of a gene encoding the protein sequence of SEQ NO:3 in plants can impart improved growth and yield properties, it may be desirable to generate further mutant AGPaseSS proteins derived from other AGPaseSS protein sequences. Alignments like those shown in FIGS. 1-4 can guide the development of such mutant AGPaseSS protein sequences. PCR-based methods are used to generate coding sequences that encode proteins with the amino acid sequence of a wild-type AGPaseSS protein sequence, such as an AGPaseSS protein sequence selected from SEQ ID NOs:55-132, but containing one or more of the mutations described in Table 7. Following the generation of these mutant AGPaseSS coding sequences, the mutant AGPaseSS coding sequence(s) of interest is/are cloned into a plant transformation construct, operably linked to a promoter that is functional in a plant cell. This construct is used to transform a cell or cells from a plant of interest, and the transformed plant cell(s) are used to regenerate plants comprising the mutant AGPaseSS coding sequence, operably linked to a promoter that is functional in a plant cell. Following regeneration of these plants, the plants are cultivated and characterized to confirm the presence and expression of the AGPaseSS coding sequence, the accumulation of AGPaseSS protein encoded by the mutant AGPaseSS coding sequence, accumulation of AGPase enzyme activity in plant tissue, altered accumulation of leaf starch, and/or altered plant growth properties including altered accumulation of biomass and/or seed. These analyses are performed in the T0, T1, T2, or later generations of transgenic plants, and characterization of plants containing mutant AGPaseSS coding sequences is compared against control plants such as wild-type or null segregant plants to determine whether the presence of the AGPaseSS coding sequence alters plant growth or metabolism.

I claim:

1. A method for increasing crop yield comprising transforming a plant with at least one ADP-glucose pyrophosphorylase small subunit (AGPaseSS) protein-encoding sequence, wherein said AGPaseSS protein-encoding sequence comprises SEQ ID NO:1 or 2, or encodes a protein comprising SEQ ID NO:3.

2. A plant having stably incorporated into its genome a promoter that drives expression in a plant operably linked to an AGPaseSS protein-encoding sequence, wherein said promoter is heterologous to said AGPaseSS protein-encoding sequence, and wherein said AGPaseSS protein-encoding sequence comprises SEQ ID NO: 1 or 2, or encodes a protein comprising SEQ ID NO: 3.

3. Transformed seed of the plant of claim 2.

4. The plant of claim 2 wherein said plant is a monocot.

5. The plant of claim 4 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena,* or *Hordeum.*

6. The plant of claim 2 wherein said plant is a dicot.

7. The plant of claim 6 wherein said plant is from the genus *Glycine, Brassica, Medicago, Helianthus, Carthamus, Nicotiana, Solanum, Gossypium, Ipomoea, Manihot, Coea, Citrus, Theobroma, Camellia, Persea, Ficus, Psidium, Mangifera, Olea, Carica, Anacardium, Macadamia, Prunus, Beta, Populus,* or *Eucalyptus.*

8. The method of claim 1, wherein said AGPaseSS protein-encoding sequence is expressed from a promoter that comprises SEQ ID NO:8.

9. The plant of claim 2, wherein said promoter that drives expression in a plant comprises SEQ ID NO:8.

10. A DNA construct comprising, in operable linkage,
   a. A promoter that is functional in a plant cell and,
   b. A nucleic acid sequence encoding an AGPaseSS protein, wherein said nucleic acid sequence encoding the AGPaseSS protein comprises SEQ ID No: 1 or 2, or encodes a protein that comprises SEQ ID NO:3.

11. The DNA construct of claim 10, wherein said promoter that is functional in a plant cell comprises SEQ ID NO:8.

12. A method for increasing crop yield comprising modulating the expression of at least one AGPaseSS protein-encoding sequence in a plant, wherein said AGPaseSS protein-encoding sequence comprises SEQ ID NO:1 or 2, or encodes a protein comprising SEQ ID NO:3.

13. The method of claim 12 wherein said modulating the expression comprises increasing the expression of at least one AGPaseSS protein-encoding sequence in a plant.

14. The DNA construct of claim 10 wherein said promoter is heterologous to said nucleic acid sequence encoding an AGPaseSS protein.

* * * * *

UNITED STATES PATENT AND TRADEMARK OFFICE
CERTIFICATE OF CORRECTION

PATENT NO. : 11,008,583 B2  
APPLICATION NO. : 16/311377  
DATED : May 18, 2021  
INVENTOR(S) : Benjamin Neil Gray Page 1 of 1

It is certified that error appears in the above-identified patent and that said Letters Patent is hereby corrected as shown below:

In the Specification

At Column 1, under the heading "Cross-Reference To Related Applications", the text at Line 9, "PCT/Il32017/053534" should be listed as -- PCT/IB2017/053534 --.

In the Claims

At Column 139, Claim 1, Line 38, the text "SEO" should be changed to -- SEQ --.

At Column 139, Claim 7, Line 57, the text "Coea," should be changed to -- Coffea --.

At Column 340, Claim 10, Line 42, the text "No:" should be changed to -- NO: --.

Signed and Sealed this  
Fifth Day of July, 2022

Katherine Kelly Vidal  
*Director of the United States Patent and Trademark Office*

SEQUENCE LISTING

<160> NUMBER OF SEQ ID NOS: 135

<210> SEQ ID NO 1
<211> LENGTH: 1566
<212> TYPE: DNA
<213> ORGANISM: Solanum tuberosum
<220> FEATURE:
<221> NAME/KEY: misc_feature
<222> LOCATION: (1)..(1566)

<223> OTHER INFORMATION: ADP-glucose pyrophosphorylase small subunit

<400> SEQUENCE: 1

| | |
|---|---|
| atggcggcga gcattggcgc cctcaaatcc agcccatcca gcaacaattg catcaatgag | 60 |
| cgcaggaacg acagcacaag ggccgtgagc tccaggaatc tgtccttcag ctccagccac | 120 |
| ctggcgggcg acaagctcat gccggtctcc agcctccgct cccaaggcgt gaggttcaac | 180 |
| gtcaggaggt ccccgatgat cgtgagcccg aaagccgtct ccgattccca gaattcccaa | 240 |
| acctgtctgg acccagacgc gagcaggtcc gtcctgggca tcatcctcgg cggggggcg | 300 |
| gggacaaggc tctacccact caccaaaaag agggccaagc cggcggtgcc gttcggggcc | 360 |
| aattatcgcc tcattgacat tccaatcagc aactgtctga actccaacat tagcaaaatc | 420 |
| tatgtgctca cacagtttaa ttccgcgtcc ctcaataggc acctgtcccg cgcgtacgcg | 480 |
| agcaacatgg gcggctataa gaatgagggg tttgtggaag tcctcgccgc ccagcagagc | 540 |
| ccggagaacc cagattggtt tcagggcaca gcggatgcgg tccgccagta tctctggctg | 600 |
| tttgaagaac acacagtgct ggaatatctg attctcgcgg gcgaccacct gtacaggatg | 660 |
| gattacgaga aatttattca ggcgcaccgc gaaaccgatg ccgacattac cgtggcggcg | 720 |
| ctgccaatgg acgagaaaag ggccacagcc tttggcctca tgaaaatcga cgaagaaggc | 780 |
| aggatcatcg agttcgccga aaagccacaa ggggagcagc tgcaagcgat gaaggtggat | 840 |
| accaccattc tcgggctcga cgataagagg gccaaggaga tgccattcat gcctccatg | 900 |
| ggcatttatg tcatttccaa ggatgtcatg ctcaacctcc tgagggataa gttcccgggc | 960 |
| gccaacgatt tcgggtccga ggtcatcccg ggcgccacca gctgggcat gcgcgtccaa | 1020 |
| gcgtatctct acgacgggta ttgggaagac attgggacaa ttgaagcctt ttacaatgcg | 1080 |
| aacctcggca ttaccaaaaa accagtcccg gacttcagcc tctatgacag gtccgcgccg | 1140 |
| atctatacac aaccaaggtg tctcccgcca agcaaaatgc tcgacgccga cgtgaccgac | 1200 |
| agcgtcatcg gggagggctg tgtgattaaa aactgcaaga ttcatcattc cgtggtcggg | 1260 |
| ctgcgctcct gcatctccga aggggcgatt attgaagatt ccctcctcat ggggcggac | 1320 |
| tattatgaaa ccgatgccga ccgcaaatcc ctggccgcca agggagcgt cccgattggg | 1380 |
| attggcaaga actgccatat caaacgcgcc atcatcgata aaaacgcccg cattggggac | 1440 |
| aacgtgaaga tcattaacaa ggacaatgtc caagaagcgg ccaggaaaac agatgggtat | 1500 |
| ttcatcaaaa gcgggatcgt gacagtcatt aaggacgccc tgatcccaag cgggatcatc | 1560 |
| atctga | 1566 |

<210> SEQ ID NO 2
<211> LENGTH: 1566
<212> TYPE: DNA
<213> ORGANISM: Solanum tuberosum
<220> FEATURE:
<221> NAME/KEY: misc_feature
<222> LOCATION: (1)..(1566)
<223> OTHER INFORMATION: ADP-glucose pyrophosphorylase small subunit

<400> SEQUENCE: 2

| | |
|---|---|
| atggctgctt ctattggagc tttgaagtct tctccttctt ctaataattg tattaatgaa | 60 |
| agaagaaatg attctactag agctgtttct tctagaaatt tgtctttttc ttcttctcat | 120 |
| ttggctggag ataagttgat gcctgtttct tctttgagat ctcaaggagt tagatttaat | 180 |
| gttagaagat ctcctatgat tgtttctcct aaggctgttt ctgattctca aaattctcaa | 240 |
| acttgtttgg atcctgatgc ttctagatct gttttgggaa ttattttggg aggaggagct | 300 |

```
ggaactagat tgtatccttt gactaagaag agagctaagc ctgctgttcc ttttggagct    360
aattatagat tgattgatat tcctatttct aattgtttga attctaatat ttctaagatt    420
tatgttttga ctcaatttaa ttctgcttct ttgaatagac atttgtctag agcttatgct    480
tctaatatgg gaggatataa gaatgaagga tttgttaaag ttttggctgc tcaacaatct    540
cctgaaaatc ctgattggtt tcaaggaact gctgatgctg ttagacaata tttgtggttg    600
tttgaagaac atactgtttt ggaatatttg attttggctg gagatcattt gtatagaatg    660
gattatgaaa agtttattca agctcataga gaaactgatg ctgatattac tgttgctgct    720
ttgcctatgg atgaaaagag agctactgct tttggattga tgaagattga tgaagaagga    780
agaattattg aatttgctga aaagcctcaa ggagaacaat gcaagctat gaaggttgat     840 actactattt tgggattgga tgataagaga gctaaggaaa tgccttttat tgcttctatg    900
ggaatttatg ttatttctaa ggatgttatg ttgaatttgt tgagagataa gtttcctgga    960
gctaatgatt ttggatctga agttattcct ggagctactt ctttgggaat gagagttcaa   1020
gcttatttgt atgatggata ttgggaagat attggaacta ttgaagcttt ttataatgct   1080
aatttgggaa ttactaagaa gcctgttcct gattttttctt tgtatgatag atctgctcct   1140
atttatactc aacctagatg tttgcctcct tctaagatgt tggatgctga tgttactgat   1200
tctgttattg gagaaggatg tgttattaag aattgtaaga ttcatcattc tgttgttgga   1260
ttgagatctt gtatttctga aggagctatt attgaagatt ctttgttgat gggagctgat   1320
tattatgaaa ctgatgctga tagaaagtct ttggctgcta agggatctgt tcctattgga   1380
attggaaaga attgtcatat taagagagct attattgata agaatgctag aattggagat   1440
aatgttaaga ttattaataa ggataatgtt caagaagctg ctagagaaac tgatggatat   1500
tttattaagt ctggaattgt tactgttatt aaggatgctt tgattccttc tggaattatt   1560
atttga                                                                   1566

<210> SEQ ID NO 3
<211> LENGTH: 521
<212> TYPE: PRT
<213> ORGANISM: Solanum tuberosum
<220> FEATURE:
<221> NAME/KEY: MISC_FEATURE
<222> LOCATION: (1)..(521)
<223> OTHER INFORMATION: ADP-glucose pyrophosphorylase small subunit
<220> FEATURE:
<221> NAME/KEY: MISC_FEATURE
<222> LOCATION: (118)..(118)
<223> OTHER INFORMATION: Leu>Phe_mutation
<220> FEATURE:
<221> NAME/KEY: MISC_FEATURE
<222> LOCATION: (129)..(129)
<223> OTHER INFORMATION: Val>Ile_mutation
<220> FEATURE:
<221> NAME/KEY: MISC_FEATURE
<222> LOCATION: (374)..(374)
<223> OTHER INFORMATION: Phe>Leu_mutation
<220> FEATURE:
<221> NAME/KEY: MISC_FEATURE
<222> LOCATION: (387)..(387)
<223> OTHER INFORMATION: Tyr>Cys_mutation
<220> FEATURE:
<221> NAME/KEY: MISC_FEATURE
<222> LOCATION: (450)..(450)
<223> OTHER INFORMATION: Leu>Ser_mutation

<400> SEQUENCE: 3

Met Ala Ala Ser Ile Gly Ala Leu Lys Ser Ser Pro Ser Ser Asn Asn
 1               5                  10                  15
```

```
Cys Ile Asn Glu Arg Arg Asn Asp Ser Thr Arg Ala Val Ser Ser Arg
        20                  25                  30

Asn Leu Ser Phe Ser Ser His Leu Ala Gly Asp Lys Leu Met Pro
        35                  40                  45

Val Ser Ser Leu Arg Ser Gln Gly Val Arg Phe Asn Val Arg Arg Ser
50                  55                  60

Pro Met Ile Val Ser Pro Lys Ala Val Ser Asp Ser Gln Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala
                100                 105                 110

Lys Pro Ala Val Pro Phe Gly Ala Asn Tyr Arg Leu Ile Asp Ile Pro
            115                 120                 125

Ile Ser Asn Cys Leu Asn Ser Asn Ile Ser Lys Ile Tyr Val Leu Thr
130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175

Ala Gln Gln Ser Pro Glu Asn Pro Asp Trp Phe Gln Gly Thr Ala Asp
            180                 185                 190

Ala Val Arg Gln Tyr Leu Trp Leu Phe Glu Glu His Thr Val Leu Glu
            195                 200                 205

Tyr Leu Ile Leu Ala Gly Asp His Leu Tyr Arg Met Asp Tyr Glu Lys
            210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Glu Glu Gly Arg Ile Ile Glu Phe Ala Glu Lys Pro Gln Gly Glu
                260                 265                 270

Gln Leu Gln Ala Met Lys Val Asp Thr Thr Ile Leu Gly Leu Asp Asp
            275                 280                 285

Lys Arg Ala Lys Glu Met Pro Phe Ile Ala Ser Met Gly Ile Tyr Val
            290                 295                 300

Ile Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Leu Gly
                325                 330                 335

Met Arg Val Gln Ala Tyr Leu Tyr Asp Gly Tyr Trp Glu Asp Ile Gly
            340                 345                 350

Thr Ile Glu Ala Phe Tyr Asn Ala Asn Leu Gly Ile Thr Lys Lys Pro
            355                 360                 365

Val Pro Asp Phe Ser Leu Tyr Asp Arg Ser Ala Pro Ile Tyr Thr Gln
            370                 375                 380

Pro Arg Cys Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
                405                 410                 415

Ser Val Val Gly Leu Arg Ser Cys Ile Ser Glu Gly Ala Ile Ile Glu
                420                 425                 430
```

Asp Ser Leu Leu Met Gly Ala Asp Tyr Tyr Glu Thr Asp Ala Asp Arg
            435                 440                 445

Lys Ser Leu Ala Ala Lys Gly Ser Val Pro Ile Gly Ile Gly Lys Asn
    450                 455                 460

Cys His Ile Lys Arg Ala Ile Ile Asp Lys Asn Ala Arg Ile Gly Asp
465                 470                 475                 480

Asn Val Lys Ile Ile Asn Lys Asp Asn Val Gln Glu Ala Ala Arg Glu
                485                 490                 495

Thr Asp Gly Tyr Phe Ile Lys Ser Gly Ile Val Thr Val Ile Lys Asp
            500                 505                 510

Ala Leu Ile Pro Ser Gly Ile Ile Ile
            515                 520

<210> SEQ ID NO 4
<211> LENGTH: 1992
<212> TYPE: DNA
<213> ORGANISM: Zea mays
<220> FEATURE:
<221> NAME/KEY: promoter
<222> LOCATION: (1)..(1992)
<223> OTHER INFORMATION: Ubiquitin promoter and 5'UTR

<400> SEQUENCE: 4
ctgcagtgca gcgtgacccg gtcgtgcccc tctctagaga taatgagcat tgcatgtcta      60
agttataaaa aattaccaca tattttttt gtcacacttg tttgaagtgc agtttatcta      120
tctttataca tatatttaaa ctttactcta cgaataatat aatctatact actacaataa    180
tatcagtgtt ttagagaatc atataaatga acagttagac atggtctaaa ggacaattga    240
gtatttttgac aacaggactc tacagttta tcttttagt gtgcatgtgt tctccttttt    300
ttttgcaaat agcttcacct atataatact tcatccattt tattagtaca tccatttagg    360
gtttagggtt aatggttttt atagactaat tttttagta catctatttt attctatttt    420
agcctctaaa ttaagaaaac taaaactcta ttttagtttt ttatttaat aatttagata    480
taaaatagaa taaaataaag tgactaaaaa ttaaacaaat acccttaag aaattaaaaa    540
aactaaggaa acattttct tgtttcgagt agataatgcc agcctgttaa acgccgtcga    600
cgagtctaac ggacaccaac cagcgaacca gcagcgtcgc gtcgggccaa gcgaagcaga    660
cggcacggca tctctgtcgc tgcctctgga ccctctcga gagttccgct ccaccgttgg    720
acttgctccg ctgtcggcat ccagaaattg cgtggcggag cggcagacgt gagccggcac    780
ggcaggcggc ctcctcctcc tctcacggca cggcagctac gggggattcc tttcccaccg    840
ctccttcgct ttcccttcct cgcccgccgt aataaataga cacccctcc acaccctctt    900
tccccaacct cgtgttgttc ggagcgcaca cacacacaac cagatctccc ccaaatccac    960
ccgtcggcac ctccgcttca aggtacgccg ctcgtcctcc cccccccccc ctctctacct    1020
tctctagatc ggcgttccgg tccatggtta gggcccggta gttctacttc tgttcatgtt    1080
tgtgttagat ccgtgtttgt gttagatccg tgctgctagc gttcgtacac ggatgcgacc    1140
tgtacgtcag acacgttctg attgctaact tgccagtgtt tctctttggg gaatcctggg    1200
atggctctag ccgttccgca gacgggatcg atttcatgat tttttttgtt tcgttgcata    1260
gggtttggtt tgccctttc ctttatttca atatatgccg tgcacttgtt tgtcgggtca    1320
tcttttcatg cttttttttg tcttggttgt gatgatgtgg tctggttggg cggtcgttct    1380
agatcggagt agaattctgt ttcaaactac ctggtggatt tattaatttt ggatctgtat    1440
gtgtgtgcca tacatattca tagttacgaa ttgaagatga tggatggaaa tatcgatcta    1500

```
ggataggtat acatgttgat gcgggtttta ctgatgcata tacagagatg cttttttgttc    1560 gcttggttgt gatgatgtgg tgtggttggg cggtcgttca ttcgttctag atcggagtag    1620
aatactgttt caaactacct ggtgtattta ttaattttgg aactgtatgt gtgtgtcata    1680
catcttcata gttacgagtt taagatggat ggaaatatcg atctaggata ggtatacatg    1740
ttgatgtggg ttttactgat gcatatacat gatggcatat gcagcatcta ttcatatgct    1800
ctaaccttga gtacctatct attataataa acaagtatgt tttataatta ttttgatctt    1860
gatatacttg gatgatggca tatgcagcag ctatatgtgg attttttttag ccctgccttc    1920 atacgctatt tatttgcttg gtactgtttc ttttgtcgat gctcaccctg ttgtttggtg    1980
ttacttctgc ag                                                        1992
```

<210> SEQ ID NO 5
<211> LENGTH: 623
<212> TYPE: DNA
<213> ORGANISM: Zea mays
<220> FEATURE:
<221> NAME/KEY: misc_feature
<222> LOCATION: (1)..(623)
<223> OTHER INFORMATION: Ubiquitin 3'UTR

<400> SEQUENCE: 5

```
gtcatgggtc gtttaagctg ccgatgtgcc tgcgtcgtct ggtgccctct ctccatatgg      60
aggttgtcaa agtatctgct gttcgtgtca tgagtcgtgt cagtgttggt ttaataatgg     120
accggttgtg ttgtgtgtgc gtactaccca gaactatgac aaaatcatgaa taagtttgat    180 gtttgaaatt aaagcctgtg ctcattatgt tctgtctttc agttgtctcc taatatttgc    240
ctgcaggtac tggctatcta ccgtttctta cttaggaggt gtttgaatgc actaaaacta    300
atagttagtg gctaaaatta gttaaaacat ccaaacacca tagctaatag ttgaactatt    360 agctatttt ggaaaattag ttaatagtga ggtagttatt tgttagctag ctaattcaac    420
taacaatttt tagccaacta acaattagtt tcagtgcatt caaacacccc cttaatgtta    480
acgtggttct atctaccgtc tcctaatata tggttgattg ttcggtttgt tgctatgcta    540
ttgggttctg attgctgcta gttcttgctg aatccagaag ttctcgtagt atagctcaga    600
ttcatattat ttatttgagt gat                                             623
```

<210> SEQ ID NO 6
<211> LENGTH: 1681
<212> TYPE: DNA
<213> ORGANISM: Zoysia japonica
<220> FEATURE:
<221> NAME/KEY: promoter
<222> LOCATION: (1)..(1681)
<223> OTHER INFORMATION: PCK promoter and 5'UTR

<400> SEQUENCE: 6

```
gtcgacaact tattttttgag accggagtat atgtttatgg aactttgtca tccatatcaa      60
gataactata cttctatttg ttaaataata aatttaaaat atactgcttc aattaagggt    120
gcacaataaa aatatacacg aaaaacgcgg caattgccgc gcagattttc tagtacaaac    180
taattactat cacaaaaggc ttatttgtca tgtgtttaat gtgtttgaga tggaacagga    240
attagtgaca aaattacttt actcttgtcc acttcacaca aattaccact cattttggat    300
ctcgtgagat taattggtat gatttcctat ggtgtgttct tcgtgaacac aatagcttgc    360
aatattgggg tgcaaatagg tatcatgtgg tttgttgtgg gtcatacaca tctgtgtaac    420
```

```
tggatgattt actacgcgtt atcgcggaaa tttataataa tgatgataat ttattatggt        480
aagatgaaaa aagctcaaaa aaataatcat aatggatgaa aaaattaaaa catatgagaa        540
ctatttaata aaatttattt gagctcattc tgatgattaa tcatatttgc ttaaaaattc        600
aaagtttttt gactgcattt attaatgaaa tttgaatata atattcaatt atcatcagta        660
gattggccaa gttgcaagat ctaaaacttc ctagttaaga ttaaaaaata gtagatataa        720
caacatctta ataaagtcga ggaaggtgga gggtcagatt gagcggaggt gcatgagagg        780
tgaggattaa atagaggata gcagcgcggg agataaagaa ggagggatga aggaagttaa        840
atggagaggt ctacaatgaa cggccatcat taggtagagc ttcatgatcg gacggtgcaa        900
acaaaaaaga tgatgtgact cgatgagaat ttatttatga tagttagtga atggacaaat        960
atatatagaa catataaatt tgcgaatata agatggattt tgatcattcc acagagtttt       1020
tgggtcagcc caaaatctaa attagaaaac caacatctct acctacaatt ggtaatcgct       1080
atactaattt gttagtacga ggtgattttc ttcgacttaa aagcatttgc ttacatggat       1140
gaagagagcg atgacatata cacaccctat atttggaaca tgtagattca cttcaagtaa       1200
ggaatcaatt aacgcaaagt catgacaaac aggattgaaa catacaacgg ttgttgtcag       1260
agaaagagag agaaaagta gtggtcgaag aaaaacccac aaccatgctc acaaaaagtc       1320
tgaacctaac ccgcaccgtc accgccggat gggtcagaat gtaaccacgg ttaggctccg       1380
gccagcccct taaaagcccg acggggctcc gccgatacgc acccatacag cttgttccat       1440
ttcacgtcga cagcgtacac cgcgacacag acagagcacg ccgttctcct cgtacgtacg       1500
tgcctcttcc ttgtgcaagc tcgatcgcag cgacgccctg ctgctgctgc tgctctctct       1560
ccaagcgtca atggcaggac gttaggatcg tgatcagtag ggtgctaacg actctgtttc       1620
cctgtcccgt ttgcaggcgg atcaacgacc accgtgccgc acgcgcgccg cgccggcga       1680 g                                                                        1681

<210> SEQ ID NO 7
<211> LENGTH: 165
<212> TYPE: DNA
<213> ORGANISM: Zoysia japonica
<220> FEATURE:
<221> NAME/KEY: misc_feature
<222> LOCATION: (1)..(165)
<223> OTHER INFORMATION: PCK 3'UTR

<400> SEQUENCE: 7
tcttgaagaa gaaggcgacg cgatggagtg ggtattcaga ataaacggtg gtgtttgtct         60
atcacgatga tgatgacgaa aaaaatatgt tgtatcggtg tgtgagtact acatttctc        120 agcttgatga cctgtgtgcg cgcttggctg tttgcagcat tgtcc                       165

<210> SEQ ID NO 8
<211> LENGTH: 974
<212> TYPE: DNA
<213> ORGANISM: Zea mays
<220> FEATURE:
<221> NAME/KEY: promoter
<222> LOCATION: (1)..(974)
<223> OTHER INFORMATION: RbcS promoter and 5'UTR

<400> SEQUENCE: 8
gagctccctt taatctggcg ctagatctgc atccgcggct tgcaaagata aatggcacat         60
ttagtgtgtt attttgcaat acctttcata gtagatatcc ttaaatgcag ttttaggcat       120
gtttgggtaa ttaaataaca tttttaggag gagtttttaga tttacctttc tttcgtgatg      180
```

```
actgatgaca gacgtgggga attcaaatgc aactctagcg aaagttcata tattttcat    240 aaatagctga ggctggggta attatttttt ttgtagaaaa atagaatagg tggaatggtt    300
ggggaaggcg taggcgctcg tggacgacgc ccgataaaag acaagaggcg gaattgccat    360
gaattcgagg tagctaagta aggcgcatat atatgccaaa aaattctact gtcactttcc    420
aatttcaatg cgctgccaaa caagccatcc tggaaactga cttgaattca gcccaattct    480
gtagatccaa acagggccgg cgtcagtgcc tcaggtgaga gagcagcaga cgatgcaaag    540
agccaaaact gcaagcagac gcagccgaag ccgaagccga agcccaagcc caaaactgtt    600
ttgtctttgc ccagaaccgc gacgagccta aactgcgctt cctcctatct acaagtccct    660
ggcacatcac gcatagtcca accatggcgc gcaggcgata aggcgcgcca cggggacgcg    720
acatgtggtg gcggacgcga tcaggatagg gccaggctgg ccgggcgcgg ccacgggaga    780
acggtggcca ctcgtcccac atccgcttcg tcctgtcctg tactgcgtcc tgccccaac    840 gagagccgga gccggccatc ccgtcgcaca ctctccccct ctatatatgc cgtcggtgtg    900
ggggagccta ctacaggacg acccaagcaa gcaagcaagc agcgagtaca tacatactag    960
gcagccaggc agcc                                                      974

<210> SEQ ID NO 9
<211> LENGTH: 439
<212> TYPE: DNA
<213> ORGANISM: Zea mays
<220> FEATURE:
<221> NAME/KEY: misc_feature
<222> LOCATION: (1)..(439)
<223> OTHER INFORMATION: RbcS 3'UTR

<400> SEQUENCE: 9
accgcgcccg ccggccgccc cccgccggct agctagctag ctagctcctg cgtgagctag     60
tagctagtgc catgcgtcgt ctctgtcgtt cggttttgct tcgggtcacc gtgtacccttt   120 tgcttgcttg gtttcttctt tccttttttc cttttttttt cttcttttcc ccggccatgg   180
ttcctttgct ttccagcagt tctctgctgg atgtgatgta tccattgttg caatcatggc   240
cttgcattgg ctacctctat acctgctaca aaactactgc aacgcctata tacttggg    300 gtgaggaaca tgtgaatgca agctccggct atcatataca tgtaatatgg atacaaacta   360
tatatataaa tccgccgagg cgccgacaat actatacgac accgtgttaa gttaatatat   420
aactggtgct ttttatta                                                  439

<210> SEQ ID NO 10
<211> LENGTH: 1571
<212> TYPE: DNA
<213> ORGANISM: Flaveria bidentis
<220> FEATURE:
<221> NAME/KEY: promoter
<222> LOCATION: (1)..(1571)
<223> OTHER INFORMATION: GLDC promoter and 5'UTR

<400> SEQUENCE: 10
aagctttact cctctcaact ttcaaatcat aacataaaag ttcgtaggtt tgtgttcttc     60
ccaaaaaaaa agtgattttt tttcatcggt taattcatga ttaacatttc gacattcatt    120
ccactatttc acatcatgtt ttgatgggag attgaaatag cgataaggcg aatgtgaaag    180
tgtgaaacag gatgagccac accatcacca catcacaatt tacccaaata atatcccaaa    240
gattcatacg cattttgatc cactgaaacc ccatccaatt ctatccaatg cccaccacat    300
```

```
gttcgacgat tgcctcagt gaatcaagac caacacatgc cactgctttc tgcttttttag    360
tccctgataa caaacgattg gctttcattg ctcactgtag aaagtggaga cacccaacaa    420
ctatcatctc cacgtggttc cgtgccgcct ttttgccttt catactgctg gtgcgtcatt    480
tgtcgtcatc aaagcactca cccactatca ttgatctcga aatcttgaat ctttaggttt    540
ttatgctttg atacttgaac tctacacaca gtctcgtatc tgacttttttg ttatctgtgt    600
tttgctttac taaagatctc accttttaatc aagttttgaa cttttgatgg atttgtcatg    660
ataatgaaga acacatagtt attattgatt atattttgac gaatcttttt tcatgatcgt    720
taaacataat ttgagttctt tttaccttgt ctttctttga ggtttaactg tacatgaaga    780
ctgtatttttg agtttattgc ataaatggtc tatatagttt gggttaaaac aactggtttt    840
aatatcaagt ttgatactag acaaaccaac tttttgatta acttttaaaa aaattaataa    900
gtctatttgg aaaaaaattg aaaatttgat tttaaggggt aaaagttctt ttttgaaaag    960
ttaataagag taacttttga aatgtaactt ttaaaaaaat actgttgata aaaaaagaaa   1020
tcctaatcat gggcttagta ttgtaagtag cttggatatt gaagctaatt tttcactttta  1080
tattttataga aaagttaatg gaagtaagag gtttggatac ttttttttctt aatttagacg  1140
aatgttacac atgaaaaata agcgttgttt tgtaagattt ttttaattcg caagcactaa   1200
actcctaatc aactttttggg gttaaggagt aggcagtaaa ccaaaagcgt ttttgcacga    1260
tacgatgttc aaacatttga tctataacga taagtccaag tgcgttacaa aatgaaactt    1320
tggtatccaa tatgaaactg ggtgtgtagt tcagtaccaa aagcataact ttcagcctcc    1380
ttagtgactt atgactaggc aagagaacat gtgagcccaa tgtactaact ttttaccccct   1440
tttattacca ccaccccagc cccccaccat gaaccgatca gaaaaagaag caagaaaaac    1500
agagcattct tgctccttct tcttcatcaa ttcaataaca ttcttcatac cattagaccc    1560
catcttacac t                                                        1571
```

<210> SEQ ID NO 11
<211> LENGTH: 658
<212> TYPE: DNA
<213> ORGANISM: Cassava vein mosaic virus
<220> FEATURE:
<221> NAME/KEY: promoter
<222> LOCATION: (1)..(658)
<223> OTHER INFORMATION: CsVMV Promoter and 5'UTR

<400> SEQUENCE: 11

```
atccaatgtt tacgggaaaa actatggaag tattatgtga gctcagcaag aagcagatca     60
atatgcggca catatgcaac ctatgttcaa aaatgaagaa tgtacagata caagatccta    120
tactgccaga atacgaagaa gaatacgtag aaattgaaaa agaagaacca ggcgaagaaa    180
agaatcttga agacgtaagc actgacgaca acaatgaaaa gaagaagata aggtcggtga    240
ttgtgaaaga gacatagagg acacatgtaa ggtggaaaat gtaagggcgg aaagtaaacct   300
tatcacaaag gaatcttatc ccccactact tatccttttta tattttttccg tgtcattttt   360
gcccttgagt tttcctatat aaggaaccaa gttcggcatt tgtgaaaaca agaaaaaatt    420
tggtgtaagc tattttctttt gaagtactga ggatacaact tcagagaaat ttgtaagttt    480
gtaaacctca cacatatcca cactcaaaat ccaacggtgt agatcctagt ccacttgaat    540
ctcatgtatc ctagaccctc cgatcactcc aaagcttgtt ctcattgttg ttatcattat    600
atatagatga ccaaagcact agaccaaacc tcagtcacac aaagagtaaa gaagaaca      658
```

<210> SEQ ID NO 12
<211> LENGTH: 307
<212> TYPE: DNA
<213> ORGANISM: Arabidopsis thaliana
<220> FEATURE:
<221> NAME/KEY: misc_feature
<222> LOCATION: (1)..(307)
<223> OTHER INFORMATION: RbcS 3'UTR

<400> SEQUENCE: 12

| | | | | | |
|---|---|---|---|---|---|
| tttcccttg | cttttgtgta | aacctcaaaa | ctttatcccc | catctttgat | tttatcccctt | 60 |
| gttttctgc | ttttttcttc | tttcttgggt | tttaatttcc | ggacttaacg | tttgttttcc | 120 |
| ggtttgcgag | acatattcta | tcggattctc | aactgtctga | tgaaataaat | atgtaatgtt | 180 |
| ctataagtct | ttcaatttga | tatgcatatc | aacaaaaaga | aaataggaca | atgcggctac | 240 |
| aaatatgaaa | tttacaagtt | taagaaccat | gagtcgctaa | agaaatcatt | aagaaaatta | 300 |
| gtttcac | | | | | | 307 |

<210> SEQ ID NO 13
<211> LENGTH: 912
<212> TYPE: DNA
<213> ORGANISM: Zea mays
<220> FEATURE:
<221> NAME/KEY: promoter
<222> LOCATION: (1)..(912)
<223> OTHER INFORMATION: RbcS Promoter

<400> SEQUENCE: 13

| | | | | | |
|---|---|---|---|---|---|
| gagctcccctt | taatctggcg | ctagatctgc | atccgcggct | tgcaaagata | aatggcacat | 60 |
| ttagtgtgtt | attttgcaat | accttttcata | gtagatatcc | ttaaatgcag | ttttaggcat | 120 |
| gtttgggtaa | ttaaataaca | ttttttaggag | gagttttaga | tttacccttc | tttcgtgatg | 180 |
| actgatgaca | gacgtgggga | attcaaatgc | aactctagcg | aaagttcata | tatttttcat | 240 |
| aaatagctga | ggctggggta | attatttttt | ttgtagaaaa | atagaatagg | tggaatggtt | 300 |
| ggggaaggcg | taggcgctcg | tggacgacgc | ccgataaaag | acaagaggcg | gaattgccat | 360 |
| gaattcgagg | tagctaagta | aggcgcatat | atatgccaaa | aaattctact | gtcactttcc | 420 |
| aatttcaatg | cgctgccaaa | caagccatcc | tggaaactga | cttgaattca | gcccaattct | 480 |
| gtagatccaa | acagggccgg | cgtcagtgcc | tcaggtgaga | gagcagcaga | cgatgcaaag | 540 |
| agccaaaact | gcaagcagac | gcagccgaag | ccgaagccga | agcccaagcc | caaaactgtt | 600 |
| ttgtctttgc | ccagaaccgc | gacgagccta | aactgcgctt | cctcctatct | acaagtccct | 660 |
| ggcacatcac | gcatagtcca | accatggcgc | gcaggcgata | aggcgcgcca | cggggacgcg | 720 |
| acatgtggtg | gcggacgcga | tcaggatagg | gccaggctgg | ccgggcgcgg | ccacgggaga | 780 |
| acggtggcca | ctcgtcccac | atccgcttcg | tcctgtcctg | tactgcgtcc | tgcccccaac | 840 |
| gagagccgga | gccggccatc | ccgtcgcaca | ctctcccccct | ctatatatgc | cgtcggtgtg | 900 |
| ggggagccta | ct | | | | | 912 |

<210> SEQ ID NO 14
<211> LENGTH: 780
<212> TYPE: DNA
<213> ORGANISM: Cauliflower Mosaic Virus
<220> FEATURE:
<221> NAME/KEY: promoter
<222> LOCATION: (1)..(780)
<223> OTHER INFORMATION: 2X35S Promoter

<400> SEQUENCE: 14

| | |
|---|---|
| atggtggagc acgacactct cgtctactcc aagaatatca agatacagt ctcagaagac | 60 |
| caaagggcta ttgagacttt tcaacaaagg gtaatatcgg gaaacctcct cggattccat | 120 |
| tgcccagcta tctgtcactt catcaaaagg acagtagaaa aggaaggtgg cacctacaaa | 180 |
| tgccatcatt gcgataaagg aaaggctatc gttcaagatg cctctgccga cagtggtccc | 240 |
| aaagatggac ccccacccac gaggagcatc gtggaaaaag aagacgttcc aaccacgtct | 300 |
| tcaaagcaag tggattgatg tgaacatggt ggagcacgac actctcgtct actccaagaa | 360 |
| tatcaaagat acagtctcag aagaccaaag gctattgag acttttcaac aaagggtaat | 420 |
| atcgggaaac ctcctcggat tccattgccc agctatctgt cacttcatca aaaggacagt | 480 |
| agaaaaggaa ggtggcacct acaaatgcca tcattgcgat aaaggaaagg ctatcgttca | 540 |
| agatgcctct gccgacagtg gtcccaaaga tggaccccca cccacgagga gcatcgtgga | 600 |
| aaaagaagac gttccaacca cgtcttcaaa gcaagtggat tgatgtgata tctccactga | 660 |
| cgtaagggat gacgcacaat cccactatcc ttcgcaagac ccttcctcta tataaggaag | 720 |
| ttcatttcat ttggagagga cacgctgaaa tcaccagtct ctctctacaa atctatctct | 780 |

<210> SEQ ID NO 15
<211> LENGTH: 209
<212> TYPE: DNA
<213> ORGANISM: Cauliflower Mosaic Virus
<220> FEATURE:
<221> NAME/KEY: misc_feature
<222> LOCATION: (1)..(209)
<223> OTHER INFORMATION: 35S polyA

<400> SEQUENCE: 15

| | |
|---|---|
| gatctgtcga tcgacaagct cgagtttctc cataataatg tgtgagtagt tcccagataa | 60 |
| gggaattagg gttcctatag gtttcgctc atgtgttgag catataagaa acccttagta | 120 |
| tgtatttgta tttgtaaaat acttctatca ataaaatttc taattcctaa accaaaatc | 180 |
| cagtactaaa atccagatcc cccgaatta | 209 |

<210> SEQ ID NO 16
<211> LENGTH: 737
<212> TYPE: DNA
<213> ORGANISM: Sorghum bicolor
<220> FEATURE:
<221> NAME/KEY: promoter
<222> LOCATION: (1)..(737)
<223> OTHER INFORMATION: 4xRGCGR Promoter and CA 5'UTR
<220> FEATURE:
<221> NAME/KEY: misc_feature
<222> LOCATION: (1)..(252)
<223> OTHER INFORMATION: 4xRGCGR_repeats
<220> FEATURE:
<221> NAME/KEY: misc_feature
<222> LOCATION: (253)..(737)
<223> OTHER INFORMATION: SbCA_5'UTR

<400> SEQUENCE: 16

| | |
|---|---|
| gaagcgagtg gcgcgctggc ggatgaggcg gcgagtggcc cggatgcacc ggcgcaggcg | 60 |
| agcgaagcga gtggcgcgct ggcggatgag gcggcgagtg gcccggatgc accggcgcag | 120 |
| gcgagcgaag cgagtggcgc gctggcggat gaggcggcga gtggcccgga tgcaccggcg | 180 |
| caggcgagcg aagcgagtgg cgcgctggcg gatgaggcgg cgagtggccc ggatgcaccg | 240 |
| gcgcaggcga gccgcacgcc gccgcccgcc gggcgctcg cgccgggacc gctgccgcct | 300 |
| gccgccacac aatgcgagcg cgcgcgcaca cacacacaca ccacccgggc gggggggctg | 360 |
| tagtagtaac ggccttgtct tgtcggcacg cgcgcgtccg tgtgtataag gaggcaggcc | 420 |

```
cgcgacaacg ataagcggca ctcgcacgat caatgtacac attgcccgtc cgcgccacca    480
catccagcat cgtcgccagc ctcgccaccc ccgcgccgtc ctcctcctcc ggctccggct    540
ccggccgccc caggcccagg ctcatccgga acgcccccgt cttcgccgcc cccgccaccg    600
tcgtgtaaac gggacggcgg gcagctgagg agtcaaacga gagagatcga gagaaagaaa    660
gggagggcat ccaccagccg ccggcgataa gggggagga gagagaggcc agagaagagg      720
aggagaagaa gaagaaa                                                     737

<210> SEQ ID NO 17
<211> LENGTH: 287
<212> TYPE: DNA
<213> ORGANISM: Zea mays
<220> FEATURE:
<221> NAME/KEY: misc_feature
<222> LOCATION: (1)..(287)
<223> OTHER INFORMATION: CA 3'UTR

<400> SEQUENCE: 17
gttcaaaact agggctacgg caattctacc ggcccgccga ctcctgcatc atcataaata    60
tatatactat actatactac tacgtaccta ccgatatgca cccgagcaat gtgaatgcgt   120
cgagtactat atatctgttt tctgcatcta catatatata ccggatcaat cgcccaatgt   180
gaatgtaata agcaatatca ttttctacca cttttcattc ctaacgctga gcttttatg    240 tactatatct tatatgatga ataataatat gaccgccttg tgatcta                287

<210> SEQ ID NO 18
<211> LENGTH: 944
<212> TYPE: DNA
<213> ORGANISM: Cauliflower Mosaic Virus and Arabidopsis thaliana
<220> FEATURE:
<221> NAME/KEY: promoter
<222> LOCATION: (1)..(944)
<223> OTHER INFORMATION: 2X35S promoter and RbcS 5'UTR
<220> FEATURE:
<221> NAME/KEY: promoter
<222> LOCATION: (1)..(679)
<223> OTHER INFORMATION: 2X35S promoter
<220> FEATURE:
<221> NAME/KEY: misc_feature
<222> LOCATION: (680)..(944)
<223> OTHER INFORMATION: RbcS_5'UTR

<400> SEQUENCE: 18
aagcttgcat gcctgcaggt caacatggtg gagcacgaca ctctcgtcta ctccaagaat    60
atcaaagata cagtctcaga agaccagagg gctattgaga cttttcaaca aagggtaata   120
tcgggaaacc tcctcggatt ccattgccca gctatctgtc acttcatcga aggacagta    180 gaaaaggaag atggcttcta caaatgccat cattgcgata aaggaaaggc tatcgttcaa   240
gatgcctcta ccgacagtgg tcccaaagat ggacccccac ccacgaggaa catcgtggaa   300
aaagaagacg ttccaaccac gtcttcaaag caagtggatt gatgtgatgg tcaacatggt   360
ggagcacgac actctcgtct actccaagaa tatcaaagat acagtctcag aagaccagag   420 gctattgag acttttcaac aaagggtaat atcgggaaac ctcctcggat tccattgccc    480
agctatctgt cacttcatcg aaaggacagt agaaaaggaa gatggcttct acaaatgcca   540
tcattgcgat aaaggaaagg ctatcgttca agatgcctct accgacagtg gtcccaaaga   600
tggaccccca cccacgagga acatcgtgga aaaagaagac gttccaacca cgtcttcaaa   660
gcaagtggat tgatgtgata tctccactga cgtaagggat gacgcacaat cccactatcc   720
```

| | |
|---|---|
| ttcgcaagac ccttcctcta tataaggaag ttcatttcat ttggagagga acctcacaca | 780 |
| tatccacact caaaatccaa cggtgtagat cctagtccac ttgaatctca tgtatcctag | 840 |
| accctccgat cactccaaag cttgttctca ttgttgttat cattatatat agatgaccaa | 900 |
| agcactagac caaacctcag tcacacaaag agtaaagaag aaca | 944 |

<210> SEQ ID NO 19
<211> LENGTH: 2300
<212> TYPE: DNA
<213> ORGANISM: Oryza sativa
<220> FEATURE:
<221> NAME/KEY: promoter
<222> LOCATION: (1)..(2300)
<223> OTHER INFORMATION: Glutelin B-2 (GluB2) Promoter and 5'UTR

<400> SEQUENCE: 19

| | |
|---|---|
| agaaggagag gaataaataa ggagaggaat agagataagg ttgaggagag gagttaaagg | 60 |
| agagaggaga taaggttgag gagaggagga gatggcctcg atccgatcgc gcacgcctct | 120 |
| ccgatctccg cgtcgatctt ttttcccggt tggtaacacc aaccggtact aaagattgaa | 180 |
| aagtaccctg gagcttttaa ccgggacaag atgttaata caactgggac tattgtgaaa | 240 |
| tctggtcgac cgatcaaaga tggtttctcc accagtgtat gtattttact cattggatta | 300 |
| acattttaca agagaccaat acttttagga tgggataaga caaagtattt catgataatc | 360 |
| tagccggtca tattttagaa tgatggacat ataccatagt ttcaggtctt ttgctctatc | 420 |
| attcgatgac aatgctgcta gttattaata ctaaacattt atattactac atatatgtta | 480 |
| ttttttact caaaagaaaa actattaatc attcatggaa gcagcagcaa aaaccacaag | 540 |
| ggtagtattg tccatctctc tctctctccc ccccccctc tcccctctat cctctctttc | 600 |
| aggatttcgg cagccggcaa aactagccaa acacttttag gccactttc aactcctact | 660 |
| agagttagag tttagagcta ggattcgaga gttagagctc tacctaatag gcctgaaata | 720 |
| tggatatcca atttcacatg tagtatctat ttcaaaattg gattggatta tgttatacca | 780 |
| aaaaagggat atggatattt agtggacagg agaagacatg tatggcccca caagttgtat | 840 |
| aaagtttccc ttctatataa taaatcatct caagccaaat ttggtaactt tttataaagc | 900 |
| gaatgtgaat ttataaatat tagatatgga ttttgcttat atcgaatggg tatggatgaa | 960 |
| aagaatatta ccatccccat accagaaact caaataacta ttttatgagt gaaatgcata | 1020 |
| ggtacttgtg cggatgtgtc atgtaggtta ctaaactctt aaaatgcatt ttttacatcc | 1080 |
| caaactctca aaatataggc tccaactcac tccatgcgct gatatgacat gccatggtgg | 1140 |
| cgccttcatg tgagtgggac ctacgtgtta gtcactagaa aaaaaataaa attaatacac | 1200 |
| atttttctc ctctctacat taatactatt ttttttattt ttttatcttt tctcctctct | 1260 |
| tcctaagagg ggaaaagacg ttttattttt tttctatgtg gctaacatgt gggttacatt | 1320 |
| gaaaatacat tttaagaatt tagggatcta atgacacac ccgcataagt tgtgagtgtg | 1380 |
| tacttcactc ataatctatc tttaccatat cctaccacaa tagtctaagt atgtataata | 1440 |
| gtccgagtat gagtaatgga tacctagtag caagctagct taaacaaatc taaatttta | 1500 |
| atatacccaa tgtcatgata attgactat gacaatgtga ttatttcatc aagtctttaa | 1560 |
| atcattaatt ctagttgaag gtttatgttt tcttatgcta aagggttatg tttatataag | 1620 |
| aatattaaag agcaaattgc aatagatcaa cacaacaaat ttgaatgttt ccagatgtgt | 1680 |
| aaaatatcca aattaattgt tttaaaatag ttttaagaag gatctgatat gcaagtttga | 1740 |
| tagttagtaa actgcaaaag ggcttattac atggaaaatt ccttattgaa tatgtttcat | 1800 |
| tgactggttt attttacatg acaacaaagt tactagtatg tcaataaaaa aatacaaggt | 1860 |
| tacttgtcaa ttgtattgtg ccaagtaaag atgacaacaa acatacaaat ttatttgttc | 1920 |
| ttttatagaa acacctaact tatcaaggat agttggccac gcaaaaatga caacatactt | 1980 |

<400> SEQUENCE: 20

```
tataactgaa tattgtatat agattttgat tatgttttca gtgttactgt ttgatttgct    60
gtaatattgg tttcactttt tctttcatat ccttttgtat tgtgtattag ggtttattct   120
gtgtcttgca cggacgtttg tggatttat tgttatattt gtcaatgctt atttaatatg   180
taaaattatg taataaacta aaattattta tggtaaacca aatagctttt ttgtgtttag   240
tagggattct agatctttct caaagttttg aatttaaaga tctcttggtt caaatccatt   300
gtggaaaggt ttatgataaa tgttggtaaa gttatagccg tatgagaggc tattgagagc   360
tattagccat taatcaaact aatgaaaatc aatttacaat aaccaaaaac tgaacaaatg   420
attttttttt ctaagttaac aaaaactaaa atgaaaata tgtaacaaaa tcttataata   480
ttccctgtca ttccttagat attaatgagg aatcttatga cattccaaaa atgtatattt   540
aataatcttt ataaatttaa aattattatt taaatcaaaa aatcaaagtg gtgcagcgga   600
agcgtgatgg gcccataacc cacaggtcac aggatcgaaa cctgtctttg atataatctt   660
tttttttttgg cagatatatt ttatacaaaa ataaacaacc aaatgtaatg ttaacttcta   720
cttgcatagc cacacaaata taatttggtt tgtatgtcat tggtgatgta aactgaaatt   780
gaagataata gaatctcata accacacaaa aaatgaatga acgcaaatca aagcctctca   840
acacatctct ttgcctcggt ctctctctcg cccaattgcc catcaccaga gcttaatcat   900
atcttcttca gttactgcca cgtgtcactc tgaccgtgaa cagcctttat ctcttccaag   960
tccacttgtg ttcttgatta ttttgtcttc accattctct ctactcaaag ctcttcttct  1020
tcgatcaaaa aacctcgagc ttctaaca                                      1048
```

<210> SEQ ID NO 21
<211> LENGTH: 219
<212> TYPE: DNA
<213> ORGANISM: Arabidopsis thaliana
<220> FEATURE:
<221> NAME/KEY: misc_feature
<222> LOCATION: (1)..(219)
<223> OTHER INFORMATION: SBPase 3'UTR

<400> SEQUENCE: 21

```
aaactcattc aaaataagtg aatgcatgtt tattttttcca taaaccggat aatctactt     60
tcccttggtt tataagagaa gcaacaaaac ttgtgataca agttttttt aaaaattatt    120
agtttggttt ggtgttaatc aaaatttaa caactaaaaa caaataatga atctgtctg     180
aaactttatt atcatatgat caaaaacaat gtttaagcc                           219
```

<210> SEQ ID NO 22
<211> LENGTH: 1584
<212> TYPE: DNA
<213> ORGANISM: Zea mays
<220> FEATURE:
<221> NAME/KEY: promoter
<222> LOCATION: (1)..(1584)
<223> OTHER INFORMATION: PepC Promoter and 5'UTR

<400> SEQUENCE: 22

```
gggggggggg ggggagggt cgtcgtctcc ctatctgacc tctcttctgc attggattgc     60
ctttttcggt actctatttta aaacttaaaa gtacaaatga ggtgccggat tgatggagtg   120
atatataagt ttgatgtgtt tttcacataa gtgacaagta ttattgaaag agaacatttg   180
cattgctact gtttgcatat gggaaaattg agaattgtat catgccatgg ccgatcagtt   240
```

```
ctttacttag ctcgatgtaa tgcacaatgt tgatagtatg tcgaggatct agcgatgtaa      300
tggtgttagg acacgtggtt agctactaat ataaatgtaa ggtcattcga tggttttttct     360 attttcaatt acctagcatt atctcatttc taattgtgat aacaaatgca ttagaccata     420
attctgtaaa tatgtacatt taagcacaca gtctatattt taaaattctt cttttttgtgt    480 ggatatccca acccaaatcc acctctctct tcaatccgtg catgttcacc gctgccaagt     540
gccaacaaca catcgcatcg tgcatatctt tgttggcttg tgcacggtcg cgccaatgg      600 aggagacacc tgtacggtgc ccttggtaga acaacatcct tatccctata tgtatggtgc    660
ccttcgtaga atgacacccc ttatccctac aatagccatg tatgcatacc aagaattaaa    720 tatactttt cttgaaccac aataatttat tatagcggca cttcttgttc aggttgaaca     780
cttatttgga acaataaaat gccgagttcc taaccacagg ttcacttttt tttttcctta    840
tcctcctagg aaactaaatt ttaaaatcat aaatttaatt taaatgttaa tggaaacaaa    900
aaattatcta caaagacgac tcttagccac agccgcctca ctgcaccctc aaccacatcc    960
tgcaaacaga caccctcgcc catccctcc agattcttca ctccgatgca gcctacttgc    1020
taacagacgc cctctccaca tcctgcaaag cattcctcca aattcttgcg atcccccgaa    1080
tccagcatta actgctaagg gacgccctct ccacatcctg ctacccaatt agccaacgga    1140
ataacacaag aaggcaggtg agcagtgaca agcacgtca acagcaccga gccaagccaa    1200
aaaggagcaa ggaggagcaa gcccaagccg cagccgcagc tctccaggtc cccttgcgat   1260
tgccgccagc agtagcagac acccctctcc acatcccctc cggccgctaa cagcagcaag   1320
ccaagccaaa aaggagcctc agccgcagcc ggttccgttg cggttaccgc cgatcacatg   1380
cccaaggccg cgccttttccg aacgccgagg gccgcccgtt cccgtgcaca gccacacaca   1440
cacccgcccg ccaacgactc cccatcccta tttgaaccca cccgcgcact gcattgatca   1500
gacaccaatc gcatcgcagc agcacgagca gcacgccgtg ccgctccaac catctcgctt   1560
ccgtgcttag cttcccgccg cgcc                                          1584
```

<210> SEQ ID NO 23
<211> LENGTH: 1584
<212> TYPE: DNA
<213> ORGANISM: Zea mays
<220> FEATURE:
<221> NAME/KEY: misc_feature
<222> LOCATION: (1)..(1584)
<223> OTHER INFORMATION: PepC 3'UTR

<400> SEQUENCE: 23

```
gggggggggg gggggagggt cgtcgtctcc ctatctgacc tctcttctgc attggattgc      60
ctttttcggt actctattta aaacttaaaa gtacaaatga ggtgccggat tgatggagtg     120
atatataagt ttgatgtgtt tttcacataa gtgacaagta ttattgaaag agaacatttg    180
cattgctact gtttgcatat gggaaaattg agaattgtat catgccatgg ccgatcagtt    240
ctttacttag ctcgatgtaa tgcacaatgt tgatagtatg tcgaggatct agcgatgtaa    300
tggtgttagg acacgtggtt agctactaat ataaatgtaa ggtcattcga tggttttttct   360 attttcaatt acctagcatt atctcatttc taattgtgat aacaaatgca ttagaccata    420
attctgtaaa tatgtacatt taagcacaca gtctatattt taaaattctt cttttttgtgt   480 ggatatccca acccaaatcc acctctctct tcaatccgtg catgttcacc gctgccaagt    540
gccaacaaca catcgcatcg tgcatatctt tgttggcttg tgcacggtcg cgccaatgg     600 aggagacacc tgtacggtgc ccttggtaga acaacatcct tatccctata tgtatggtgc    660
```

```
ccttcgtaga atgacacccc ttatccctac aatagccatg tatgcatacc aagaattaaa      720
tatacttttt cttgaaccac aataaatttat tatagcggca cttcttgttc aggttgaaca      780
cttatttgga acaataaaat gccgagttcc taaccacagg ttcactttttt tttttcctta      840 tcctcctagg aaactaaatt ttaaaatcat aaatttaatt taaatgttaa tggaaacaaa      900
aaattatcta caaagacgac tcttagccac agccgcctca ctgcaccctc aaccacatcc      960
tgcaaacaga caccctcgcc catccctcc agattcttca ctccgatgca gcctacttgc     1020
taacagacgc cctctccaca tcctgcaaag cattcctcca aattcttgcg atccccgaa     1080 tccagcatta actgctaagg gacgccctct ccacatcctg ctacccaatt agccaacgga     1140
ataacacaag aaggcaggtg agcagtgaca agcacgtca acagcaccga gccaagccaa     1200
aaaggagcaa ggaggagcaa gcccaagccg cagccgcagc tctccaggtc cccttgcgat     1260
tgccgccagc agtagcagac acccctctcc acatcccctc cggccgctaa cagcagcaag     1320
ccaagccaaa aaggagcctc agccgcagcc ggttccgttg cggttaccgc cgatcacatg     1380
cccaaggccg cgccttttccg aacgccgagg gccgcccgtt cccgtgcaca gccacacaca     1440
cacccgcccg ccaacgactc cccatcccta tttgaaccca cccgcgcact gcattgatca     1500
gacaccaatc gcatcgcagc agcacgagca gcacgccgtg ccgctccaac catctcgctt     1560
ccgtgcttag cttcccgccg cgcc                                            1584

<210> SEQ ID NO 24
<211> LENGTH: 1412
<212> TYPE: DNA
<213> ORGANISM: Oryza sativa
<220> FEATURE:
<221> NAME/KEY: promoter
<222> LOCATION: (1)..(1412)
<223> OTHER INFORMATION: Os01g45274 promoter and 5'UTR

<400> SEQUENCE: 24
atcttggcta tttcccatgg cttctccgct ctactcttgt ccctgtttgg atgacgccgt       60
ccagaccaag acatcaaaac ggggcgacac tgtgaggtta cggtgtcgcc attcgccaca      120
atgagctcac catgtcacct tgtcgacatt tcgccgcata caagtcgctg tgcgaccgcc      180
aggtgggccc cactgtgagc agcacgagtg tggcgcgtat ataaatttgt cggatggaga      240
ggcagctgaa ggttttttcgc catggcaact gcgtccttcg acatctgcgc gaaggttggg      300
ctcggaattt cgacaggata ctcacagcga aatcaatact ctgctatggc aaatggtacg      360
cactcgtttc gattgttctg ccttcttctg ttttatttttt tttcccgtat gtagctgtag      420
ctgctgataa acgtgccatg tattccatct cgttcttgca agcagtttct tagatgagtt      480
aaaatatgta ttccatgtca actgttcact ttagttaggt agaactttct tacattatga      540
ttagttatct acttactctc tctgtccgat aataattatc gcattgattt ttttttataat     600 gtttgatcat tcgtcttatt aaaaaaaatt atagaattat tttttttttatt ttgtttgtga     660 cttgctttat tatcaaaaaa ataatttaaa tatggcatat ctttttttat atttacaata      720 attttttcaaa aaagatgaat ggtcaaacgt tacacgaaaa aatcaaagcg accactatttt    780 tggaatggaa gtagtacctg tagagaaaaa ttaaatatta gttcttaagt gagtgtggac     840
cgaaaaaatt ccttatttat cataaacacg ttttccaaac ttttaaatga tatgttttttt    900 taaatatata aatgaacatg ttcttttcaaa aatcaaataa atcactttt caagtttgta      960 ctgattaata ctagactaat catttgctaa ttgtttatat tgttttactt gccatcataa    1020
```

```
ctcatgccaa attgctttc caaacccacc attagccgct gtggcaagct cagttgctag    1080
cttgaggagg actatacaaa gttgcacaca cgccatggta ctaacgagaa ctggaaaata    1140
tgttgactgg aaaaattgta tcagttcata ttagaaacaa attactgtca gaatgaggaa    1200
aaactcagtc catgccacta aaggcatcag atgcgaattg cgctcctttt ctcctttcaa    1260
ggagtaggca taaacatagg ctctgcagta gtttcatctg agacagtcgg cacgcggggg    1320
cgcgggcgtc tatttgttgc gcgcgcgggc gcggcggcga dacgcgtgtg tagctactgc    1380
tataaggagc gcgccgtgca ccgcctctca ca                                1412

<210> SEQ ID NO 25
<211> LENGTH: 310
<212> TYPE: DNA
<213> ORGANISM: Oryza sativa
<220> FEATURE:
<221> NAME/KEY: misc_feature
<222> LOCATION: (1)..(310)
<223> OTHER INFORMATION: Os01g45274 3'UTR

<400> SEQUENCE: 25
atccgaccgt ccgtccgttc agttcgtcag tttacgccaa cgcttttgca taagtactac     60
ctgaggatat cgtccccgat catcgatgtg aacgcgtgga gtactactac gtacgtaccg    120
gatggttcga tatatgtgaa tgctgtatta agtaataaca agaaatatat ctcctctact    180
ttttcctgac gcggagttgt actgcctatg atgcataatt tgatcgcagt gtgatcaaaa    240
gacatcagct ataatgtctt aataatatta ttatgaagag tttacctttt tactaccttt    300
tactctggta                                                         310

<210> SEQ ID NO 26
<211> LENGTH: 1585
<212> TYPE: DNA
<213> ORGANISM: Oryza sativa
<220> FEATURE:
<221> NAME/KEY: promoter
<222> LOCATION: (1)..(1585)
<223> OTHER INFORMATION: Os12g17600 promoter and 5'UTR

<400> SEQUENCE: 26
gcttgttaaa atgcctgcaa ggagggagag agaaaggaag gtgggggagg gatggggcac     60
tggtgcggct ggcatgtggg gtccagggct cctgggctca ccgctcagag aggaggagaa    120
gaaagagagg agaggcgatt ttcctgaaaa ttttggtgaa aactgagagt gtgatcgaat    180
tttcaggata tgctacagtg tagcaaacac ctgtgcatag ataactggga ataaatgcga    240
tcatgaactt ctttttggtga atttttgaga ctttttgtcat gtgtacttct gtgaaaattc    300
agagaagttc actgtttcat ttcaatttga actggttttcg attgttttga catatttaat    360
tgacgtgcaa aactaaggta caaagttgtc aaacttttcc agaacattat tgaaggtgtc    420
tactgtttat aaaaaaccca tatttttact cctcttagat ttaatactttt cacttttctg    480 tttttcaatg caagttcatt ttctgcagcc gtaacaggat gcccagcttg ctggcgctgc    540
agcagccagc agaaacgatc aagcccatgg agcacagaga aaacgctttg gaaataaaag    600
tagtgcatat aatacttgca gagaagcagc cgtagaataa ctgatggcat tagatgaagc    660
acccgatatt cttatacgga tcaggtgacc gattacgagc aatctccaaa actaatccta    720
cctggatggg acaaccagcg tttcactact ctgcagaggc cacaaaccac atccagtcca    780
atgaaccaag aacatcttca gggatacaaa actaacagcc agcctaatag cagaggcaag    840
aaacaaatta tagacctgat gtcgactggt ctcagactct cggtcgttcg agaacccttt    900
```

```
tgctccatgt atccaggcac ctcctctcat cagcaatttg ctccatctct gcaggaaaga    960
aaccttatta gttggtgata ttatttggta ccacttaaat tttggtgaca ggaatgtagt   1020
tttctgacaa agtcaattac tgaatataaa aaatatttgc acagctctgc atcaacagtt   1080
gtccaaggga tgcctcaaaa atctgtgcag attatcagtc gtcacgcaga agcagaacat   1140
cgtggtgtgc taggtctgct tcttgcactg ggccatgaat ccggtgggtt gttaggtggt   1200
gtttaggaag gagggactaa actttagtcc cttttacaaa agcaagtctt tatgggaggg   1260
actaaaatct ctcctctctt agggcatcag caatttatgc tgacaaccac agccagagcc   1320
cgggtcgaga tgccaccacg gccacaatcc acgagcccgg cgcgacacca ccgcgcgcgc   1380
gtgagccagc cacaaacgcc cgcggatagg cgcgcgcacg ccggccaatc ctaccacatc   1440
cccggcctcc gcggctcgcg agcgccgctg ccatccgatc cgctgagttt tggctattta   1500
tacgtaccgc gggagcctgt gtgcagagca gtgcatctca agaagtactc gagcaaagaa   1560
ggagagagct tggtgagctg cagag                                         1585

<210> SEQ ID NO 27
<211> LENGTH: 353
<212> TYPE: DNA
<213> ORGANISM: Oryza sativa
<220> FEATURE:
<221> NAME/KEY: misc_feature
<222> LOCATION: (1)..(353)
<223> OTHER INFORMATION: Os12g17600 3'UTR

<400> SEQUENCE: 27
gccgtcatcg tcatatatag ccttgtttaa ttgttcatct ctgattcgat gatgtctccc     60
accttgtttc gtgtgttccc agtttgttca tcgtctttg attttaccgg ccgtgctctg    120
cttttgtttt tgtttcacct gatctctctc tgacttgatg taagagtggt atctgctacg    180
actatatgtt gttgggtgag gcatatgtga atgaaaatata tggaagctcc ggctatatat    240
atttatacaa agggtacgag atggatgtga atcctagagc atatgtgtcc aacaatcaat    300
tcgtcgacaa tgaaaatttg atcatggaat taaaaaatca tgcttctgtt gtt           353

<210> SEQ ID NO 28
<211> LENGTH: 1176
<212> TYPE: DNA
<213> ORGANISM: Brachypodium distachyon
<220> FEATURE:
<221> NAME/KEY: misc_feature
<222> LOCATION: (1)..(1176)
<223> OTHER INFORMATION: SBPase

<400> SEQUENCE: 28
atggagaccg tggccgcctc cggctacgcc aggggcgccg ccaccaggtc cccggcctgc     60
tgcgccgcca tgtccttctc ccagtcctac aggccgaagg ccgccaggcc gccgaccacc    120
ttctacggcg agtccgtgag ggccaacacc gccaggaccc tcccgggcag gcagtccaag    180
gccgcctcca gggccgccct caccaccagg tgcgccatcg gcgactccct cgaggagttc    240
ctcaccaagg ccaccccgga caagaacctc atcaggctcc tcatctgcat gggcgaggcc    300
atgaggacca tcgccttcaa ggtgaggacc gcctcctgcg gcggcaccgc tgcgtgaac    360 tccttcggcg acgagcagct cgccgtggac atgctcgccg acaagctcct cttcgaggcc    420
ctcgagtact cccacgtgtg caagtacgcc tgctccgagg aggtgccgga gctccaggac    480
atgggcggcc cggtggacgg cggcttctcc gtggccttcg acccgctcga cggctcctcc    540
```

-continued

```
atcgtggaca ccaacttcac cgtgggcacc atcttcggcg tgtggccggg cgacaagctc    600
accggcgtga ccggcggcga ccaggtggcc gccgccatgg gcatctacgg cccgaggacc    660
accttcgtgg tggccctcaa ggactgcccg ggcacccacg agttcctcct cctcgacgag    720
ggcaagtggc agcacgtgaa ggacaccacc accatcggcg agggcaagat gttctccccg    780
ggcaacctca gggccacctt cgacaacccg gactacgaca agctcgtgaa ctactacgtg    840
aaggagaagt acaccctcag gtacaccggc ggcatggtgc cggacgtgaa ccagatcatc    900
gtgaaggaga agggcatctt caccaacgtg acctccccga ccgccaaggc caagctcagg    960
ctcctcttcg aggtggcccc gctcggcttc ctcatcgaga aggccggcgg ccactcctcc   1020
gacggcaagc agtccgtgct cgacaaggtg atcaccgtgc tcgacgagag gacccaggtg   1080
gcctacggct ccaagaacga gatcatcagg ttcgaggaga ccctctacgg ctcctccagg   1140
ctcgccgccg cgccaccgt gggcgccacc gtgtga                              1176
```

<210> SEQ ID NO 29
<211> LENGTH: 391
<212> TYPE: PRT
<213> ORGANISM: Brachypodium distachyon
<220> FEATURE:
<221> NAME/KEY: MISC_FEATURE
<222> LOCATION: (1)..(391)
<223> OTHER INFORMATION: SBPase

<400> SEQUENCE: 29

```
Met Glu Thr Val Ala Ala Ser Gly Tyr Ala Arg Gly Ala Ala Thr Arg
1               5                   10                  15

Ser Pro Ala Cys Cys Ala Ala Met Ser Phe Ser Gln Ser Tyr Arg Pro
            20                  25                  30

Lys Ala Ala Arg Pro Pro Thr Thr Phe Tyr Gly Glu Ser Val Arg Ala
        35                  40                  45

Asn Thr Ala Arg Thr Leu Pro Gly Arg Gln Ser Lys Ala Ala Ser Arg
    50                  55                  60

Ala Ala Leu Thr Thr Arg Cys Ala Ile Gly Asp Ser Leu Glu Glu Phe
65                  70                  75                  80

Leu Thr Lys Ala Thr Pro Asp Lys Asn Leu Ile Arg Leu Leu Ile Cys
                85                  90                  95

Met Gly Glu Ala Met Arg Thr Ile Ala Phe Lys Val Arg Thr Ala Ser
            100                 105                 110

Cys Gly Gly Thr Ala Cys Val Asn Ser Phe Gly Asp Glu Gln Leu Ala
        115                 120                 125

Val Asp Met Leu Ala Asp Lys Leu Leu Phe Glu Ala Leu Glu Tyr Ser
    130                 135                 140

His Val Cys Lys Tyr Ala Cys Ser Glu Glu Val Pro Glu Leu Gln Asp
145                 150                 155                 160

Met Gly Gly Pro Val Asp Gly Phe Ser Val Ala Phe Asp Pro Leu
                165                 170                 175

Asp Gly Ser Ser Ile Val Asp Thr Asn Phe Thr Val Gly Thr Ile Phe
            180                 185                 190

Gly Val Trp Pro Gly Asp Lys Leu Thr Gly Val Thr Gly Gly Asp Gln
        195                 200                 205

Val Ala Ala Ala Met Gly Ile Tyr Gly Pro Arg Thr Phe Val Val
    210                 215                 220

Ala Leu Lys Asp Cys Pro Gly Thr His Glu Phe Leu Leu Leu Asp Glu
225                 230                 235                 240
```

| | | | | | | | | | | | |
|---|---|---|---|---|---|---|---|---|---|---|---|
|Gly|Lys|Trp|Gln|His|Val|Lys|Asp|Thr|Thr|Thr|Ile|Gly|Glu|Gly|Lys|
| | | | |245| | | |250| | | |255| | | |

Met Phe Ser Pro Gly Asn Leu Arg Ala Thr Phe Asp Asn Pro Asp Tyr
    260                        265                    270

Asp Lys Leu Val Asn Tyr Tyr Val Lys Glu Lys Tyr Thr Leu Arg Tyr
    275                        280                    285

Thr Gly Gly Met Val Pro Asp Val Asn Gln Ile Ile Val Lys Glu Lys
    290                        295                  300

Gly Ile Phe Thr Asn Val Thr Ser Pro Thr Ala Lys Ala Lys Leu Arg
305                    310                    315                  320

Leu Leu Phe Glu Val Ala Pro Leu Gly Phe Leu Ile Glu Lys Ala Gly
    325                        330                    335

Gly His Ser Ser Asp Gly Lys Gln Ser Val Leu Asp Lys Val Ile Thr
        340                    345                    350

Val Leu Asp Glu Arg Thr Gln Val Ala Tyr Gly Ser Lys Asn Glu Ile
    355                        360                    365

Ile Arg Phe Glu Glu Thr Leu Tyr Gly Ser Ser Arg Leu Ala Ala Gly
        370                    375                    380

Ala Thr Val Gly Ala Thr Val
385                    390

<210> SEQ ID NO 30
<211> LENGTH: 1164
<212> TYPE: DNA
<213> ORGANISM: Glycine max
<220> FEATURE:
<221> NAME/KEY: misc_feature
<222> LOCATION: (1)..(1164)
<223> OTHER INFORMATION: SBPase

<400> SEQUENCE: 30

```
atggaaactg gaattgcttg ttatactaga ggaccttttt tgccttctgt ttcttctaag     60
cattctcctc cttctatttc tccttctttt ggattgagat ctttgaagtc ttcttctttg    120
tttggagaat ctttgagagt tgcttctaag tctactatta aggtttctaa gactaagaat    180
acttctttgg ttactagatg tgaaattgga gattctttgg aagaattttt gactaaggct    240
actcctgata agggattgat tagattgttg gtttctatgg agaagctttt gagaactatt    300
tcttttaagg ttaagactgc ttcttgtgga ggaactcaat gtgttaatac ttttggagat    360
gaacaattgg ctgttgattt gttggctaat caattgttgt ttgaagcttt gaattattct    420
cattttgta agtatgcttg ttctgaagaa aatcctgaat tgttggatat gggaggacct     480
gttgaaggag gattttctgt tgcttttgat cctttggatg gatcttctat tgttgatact    540
aattttactg ttggaactat ttttggagtt tggcctggag ataagttgac tggaattact    600
ggaagagatc aagttgctgc tgctatggga gttttgggac tagaactac ttatgttttg     660
gctttgaagg attttcctgg aactcatgaa tttttgttgt tggatgaagg aaagtggcaa    720
catgttaagg aaactactga attggagaa ggaaagttgt tttctcctgg aaatttgaga     780
gctacttctg ataatcctga ttatgctaag ttgattgatt attatgttaa tgaaaagtat    840
actttgagat atactggagg aatggttcct gatgttaatc aaattattgt taaggaaaag    900
ggaattttta ctaatgttac ttctccttct gctaaggcta agttgagatt gttgtttgaa    960
gttgctcctt tgggattttt gattgaaaag gctggaggat attcttctga tggacatcaa   1020
tctgttttgg ataaggttat tactaatatt gatgaaagaa ctcaagttgc ttatggatct   1080
aagaatgaaa ttattagatt tgaagaaact ttgtatggaa agtctagatt gaaggatgga   1140
```
gttgctgttg gagctgctgc ttga                                                                                      1164

<210> SEQ ID NO 31
<211> LENGTH: 387
<212> TYPE: PRT
<213> ORGANISM: Glycine max
<220> FEATURE:
<221> NAME/KEY: MISC_FEATURE
<222> LOCATION: (1)..(387)
<223> OTHER INFORMATION: SBPase

<400> SEQUENCE: 31

Met Glu Thr Gly Ile Ala Cys Tyr Thr Arg Gly Pro Phe Leu Pro Ser
1               5                   10                  15

Val Ser Ser Lys His Ser Pro Ser Ile Ser Pro Ser Phe Gly Leu
            20                  25                  30

Arg Ser Leu Lys Ser Ser Leu Phe Gly Glu Ser Leu Arg Val Ala
        35                  40                  45

Ser Lys Ser Thr Ile Lys Val Ser Lys Thr Lys Asn Thr Ser Leu Val
50                  55                  60

Thr Arg Cys Glu Ile Gly Asp Ser Leu Glu Glu Phe Leu Thr Lys Ala
65                  70                  75                  80

Thr Pro Asp Lys Gly Leu Ile Arg Leu Leu Val Ser Met Gly Glu Ala
                85                  90                  95

Leu Arg Thr Ile Ser Phe Lys Val Lys Thr Ala Ser Cys Gly Gly Thr
            100                 105                 110

Gln Cys Val Asn Thr Phe Gly Asp Glu Gln Leu Ala Val Asp Leu Leu
        115                 120                 125

Ala Asn Gln Leu Leu Phe Glu Ala Leu Asn Tyr Ser His Phe Cys Lys
130                 135                 140

Tyr Ala Cys Ser Glu Glu Asn Pro Glu Leu Leu Asp Met Gly Gly Pro
145                 150                 155                 160

Val Glu Gly Gly Phe Ser Val Ala Phe Asp Pro Leu Asp Gly Ser Ser
                165                 170                 175

Ile Val Asp Thr Asn Phe Thr Val Gly Thr Ile Phe Gly Val Trp Pro
            180                 185                 190

Gly Asp Lys Leu Thr Gly Ile Thr Gly Arg Asp Gln Val Ala Ala Ala
        195                 200                 205

Met Gly Val Leu Gly Pro Arg Thr Thr Tyr Val Leu Ala Leu Lys Asp
210                 215                 220

Phe Pro Gly Thr His Glu Phe Leu Leu Leu Asp Glu Gly Lys Trp Gln
225                 230                 235                 240

His Val Lys Glu Thr Thr Glu Ile Gly Glu Gly Lys Leu Phe Ser Pro
                245                 250                 255

Gly Asn Leu Arg Ala Thr Ser Asp Asn Pro Asp Tyr Ala Lys Leu Ile
            260                 265                 270

Asp Tyr Tyr Val Asn Glu Lys Tyr Thr Leu Arg Tyr Thr Gly Gly Met
        275                 280                 285

Val Pro Asp Val Asn Gln Ile Ile Val Lys Glu Lys Gly Ile Phe Thr
290                 295                 300

Asn Val Thr Ser Pro Ser Ala Lys Ala Lys Leu Arg Leu Leu Phe Glu
305                 310                 315                 320

Val Ala Pro Leu Gly Phe Leu Ile Glu Lys Ala Gly Gly Tyr Ser Ser
                325                 330                 335

Asp Gly His Gln Ser Val Leu Asp Lys Val Ile Thr Asn Ile Asp Glu

```
                340             345             350
Arg Thr Gln Val Ala Tyr Gly Ser Lys Asn Glu Ile Ile Arg Phe Glu
        355             360             365
Glu Thr Leu Tyr Gly Lys Ser Arg Leu Lys Asp Gly Val Ala Val Gly
        370             375             380
Ala Ala Ala
385

<210> SEQ ID NO 32
<211> LENGTH: 1647
<212> TYPE: DNA
<213> ORGANISM: Pisum sativum and Synechococcus sp. PCC 7942
<220> FEATURE:
<221> NAME/KEY: misc_feature
<222> LOCATION: (1)..(1647)
<223> OTHER INFORMATION: RbcS signal peptide-ictB
<220> FEATURE:
<221> NAME/KEY: misc_feature
<222> LOCATION: (1)..(243)
<223> OTHER INFORMATION: P.sativum_RbcS_signal_peptide
<220> FEATURE:
<221> NAME/KEY: misc_feature
<222> LOCATION: (244)..(1647)
<223> OTHER INFORMATION: ictB

<400> SEQUENCE: 32
atggcttcta tgatttcttc ttctgctgtt actactgttt ctagagcttc tagaggacaa      60
tctgctgctg ttgctccttt tggaggattg aagtctatga ctggatttcc tgttaagaag     120
gttaatactg atattacttc tattacttct aatggaggaa gagttaagtg tatgcaagtt     180
tggcctccta ttggaaagaa gaagtttgaa actttgtctt atttgcctcc tttgactaga     240
gatatgactg tttggcaaac tttgactttt gctcattatc aacctcaaca atggggacat     300
tcttcttttt tgcatagatt gtttggatct ttgagagctt ggagagcttc ttctcaattg     360 ttggttttggt ctgaagcttt gggaggattt tgttggctg ttgtttatgg atctgctcct     420
tttgttcctt cttctgcttt gggattggga ttggctgcta ttgctgctta ttgggctttg     480
ttgtctttga ctgatattga tttgagacaa gctactccta ttcattggtt ggttttgttg     540
tattggggag ttgatgcttt ggctactgga ttgtctcctg ttagagctgc tgcttttggtt     600 ggattggcta agttgacttt gtatttgttg ttttttgctt tggctgctag agttttgaga     660
aatcctagat gagatctttt gttgttttct gttgttgtta ttacttcttt gtttgtttct     720
gtttatggat tgaatcaatg gatttatgga gttgaagaat tggctacttg ggttgataga     780
aattctgttg ctgattttac ttctagagtt tattcttatt gggaaatcc taattgtttg     840 gctgcttatt ggttcctac tactgctttt tctgctgctg ctattggagt ttggagagga     900
tggttgccta agttgttggc tattgctgct actggagctt cttctttgtg tttgattttg     960
acttattcta gaggaggatg gttgggattt gttgctatga ttttgtttg ggctttgttg    1020 ggattgtatt ggtttcaacc tagattgcct gctccttgga gagatggtt gtttcctgtt    1080 gttttgggag gattggttgc tgtttttgttg gttgctgttt tgggattgga acctttgaga    1140
gttagagttt tgtctatttt tgttggaaga gaagattctt ctaataattt tagaattaat    1200
gtttggttgg ctgtttttgca aatgattcaa gatagacctt ggttgggaat tggacctgga    1260
aatactgctt ttaatttggt ttatcctttg tatcaacaag ctagatttac tgctttgtct    1320
gcttattctg ttcctttgga agttgctgtt gaaggaggat gtttgggatt gactgctttt    1380
gcttggttgt tgttggttac tgctgttact gctgttagac aagtttctag attgagaaga    1440
```

```
gatagaaatc ctcaagcttt ttggttgatg gcttctttgg ctggattggc tggaatgttg    1500
ggacatggat tgttttgatac tgtttgtat agacctgaag cttctacttt gtggtggttg    1560
tgtattggag ctattgcttc tttttggcaa cctcaacctt ctaagcaatt gcctcctgaa    1620
gctgaacatt ctgatgaaaa gatgtga                                        1647
```

<210> SEQ ID NO 33
<211> LENGTH: 548
<212> TYPE: PRT
<213> ORGANISM: Pisum sativum and Synechococcus sp. PCC 7942
<220> FEATURE:
<221> NAME/KEY: MISC_FEATURE
<222> LOCATION: (1)..(548)
<223> OTHER INFORMATION: RbcS signal peptide-ictB
<220> FEATURE:
<221> NAME/KEY: MISC_FEATURE
<222> LOCATION: (1)..(81)
<223> OTHER INFORMATION: P.sativum RbcS signal peptide
<220> FEATURE:
<221> NAME/KEY: MISC_FEATURE
<222> LOCATION: (82)..(548)
<223> OTHER INFORMATION: ictB

<400> SEQUENCE: 33

```
Met Ala Ser Met Ile Ser Ser Ser Ala Val Thr Thr Val Ser Arg Ala
1               5                   10                  15

Ser Arg Gly Gln Ser Ala Ala Val Ala Pro Phe Gly Gly Leu Lys Ser
            20                  25                  30

Met Thr Gly Phe Pro Val Lys Lys Val Asn Thr Asp Ile Thr Ser Ile
        35                  40                  45

Thr Ser Asn Gly Gly Arg Val Lys Cys Met Gln Val Trp Pro Pro Ile
    50                  55                  60

Gly Lys Lys Lys Phe Glu Thr Leu Ser Tyr Leu Pro Pro Leu Thr Arg
65                  70                  75                  80

Asp Met Thr Val Trp Gln Thr Leu Thr Phe Ala His Tyr Gln Pro Gln
                85                  90                  95

Gln Trp Gly His Ser Ser Phe Leu His Arg Leu Phe Gly Ser Leu Arg
            100                 105                 110

Ala Trp Arg Ala Ser Ser Gln Leu Leu Val Trp Ser Glu Ala Leu Gly
        115                 120                 125

Gly Phe Leu Leu Ala Val Val Tyr Gly Ser Ala Pro Phe Val Pro Ser
    130                 135                 140

Ser Ala Leu Gly Leu Gly Leu Ala Ala Ile Ala Ala Tyr Trp Ala Leu
145                 150                 155                 160

Leu Ser Leu Thr Asp Ile Asp Leu Arg Gln Ala Thr Pro Ile His Trp
                165                 170                 175

Leu Val Leu Leu Tyr Trp Gly Val Asp Ala Leu Ala Thr Gly Leu Ser
            180                 185                 190

Pro Val Arg Ala Ala Ala Leu Val Gly Leu Ala Lys Leu Thr Leu Tyr
        195                 200                 205

Leu Leu Val Phe Ala Leu Ala Ala Arg Val Leu Arg Asn Pro Arg Leu
    210                 215                 220

Arg Ser Leu Leu Phe Ser Val Val Val Ile Thr Ser Leu Phe Val Ser
225                 230                 235                 240

Val Tyr Gly Leu Asn Gln Trp Ile Tyr Gly Val Glu Glu Leu Ala Thr
                245                 250                 255

Trp Val Asp Arg Asn Ser Val Ala Asp Phe Thr Ser Arg Val Tyr Ser
            260                 265                 270
```

```
Tyr Leu Gly Asn Pro Asn Leu Ala Ala Tyr Leu Val Pro Thr Thr
            275                 280                 285
Ala Phe Ser Ala Ala Ile Gly Val Trp Arg Gly Trp Leu Pro Lys
290                 295                 300
Leu Leu Ala Ile Ala Ala Thr Gly Ala Ser Ser Leu Cys Leu Ile Leu
305                 310                 315                 320
Thr Tyr Ser Arg Gly Gly Trp Leu Gly Phe Val Ala Met Ile Phe Val
            325                 330                 335
Trp Ala Leu Leu Gly Leu Tyr Trp Phe Gln Pro Arg Leu Pro Ala Pro
                340                 345                 350
Trp Arg Arg Trp Leu Phe Pro Val Val Leu Gly Gly Leu Val Ala Val
            355                 360                 365
Leu Leu Val Ala Val Leu Gly Leu Glu Pro Leu Arg Val Arg Val Leu
370                 375                 380
Ser Ile Phe Val Gly Arg Glu Asp Ser Ser Asn Asn Phe Arg Ile Asn
385                 390                 395                 400
Val Trp Leu Ala Val Leu Gln Met Ile Gln Asp Arg Pro Trp Leu Gly
                405                 410                 415
Ile Gly Pro Gly Asn Thr Ala Phe Asn Leu Val Tyr Pro Leu Tyr Gln
            420                 425                 430
Gln Ala Arg Phe Thr Ala Leu Ser Ala Tyr Ser Val Pro Leu Glu Val
            435                 440                 445
Ala Val Glu Gly Gly Leu Leu Gly Leu Thr Ala Phe Ala Trp Leu Leu
            450                 455                 460
Leu Val Thr Ala Val Thr Ala Val Arg Gln Val Ser Arg Leu Arg Arg
465                 470                 475                 480
Asp Arg Asn Pro Gln Ala Phe Trp Leu Met Ala Ser Leu Ala Gly Leu
                485                 490                 495
Ala Gly Met Leu Gly His Gly Leu Phe Asp Thr Val Leu Tyr Arg Pro
            500                 505                 510
Glu Ala Ser Thr Leu Trp Trp Leu Cys Ile Gly Ala Ile Ala Ser Phe
            515                 520                 525
Trp Gln Pro Gln Pro Ser Lys Gln Leu Pro Pro Glu Ala Glu His Ser
530                 535                 540
Asp Glu Lys Met
545
```

<210> SEQ ID NO 34
<211> LENGTH: 1584
<212> TYPE: DNA
<213> ORGANISM: Solanum tuberosum
<220> FEATURE:
<221> NAME/KEY: misc_feature
<222> LOCATION: (1)..(1584)
<223> OTHER INFORMATION: AGPase large subunit

<400> SEQUENCE: 34

```
atggatactt gttgtgttcc tatgaagtct actgttcatt tgggaagagt ttctactgga    60
ggatttaata atggagaaaa ggattttttt ggagaaaaga ttagaggatc tttgaattct   120
aatttgagaa ttaatcaatt gtctaagtct ttgaagttgg aaaagaagga aaataagatt   180
aagcctggag ttgcttattc tgttattact actgaaaatg atactcaaac tgttttttgtt   240 gatatgccta gattggaaag aagaagagct aatcctaagg atgttgctgc tgttattttg   300
ggaggaggaa agggaactaa gttgtttcct ttgacttcta gaactgctac tcctgctgtt   360
cctgttggag gatgttatag attgattgat attcctatgt ctaattgtat taattctgct   420
```

```
attaataaga tttttgtttt gactcaatat aattctgctc ctttgaatag acatattgct    480
agaacttatt ttggaaatgg agtttctttt ggagatggat tgttgaagt tttggctgct     540 actcaaactc ctggagaagc tggaaagaag tggtttcaag gaactgctga tgctgttaga    600
aagtttattt gggttttga agatgctaag aataagaata ttgaaaatat tgttgtttg    660 tctggagatc atttgtatag aatggattat atggaattgg ttcaaaatca tattgataga    720
aatgctgata ttactttgtc ttgtgctcct gctgaagatt ctagagcttc tgattttgga    780
ttggttaaga ttgattctag aggaagagtt gttcaatttg ctgaaaagcc taagggattt    840
gatttgaagg ctatgcaagt tgatactact ttggttggat tgtctcctca agatgctaag    900
aagtctcctt atattgcttc tatgggagtt tatgttttta agactgatgt tttgttgaag    960
ttgttgaagt ggtcttatcc tacttctaat gattttggat ctgaaattat tcctgctgct    1020
attgatgatt ataatgttca agcttatatt tttaaggatt attgggaaga tattggaact    1080
attaagtctt tttataatgc ttctttggct ttgactcaag aatttcctga atttcaattt    1140
tatgatccta agactccttt ttatacttct cctagatttt tgcctcctac taagattgat    1200
aattgtaaga ttaaggatgc tattatttct catggatgtt ttttgagaga ttgttctgtt    1260
gaacattcta ttgttggaga aagatctaga ttggattgtg gagttgaatt gaaggatact    1320
tttatgatgg gagctgatta ttatcaaact gaatctgaaa ttgcttcttt gttggctgaa    1380
ggaaaggttc ctattggaat tggagaaaat actaagatta gaagtgtat tattgataag    1440 aatgctaaga ttggaaagaa tgtttctatt attaataagg atggagttca agaagctgat    1500
agacctgaag aaggatttta tattagatct ggaattatta ttatttggga aaaggctact    1560
attagagatg gaactgttat ttga                                           1584
```

<210> SEQ ID NO 35
<211> LENGTH: 527
<212> TYPE: PRT
<213> ORGANISM: Solanum tuberosum
<220> FEATURE:
<221> NAME/KEY: MISC_FEATURE
<222> LOCATION: (1)..(527)
<223> OTHER INFORMATION: AGPase large subunit

<400> SEQUENCE: 35

```
Met Asp Thr Cys Cys Val Pro Met Lys Ser Thr Val His Leu Gly Arg
1               5                   10                  15

Val Ser Thr Gly Gly Phe Asn Asn Gly Glu Lys Glu Phe Gly Glu
            20                  25                  30

Lys Ile Arg Gly Ser Leu Asn Ser Asn Leu Arg Ile Asn Gln Leu Ser
        35                  40                  45

Lys Ser Leu Lys Leu Glu Lys Lys Glu Asn Lys Ile Lys Pro Gly Val
    50                  55                  60

Ala Tyr Ser Val Ile Thr Thr Glu Asn Asp Thr Gln Thr Val Phe Val
65                  70                  75                  80

Asp Met Pro Arg Leu Glu Arg Arg Ala Asn Pro Lys Asp Val Ala
                85                  90                  95

Ala Val Ile Leu Gly Gly Gly Lys Gly Thr Lys Leu Phe Pro Leu Thr
            100                 105                 110

Ser Arg Thr Ala Thr Pro Ala Val Pro Val Gly Gly Cys Tyr Arg Leu
        115                 120                 125

Ile Asp Ile Pro Met Ser Asn Cys Ile Asn Ser Ala Ile Asn Lys Ile
    130                 135                 140
```

-continued

Phe Val Leu Thr Gln Tyr Asn Ser Ala Pro Leu Asn Arg His Ile Ala
145                 150                 155                 160

Arg Thr Tyr Phe Gly Asn Gly Val Ser Phe Gly Asp Gly Phe Val Glu
            165                 170                 175

Val Leu Ala Ala Thr Gln Thr Pro Gly Glu Ala Gly Lys Lys Trp Phe
        180                 185                 190

Gln Gly Thr Ala Asp Ala Val Arg Lys Phe Ile Trp Val Phe Glu Asp
        195                 200                 205

Ala Lys Asn Lys Asn Ile Glu Asn Ile Val Val Leu Ser Gly Asp His
        210                 215                 220

Leu Tyr Arg Met Asp Tyr Met Glu Leu Val Gln Asn His Ile Asp Arg
225                 230                 235                 240

Asn Ala Asp Ile Thr Leu Ser Cys Ala Pro Ala Glu Asp Ser Arg Ala
                245                 250                 255

Ser Asp Phe Gly Leu Val Lys Ile Asp Ser Arg Gly Arg Val Val Gln
            260                 265                 270

Phe Ala Glu Lys Pro Lys Gly Phe Asp Leu Lys Ala Met Gln Val Asp
        275                 280                 285

Thr Thr Leu Val Gly Leu Ser Pro Gln Asp Ala Lys Lys Ser Pro Tyr
        290                 295                 300

Ile Ala Ser Met Gly Val Tyr Val Phe Lys Thr Asp Val Leu Leu Lys
305                 310                 315                 320

Leu Leu Lys Trp Ser Tyr Pro Thr Ser Asn Asp Phe Gly Ser Glu Ile
                325                 330                 335

Ile Pro Ala Ala Ile Asp Asp Tyr Asn Val Gln Ala Tyr Ile Phe Lys
            340                 345                 350

Asp Tyr Trp Glu Asp Ile Gly Thr Ile Lys Ser Phe Tyr Asn Ala Ser
        355                 360                 365

Leu Ala Leu Thr Gln Glu Phe Pro Glu Phe Gln Phe Tyr Asp Pro Lys
        370                 375                 380

Thr Pro Phe Tyr Thr Ser Pro Arg Phe Leu Pro Pro Thr Lys Ile Asp
385                 390                 395                 400

Asn Cys Lys Ile Lys Asp Ala Ile Ile Ser His Gly Cys Phe Leu Arg
                405                 410                 415

Asp Cys Ser Val Glu His Ser Ile Val Gly Glu Arg Ser Arg Leu Asp
            420                 425                 430

Cys Gly Val Glu Leu Lys Asp Thr Phe Met Met Gly Ala Asp Tyr Tyr
        435                 440                 445

Gln Thr Glu Ser Glu Ile Ala Ser Leu Leu Ala Glu Gly Lys Val Pro
        450                 455                 460

Ile Gly Ile Gly Glu Asn Thr Lys Ile Arg Lys Cys Ile Ile Asp Lys
465                 470                 475                 480

Asn Ala Lys Ile Gly Lys Asn Val Ser Ile Ile Asn Lys Asp Gly Val
                485                 490                 495

Gln Glu Ala Asp Arg Pro Glu Glu Gly Phe Tyr Ile Arg Ser Gly Ile
            500                 505                 510

Ile Ile Ile Leu Glu Lys Ala Thr Ile Arg Asp Gly Thr Val Ile
        515                 520                 525

<210> SEQ ID NO 36
<211> LENGTH: 855
<212> TYPE: DNA
<213> ORGANISM: Glycine max
<220> FEATURE:

<221> NAME/KEY: misc_feature
<222> LOCATION: (1)..(855)
<223> OTHER INFORMATION: PHB8

<400> SEQUENCE: 36

```
atgggaaatt tgttttgttg tgttcaagtt gatcaatcta ctgttgctat tagagaagga      60
tttggaagat ttgaaaaggt tttgcaacct ggatgtcatt gtatgccttg gttttggga      120
aagcaattgg ctggacattt gtctttgaga ttgcaacaat tggatttgag atgtgaaact     180
aagactaagg ataatgtttt tgttaatgtt gttgcttcta ttcaatatag gctttggct      240
gaaaaggcta atgatgcttt ttataagttg tctaatacta agactcaaat tcaagcttat     300
gtttttgatg ttattagagc ttctgttcct aagttgaatt tggatgatgc ttttgaacaa     360
aagaatgaaa ttgctaaggc tgttgaagaa gaattggaaa aggctatgtc tgcttatgga     420
tatgaaattg ttcaaacttt gattgttgat attgatcctg atgaacatgt taagagagct     480
atgaatgaaa ttaatgctgc tgctagattg agaatggctg ctaatgaaaa ggctgaagct     540
gaaagatttt gttgattaa gagagctgaa ggagaagctg aatctaagta tttgtctgga     600
ttgggaattg ctagacaaag acaagctatt gttgatggat tgagagattc tgttttggga    660
ttttctgtta atgttcctgg aactactgct aaggatgtta tggatatggt tttggttact    720
caatattttg atactatgaa ggaaattgga gctgcttcta agtcttctgc tgtttttatt    780
cctcatggac ctggagctgt tagagatgtt gctggacaaa ttagagaagg attgttgcaa    840
gcttctcatc aatga                                                    855
```

<210> SEQ ID NO 37
<211> LENGTH: 284
<212> TYPE: PRT
<213> ORGANISM: Glycine max
<220> FEATURE:
<221> NAME/KEY: MISC_FEATURE
<222> LOCATION: (1)..(284)
<223> OTHER INFORMATION: PHB8

<400> SEQUENCE: 37

```
Met Gly Asn Leu Phe Cys Cys Val Gln Val Asp Gln Ser Thr Val Ala
1               5                   10                  15

Ile Arg Glu Gly Phe Gly Arg Phe Glu Lys Val Leu Gln Pro Gly Cys
            20                  25                  30

His Cys Met Pro Trp Phe Leu Gly Lys Gln Leu Ala Gly His Leu Ser
        35                  40                  45

Leu Arg Leu Gln Gln Leu Asp Leu Arg Cys Glu Thr Lys Thr Lys Asp
    50                  55                  60

Asn Val Phe Val Asn Val Val Ala Ser Ile Gln Tyr Arg Ala Leu Ala
65                  70                  75                  80

Glu Lys Ala Asn Asp Ala Phe Tyr Lys Leu Ser Asn Thr Lys Thr Gln
                85                  90                  95

Ile Gln Ala Tyr Val Phe Asp Val Ile Arg Ala Ser Val Pro Lys Leu
            100                 105                 110

Asn Leu Asp Asp Ala Phe Glu Gln Lys Asn Glu Ile Ala Lys Ala Val
        115                 120                 125

Glu Glu Glu Leu Glu Lys Ala Met Ser Ala Tyr Gly Tyr Glu Ile Val
    130                 135                 140

Gln Thr Leu Ile Val Asp Ile Asp Pro Asp Glu His Val Lys Arg Ala
145                 150                 155                 160

Met Asn Glu Ile Asn Ala Ala Ala Arg Leu Arg Met Ala Ala Asn Glu
```

```
                         165                 170                 175
Lys Ala Glu Ala Glu Lys Ile Leu Leu Ile Lys Arg Ala Gly Glu
                180                 185                 190

Ala Glu Ser Lys Tyr Leu Ser Gly Leu Gly Ile Ala Arg Gln Arg Gln
            195                 200                 205

Ala Ile Val Asp Gly Leu Arg Asp Ser Val Leu Gly Phe Ser Val Asn
        210                 215                 220

Val Pro Gly Thr Thr Ala Lys Asp Val Met Asp Met Val Leu Val Thr
225                 230                 235                 240

Gln Tyr Phe Asp Thr Met Lys Glu Ile Gly Ala Ala Ser Lys Ser Ser
                245                 250                 255

Ala Val Phe Ile Pro His Gly Pro Gly Ala Val Arg Asp Val Ala Gly
            260                 265                 270

Gln Ile Arg Glu Gly Leu Leu Gln Ala Ser His Gln
        275                 280

<210> SEQ ID NO 38
<211> LENGTH: 1647
<212> TYPE: DNA
<213> ORGANISM: Pisum sativum and Synechococcus sp. PCC 7942
<220> FEATURE:
<221> NAME/KEY: misc_feature
<222> LOCATION: (1)..(1647)
<223> OTHER INFORMATION: RbcS signal peptide-ictB
<220> FEATURE:
<221> NAME/KEY: misc_feature
<222> LOCATION: (1)..(243)
<223> OTHER INFORMATION: P.sativum_RbcS signal peptide
<220> FEATURE:
<221> NAME/KEY: misc_feature
<222> LOCATION: (244)..(1647)
<223> OTHER INFORMATION: ictB

<400> SEQUENCE: 38
atggcttcta tgatttcttc ttctgctgtg acaacagtgt ctagggcttc taggggccag      60
tctgctgctg tggctccttt cggcggcctc aagtctatga caggcttccc tgtgaagaag     120
gtgaatacag atattacatc tattacatct aatggcggca gggtgaagtg catgcaggtg     180
tggcctccta ttggcaagaa gaagttcgag acactctctt acctccctcc tctcacaagg     240
gatatgacag tgtggcagac actcacattc gctcattacc agcctcagca gtggggccat     300
tcttctttcc tccataggct cttcggctct ctcaggcttg gaggggcttc ttctcagctc     360
ctcgtgtggt ctgaggctct cggcggcttc ctcctcgctg tggtgtacgg ctctgctcct     420
ttcgtgcctt cttctgctct cggcctcggc ctcgctgcta ttgctgctta ctgggctctc     480
ctctctctca cagatattga tctcaggcag gctacaccta ttcattggct cgtgctcctc     540
tactggggcg tggatgctct cgctacaggc ctctctcctg tgagggctgc tgctctcgtg     600
ggcctcgcta agctcacact ctacctcctc gtgttcgctc tcgctgctag ggtgctcagg     660
aatcctaggc tcaggtctct cctcttctct gtggtggtga ttacatctct cttcgtgtct     720
gtgtacggcc tcaatcagtg gatttacggc gtggaggagc tcgctacatg ggtggatagg     780
aattctgtgg ctgatttcac atctagggtg tactcttacc tcggcaatcc taatctcctc     840
gctgcttacc tcgtgcctac aacagctttc tctgctgctg ctattggcgt gtggaggggc     900
tggctcccta agctcctcgc tattgctgct acaggcgctt cttctctctg cctcattctc     960
acatactcta ggggcggctg gctcggcttc gtggctatga ttttcgtgtg ggctctcctc    1020
ggcctctact ggttccagcc taggctccct gctccttgga ggaggtggct cttccctgtg    1080
```

| | |
|---|---|
| gtgctcggcg gcctcgtggc tgtgctcctc gtggctgtgc tcggcctcga gcctctcagg | 1140 |
| gtgagggtgc tctctatttt cgtgggcagg gaggattctt ctaataattt caggattaat | 1200 |
| gtgtggctcg ctgtgctcca gatgattcag gataggcctt ggctcggcat tggccctggc | 1260 |
| aatacagctt tcaatctcgt gtaccctctc taccagcagg ctaggttcac agctctctct | 1320 |
| gcttactctg tgcctctcga ggtggctgtg gagggcggcc tcctcggcct cacagctttc | 1380 |
| gcttggctcc tcctcgtgac agctgtgaca gctgtgcgcc aggtgtctag gctcaggagg | 1440 |
| gataggaatc ctcaggcttt ctggctcatg gcttctctcg ctggcctcgc tggcatgctc | 1500 |
| ggccatggcc tcttcgatac agtgctctac aggcctgagg cttctacact ctggtggctc | 1560 |
| tgcattggcg ctattgcttc tttctggcag cctcagcctt taagcagct ccctcctgag | 1620 |
| gctgagcatt ctgatgagaa gatgtga | 1647 |

<210> SEQ ID NO 39
<211> LENGTH: 1551
<212> TYPE: DNA
<213> ORGANISM: Zea mays
<220> FEATURE:
<221> NAME/KEY: misc_feature
<222> LOCATION: (1)..(1551)
<223> OTHER INFORMATION: ism2 mutant of sh2

<400> SEQUENCE: 39

| | |
|---|---|
| atgcagttcg ctctcgctct cgatacaaat tctggccctc atcagattag gtcttgcgag | 60 |
| ggcgatggca ttgataggct cgagaagctc tctattggcg gcaggaagca ggagaaggct | 120 |
| ctcaggaata ggtgcttcgg cggcagggtg gctgctacaa cacagtgcat tctcacatct | 180 |
| gatgcttgcc ctgagacact ccattctcag acacagtctt ctaggaagaa ttacgctgat | 240 |
| gctaataggg tgtctgctat tattctcggc ggcggcacag gctctggcct cttccctctc | 300 |
| acatctacaa gggctacacc tgctgtgcct gtgggcggct gctacaggct cattgatatt | 360 |
| cctatgtcta attgcttcaa ttctggcatt aataagattt cgtgatgtc tcagttcaat | 420 |
| tctacatctc tcaataggca tattcatagg acatacctcg agggcggcat taatttcgct | 480 |
| ggcggctctg tgcaggtgct cgctgctaca cagatgcctg aggagcctgc tggctggttc | 540 |
| cagggcacag ctgattctat taggaagttc atttgggtgc tcgaggatta ctactctcat | 600 |
| aagtctattg ataatattgt gattctctct ggcgatcagc tctacaggat gaattacatg | 660 |
| gagctcgtgc agaagcatgt ggaggatgat gctgatatta caatttcttg cgctcctgtg | 720 |
| gatgagtcta gggcttctaa gaatggcctc gtgaagattg atcatacagg cagggtgctc | 780 |
| cagttcttcg agaagcctaa gggcgctgat ctcaattcta tgagggtgga gacaaatttc | 840 |
| ctctcttacg ctattgatga tgctcagaag tacccttacc tcgcttctat ggcatttac | 900 |
| gtgttcaaga aggatgctct cctcgatctc ctcaagtcta agtacacaca gctccatgat | 960 |
| ttcggctctg agattctccc tagggctgtg ctcgatcatt ctgtgcaggc ttgcattttc | 1020 |
| acaggctact gggaggatgt gggcacaatt aagtctttct tcgatgctaa tctcgctctc | 1080 |
| acagagcagc cttctaagtt cgatttctac gatcctaaga caccttttctt cacagctcct | 1140 |
| aggtgcctcc ctcctacaca gctcgataag tgcaagatga agtacgcttt catttctgat | 1200 |
| ggctgcctcc tcagggagtg caatattgag cattctgtga ttggcgtgtg ctctagggtg | 1260 |
| tcttctggct gcgagctcaa ggattctgtg atgatgggcg ctgatacata cgagacagag | 1320 |
| gaggagaggt ctaagctcct cctcgctggc aaggtgcctg tgggcattgg caggaataca | 1380 |
| aagattagga attgcattat tgatatgaat gctaggattg gcaagaatgt ggtgattaca | 1440 |

```
aattctaagg gcattcagga ggctgatcat cctgaggagg gctactacat taggtctggc    1500
attgtggtga ttctcaagaa tgctacaatt aatgatggct ctgtgatttg a             1551
```

<210> SEQ ID NO 40
<211> LENGTH: 516
<212> TYPE: PRT
<213> ORGANISM: Zea mays
<220> FEATURE:
<221> NAME/KEY: MISC_FEATURE
<222> LOCATION: (1)..(516)
<223> OTHER INFORMATION: ism2 mutant of sh2

<400> SEQUENCE: 40

```
Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys Phe Gly Gly
        35                  40                  45

Arg Val Ala Ala Thr Thr Gln Cys Ile Leu Thr Ser Asp Ala Cys Pro
    50                  55                  60

Glu Thr Leu His Ser Gln Thr Gln Ser Ser Arg Lys Asn Tyr Ala Asp
65                  70                  75                  80

Ala Asn Arg Val Ser Ala Ile Ile Leu Gly Gly Gly Thr Gly Ser Gly
                85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Gly Ile Asn Phe Ala
145                 150                 155                 160

Gly Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
            260                 265                 270

Ser Met Arg Val Glu Thr Asn Phe Leu Ser Tyr Ala Ile Asp Asp Ala
        275                 280                 285

Gln Lys Tyr Pro Tyr Leu Ala Ser Met Gly Ile Tyr Val Phe Lys Lys
    290                 295                 300

Asp Ala Leu Leu Asp Leu Leu Lys Ser Lys Tyr Thr Gln Leu His Asp
305                 310                 315                 320

Phe Gly Ser Glu Ile Leu Pro Arg Ala Val Leu Asp His Ser Val Gln
                325                 330                 335
```

```
Ala Cys Ile Phe Thr Gly Tyr Trp Glu Asp Val Gly Thr Ile Lys Ser
                340                 345                 350

Phe Phe Asp Ala Asn Leu Ala Leu Thr Glu Gln Pro Ser Lys Phe Asp
            355                 360                 365

Phe Tyr Asp Pro Lys Thr Pro Phe Phe Thr Ala Pro Arg Cys Leu Pro
        370                 375                 380

Pro Thr Gln Leu Asp Lys Cys Lys Met Lys Tyr Ala Phe Ile Ser Asp
385                 390                 395                 400

Gly Cys Leu Leu Arg Glu Cys Asn Ile Glu His Ser Val Ile Gly Val
                405                 410                 415

Cys Ser Arg Val Ser Ser Gly Cys Glu Leu Lys Asp Ser Val Met Met
                420                 425                 430

Gly Ala Asp Thr Tyr Glu Thr Glu Glu Glu Arg Ser Lys Leu Leu Leu
                435                 440                 445

Ala Gly Lys Val Pro Val Gly Ile Gly Arg Asn Thr Lys Ile Arg Asn
            450                 455                 460

Cys Ile Ile Asp Met Asn Ala Arg Ile Gly Lys Asn Val Val Ile Thr
465                 470                 475                 480

Asn Ser Lys Gly Ile Gln Glu Ala Asp His Pro Glu Glu Gly Tyr Tyr
                485                 490                 495

Ile Arg Ser Gly Ile Val Val Ile Leu Lys Asn Ala Thr Ile Asn Asp
                500                 505                 510

Gly Ser Val Ile
        515

<210> SEQ ID NO 41
<211> LENGTH: 1647
<212> TYPE: DNA
<213> ORGANISM: Pisum sativum and Synechococcus sp. PCC 7942
<220> FEATURE:
<221> NAME/KEY: misc_feature
<222> LOCATION: (1)..(1647)
<223> OTHER INFORMATION: RbcS signal peptide-ictB
<220> FEATURE:
<221> NAME/KEY: misc_feature
<222> LOCATION: (1)..(243)
<223> OTHER INFORMATION: misc_feature
<220> FEATURE:
<221> NAME/KEY: misc_feature
<222> LOCATION: (244)..(1647)
<223> OTHER INFORMATION: ictB

<400> SEQUENCE: 41
atggcttcta tgatttcttc ttctgctgtg acaacagtgt ctagggcttc taggggccag      60
tctgctgctg tggctccttt cggcggcctc aagtctatga caggcttccc tgtgaagaag     120
gtgaatacag atattacatc tattacatct aatggcggca gggtgaagtg catgcaggtg     180
tggcctccta ttggcaagaa gaagttcgag acactctctt acctccctcc tctcacaagg     240
gatatgacag tgtggcagac actcacattg gctcattacc agcctcagca gtggggccat     300
tcttctttcc tccataggct cttcggctct tcagggcttg gagggcttcc ttctcagctc     360
ctcgtgtggt ctgaggctct cggcggcttc ctcctcgctg tggtgtacgg ctctgctcct     420
ttcgtgcctt cttctgctct cggcctcggc ctcgctgcta ttgctgctta ctgggctctc     480
ctctctctca cagatattga tctcaggcag gctacaccta ttcattggct cgtgctcctc     540
tactggggcg tggatgctct cgctacaggc ctctctcctg tgaggctgc tgctctcgtg     600 ggcctcgcta agctcacact ctacctcctc gtgttcgctc tcgctgctag ggtgctcagg     660
```

```
aatcctaggc tcaggtctct cctcttctct gtggtggtga ttacatctct cttcgtgtct    720
gtgtacggcc tcaatcagtg gatttacggc gtggaggagc tcgctacatg ggtggatagg    780
aattctgtgg ctgatttcac atctagggtg tactcttacc tcggcaatcc taatctcctc    840
gctgcttacc tcgtgcctac aacagctttc tctgctgctg ctattggcgt gtggaggggc    900
tggctcccta agctcctcgc tattgctgct acaggcgctt cttctctctg cctcattctc    960
acatactcta ggggcggctg gctcggcttc gtggctatga ttttcgtgtg ggctctcctc   1020
ggcctctact ggttccagcc taggctccct gctccttgga ggaggtggct cttccctgtg   1080
gtgctcggcg gcctcgtggc tgtgctcctc gtggctgtgc tcggcctcga gcctctcagg   1140
gtgagggtgc tctctatttt cgtgggcagg gaggattctt ctaataattt caggattaat   1200
gtgtggctcg ctgtgctcca gatgattcag gataggcctt ggctcggcat ggccctggc    1260
aatacagctt tcaatctcgt gtaccctctc taccagcagg ctaggttcac agctctctct   1320
gcttactctg tgcctctcga ggtggctgtg gagggcggcc tcctcggcct cacagctttc   1380
gcttggctcc tcctcgtgac agctgtgaca gctgtgcgcc aggtgtctag gctcaggagg   1440
gataggaatc ctcaggcttt ctggctcatg gcttctctcg ctggcctcgc tggcatgctc   1500
ggccatggcc tcttcgatac agtgctctac aggcctgagg cttctacact ctggtggctc   1560
tgcattggcg ctattgcttc tttctggcag cctcagcctt ctaagcagct ccctcctgag   1620
gctgagcatt ctgatgagaa gatgtga                                      1647

<210> SEQ ID NO 42
<211> LENGTH: 231
<212> TYPE: DNA
<213> ORGANISM: Populus sp.
<220> FEATURE:
<221> NAME/KEY: misc_feature
<222> LOCATION: (1)..(231)
<223> OTHER INFORMATION: hc1

<400> SEQUENCE: 42
atgtctgatt ggggccctgt gttcgtggct gtggtgctct tcattctcct cacacctggc     60
ctcctcattc agattcctgg caggcagagg ctcgtggagt tcggcaattt ccagacatct    120
ggcgtgtcta ttctcgtgca ttctattctc tacttcgctc tcatttgcat tttcctcctc    180
gctgtgggcg tgcatgtgtg ctctctctgc acaccttcta tgctcgattg a             231

<210> SEQ ID NO 43
<211> LENGTH: 76
<212> TYPE: PRT
<213> ORGANISM: Populus sp.
<220> FEATURE:
<221> NAME/KEY: MISC_FEATURE
<222> LOCATION: (1)..(76)
<223> OTHER INFORMATION: hc1

<400> SEQUENCE: 43

Met Ser Asp Trp Gly Pro Val Phe Val Ala Val Leu Phe Ile Leu
1               5                   10                  15

Leu Thr Pro Gly Leu Leu Ile Gln Ile Pro Gly Arg Gln Arg Leu Val
                20                  25                  30

Glu Phe Gly Asn Phe Gln Thr Ser Gly Val Ser Ile Leu Val His Ser
            35                  40                  45

Ile Leu Tyr Phe Ala Leu Ile Cys Ile Phe Leu Leu Ala Val Gly Val
        50                  55                  60

His Val Cys Ser Leu Cys Thr Pro Ser Met Leu Asp
```

<210> SEQ ID NO 44
<211> LENGTH: 210
<212> TYPE: DNA
<213> ORGANISM: Sorghum bicolor
<220> FEATURE:
<221> NAME/KEY: misc_feature
<222> LOCATION: (1)..(210)
<223> OTHER INFORMATION: hc1

<400> SEQUENCE: 44

```
atggctgatt ggggccctgt gctcattggc ctcgtgctct tcattctcct ctctcctggc     60
ctcctcttcc agattcctgg caagggcagg attattgagt tcggcaattt ccagacatct    120
ggcctctcta ttctcattca tgctgtgatt tacttcgctc tcctcgctat tttcctcctc    180
gctgtgggcg tgcatattta cctcggctga                                      210
```

<210> SEQ ID NO 45
<211> LENGTH: 69
<212> TYPE: PRT
<213> ORGANISM: Sorghum bicolor
<220> FEATURE:
<221> NAME/KEY: MISC_FEATURE
<222> LOCATION: (1)..(69)
<223> OTHER INFORMATION: hc1

<400> SEQUENCE: 45

Met Ala Asp Trp Gly Pro Val Leu Ile Gly Leu Val Leu Phe Ile Leu
1               5                   10                  15

Leu Ser Pro Gly Leu Leu Phe Gln Ile Pro Gly Lys Gly Arg Ile Ile
            20                  25                  30

Glu Phe Gly Asn Phe Gln Thr Ser Gly Leu Ser Ile Leu Ile His Ala
        35                  40                  45

Val Ile Tyr Phe Ala Leu Leu Ala Ile Phe Leu Leu Ala Val Gly Val
    50                  55                  60

His Ile Tyr Leu Gly
65

<210> SEQ ID NO 46
<211> LENGTH: 1584
<212> TYPE: DNA
<213> ORGANISM: Solanum tuberosum
<220> FEATURE:
<221> NAME/KEY: misc_feature
<222> LOCATION: (1)..(1584)
<223> OTHER INFORMATION: AGPase large subunit

<400> SEQUENCE: 46

```
atggatacct gctgcgtgcc aatgaagtcc accgtgcacc tgggcagggt gtccaccggg     60
ggcttcaaca atggggagaa agagttcttt ggcgaaaaaa tccgcgggag cctcaacagc    120
aatctgcgca tcaatcaact gtccaagtcc ctgaagctcg agaagaaaga aaataaaatc    180
aagccaggcg tcgcctacag cgtgatcaca acagagaatg acacacaaac agtgtttgtg    240
gatatgccaa ggctggaacg ccgccgcgcg aatccaaagg acgtcgccgc cgtgattctc    300
ggggggggca aggggacaaa gctcttccca ctgaccagca ggaccgccac cctcgcggtc    360
ccggtggggg gctgctatag gctcattgac attccgatgt ccaactgcat caacagcgcg    420
atcaacaaaa tcttcgtgct gacccaatac aattccgccc cgctgaacag gcacatcgcc    480
cgcacatatt tcgggaatgg cgtgtccttc ggcgatggct cgtcgaagt cctggcggcg    540
```

```
acacagaccc cggggaagc cggcaaaaag tggttccagg gcacagcgga tgccgtgcgc      600
aaatttatct gggtgttcga agatgccaag aacaaaaaca tcgagaacat tgtcgtgctg    660
agcggggatc acctctatag gatggactac atggaactgg tgcagaatca catcgaccgc    720
aatgccgaca ttaccctgag ctgcgcccca gcggaagaca gcagggcctc cgacttcggc    780
ctcgtgaaaa ttgatagccg cggccgcgtg gtgcagttcg ccgagaagcc aaagggcttt    840
gatctcaaag ccatgcaagt cgatacaaca ctggtcggcc tgtccccaca agatgcgaaa    900
aagtccccgt acatcgcgag catgggggtg tacgtcttta aaacagacgt cctgctcaag    960
ctgctcaagt ggtcctaccc aaccagcaat gactttggca gcgagattat cccagcggcc   1020
attgatgact acaacgtgca ggcctatatt ttcaaggatt actgggagga tattgggaca   1080
attaagagct tttataacgc gtccctcgcc ctgacacaag aattcccaga attccaattc   1140
tatgacccga agacaccatt ctatacatcc ccaaggtttc tcccaccgac aaaaatcgac   1200
aactgtaaga tcaaggacgc catcattagc cacggctgct cctgcgcgca ttgtagcgtg   1260
gaacatagca tcgtcgggga acgctcccgc ctcgactgtg gcgtggagct gaaagatacc   1320
ttcatgatgg gggcggacta ttatcaaaca gagtccgaga tcgcgagcct gctggccgag   1380
gggaaagtgc caattggcat tggcgaaaat acaaaaatcc gcaaatgtat catcgacaaa   1440
aacgccaaaa ttggcaaaaa cgtgagcatt attaacaaag atggcgtgca ggaggccgac   1500
cgcccagagg aagggttcta tattcgcagc gggatcatta ttattctgga aaaggccacc   1560
attagggacg ggacagtgat ctga                                          1584

<210> SEQ ID NO 47
<211> LENGTH: 1242
<212> TYPE: DNA
<213> ORGANISM: Zea mays
<220> FEATURE:
<221> NAME/KEY: misc_feature
<222> LOCATION: (1)..(1242)
<223> OTHER INFORMATION: FBPase

<400> SEQUENCE: 47
atggctgctg ctgctacaac atcttcttct tctcatctcc tcctcctctc taggcagcag     60
gctgcttctc tcaggtgcag gctctctttc ctcggccagc ctaggaggcc tggcagggtg    120
acagctcagg ctcctgctgc taaggatgtg aggtgcatgg ctgctgtgga tacagctgct    180
tctgctgctg ctgctgagac atctcctaag tcttcttctt cttacgagat tgtgacactc    240
acaacatggc tcctccagca ggagaggaca ggcgctattg ataatgagat gacaattgtg    300
ctcgcttcta tttctacagc ttgcaagcag attgctgctc tcgtgcagag ggctcctatt    360
tctaatctca caggcgtgca gggcgctgtg aatgtgcagg gcgaggatca gaagaagctc    420
gatgtggtgt ctaatgaggt gttctctaat tgcctcaagt cttctggcag acaggcgtg    480
attgcttctg aggaggagga tgtgcctgtg gctgtggagc agtcttactc tggcaattac    540
attgtggtgt tcgatcctct cgatggctct tctaatattg atgctgctgt gtctacaggc    600
tctatttttcg gcatttacaa tcctaatgat gagtgcctcg ctgatgtgga tgataatgat    660
acactcgatt ctgtgggagca gaggtgcatt gtgaatgtgt gccagcctgg ctctaatctc    720
ctcgctgctg gctactgcat gtactcttct tctgtgattt tcgtgctcac agtgggcaca    780
ggcgtgtacg tgttcacact cgatcctatg tacggcgagt tcgtgctcac acaggagaag    840
gtgcagattc ctaaggctgg caagatttac gctttcaatg agggcaatta cgctctctgg    900
gatgataagc tcaagctcta catggattct ctcaaggagc ctggcgattc tggcaagcct    960
```

```
tactctgcta ggtacattgg ctctctcgtg ggcgatttcc ataggacact cctctacggc   1020
ggcatttacg gctaccctag ggataagaag tctaagaatg caagctcag gctcctctac    1080 gagtgcgctc ctatgtcttt cattgtggag caggctggcg gcaagggctc tgatggccat   1140
cagaggattc tcgatattac acctacagag attcatcaga gggtgcctct ctacattggc   1200
tctgtggagg aggtggataa ggtggagaag ttcctcgctt ga                      1242
```

<210> SEQ ID NO 48
<211> LENGTH: 413
<212> TYPE: PRT
<213> ORGANISM: Zea mays
<220> FEATURE:
<221> NAME/KEY: MISC_FEATURE
<222> LOCATION: (1)..(413)
<223> OTHER INFORMATION: FBPase

<400> SEQUENCE: 48

```
Met Ala Ala Ala Thr Thr Ser Ser Ser His Leu Leu Leu Leu
1               5                   10                  15

Ser Arg Gln Gln Ala Ala Ser Leu Arg Cys Arg Leu Ser Phe Leu Gly
                20                  25                  30

Gln Pro Arg Arg Pro Gly Arg Val Thr Ala Gln Ala Pro Ala Ala Lys
            35                  40                  45

Asp Val Arg Cys Met Ala Ala Val Asp Thr Ala Ala Ser Ala Ala Ala
        50                  55                  60

Ala Glu Thr Ser Pro Lys Ser Ser Ser Tyr Glu Ile Val Thr Leu
65                  70                  75                  80

Thr Thr Trp Leu Leu Gln Gln Glu Arg Thr Gly Ala Ile Asp Asn Glu
                85                  90                  95

Met Thr Ile Val Leu Ala Ser Ile Ser Thr Ala Cys Lys Gln Ile Ala
            100                 105                 110

Ala Leu Val Gln Arg Ala Pro Ile Ser Asn Leu Thr Gly Val Gln Gly
        115                 120                 125

Ala Val Asn Val Gln Gly Glu Asp Gln Lys Lys Leu Asp Val Val Ser
    130                 135                 140

Asn Glu Val Phe Ser Asn Cys Leu Lys Ser Ser Gly Arg Thr Gly Val
145                 150                 155                 160

Ile Ala Ser Glu Glu Asp Val Pro Val Ala Val Glu Gln Ser Tyr
                165                 170                 175

Ser Gly Asn Tyr Ile Val Val Phe Asp Pro Leu Asp Gly Ser Ser Asn
            180                 185                 190

Ile Asp Ala Ala Val Ser Thr Gly Ser Ile Phe Gly Ile Tyr Asn Pro
        195                 200                 205

Asn Asp Glu Cys Leu Ala Asp Val Asp Asp Asn Asp Thr Leu Asp Ser
    210                 215                 220

Val Glu Gln Arg Cys Ile Val Asn Val Cys Gln Pro Gly Ser Asn Leu
225                 230                 235                 240

Leu Ala Ala Gly Tyr Cys Met Tyr Ser Ser Ser Val Ile Phe Val Leu
                245                 250                 255

Thr Val Gly Thr Gly Val Tyr Val Phe Thr Leu Asp Pro Met Tyr Gly
            260                 265                 270

Glu Phe Val Leu Thr Gln Glu Lys Val Gln Ile Pro Lys Ala Gly Lys
        275                 280                 285

Ile Tyr Ala Phe Asn Glu Gly Asn Tyr Ala Leu Trp Asp Asp Lys Leu
    290                 295                 300
```

Lys Leu Tyr Met Asp Ser Leu Lys Glu Pro Gly Asp Ser Gly Lys Pro
305                 310                 315                 320

Tyr Ser Ala Arg Tyr Ile Gly Ser Leu Val Gly Asp Phe His Arg Thr
            325                 330                 335

Leu Leu Tyr Gly Gly Ile Tyr Tyr Pro Arg Asp Lys Lys Ser Lys
        340                 345                 350

Asn Gly Lys Leu Arg Leu Leu Tyr Glu Cys Ala Pro Met Ser Phe Ile
            355                 360                 365

Val Glu Gln Ala Gly Lys Gly Ser Asp Gly His Gln Arg Ile Leu
    370                 375                 380

Asp Ile Thr Pro Thr Glu Ile His Gln Arg Val Pro Leu Tyr Ile Gly
385                 390                 395                 400

Ser Val Glu Glu Val Asp Lys Val Glu Lys Phe Leu Ala
                405                 410

<210> SEQ ID NO 49
<211> LENGTH: 1167
<212> TYPE: DNA
<213> ORGANISM: Zea mays
<220> FEATURE:
<221> NAME/KEY: misc_feature
<222> LOCATION: (1)..(1167)
<223> OTHER INFORMATION: FBP aldolase

<400> SEQUENCE: 49
atggcttctg ctacagtgct caagtcttct ttcctcccta agaagtctga gtggggcgct      60
acaaggcagg ctgctgctcc taggcctcct acagtgtcta tggtggtgag ggcttctgct     120
tacgctgatg agctcgtgaa gacagctaag acaattgctt ctcctggcag gggcattctc     180
gctatggatg agtctaatgc tacatgcggc aagaggctcg cttctattgg cctcgagaat     240
acagaggcta ataggcaggc ttacaggaca ctcctcgtga cagctcctgg cctcggccag     300
tacatttctg gcgctattct cttcgaggag acactctacc agtctgctgt ggatggcagg     360
aagattgtgg atattctcgt ggagcagggc attgtgcctg gcattaaggt ggataagggc     420
ctcgtgcctc tcgctggctc taataatgag tcttggtgcc agggcctcga tggcctcgct     480
tctagggagg ctgcttacta ccagcagggc gctaggttcg ctaagtggag gacagtggtg     540
tctattccta atggcccttc tgagctcgct gtgaaggagg ctgcttgggg cctcgctagg     600
tacgctgcta tttctcagga taatggcctc gtgcctattg tggagcctga gattctcctc     660
gatggcgagc atggcattga gaggacattc gaggtggctc agaaggtgtg ggctgagaca     720
ttctacgcta tggctgagaa taatgtgatg ttcgagggca ttctcctcaa gccttctatg     780
gtgacacctg cgctgaggc taaggatagg gctacacctg agcaggtggc tgcttacaca     840
ctcaagctcc tccataggag gattcctcct tctgtgcctg gcattatgtt cctctctggc     900
ggccagtctg aggtggaggc tacacagaat ctcaatgcta tgaatcaggg ccctaatcct     960
tggcatgtgt ctttctctta cgctagggct ctccagaata catgcctcaa gacatggggc    1020
ggccagcctg ataaggtgaa ggctgctcag gatgctctcc tcctcagggc taaggctaat    1080
tctctcgctc agctcggcaa gtacacatct gatggcgagg ctgctgaggc taaggagggc    1140
atgttcgtga agaattactc ttactga                                        1167

<210> SEQ ID NO 50
<211> LENGTH: 388
<212> TYPE: PRT
<213> ORGANISM: Zea mays

<220> FEATURE:
<221> NAME/KEY: MISC_FEATURE
<222> LOCATION: (1)..(388)
<223> OTHER INFORMATION: FBP aldolase

<400> SEQUENCE: 50

| | | | | | | | | | | | | | | |
|---|---|---|---|---|---|---|---|---|---|---|---|---|---|---|
| Met | Ala | Ser | Ala | Thr | Val | Leu | Lys | Ser | Ser | Phe | Leu | Pro | Lys | Lys | Ser |
| 1 | | | | 5 | | | | | 10 | | | | | 15 | |
| Glu | Trp | Gly | Ala | Thr | Arg | Gln | Ala | Ala | Pro | Arg | Pro | Thr | Val |
| | | | 20 | | | | | 25 | | | | | 30 |
| Ser | Met | Val | Val | Arg | Ala | Ser | Ala | Tyr | Ala | Asp | Glu | Leu | Val | Lys | Thr |
| | | | | 35 | | | | | 40 | | | | | 45 |
| Ala | Lys | Thr | Ile | Ala | Ser | Pro | Gly | Arg | Gly | Ile | Leu | Ala | Met | Asp | Glu |
| | 50 | | | | | 55 | | | | | 60 |
| Ser | Asn | Ala | Thr | Cys | Gly | Lys | Arg | Leu | Ala | Ser | Ile | Gly | Leu | Glu | Asn |
| 65 | | | | | 70 | | | | | 75 | | | | | 80 |
| Thr | Glu | Ala | Asn | Arg | Gln | Ala | Tyr | Arg | Thr | Leu | Leu | Val | Thr | Ala | Pro |
| | | | | 85 | | | | | 90 | | | | | 95 |
| Gly | Leu | Gly | Gln | Tyr | Ile | Ser | Gly | Ala | Ile | Leu | Phe | Glu | Glu | Thr | Leu |
| | | | 100 | | | | | 105 | | | | | 110 |
| Tyr | Gln | Ser | Ala | Val | Asp | Gly | Arg | Lys | Ile | Val | Asp | Ile | Leu | Val | Glu |
| | | | 115 | | | | | 120 | | | | | 125 |
| Gln | Gly | Ile | Val | Pro | Gly | Ile | Lys | Val | Asp | Lys | Gly | Leu | Val | Pro | Leu |
| | 130 | | | | | 135 | | | | | 140 |
| Ala | Gly | Ser | Asn | Asn | Glu | Ser | Trp | Cys | Gln | Gly | Leu | Asp | Gly | Leu | Ala |
| 145 | | | | | 150 | | | | | 155 | | | | | 160 |
| Ser | Arg | Glu | Ala | Ala | Tyr | Tyr | Gln | Gln | Gly | Ala | Arg | Phe | Ala | Lys | Trp |
| | | | | 165 | | | | | 170 | | | | | 175 |
| Arg | Thr | Val | Val | Ser | Ile | Pro | Asn | Gly | Pro | Ser | Glu | Leu | Ala | Val | Lys |
| | | | 180 | | | | | 185 | | | | | 190 |
| Glu | Ala | Ala | Trp | Gly | Leu | Ala | Arg | Tyr | Ala | Ala | Ile | Ser | Gln | Asp | Asn |
| | | | 195 | | | | | 200 | | | | | 205 |
| Gly | Leu | Val | Pro | Ile | Val | Glu | Pro | Glu | Ile | Leu | Leu | Asp | Gly | Glu | His |
| | 210 | | | | | 215 | | | | | 220 |
| Gly | Ile | Glu | Arg | Thr | Phe | Glu | Val | Ala | Gln | Lys | Val | Trp | Ala | Glu | Thr |
| 225 | | | | | 230 | | | | | 235 | | | | | 240 |
| Phe | Tyr | Ala | Met | Ala | Glu | Asn | Asn | Val | Met | Phe | Glu | Gly | Ile | Leu | Leu |
| | | | | 245 | | | | | 250 | | | | | 255 |
| Lys | Pro | Ser | Met | Val | Thr | Pro | Gly | Ala | Glu | Ala | Lys | Asp | Arg | Ala | Thr |
| | | | 260 | | | | | 265 | | | | | 270 |
| Pro | Glu | Gln | Val | Ala | Ala | Tyr | Thr | Leu | Lys | Leu | Leu | His | Arg | Arg | Ile |
| | | | 275 | | | | | 280 | | | | | 285 |
| Pro | Pro | Ser | Val | Pro | Gly | Ile | Met | Phe | Leu | Ser | Gly | Gly | Gln | Ser | Glu |
| | 290 | | | | | 295 | | | | | 300 |
| Val | Glu | Ala | Thr | Gln | Asn | Leu | Asn | Ala | Met | Asn | Gln | Gly | Pro | Asn | Pro |
| 305 | | | | | 310 | | | | | 315 | | | | | 320 |
| Trp | His | Val | Ser | Phe | Ser | Tyr | Ala | Arg | Ala | Leu | Gln | Asn | Thr | Cys | Leu |
| | | | | 325 | | | | | 330 | | | | | 335 |
| Lys | Thr | Trp | Gly | Gly | Gln | Pro | Asp | Lys | Val | Lys | Ala | Ala | Gln | Asp | Ala |
| | | | 340 | | | | | 345 | | | | | 350 |
| Leu | Leu | Leu | Arg | Ala | Lys | Ala | Asn | Ser | Leu | Ala | Gln | Leu | Gly | Lys | Tyr |
| | | | 355 | | | | | 360 | | | | | 365 |
| Thr | Ser | Asp | Gly | Glu | Ala | Ala | Glu | Ala | Lys | Glu | Gly | Met | Phe | Val | Lys |
| | 370 | | | | | 375 | | | | | 380 |

Asn Tyr Ser Tyr
385

<210> SEQ ID NO 51
<211> LENGTH: 1359
<212> TYPE: DNA
<213> ORGANISM: Zea mays
<220> FEATURE:
<221> NAME/KEY: misc_feature
<222> LOCATION: (1)..(1359)
<223> OTHER INFORMATION: Carbonic anhydrase

<400> SEQUENCE: 51

| | | | | |
|---|---|---|---|---|
| atgagcagct | gcctctgcct | cccgaagaag | aaggagggcc | cggccaagga gaagccgagc | 60 |
| accgacaccc | cgaccagcag | cctcctccag | aaccagaagc | cgagccagcc gccgccgccg | 120 |
| ccgagcaagg | ccagcagcaa | gggcatggac | ccgaccgtgg | agcgcctcaa gagcggcttc | 180 |
| cagaagttca | agaccgaggt | gtacgacaag | aagccggagc | tcttcgagcc gctcaagagc | 240 |
| ggccagagcc | cgcgctacat | ggtgttcgcc | tgcagcgaca | gccgcgtgtg cccgagcgtg | 300 |
| accctcggcc | tccagccggg | cgaggccttc | accgtgcgca | catcgccag catggtgccg | 360 |
| ccgtacgaca | agatcaagta | cgccggcacc | ggcagcgcca | tcgagtacgc cgtgtgcgcc | 420 |
| ctcaaggtgc | aggtcatcgt | ggtgatcggc | cacagctgct | gcggcggcat ccgcgccctc | 480 |
| ctcagcctca | aggacggcgc | cccggacaac | ttccacttcg | tggaggactg ggtgcgcatc | 540 |
| ggcagcccgg | ccaagaacaa | ggtgaagaag | gagcacgcca | gcgtgccgtt cgacgaccag | 600 |
| tgcagcatcc | tcgagaagga | ggccgtgaac | gtgagcctcc | agaacctcaa gagctacccg | 660 |
| ttcgtgaagg | agggcctcgc | cggcggcacc | ctcaagctcg | tgggcgccca ctacgacttc | 720 |
| gtgaagggcc | agttcgtgac | ctgggagccg | ccgcaggacg | ccatcgagcg cctcaccagc | 780 |
| ggcttccagc | agttcaaggt | gaacgtgtac | gacaagaagc | cggagctctt cggcccgctc | 840 |
| aagagcggcc | aggccccgaa | gtacatggtg | ttcgcctgca | gcgacagccg cgtgtgcccg | 900 |
| agcgtgaccc | tcggcctcca | gccgggcgag | gccttcaccg | tgcgcaacat cgccgccatg | 960 |
| gtgccgggct | acgacaagac | caagtacacc | ggcatcggca | gcgccatcga gtacgccgtg | 1020 |
| tgcgccctca | aggtggaggt | gctcgtggtg | atcggccaca | gctgctgcgg cggcatccgc | 1080 |
| gccctcctca | gcctccagga | cggcgccccg | gacaccttcc | acttcgtgga ggactgggtg | 1140 |
| aagatcggct | tcatcgccaa | gatgaaggtg | aagaaggagc | acgccagcgt gccgttcgac | 1200 |
| gaccagtgca | gcatcctcga | gaaggaggcc | gtgaacgtga | gcctcgagaa cctcaagacc | 1260 |
| tacccgttcg | tgaaggaggg | cctcgccaac | ggcacccctca | agctcatcgg cgcccactac | 1320 |
| gacttcgtga | gcggcgagtt | cctcacctgg | aagaagtga | | 1359 |

<210> SEQ ID NO 52
<211> LENGTH: 452
<212> TYPE: PRT
<213> ORGANISM: Zea mays
<220> FEATURE:
<221> NAME/KEY: MISC_FEATURE
<222> LOCATION: (1)..(452)
<223> OTHER INFORMATION: Carbonic anhydrase

<400> SEQUENCE: 52

Met Ser Ser Cys Leu Cys Leu Pro Lys Lys Glu Gly Pro Ala Lys
1               5                   10                  15

Glu Lys Pro Ser Thr Asp Thr Pro Thr Ser Ser Leu Leu Gln Asn Gln
            20                  25                  30

```
Lys Pro Ser Gln Pro Pro Pro Pro Ser Lys Ala Ser Ser Lys Gly
         35                  40                  45

Met Asp Pro Thr Val Glu Arg Leu Lys Ser Gly Phe Gln Lys Phe Lys
 50                  55                  60

Thr Glu Val Tyr Asp Lys Lys Pro Glu Leu Phe Glu Pro Leu Lys Ser
 65                  70                  75                  80

Gly Gln Ser Pro Arg Tyr Met Val Phe Ala Cys Ser Asp Ser Arg Val
                 85                  90                  95

Cys Pro Ser Val Thr Leu Gly Leu Gln Pro Gly Glu Ala Phe Thr Val
                100                 105                 110

Arg Asn Ile Ala Ser Met Val Pro Pro Tyr Asp Lys Ile Lys Tyr Ala
             115                 120                 125

Gly Thr Gly Ser Ala Ile Glu Tyr Ala Val Cys Ala Leu Lys Val Gln
 130                 135                 140

Val Ile Val Val Ile Gly His Ser Cys Cys Gly Gly Ile Arg Ala Leu
145                 150                 155                 160

Leu Ser Leu Lys Asp Gly Ala Pro Asp Asn Phe His Phe Val Glu Asp
                 165                 170                 175

Trp Val Arg Ile Gly Ser Pro Ala Lys Asn Lys Val Lys Lys Glu His
                 180                 185                 190

Ala Ser Val Pro Phe Asp Asp Gln Cys Ser Ile Leu Glu Lys Glu Ala
             195                 200                 205

Val Asn Val Ser Leu Gln Asn Leu Lys Ser Tyr Pro Phe Val Lys Glu
210                 215                 220

Gly Leu Ala Gly Gly Thr Leu Lys Leu Val Gly Ala His Tyr Asp Phe
225                 230                 235                 240

Val Lys Gly Gln Phe Val Thr Trp Glu Pro Pro Gln Asp Ala Ile Glu
                 245                 250                 255

Arg Leu Thr Ser Gly Phe Gln Gln Phe Lys Val Asn Val Tyr Asp Lys
             260                 265                 270

Lys Pro Glu Leu Phe Gly Pro Leu Lys Ser Gly Gln Ala Pro Lys Tyr
         275                 280                 285

Met Val Phe Ala Cys Ser Asp Ser Arg Val Cys Pro Ser Val Thr Leu
 290                 295                 300

Gly Leu Gln Pro Gly Glu Ala Phe Thr Val Arg Asn Ile Ala Ala Met
305                 310                 315                 320

Val Pro Gly Tyr Asp Lys Thr Lys Tyr Thr Gly Ile Gly Ser Ala Ile
                 325                 330                 335

Glu Tyr Ala Val Cys Ala Leu Lys Val Glu Val Leu Val Ile Gly
             340                 345                 350

His Ser Cys Cys Gly Gly Ile Arg Ala Leu Leu Ser Leu Gln Asp Gly
             355                 360                 365

Ala Pro Asp Thr Phe His Phe Val Glu Asp Trp Val Lys Ile Gly Phe
370                 375                 380

Ile Ala Lys Met Lys Val Lys Lys Glu His Ala Ser Val Pro Phe Asp
385                 390                 395                 400

Asp Gln Cys Ser Ile Leu Glu Lys Glu Ala Val Asn Val Ser Leu Glu
             405                 410                 415

Asn Leu Lys Thr Tyr Pro Phe Val Lys Glu Gly Leu Ala Asn Gly Thr
             420                 425                 430

Leu Lys Leu Ile Gly Ala His Tyr Asp Phe Val Ser Gly Glu Phe Leu
435                 440                 445

Thr Trp Lys Lys
```

<210> SEQ ID NO 53
<211> LENGTH: 864
<212> TYPE: DNA
<213> ORGANISM: Brachypodium distachyon
<220> FEATURE:
<221> NAME/KEY: misc_feature
<222> LOCATION: (1)..(864)
<223> OTHER INFORMATION: PHB8

<400> SEQUENCE: 53

```
atgggcaatc tctgctgctg cgtgcaggtc gatcagtcta cagtggctat tagggagcag    60
ttcggcaggt tcgattctgt gctcgagcct ggctgccatt gcctcccttg gatgattggc   120
aagaggattg tgggccatct cacactcagg ctccagcagc tcgatgtgag gtgcgagaca   180
aagacaaagg ataatgtgtt cgtgacagtg gtggcttcta ttcagtacag gcctctcgct   240
ggcaaggagt ctgatgcttt ctacaagctc acaaatacaa ggtctcagat tcaggcttac   300
gtgttcgatg tgattagggc ttctgtgcct aagctcaatc tcgatgatgc tttcgagcag   360
aagaatgata ttgctaaggc tgtggaggat gagctcgaga aggctatgtc tgcttacggc   420
ttcgagattg tgcagacact cattgtggat attgagcctg atgagcatgt gaagagggct   480
atgaatgaga ttaatgctgc tgctaggatg agggtggctg ctaatgagaa ggctgaggct   540
gagaagattg tgcagattaa gagggctgag gcgaggctg aggctaagta cctctctggc   600
ctcggcattg ctaggcagag gcaggctatt gtggatggcc tcagggattc tgtgctcggc   660
ttctctgtga atgtgcctgg cacaacagct aaggatgtga tggatatggt gctcattaca   720
cagtacttcg atacaatgaa ggagattggc gcttcttcta agtcttctgc tgtgttcatt   780
cctcatggcc ctggcgctgt gagggatatt gctacacaga ttagggatgg cctcctccag   840
ggccagtctg ctgctcatca gtga                                         864
```

<210> SEQ ID NO 54
<211> LENGTH: 287
<212> TYPE: PRT
<213> ORGANISM: Brachypodium distachyon
<220> FEATURE:
<221> NAME/KEY: MISC_FEATURE
<222> LOCATION: (1)..(287)
<223> OTHER INFORMATION: PHB8

<400> SEQUENCE: 54

```
Met Gly Asn Leu Cys Cys Cys Val Gln Val Asp Gln Ser Thr Val Ala
1               5                   10                  15

Ile Arg Glu Gln Phe Gly Arg Phe Asp Ser Val Leu Glu Pro Gly Cys
            20                  25                  30

His Cys Leu Pro Trp Met Ile Gly Lys Arg Ile Val Gly His Leu Thr
        35                  40                  45

Leu Arg Leu Gln Gln Leu Asp Val Arg Cys Glu Thr Lys Thr Lys Asp
    50                  55                  60

Asn Val Phe Val Thr Val Val Ala Ser Ile Gln Tyr Arg Pro Leu Ala
65                  70                  75                  80

Gly Lys Glu Ser Asp Ala Phe Tyr Lys Leu Thr Asn Thr Arg Ser Gln
                85                  90                  95

Ile Gln Ala Tyr Val Phe Asp Val Ile Arg Ala Ser Val Pro Lys Leu
            100                 105                 110

Asn Leu Asp Asp Ala Phe Glu Gln Lys Asn Asp Ile Ala Lys Ala Val
        115                 120                 125
```

```
Glu Asp Glu Leu Glu Lys Ala Met Ser Ala Tyr Gly Phe Glu Ile Val
    130                 135                 140

Gln Thr Leu Ile Val Asp Ile Glu Pro Asp Glu His Val Lys Arg Ala
145                 150                 155                 160

Met Asn Glu Ile Asn Ala Ala Ala Arg Met Arg Val Ala Ala Asn Glu
                165                 170                 175

Lys Ala Glu Ala Glu Lys Ile Val Gln Ile Lys Arg Ala Glu Gly Glu
            180                 185                 190

Ala Glu Ala Lys Tyr Leu Ser Gly Leu Gly Ile Ala Arg Gln Arg Gln
        195                 200                 205

Ala Ile Val Asp Gly Leu Arg Asp Ser Val Leu Gly Phe Ser Val Asn
    210                 215                 220

Val Pro Gly Thr Thr Ala Lys Asp Val Met Asp Met Val Leu Ile Thr
225                 230                 235                 240

Gln Tyr Phe Asp Thr Met Lys Glu Ile Gly Ala Ser Ser Lys Ser Ser
                245                 250                 255

Ala Val Phe Ile Pro His Gly Pro Gly Ala Val Arg Asp Ile Ala Thr
            260                 265                 270

Gln Ile Arg Asp Gly Leu Leu Gln Gly Gln Ser Ala Ala His Gln
        275                 280                 285

<210> SEQ ID NO 55
<211> LENGTH: 521
<212> TYPE: PRT
<213> ORGANISM: Solanum tuberosum
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 55

Met Ala Ala Ser Ile Gly Ala Leu Lys Ser Ser Pro Ser Ser Asn Asn
1               5                   10                  15

Cys Ile Asn Glu Arg Arg Asn Asp Ser Thr Arg Ala Val Ser Ser Arg
            20                  25                  30

Asn Leu Ser Phe Ser Ser Ser His Leu Ala Gly Asp Lys Leu Met Pro
        35                  40                  45

Val Ser Ser Leu Arg Ser Gln Gly Val Arg Phe Asn Val Arg Arg Ser
    50                  55                  60

Pro Met Ile Val Ser Pro Lys Ala Val Ser Asp Ser Gln Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
        115                 120                 125

Val Ser Asn Cys Leu Asn Ser Asn Ile Ser Lys Ile Tyr Val Leu Thr
    130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175

Ala Gln Gln Ser Pro Glu Asn Pro Asp Trp Phe Gln Gly Thr Ala Asp
            180                 185                 190
```

```
Ala Val Arg Gln Tyr Leu Trp Leu Phe Glu Glu His Thr Val Leu Glu
            195                 200                 205

Tyr Leu Ile Leu Ala Gly Asp His Leu Tyr Arg Met Asp Tyr Glu Lys
210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
            245                 250                 255

Asp Glu Glu Gly Arg Ile Ile Glu Phe Ala Glu Lys Pro Gln Gly Glu
                260                 265                 270

Gln Leu Gln Ala Met Lys Val Asp Thr Thr Ile Leu Gly Leu Asp Asp
            275                 280                 285

Lys Arg Ala Lys Glu Met Pro Phe Ile Ala Ser Met Gly Ile Tyr Val
290                 295                 300

Ile Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Leu Gly
                325                 330                 335

Met Arg Val Gln Ala Tyr Leu Tyr Asp Gly Tyr Trp Glu Asp Ile Gly
            340                 345                 350

Thr Ile Glu Ala Phe Tyr Asn Ala Asn Leu Gly Ile Thr Lys Lys Pro
        355                 360                 365

Val Pro Asp Phe Ser Phe Tyr Asp Arg Ser Ala Pro Ile Tyr Thr Gln
370                 375                 380

Pro Arg Tyr Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
                405                 410                 415

Ser Val Val Gly Leu Arg Ser Cys Ile Ser Glu Gly Ala Ile Ile Glu
            420                 425                 430

Asp Ser Leu Leu Met Gly Ala Asp Tyr Tyr Glu Thr Asp Ala Asp Arg
        435                 440                 445

Lys Leu Leu Ala Ala Lys Gly Ser Val Pro Ile Gly Ile Gly Lys Asn
450                 455                 460

Cys His Ile Lys Arg Ala Ile Ile Asp Lys Asn Ala Arg Ile Gly Asp
465                 470                 475                 480

Asn Val Lys Ile Ile Asn Lys Asp Asn Val Gln Glu Ala Ala Arg Glu
                485                 490                 495

Thr Asp Gly Tyr Phe Ile Lys Ser Gly Ile Val Thr Val Ile Lys Asp
            500                 505                 510

Ala Leu Ile Pro Ser Gly Ile Ile Ile
        515                 520

<210> SEQ ID NO 56
<211> LENGTH: 521
<212> TYPE: PRT
<213> ORGANISM: Solanum pennellii
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 56

Met Ala Ala Ser Ile Gly Ala Leu Lys Ser Ser Pro Ser Ser His Asn
1               5                   10                  15

Cys Ile Asn Glu Arg Lys Asn Asp Ser Thr Arg Ala Ile Ser Ser Arg
```

```
                20                  25                  30
Asn Leu Ser Phe Ser Ser His Leu Ala Gly Asp Lys Leu Met Pro
             35                  40                  45

Val Ser Ser Leu Arg Ser Gln Gly Val Arg Phe Asn Val Arg Arg Ser
 50                  55                  60

Pro Leu Ile Val Ser Pro Lys Ala Val Ser Asp Ser Gln Asn Ser Gln
 65                  70                  75                  80

Thr Cys Leu Asp Pro Asp Ala Ser Arg Ser Val Leu Gly Ile Ile Leu
                 85                  90                  95

Gly Gly Gly Ala Gly Thr Arg Leu Tyr Pro Leu Thr Lys Lys Arg Ala
                100                 105                 110

Lys Pro Ala Val Pro Leu Gly Ala Asn Tyr Arg Leu Ile Asp Ile Pro
            115                 120                 125

Val Ser Asn Cys Leu Asn Ser Asn Ile Ser Lys Ile Tyr Val Leu Thr
            130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175

Ala Gln Gln Ser Pro Glu Asn Pro Asp Trp Phe Gln Gly Thr Ala Asp
            180                 185                 190

Ala Val Arg Gln Tyr Leu Trp Leu Phe Glu Glu His Asn Val Leu Glu
            195                 200                 205

Tyr Leu Ile Leu Ala Gly Asp His Leu Tyr Arg Met Asp Tyr Glu Lys
            210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Glu Glu Gly Arg Ile Ile Glu Phe Ala Glu Lys Pro Gln Gly Glu
            260                 265                 270

Gln Leu Gln Ala Met Lys Val Asp Thr Thr Ile Leu Gly Leu Asp Asp
            275                 280                 285

Lys Arg Ala Lys Glu Met Pro Phe Ile Ala Ser Met Gly Ile Tyr Val
            290                 295                 300

Ile Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Leu Gly
                325                 330                 335

Met Arg Val Gln Ala Tyr Leu Tyr Asp Gly Tyr Trp Glu Asp Ile Gly
            340                 345                 350

Thr Ile Glu Ala Phe Tyr Asn Ala Asn Leu Gly Ile Thr Lys Lys Pro
            355                 360                 365

Val Pro Asp Phe Ser Phe Tyr Asp Arg Ser Ala Pro Ile Tyr Thr Gln
            370                 375                 380

Pro Arg Tyr Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
                405                 410                 415

Ser Val Val Gly Leu Arg Ser Cys Ile Ser Glu Gly Ala Ile Ile Glu
            420                 425                 430

Asp Ser Leu Leu Met Gly Ala Asp Tyr Tyr Glu Thr Asp Ala Asp Arg
            435                 440                 445
```

```
Lys Leu Leu Ala Ala Lys Gly Ser Val Pro Ile Gly Ile Gly Lys Asn
            450                 455                 460

Cys His Ile Lys Arg Ala Ile Ile Asp Lys Asn Ala Arg Ile Gly Asp
465                 470                 475                 480

Asn Val Lys Ile Ile Asn Lys Asp Asn Val Gln Glu Ala Ala Arg Glu
                485                 490                 495

Thr Asp Gly Tyr Phe Ile Lys Ser Gly Ile Val Thr Val Ile Lys Asp
                500                 505                 510

Ala Leu Ile Pro Ser Gly Ile Val Ile
            515                 520

<210> SEQ ID NO 57
<211> LENGTH: 521
<212> TYPE: PRT
<213> ORGANISM: Solanum lycopersicum
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 57

Met Ala Ala Ser Ile Gly Ala Leu Lys Ser Ser Pro Ser Ser His Asn
1               5                   10                  15

Cys Ile Asn Glu Arg Arg Asn Asp Ser Thr Arg Ala Ile Ser Ser Arg
            20                  25                  30

Asn Leu Ser Phe Ser Ser Ser His Leu Ala Gly Asp Lys Leu Met Pro
        35                  40                  45

Val Ser Ser Leu Arg Ser Gln Gly Val Arg Phe Asn Val Arg Arg Ser
50                  55                  60

Pro Leu Ile Val Ser Pro Lys Ala Val Ser Asp Ser Gln Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
        115                 120                 125

Val Ser Asn Cys Leu Asn Ser Asn Ile Ser Lys Ile Tyr Val Leu Thr
130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175

Ala Gln Gln Ser Pro Glu Asn Pro Asp Trp Phe Gln Gly Thr Ala Asp
            180                 185                 190

Ala Val Arg Gln Tyr Leu Trp Leu Phe Glu Glu His Asn Val Leu Glu
        195                 200                 205

Tyr Leu Ile Leu Ala Gly Asp His Leu Tyr Arg Met Asp Tyr Glu Lys
210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Glu Glu Gly Arg Ile Ile Glu Phe Ala Glu Lys Pro Gln Gly Glu
            260                 265                 270
```

Gln Leu Gln Ala Met Lys Val Asp Thr Thr Ile Leu Gly Leu Asp Asp
                275                 280                 285

Lys Arg Ala Lys Glu Met Pro Phe Ile Ala Ser Met Gly Ile Tyr Val
290                 295                 300

Ile Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Phe Gly
                325                 330                 335

Met Arg Val Gln Ala Tyr Leu Tyr Asp Gly Tyr Trp Glu Asp Ile Gly
                340                 345                 350

Thr Ile Glu Ala Phe Tyr Asn Ala Asn Leu Gly Ile Thr Lys Lys Pro
                355                 360                 365

Val Pro Asp Phe Ser Phe Tyr Asp Arg Ser Ala Pro Ile Tyr Thr Gln
                370                 375                 380

Pro Arg Tyr Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
                405                 410                 415

Ser Val Val Gly Leu Arg Ser Cys Ile Ser Glu Gly Ala Ile Ile Glu
                420                 425                 430

Asp Ser Leu Leu Met Gly Ala Asp Tyr Tyr Glu Thr Asp Ala Asp Arg
                435                 440                 445

Lys Leu Leu Ala Ala Lys Gly Ser Val Pro Ile Gly Ile Gly Lys Asn
                450                 455                 460

Cys His Ile Lys Arg Ala Ile Ile Asp Lys Asn Ala Arg Ile Gly Asp
465                 470                 475                 480

Asn Val Lys Ile Ile Asn Lys Asp Asn Val Gln Glu Ala Ala Arg Glu
                485                 490                 495

Thr Asp Gly Tyr Phe Ile Lys Ser Gly Ile Val Thr Val Ile Lys Asp
                500                 505                 510

Ala Leu Ile Pro Ser Gly Ile Val Ile
                515                 520

<210> SEQ ID NO 58
<211> LENGTH: 521
<212> TYPE: PRT
<213> ORGANISM: Solanum tuberosum
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 58

Met Ala Ala Ser Ile Gly Ala Leu Lys Ser Ser Pro Ser Ser Asn Asn
1               5                   10                  15

Cys Ile Asn Glu Arg Arg Asn Asp Ser Thr Arg Ala Val Ser Ser Arg
                20                  25                  30

Asn Leu Ser Phe Ser Ser His Leu Thr Gly Asp Lys Leu Met Pro
                35                  40                  45

Ile Ser Ser Leu Arg Ser Gln Gly Val Arg Phe Asn Val Arg Arg Ser
            50                  55                  60

Ser Leu Ile Val Ser Pro Lys Ala Val Ser Asp Ser Gln Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala

```
            100                 105                 110
Lys Pro Ala Val Pro Leu Gly Ala Asn Tyr Arg Leu Ile Asp Ile Pro
            115                 120                 125
Val Ser Asn Cys Leu Asn Ser Asn Ile Ser Lys Ile Tyr Val Leu Thr
            130                 135                 140
Gln Phe Asn Ser Ala Ser Leu Asn Arg His Leu Ser Arg Ala Tyr Ala
145                 150                 155                 160
Ser Asn Met Gly Gly Tyr Lys Asn Glu Gly Leu Val Glu Val Leu Ala
                165                 170                 175
Ala Gln Gln Ser Pro Glu Asn Pro Asp Trp Phe Gln Gly Thr Ala Asp
                180                 185                 190
Ala Val Arg Gln Tyr Leu Trp Leu Phe Glu Glu His Thr Val Leu Glu
                195                 200                 205
Tyr Leu Ile Leu Ala Gly Asp His Leu Tyr Arg Met Asp Tyr Glu Lys
            210                 215                 220
Phe Ile Gln Ala His Arg Glu Thr Asp Ala Asp Ile Thr Val Ala Ala
225                 230                 235                 240
Leu Pro Met Asp Glu Lys Arg Ala Thr Ala Phe Gly Leu Met Lys Ile
                245                 250                 255
Asp Glu Glu Gly Arg Ile Ile Glu Phe Ala Glu Lys Pro Gln Gly Glu
                260                 265                 270
Gln Leu Gln Ala Met Lys Val Asp Thr Thr Ile Leu Gly Leu Asp Asp
            275                 280                 285
Lys Arg Ala Lys Glu Met Pro Leu Val Ala Ser Met Gly Ile Tyr Val
            290                 295                 300
Ile Ser Lys Asp Val Met Leu Asn Leu Leu Arg Asp Lys Phe Pro Gly
305                 310                 315                 320
Ala Asn Asp Phe Gly Ser Glu Val Ile Pro Gly Ala Thr Ser Leu Gly
                325                 330                 335
Met Arg Val Gln Ala Tyr Leu Tyr Asp Gly Tyr Trp Glu Asp Ile Gly
                340                 345                 350
Thr Ile Glu Ala Phe Tyr Asn Ala Asn Leu Gly Ile Thr Lys Lys Pro
            355                 360                 365
Val Pro Asp Phe Ser Phe Tyr Asp Arg Ser Ala Pro Ile Tyr Thr Gln
370                 375                 380
Pro Arg Tyr Leu Pro Pro Ser Lys Met Leu Asp Ala Asp Val Thr Asp
385                 390                 395                 400
Ser Val Ile Gly Glu Gly Cys Val Ile Lys Asn Cys Lys Ile His His
                405                 410                 415
Ser Val Val Gly Leu Arg Ser Cys Ile Ser Glu Gly Ala Ile Ile Glu
                420                 425                 430
Asp Ser Leu Leu Met Gly Ala Asp Tyr Tyr Glu Thr Asp Ala Asp Arg
            435                 440                 445
Lys Leu Leu Ala Ala Lys Gly Ser Val Pro Ile Gly Ile Gly Lys Asn
            450                 455                 460
Cys His Ile Lys Arg Ala Ile Ile Asp Lys Asn Ala Arg Ile Gly Asp
465                 470                 475                 480
Asn Val Glu Ile Ile Asn Lys Asp Asn Val Gln Glu Ala Ala Arg Glu
                485                 490                 495
Thr Asp Gly Tyr Phe Ile Lys Ser Gly Ile Val Thr Val Ile Lys Asp
            500                 505                 510
Ala Leu Ile Pro Ser Gly Ile Ile Ile
            515                 520
```

```
<210> SEQ ID NO 59
<211> LENGTH: 521
<212> TYPE: PRT
<213> ORGANISM: Solanum lycopersicum
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 59

Met Ala Ala Ser Ile Gly Ala Leu Lys Ser Ser Pro Ser Ser His Asn
1               5                   10                  15

Cys Ile Asn Glu Arg Arg Asn Asp Ser Thr Arg Ala Ile Ser Ser Arg
            20                  25                  30

Asn Leu Ser Phe Ser Ser Ser His Leu Ala Gly Asp Lys Leu Met Pro
        35                  40                  45

Val Ser Ser Leu Arg Ser Gln Gly Val Arg Phe Asn Val Arg Arg Ser
    50                  55                  60

Pro Leu Ile Val Ser Pro Lys Ala Val Ser Asp Ser Gln Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
        115                 120                 125

Val Ser Asn Cys Leu Asn Ser Asn Ile Ser Lys Ile Tyr Val Leu Thr
130                 135                 140

Gln Phe Asn Ser Ala Ser Leu Asn Arg His Leu Ser Arg Ala Tyr Ala
145                 150                 155                 160

Ser Asn Met Gly Glu Tyr Lys Asn Glu Gly Phe Val Glu Val Leu Ala
                165                 170                 175

Ala Gln Gln Ser Pro Glu Asn Pro Asp Trp Phe Gln Gly Thr Ala Asp
            180                 185                 190

Ala Val Arg Gln Tyr Leu Trp Leu Phe Glu Glu His Asn Val Leu Glu
        195                 200                 205

Tyr Leu Ile Leu Ala Gly Asp His Leu Tyr Arg Met Asp Tyr Glu Lys
210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Glu Glu Gly Arg Ile Ile Glu Phe Ala Glu Lys Pro Gln Gly Glu
            260                 265                 270

Gln Leu Gln Ala Met Lys Val Asp Thr Thr Ile Leu Gly Leu Asp Asp
        275                 280                 285

Lys Arg Ala Lys Glu Met Pro Phe Ile Ala Ser Met Gly Ile Tyr Val
290                 295                 300

Ile Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Leu Gly
                325                 330                 335

Met Arg Val Gln Ala Tyr Leu Tyr Asp Gly Tyr Trp Glu Asp Ile Gly
            340                 345                 350
```

```
Thr Ile Glu Ala Phe Tyr Asn Ala Asn Leu Gly Ile Thr Lys Lys Pro
            355                 360                 365

Val Pro Asp Phe Ser Phe Tyr Asp Arg Ser Ala Pro Ile Tyr Thr Gln
370                 375                 380

Pro Arg Tyr Leu Pro Ser Lys Met Leu Asp Ala Asp Val Thr Asp
385                 390                 395                 400

Ser Val Ile Gly Glu Gly Cys Val Ile Lys Asn Cys Lys Ile His His
            405                 410                 415

Ser Val Val Gly Leu Arg Ser Cys Ile Ser Glu Gly Ala Ile Ile Glu
            420                 425                 430

Asp Ser Leu Leu Met Gly Ala Asp Tyr Tyr Glu Thr Asp Ala Glu Arg
            435                 440                 445

Lys Leu Leu Ala Ala Lys Gly Ser Val Pro Ile Gly Ile Gly Lys Asn
450                 455                 460

Cys Leu Tyr Lys Arg Ala Ile Ile Asp Lys Asn Ala Arg Ile Gly Asp
465                 470                 475                 480

Asn Val Lys Ile Ile Asn Lys Asp Asn Val Gln Glu Ala Ala Arg Glu
            485                 490                 495

Thr Asp Gly Tyr Phe Ile Lys Ser Gly Ile Val Thr Val Ile Lys Asp
            500                 505                 510

Ala Leu Ile Pro Ser Gly Ile Val Ile
            515                 520

<210> SEQ ID NO 60
<211> LENGTH: 520
<212> TYPE: PRT
<213> ORGANISM: Nicotiana sylvestris
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 60

Met Ala Ser Ile Gly Ala Leu Lys Ser Ser Pro Ser Pro Lys Asn Cys
1               5                   10                  15

Ile Asn Glu Arg Arg Asn Asp Ala Thr Arg Ala Met Ser Phe Arg Asn
            20                  25                  30

Leu Ser Phe Ser Ser Ser His Leu Ser Gly Asp Lys Leu Met Ser Met
        35                  40                  45

Ala Thr Leu His Ser Gln Gln Arg His Ser Ser Glu Arg Arg Ser Pro
    50                  55                  60

Leu Ile Val Ser Pro Lys Ala Val Ser Asp Ser Gln Asn Ser Gln Thr
65                  70                  75                  80

Cys Leu Asp Pro Asp Ala Ser Arg Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Ile Ser Lys Ile Tyr Val Leu Thr Gln
    130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
```

```
                180             185             190
Val Arg Gln Tyr Leu Trp Leu Phe Glu Glu His Asn Val Leu Glu Phe
            195             200             205

Leu Val Leu Ala Gly Asp His Leu Tyr Arg Met Asp Tyr Glu Lys Phe
        210             215             220

Ile Gln Ala His Arg Glu Thr Asp Ala Asp Ile Thr Val Ala Ala Leu
225             230             235             240

Pro Met Asp Glu Lys Arg Ala Thr Ala Phe Gly Leu Met Lys Ile Asp
            245             250             255

Glu Glu Gly Arg Ile Ile Glu Phe Ala Glu Lys Pro Lys Gly Glu Gln
            260             265             270

Leu Lys Ala Met Lys Val Asp Thr Thr Ile Leu Gly Leu Asp Asp Glu
        275             280             285

Arg Ala Lys Glu Met Pro Phe Ile Ala Ser Met Gly Ile Tyr Val Ile
        290             295             300

Ser Lys Asp Val Met Leu Asn Leu Leu Arg Asp Lys Phe Pro Gly Ala
305             310             315             320

Asn Asp Phe Gly Ser Glu Val Ile Pro Gly Ala Thr Ser Leu Gly Met
            325             330             335

Arg Val Gln Ala Tyr Leu Tyr Asp Gly Tyr Trp Glu Asp Ile Gly Thr
        340             345             350

Ile Glu Ala Phe Tyr Asn Ala Asn Leu Gly Ile Thr Lys Lys Pro Val
        355             360             365

Pro Asp Phe Ser Phe Tyr Asp Arg Ser Ala Pro Ile Tyr Thr Gln Pro
        370             375             380

Arg Tyr Leu Pro Pro Ser Lys Met Leu Asp Ala Asp Val Thr Asp Ser
385             390             395             400

Val Ile Gly Glu Gly Cys Val Ile Lys Asn Cys Lys Ile His His Ser
            405             410             415

Val Val Gly Leu Arg Ser Cys Ile Ser Glu Gly Ala Ile Ile Glu Asp
        420             425             430

Ser Leu Leu Met Gly Ala Asp Tyr Tyr Glu Thr Asp Ala Asp Arg Arg
        435             440             445

Phe Leu Ala Ala Lys Gly Ser Val Pro Ile Gly Ile Gly Lys Asn Ser
        450             455             460

His Ile Lys Arg Ala Ile Ile Asp Lys Asn Ala Arg Ile Gly Asp Asn
465             470             475             480

Val Lys Ile Ile Asn Ser Asp Asn Val Gln Glu Ala Ala Arg Glu Thr
            485             490             495

Asp Gly Tyr Phe Ile Lys Ser Gly Ile Val Thr Val Ile Lys Asp Ala
            500             505             510

Leu Ile Pro Ser Gly Ile Ile Ile
        515             520
```

<210> SEQ ID NO 61
<211> LENGTH: 520
<212> TYPE: PRT
<213> ORGANISM: Nicotiana tomentosiformis
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 61

```
Met Ala Ser Val Gly Ala Leu Lys Ser Ser Pro Ser Pro Gln Asn Cys
1               5                   10                  15
```

```
Ile Asn Glu Lys Arg Asn Asp Ala Thr Arg Ala Met Ser Phe Arg Asn
            20                  25                  30

Leu Ser Phe Ser Ser His Leu Ser Gly Asp Lys Leu Met Ser Met
        35                  40                  45

Ala Thr Leu His Ser Gln Gln Arg His Ser Ser Glu Arg Arg Ser Pro
 50                  55                  60

Leu Ile Val Ser Pro Lys Ala Val Ser Asp Ser Gln Asn Ser Gln Thr
 65                  70                  75                  80

Cys Leu Asp Pro Asp Ala Ser Arg Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
            115                 120                 125

Ser Asn Cys Leu Asn Ser Asn Ile Ser Lys Ile Tyr Val Leu Thr Gln
130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
            165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Phe
            195                 200                 205

Leu Val Leu Ala Gly Asp His Leu Tyr Arg Met Asp Tyr Glu Lys Phe
            210                 215                 220

Ile Gln Ala His Arg Glu Thr Asp Ala Asp Ile Thr Val Ala Ala Leu
225                 230                 235                 240

Pro Met Asp Glu Lys Arg Ala Thr Ala Phe Gly Leu Met Lys Ile Asp
            245                 250                 255

Glu Glu Gly Arg Ile Ile Glu Phe Ala Glu Lys Pro Lys Gly Glu Gln
            260                 265                 270

Leu Lys Ala Met Lys Val Asp Thr Thr Ile Leu Gly Leu Asp Asp Glu
            275                 280                 285

Arg Ala Lys Glu Met Pro Phe Ile Ala Ser Met Gly Ile Tyr Val Ile
            290                 295                 300

Ser Lys Asp Val Met Leu Asn Leu Leu Arg Asp Lys Phe Pro Gly Ala
305                 310                 315                 320

Asn Asp Phe Gly Ser Glu Val Ile Pro Gly Ala Thr Ser Leu Gly Met
            325                 330                 335

Arg Val Gln Ala Tyr Leu Tyr Asp Gly Tyr Trp Glu Asp Ile Gly Thr
            340                 345                 350

Ile Glu Ala Phe Tyr Asn Ala Asn Leu Gly Ile Thr Lys Lys Pro Val
            355                 360                 365

Pro Asp Phe Ser Phe Tyr Asp Arg Ser Ala Pro Ile Tyr Thr Gln Pro
            370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
            405                 410                 415

Val Val Gly Leu Arg Ser Cys Ile Ser Glu Gly Ala Ile Ile Glu Asp
            420                 425                 430
```

```
Ser Leu Leu Met Gly Ala Asp Tyr Tyr Glu Thr Asp Ala Asp Arg Arg
            435                 440                 445

Phe Leu Ala Ala Lys Gly Ser Val Pro Ile Gly Ile Gly Lys Asn Ser
        450                 455                 460

His Ile Lys Arg Ala Ile Ile Asp Lys Asn Ala Arg Ile Gly Asp Asn
465                 470                 475                 480

Val Lys Ile Ile Asn Ser Asp Asn Val Gln Glu Ala Ala Arg Glu Thr
                485                 490                 495

Asp Gly Tyr Phe Ile Lys Ser Gly Ile Val Thr Val Ile Lys Asp Ala
            500                 505                 510

Leu Ile Pro Ser Gly Ile Ile Ile
            515                 520

<210> SEQ ID NO 62
<211> LENGTH: 520
<212> TYPE: PRT
<213> ORGANISM: Nicotiana tabacum
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 62

Met Ala Ser Ile Gly Ala Leu Lys Ser Ser Pro Ser Pro Lys Asn Cys
1               5                   10                  15

Ile Asn Glu Arg Arg Asn Asp Ala Thr Arg Ala Met Ser Phe Arg Asn
            20                  25                  30

Leu Ser Phe Ser Ser Ser His Ile Tyr Gly Asp Lys Leu Met Ser Met
        35                  40                  45

Ala Thr Leu His Ser Gln Gln Arg His Ser Ser Glu Arg Arg Ser Pro
    50                  55                  60

Leu Ile Val Ser Pro Lys Ala Val Ser Asp Ser Gln Asn Ser Gln Thr
65                  70                  75                  80

Cys Leu Asp Pro Asp Ala Ser Arg Ser Val Leu Gly Ile Ile Leu Gly
            85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Ile Ser Lys Ile Tyr Val Leu Thr Gln
    130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Phe
        195                 200                 205

Leu Val Leu Ala Gly Asp His Leu Tyr Arg Met Asp Tyr Glu Lys Phe
    210                 215                 220

Ile Gln Ala His Arg Glu Thr Asp Ala Asp Ile Thr Val Ala Ala Leu
225                 230                 235                 240

Pro Met Asp Glu Lys Arg Ala Thr Ala Phe Gly Leu Met Lys Ile Asp
                245                 250                 255

Glu Glu Gly Arg Ile Ile Glu Phe Ala Glu Lys Pro Lys Gly Glu Gln
```

```
                260                 265                 270
Leu Lys Ala Met Lys Val Asp Thr Thr Ile Leu Gly Leu Asp Asp Glu
        275                 280                 285

Arg Ala Lys Glu Met Pro Phe Ile Ala Ser Met Gly Ile Tyr Val Ile
    290                 295                 300

Ser Lys Asp Val Met Leu Asn Leu Leu Arg Asp Lys Phe Pro Gly Ala
305                 310                 315                 320

Asn Asp Phe Gly Ser Glu Val Ile Pro Gly Ala Thr Ser Leu Gly Met
                325                 330                 335

Arg Val Gln Ala Tyr Leu Tyr Asp Gly Tyr Trp Glu Asp Ile Gly Thr
            340                 345                 350

Ile Glu Ala Phe Tyr Asn Ala Asn Leu Gly Ile Thr Lys Lys Pro Val
        355                 360                 365

Pro Asp Phe Ser Phe Tyr Asp Arg Ser Ala Pro Ile Tyr Thr Gln Pro
    370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
                405                 410                 415

Val Val Gly Leu Arg Ser Cys Ile Ser Glu Gly Ala Ile Ile Glu Asp
            420                 425                 430

Ser Leu Leu Met Gly Ala Asp Tyr Tyr Glu Thr Asp Ala Asp Arg Arg
        435                 440                 445

Phe Leu Ala Ala Lys Gly Ser Val Pro Ile Gly Ile Gly Lys Asn Ser
    450                 455                 460

His Ile Lys Arg Ala Ile Ile Asp Lys Asn Ala Arg Ile Gly Asp Asn
465                 470                 475                 480

Val Lys Ile Ile Asn Ser Asp Asn Val Gln Ala Ala Arg Glu Thr
                485                 490                 495

Asp Gly Tyr Phe Ile Lys Ser Gly Ile Val Thr Val Ile Lys Asp Ala
            500                 505                 510

Leu Ile Pro Ser Gly Ile Ile Ile
        515                 520

<210> SEQ ID NO 63
<211> LENGTH: 517
<212> TYPE: PRT
<213> ORGANISM: Capsicum annuum
<220> FEATURE:
<221> NAME/KEY: MISC_FEATURE
<222> LOCATION: (1)..(517)
<223> OTHER INFORMATION: ADP-glucose pyrophosphorylase small subunit

<400> SEQUENCE: 63

Met Ala Ala Ser Ile Gly Ala Leu Lys Ser Ser Pro Ser Ser Thr His
1               5                   10                  15

Asn Cys Ile Arg Asn Glu Phe Ala Cys Ala Val Pro Ser Arg Asn Leu
            20                  25                  30

Ser Phe Ser Ser Ser His Leu Ser Gly Asp Lys Leu Met Met Pro Val
        35                  40                  45

Ala Ser Gln Gly Leu Arg Phe Cys Glu Arg Arg Thr Pro Val Ile Val
    50                  55                  60

Ser Pro Lys Ala Val Ser Asp Ser Gln Asn Ser Gln Thr Cys Leu Asp
65                  70                  75                  80

Pro Asp Ala Ser Arg Ser Val Leu Gly Ile Ile Leu Gly Gly Gly Ala
                85                  90                  95
```

```
Gly Thr Arg Leu Tyr Pro Leu Thr Lys Lys Arg Ala Lys Pro Ala Val
            100                 105                 110

Pro Leu Gly Ala Asn Tyr Arg Leu Ile Asp Ile Pro Val Ser Asn Cys
            115                 120                 125

Leu Asn Ser Asn Ile Ser Lys Ile Tyr Val Leu Thr Gln Phe Asn Ser
        130                 135                 140

Ala Ser Leu Asn Arg His Leu Ser Arg Ala Tyr Ala Ser Asn Met Gly
145                 150                 155                 160

Gly Tyr Lys Asn Glu Gly Phe Val Glu Val Leu Ala Ala Gln Gln Ser
                165                 170                 175

Pro Glu Asn Pro Asp Trp Phe Gln Gly Thr Ala Asp Ala Val Arg Gln
            180                 185                 190

Tyr Leu Trp Leu Phe Glu Glu His Asn Val Leu Glu Tyr Leu Ile Leu
            195                 200                 205

Ala Gly Asp His Leu Tyr Arg Met Asp Tyr Glu Lys Phe Ile Gln Ala
        210                 215                 220

His Arg Glu Thr Asp Ala Asp Ile Thr Val Ala Ala Leu Pro Met Asp
225                 230                 235                 240

Glu Lys Arg Ala Thr Ala Phe Gly Leu Met Lys Ile Asp Glu Glu Gly
                245                 250                 255

Arg Ile Ile Glu Phe Ala Glu Lys Pro Lys Gly Glu Gln Leu Gln Ala
            260                 265                 270

Met Lys Val Asp Thr Thr Ile Leu Gly Leu Asp Asp Lys Arg Ala Lys
        275                 280                 285

Glu Met Pro Phe Ile Ala Ser Met Gly Ile Tyr Val Ile Ser Lys Asp
        290                 295                 300

Val Met Leu Asn Leu Leu Arg Asp Lys Phe Pro Gly Ala Asn Asp Phe
305                 310                 315                 320

Gly Ser Glu Val Ile Pro Gly Ala Thr Ser Leu Gly Met Arg Val Gln
                325                 330                 335

Ala Tyr Leu Tyr Asp Gly Tyr Trp Glu Asp Ile Gly Thr Ile Glu Ala
            340                 345                 350

Phe Tyr Asn Ala Asn Leu Gly Ile Thr Lys Lys Pro Val Pro Asp Phe
        355                 360                 365

Ser Phe Tyr Asp Arg Ser Ala Pro Ile Tyr Thr Gln Pro Arg Tyr Leu
    370                 375                 380

Pro Pro Ser Lys Met Leu Asp Ala Asp Val Thr Asp Ser Val Ile Gly
385                 390                 395                 400

Glu Gly Cys Val Ile Lys Asn Cys Lys Ile His His Ser Val Val Gly
                405                 410                 415

Leu Arg Ser Cys Ile Ser Glu Gly Ala Ile Ile Glu Asp Thr Leu Leu
            420                 425                 430

Met Gly Ala Asp Tyr Tyr Glu Thr Asp Ala Asp Arg Lys Leu Leu Ala
        435                 440                 445

Ser Lys Gly Gly Val Pro Ile Gly Ile Gly Lys Asn Ser His Val Lys
    450                 455                 460

Arg Ala Ile Ile Asp Lys Asn Ala Arg Ile Gly Asp Asn Val Lys Ile
465                 470                 475                 480

Ile Asn Arg Asp Asn Val Gln Glu Ala Ala Arg Glu Thr Asp Gly Tyr
                485                 490                 495

Phe Ile Lys Ser Gly Ile Val Thr Ile Ile Lys Asp Ala Leu Ile Pro
            500                 505                 510
```

Ser Gly Ile Val Ile
        515

<210> SEQ ID NO 64
<211> LENGTH: 520
<212> TYPE: PRT
<213> ORGANISM: Nicotiana langsdorffii x Nicotiana sanderae
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 64

Met Ala Ser Ile Gly Ala Leu Lys Ser Ser Pro Ser Pro Gln Asn Cys
1               5                   10                  15

Ile Asn Glu Arg Arg Asn Asp Ala Thr Arg Ala Met Ser Phe Arg Asn
            20                  25                  30

Leu Ser Phe Ser Ser Ser His Leu Ser Gly Asp Lys Leu Met Ser Met
        35                  40                  45

Ala Thr Leu His Ser Gln Arg Arg Arg Ser Ser Asp Ser Ser Arg Pro
    50                  55                  60

Leu Ile Val Ser Pro Lys Ala Val Ser Asp Ser Gln Asn Ser Gln Thr
65                  70                  75                  80

Cys Leu Asp Pro Asp Ala Ser Arg Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Ile Ser Lys Ile Tyr Val Leu Thr Gln
    130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Phe
        195                 200                 205

Leu Ile Leu Ala Gly Asp His Leu Tyr Arg Met Asp Tyr Glu Lys Phe
    210                 215                 220

Ile Gln Ala His Arg Glu Thr Asp Ala Asp Ile Thr Val Ala Ala Leu
225                 230                 235                 240

Pro Met Asp Glu Lys Arg Ala Thr Ala Phe Gly Leu Met Lys Ile Asp
                245                 250                 255

Glu Glu Gly Arg Ile Ile Glu Phe Ala Glu Lys Pro Lys Gly Glu Gln
            260                 265                 270

Leu Lys Ala Met Lys Val Asp Thr Thr Ile Leu Gly Leu Asp Asp Glu
        275                 280                 285

Arg Ala Lys Glu Met Pro Phe Ile Ala Ser Met Gly Ile Tyr Val Ile
    290                 295                 300

Ser Lys Asp Val Met Leu Asn Leu Leu Arg Asp Lys Phe Pro Gly Ala
305                 310                 315                 320

Asn Asp Phe Gly Ser Glu Val Ile Pro Gly Ala Thr Ser Leu Gly Met
                325                 330                 335

Arg Val Gln Ala Tyr Leu Tyr Asp Gly Tyr Trp Glu Asp Ile Gly Thr

```
                340                 345                 350
Ile Glu Ala Phe Tyr Asn Ala Asn Leu Gly Ile Thr Lys Lys Pro Val
                355                 360                 365

Pro Asp Phe Ser Phe Tyr Asp Arg Ser Ala Pro Ile Tyr Thr Gln Pro
            370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
                405                 410                 415

Val Val Gly Leu Arg Ser Cys Ile Ser Glu Gly Ala Ile Ile Glu Asp
            420                 425                 430

Ser Leu Leu Met Gly Ala Asp Tyr Cys Glu Thr Asp Ala Asp Arg Arg
                435                 440                 445

Phe Leu Ala Ala Lys Gly Ser Val Pro Ile Gly Ile Gly Lys Asn Ser
            450                 455                 460

His Ile Lys Gly Ala Ile Ile Asp Lys Asn Ala Arg Ile Gly Asp Asn
465                 470                 475                 480

Val Lys Ile Ile Asn Ser Asp Asp Val Gln Glu Ala Ala Arg Glu Thr
                485                 490                 495

Asp Gly Tyr Phe Ile Lys Ser Gly Ile Val Thr Val Ile Lys Asp Ala
            500                 505                 510

Leu Ile Pro Ser Gly Ile Ile Ile
            515                 520

<210> SEQ ID NO 65
<211> LENGTH: 523
<212> TYPE: PRT
<213> ORGANISM: Perilla frutescens
<220> FEATURE:
<221> NAME/KEY: MISC_FEATURE
<222> LOCATION: (1)..(523)
<223> OTHER INFORMATION: ADP-glucose pyrophosphorylase small subunit

<400> SEQUENCE: 65

Met Ala Ala Thr Ala Val Phe Lys Ser Thr Pro Gly Lys Thr Ala Ile
1               5                   10                  15

Ala Asn Tyr Ser Ser Leu Glu Asp Val Asn Ser Thr Ser Phe Lys Arg
            20                  25                  30

Leu Ser Phe Ala Ala Ser Asn Val Ala Gly Glu Arg Ile Thr Ser Pro
        35                  40                  45

Pro Arg Leu Arg Val Arg Arg Ser Arg Ala Gly Gly Glu Leu Glu Arg
    50                  55                  60

Arg Ser Pro Val Ile Val Ser Pro Lys Ala Val Ser Asp Ser Gln Asn
65                  70                  75                  80

Ser Gln Thr Cys Leu Asp Pro Asp Ala Ser Arg Ser Val Leu Gly Ile
                85                  90                  95

Ile Leu Gly Ser Gly Ala Gly Thr Lys Leu Tyr Pro Leu Thr Lys Lys
            100                 105                 110

Arg Ala Lys Pro Ala Val Pro Phe Gly Ala Asn Tyr Arg Leu Ile Asp
        115                 120                 125

Ile Pro Val Ser Asn Cys Leu Asn Ser Asn Ile Ser Lys Ile Tyr Val
    130                 135                 140

Leu Thr Gln Phe Asn Ser Ala Ser Leu Asn Arg His Leu Ser Arg Ala
145                 150                 155                 160

Tyr Ala Ser Asn Met Gly Gly Tyr Lys Asn Glu Gly Phe Val Glu Val
                165                 170                 175
```

Leu Ala Ala Gln Gln Ser Pro Glu Asn Pro Asn Trp Phe Gln Gly Thr
            180                 185                 190

Ala Asp Ala Val Arg Gln Tyr Leu Trp Leu Phe Glu Glu His Asn Val
        195                 200                 205

Leu Glu Phe Leu Ile Leu Ala Gly Asp His Leu Tyr Arg Met Asp Tyr
    210                 215                 220

Glu Arg Phe Ile Gln Ala His Arg Glu Thr Asp Ala Asp Ile Thr Val
225                 230                 235                 240

Ala Ala Leu Pro Met Asp Glu Lys Arg Pro Thr Ala Phe Gly Leu Met
                245                 250                 255

Lys Ile Asp Glu Glu Gly Arg Ile Ile Glu Phe Ala Glu Lys Pro Lys
            260                 265                 270

Gly Glu Gln Leu Lys Ala Met Lys Val Asp Thr Thr Ile Leu Gly Leu
        275                 280                 285

Asp Asp Lys Arg Ala Lys Glu Met Pro Tyr Ile Ala Ser Met Gly Ile
    290                 295                 300

Tyr Val Val Ser Lys Asp Val Met Leu Asn Leu Leu Arg Asp Glu Phe
305                 310                 315                 320

Pro Ala Ala Asn Asp Phe Gly Ser Glu Val Ile Pro Gly Ala Thr Ala
                325                 330                 335

Met Gly Leu Arg Val Gln Ala Tyr Leu Phe Asp Gly Tyr Trp Glu Asp
            340                 345                 350

Ile Gly Thr Ile Glu Ala Phe Tyr Asn Ala Asn Leu Gly Ile Thr Lys
        355                 360                 365

Lys Pro Val Pro Asp Phe Ser Phe Tyr Asp Arg Ser Ala Pro Ile Tyr
    370                 375                 380

Thr Gln Pro Arg Tyr Leu Pro Pro Ser Lys Met Leu Asp Ala Asp Val
385                 390                 395                 400

Thr Asp Ser Val Ile Gly Glu Gly Cys Val Ile Lys Asn Cys Lys Ile
                405                 410                 415

His His Ser Val Val Gly Leu Arg Ser Cys Ile Ala Glu Gly Ala Ile
            420                 425                 430

Ile Glu Asp Thr Leu Leu Met Gly Ala Asp Tyr Tyr Glu Thr Asp Ala
        435                 440                 445

Asp Arg Arg Phe Leu Ala Ala Lys Gly Gly Val Pro Ile Gly Ile Gly
    450                 455                 460

Lys Asn Thr His Ile Lys Arg Ala Ile Ile Asp Lys Asn Ala Arg Ile
465                 470                 475                 480

Gly Glu Asn Val Lys Ile Val Asn Gly Asp Asn Val Gln Glu Ala Ala
                485                 490                 495

Arg Glu Thr Asp Gly Tyr Phe Ile Lys Ser Gly Ile Val Thr Val Ile
            500                 505                 510

Lys Asp Ala Leu Ile Pro Ser Gly Thr Met Ile
        515                 520

<210> SEQ ID NO 66
<211> LENGTH: 522
<212> TYPE: PRT
<213> ORGANISM: Ipomoea batatas
<220> FEATURE:
<221> NAME/KEY: MISC_FEATURE
<222> LOCATION: (1)..(522)
<223> OTHER INFORMATION: ADP-glucose pyrophosphorylase small subunit

<400> SEQUENCE: 66

```
Met Ala Ala Ala Thr Ile Gly Ala Leu Ser Pro Tyr Thr Gly Gly
1               5                   10                  15

Val Gly Glu Arg Ile Asp Gly Asp Val Ser Lys Ala Ser Phe Arg Arg
            20                  25                  30

Leu Ser Phe Ala Ser Ser His Leu Ser Gly Asp Lys Leu Met Pro Leu
        35                  40                  45

Pro Pro Arg Arg Leu Arg Ser Gly Gly Lys Ser Ser Glu Val Arg Thr
50                  55                  60

Ala Pro Phe Ile Val Ser Pro Lys Ala Val Ser Asp Ser Gln Asn Ser
65                  70                  75                  80

Gln Thr Cys Leu Asp Pro Asp Ala Ser Arg Ser Val Leu Gly Ile Ile
                85                  90                  95

Leu Gly Gly Gly Ala Gly Thr Arg Leu Tyr Pro Leu Thr Lys Lys Arg
                100                 105                 110

Ala Lys Pro Ala Val Pro Leu Gly Ala Asn Tyr Arg Leu Ile Asp Ile
            115                 120                 125

Pro Val Ser Asn Cys Leu Asn Ser Asn Ile Ser Lys Ile Tyr Val Leu
        130                 135                 140

Thr Gln Phe Asn Ser Ala Ser Leu Asn Arg His Leu Ser Arg Ala Tyr
145                 150                 155                 160

Ala Ser Asn Met Gly Gly Tyr Lys Asn Glu Gly Phe Val Glu Val Leu
                165                 170                 175

Ala Ala Gln Gln Ser Pro Glu Asn Pro Asn Trp Phe Gln Gly Thr Ala
            180                 185                 190

Asp Ala Val Arg Gln Tyr Leu Trp Leu Phe Glu Glu His Asn Val Leu
        195                 200                 205

Glu Phe Leu Val Leu Ala Gly Asp His Leu Tyr Arg Met Asp Tyr Glu
210                 215                 220

Arg Phe Ile Gln Ala His Arg Glu Thr Asp Ala Asp Ile Thr Val Ala
225                 230                 235                 240

Ala Leu Pro Met Asp Glu Lys Arg Ala Thr Ala Phe Gly Leu Met Lys
                245                 250                 255

Ile Asp Glu Glu Gly Arg Ile Ile Glu Phe Ala Glu Lys Pro Lys Gly
            260                 265                 270

Glu Gln Leu Lys Ala Met Lys Val Asp Thr Thr Ile Leu Gly Leu Asp
        275                 280                 285

Asp Gln Arg Ala Lys Glu Met Pro Tyr Ile Ala Ser Met Gly Ile Tyr
        290                 295                 300

Val Val Ser Lys Asp Val Met Val Asn Leu Leu Arg Gln Lys Phe Pro
305                 310                 315                 320

Gly Ala Asn Asp Phe Gly Ser Glu Val Ile Pro Gly Ala Thr Ser Ile
                325                 330                 335

Gly Leu Arg Val Gln Ala Tyr Leu Phe Asp Gly Tyr Trp Glu Asp Ile
            340                 345                 350

Gly Thr Ile Glu Ala Phe Tyr Asn Ala Asn Leu Gly Ile Thr Lys Lys
        355                 360                 365

Pro Val Pro Asp Phe Ser Phe Tyr Asp Arg Ser Ala Pro Ile Tyr Thr
370                 375                 380

Gln Pro Arg Tyr Leu Pro Pro Ser Lys Met Leu Asp Ala Asp Val Thr
385                 390                 395                 400

Asp Ser Val Ile Gly Glu Gly Cys Val Ile Lys Asn Cys Lys Ile His
                405                 410                 415

His Ser Val Val Gly Leu Arg Ser Cys Ile Ser Glu Gly Ala Ile Ile
```

```
                420            425             430
Glu Asp Thr Leu Leu Met Gly Ala Asp Tyr Tyr Glu Thr Asp Ala Asp
            435                 440                 445

Arg Arg Leu Leu Ala Ala Lys Gly Ser Val Pro Ile Gly Ile Gly Arg
    450                 455                 460

Asn Ser His Ile Lys Arg Ala Ile Ile Asp Lys Asn Ala Arg Ile Gly
465                 470                 475                 480

Asn Asp Val Lys Ile Ile Asn Asn Asp Asn Val Gln Glu Ala Ala Arg
                485                 490                 495

Glu Thr Glu Gly Tyr Phe Ile Lys Ser Gly Ile Val Thr Ile Ile Lys
            500                 505                 510

Asp Ala Leu Ile Pro Ser Gly Thr Ile Ile
            515                 520

<210> SEQ ID NO 67
<211> LENGTH: 522
<212> TYPE: PRT
<213> ORGANISM: Ipomoea batatas
<220> FEATURE:
<221> NAME/KEY: MISC_FEATURE
<222> LOCATION: (1)..(522)
<223> OTHER INFORMATION: ADP-glucose pyrophosphorylase small subunit

<400> SEQUENCE: 67

Met Ala Ala Ala Thr Ile Gly Ala Leu Ser Ser Pro Tyr Thr Gly Gly
1               5                   10                  15

Val Gly Glu Arg Ile Asp Gly Asp Val Ser Lys Ala Ser Phe Arg Arg
            20                  25                  30

Leu Ser Phe Ala Ser Ser His Leu Ser Gly Asp Lys Leu Met Pro Leu
        35                  40                  45

Pro Pro Arg Arg Leu Arg Ser Gly Gly Lys Ser Ser Glu Val Arg Thr
    50                  55                  60

Ala Pro Phe Ile Val Ser Pro Lys Ala Val Ser Asp Ser Gln Asn Ser
65                  70                  75                  80

Gln Thr Cys Leu Asp Pro Asp Ala Ser Arg Ser Val Leu Gly Ile Ile
                85                  90                  95

Leu Gly Gly Gly Ala Gly Thr Arg Leu Tyr Pro Leu Thr Lys Lys Arg
            100                 105                 110

Ala Lys Pro Ala Val Pro Leu Gly Ala Asn Tyr Arg Leu Ile Asp Ile
        115                 120                 125

Pro Val Ser Asn Cys Leu Asn Ser Asn Ile Ser Lys Ile Tyr Val Leu
    130                 135                 140

Thr Gln Phe Asn Ser Ala Ser Leu Asn Arg His Leu Ser Arg Ala Tyr
145                 150                 155                 160

Ala Ser Asn Met Gly Gly Tyr Lys Asn Glu Gly Phe Val Glu Val Leu
                165                 170                 175

Ala Ala Gln Gln Ser Pro Glu Asn Pro Asn Trp Phe Gln Gly Thr Ala
            180                 185                 190

Asp Ala Val Arg Gln Tyr Leu Trp Leu Phe Glu Glu His Asn Val Leu
        195                 200                 205

Glu Phe Leu Val Leu Ala Gly Asp His Leu Tyr Arg Met Asp Tyr Glu
    210                 215                 220

Arg Phe Ile Gln Ala His Arg Glu Thr Asp Ala Asp Ile Thr Val Ala
225                 230                 235                 240

Ala Leu Pro Met Asp Glu Lys Arg Ala Thr Ala Phe Gly Leu Met Lys
                245                 250                 255
```

Ile Asp Glu Glu Gly Arg Ile Ile Glu Phe Ala Glu Lys Pro Lys Gly
                260                 265                 270

Glu Gln Leu Lys Ala Met Lys Val Asp Thr Thr Ile Leu Gly Leu Asp
            275                 280                 285

Asp Gln Arg Ala Lys Glu Met Pro Tyr Ile Ala Ser Met Gly Ile Tyr
        290                 295                 300

Val Val Ser Lys Asp Val Met Val Asn Leu Leu Arg Gln Lys Phe Pro
305                 310                 315                 320

Gly Ala Asn Asp Phe Gly Ser Glu Val Ile Pro Gly Ala Thr Ser Ile
                325                 330                 335

Gly Leu Arg Val Gln Ala Tyr Leu Phe Asp Gly Tyr Trp Glu Asp Ile
            340                 345                 350

Gly Thr Ile Glu Ala Phe Tyr Asn Ala Asn Leu Gly Ile Thr Lys Lys
        355                 360                 365

Pro Val Pro Asp Phe Ser Phe Tyr Asp Arg Ser Ala Pro Ile Tyr Thr
370                 375                 380

Gln Pro Arg Tyr Leu Pro Pro Ser Lys Met Leu Asp Ala Asp Val Thr
385                 390                 395                 400

Asp Ser Val Ile Gly Glu Gly Cys Val Ile Lys Asn Cys Lys Ile His
                405                 410                 415

His Ser Val Val Gly Leu Arg Ser Cys Ile Ser Glu Gly Ala Ile Ile
            420                 425                 430

Glu Asp Thr Leu Leu Met Gly Ala Asp Tyr Tyr Glu Thr Asp Ala Asp
        435                 440                 445

Arg Arg Leu Leu Ala Ala Lys Gly Ser Val Pro Ile Gly Ile Gly Arg
450                 455                 460

Asn Ser His Ile Lys Arg Ala Ile Ile Asp Lys Asn Ala Arg Ile Gly
465                 470                 475                 480

Asn Asp Val Lys Ile Thr Asn Asn Asp Asn Val Gln Glu Ala Ala Arg
                485                 490                 495

Glu Thr Glu Gly Tyr Phe Ile Lys Ser Gly Ile Val Thr Ile Ile Lys
            500                 505                 510

Asp Ala Leu Ile Pro Ser Gly Thr Ile Ile
        515                 520

<210> SEQ ID NO 68
<211> LENGTH: 523
<212> TYPE: PRT
<213> ORGANISM: Ipomoea batatas
<220> FEATURE:
<221> NAME/KEY: MISC_FEATURE
<222> LOCATION: (1)..(523)
<223> OTHER INFORMATION: ADP-glucose pyrophosphorylase small subunit

<400> SEQUENCE: 68

Met Ala Ala Ala Ile Gly Ala Pro Lys Leu Ala Pro Tyr Thr Cys Ala
1               5                   10                  15

Ala Glu Arg Asn Asp Gly Ser Ala Arg Arg Ala Ala Arg Phe Lys Ser
            20                  25                  30

Leu Ser Phe Ala Ser Ser Asn Leu Ser Gly Asp Lys Leu Ala Ser Leu
        35                  40                  45

Val Ser Arg Arg Cys Ser Arg Ser Gly Gly Lys Ser Ser Glu Arg Arg
    50                  55                  60

Asn Ala Pro Ile Ile Val Ser Pro Lys Ala Val Ser Asp Ser Gln Asn
65                  70                  75                  80

```
Ser Gln Thr Cys Leu Asp Pro Asp Ala Ser Arg Ser Val Leu Gly Ile
                85                  90                  95

Ile Leu Gly Gly Gly Ala Gly Thr Arg Leu Tyr Pro Leu Thr Lys Lys
            100                 105                 110

Arg Ala Lys Pro Ala Val Pro Leu Gly Ala Asn Tyr Arg Leu Ile Asp
            115                 120                 125

Ile Pro Val Ser Asn Cys Leu Asn Ser Asn Val Ser Lys Ile Tyr Val
            130                 135                 140

Leu Thr Gln Phe Asn Ser Ala Ser Leu Asn Arg His Leu Ser Arg Ala
145                 150                 155                 160

Tyr Ala Ser Asn Met Gly Gly Tyr Lys Asn Glu Gly Phe Val Glu Val
                165                 170                 175

Leu Ala Ala Gln Gln Ser Pro Glu Asn Pro Asn Trp Phe Gln Gly Thr
            180                 185                 190

Ala Asp Ala Val Arg Gln Tyr Leu Trp Leu Phe Glu Glu His Asn Val
            195                 200                 205

Leu Glu Phe Leu Val Leu Ala Gly Asp His Leu Tyr Arg Met Asp Tyr
            210                 215                 220

Glu Arg Phe Ile Gln Ala His Arg Glu Thr Asp Ala Asp Ile Thr Val
225                 230                 235                 240

Ala Ala Leu Pro Met Asp Glu Lys Arg Ala Thr Ala Phe Gly Leu Met
                245                 250                 255

Lys Ile Asp Glu Glu Gly Arg Ile Ile Glu Phe Ala Glu Lys Pro Lys
                260                 265                 270

Gly Glu Gln Leu Lys Ala Met Lys Val Asp Thr Thr Ile Leu Gly Leu
            275                 280                 285

Asp Asp Gln Arg Ala Lys Glu Leu Pro Phe Ile Ala Ser Met Gly Ile
            290                 295                 300

Tyr Val Ile Ser Lys Asn Val Met Leu Asn Leu Leu Arg Glu Lys Phe
305                 310                 315                 320

Pro Gly Ala Asn Asp Phe Gly Ser Glu Val Ile Pro Gly Ala Thr Ser
                325                 330                 335

Ile Gly Met Arg Val Gln Ala Tyr Leu Phe Asp Gly Tyr Trp Glu Asp
            340                 345                 350

Ile Gly Thr Ile Glu Ala Phe Tyr Asn Ala Asn Leu Gly Ile Thr Lys
            355                 360                 365

Lys Pro Val Pro Asp Phe Ser Phe Tyr Asp Arg Ser Ala Pro Ile Tyr
            370                 375                 380

Thr Gln Pro Arg Tyr Leu Pro Pro Ser Lys Met Leu Asp Ala Asp Val
385                 390                 395                 400

Thr Asp Ser Val Ile Gly Glu Gly Cys Val Ile Lys Asn Cys Lys Ile
                405                 410                 415

His His Ser Val Val Gly Leu Arg Ser Cys Ile Ser Glu Gly Ala Ile
            420                 425                 430

Ile Glu Asp Ser Leu Leu Met Gly Ala Asp Tyr Tyr Glu Thr Asp Ala
            435                 440                 445

Asp Arg Arg Leu Leu Ala Ala Lys Gly Ser Ile Pro Ile Gly Ile Gly
            450                 455                 460

Arg Asn Ser His Ile Lys Arg Ala Ile Asp Lys Asn Ala Arg Ile
465                 470                 475                 480

Gly Asp Asn Val Lys Ile Ile Asn Ser Asp Asp Val Gln Glu Ala Ala
            485                 490                 495

Arg Glu Thr Asp Gly Tyr Phe Ile Lys Ser Gly Ile Val Thr Val Ile
```

```
                    500                 505                 510
Lys Asp Ala Leu Ile Pro Ser Gly Thr Val Ile
            515                 520

<210> SEQ ID NO 69
<211> LENGTH: 520
<212> TYPE: PRT
<213> ORGANISM: Brassica napus
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 69

Met Ala Thr Met Ala Ala Ile Gly Ser Leu Lys Val Pro Ser Ser Ser
1               5                   10                  15

Ser Asn His Thr Arg Arg Leu Ser Ser Ser Gln Arg Lys Thr Leu
            20                  25                  30

Ser Phe Ser Ser Ser Ser Leu Ala Gly Glu Lys Ile Asn Pro Thr Gln
        35                  40                  45

Glu Ile Ile Ile Ser Asn Leu Pro Gly Arg Asn Glu Arg Arg Arg Pro
50                  55                  60

Ser Ile Val Ser Pro Lys Ala Val Ser Asp Ser Gln Asn Ser Gln Thr
65                  70                  75                  80

Cys Leu Asp Pro Asp Ala Ser Arg Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Ile Ser Lys Ile Tyr Val Leu Thr Gln
130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Phe
        195                 200                 205

Leu Val Leu Ala Gly Asp His Leu Tyr Arg Met Asp Tyr Glu Lys Phe
210                 215                 220

Ile Gln Ala His Arg Glu Thr Asp Ala Asp Ile Thr Val Ala Ala Leu
225                 230                 235                 240

Pro Met Asp Glu Lys Arg Ala Thr Ala Phe Gly Leu Met Lys Ile Asp
                245                 250                 255

Asp Glu Gly Arg Ile Ile Glu Phe Ala Glu Lys Pro Lys Gly Glu Gln
            260                 265                 270

Leu Lys Ala Met Lys Val Asp Thr Thr Ile Leu Gly Leu Asp Asp Glu
        275                 280                 285

Arg Ala Lys Glu Met Pro Phe Ile Ala Ser Met Gly Ile Tyr Val Val
290                 295                 300

Ser Lys Asn Val Met Leu Asp Leu Leu Arg Asp Gln Phe Pro Gly Ala
305                 310                 315                 320

Asn Asp Phe Gly Ser Glu Val Ile Pro Gly Ala Thr Asp Leu Gly Leu
                325                 330                 335
```

```
Arg Val Gln Ala Tyr Leu Tyr Asp Gly Tyr Trp Glu Asp Ile Gly Thr
                340                 345                 350

Ile Glu Ala Phe Tyr Asn Ala Asn Leu Gly Ile Thr Lys Lys Pro Val
            355                 360                 365

Pro Asp Phe Ser Phe Tyr Asp Arg Ser Ala Pro Ile Tyr Thr Gln Pro
        370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
                405                 410                 415

Val Ile Gly Leu Arg Ser Cys Ile Ser Glu Gly Ala Ile Ile Glu Asp
            420                 425                 430

Thr Leu Leu Met Gly Ala Asp Tyr Tyr Glu Thr Asp Ala Asp Arg Thr
        435                 440                 445

Leu Leu Ala Ala Lys Gly Ser Ile Pro Ile Gly Ile Gly Arg Asp Ser
450                 455                 460

His Ile Lys Arg Ala Ile Ile Asp Lys Asn Ala Arg Ile Gly Asp Asn
465                 470                 475                 480

Val Lys Ile Ile Asn Thr Asp Asn Val Gln Glu Ala Ala Arg Glu Thr
                485                 490                 495

Asp Gly Tyr Phe Ile Lys Ser Gly Ile Val Thr Val Ile Lys Asp Ala
            500                 505                 510

Leu Ile Pro Ser Gly Thr Val Ile
        515                 520

<210> SEQ ID NO 70
<211> LENGTH: 520
<212> TYPE: PRT
<213> ORGANISM: Gossypium hirsutum
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 70

Met Ala Ser Thr Ala Ala Leu Arg Leu Ile Thr Thr Thr Lys Ser Ser
1               5                   10                  15

Ser Ser Ser Asn Ala Ala Ser Val Ser Pro Ser Ser Gly Ile Phe Leu
            20                  25                  30

Ala Pro Arg Thr Leu Ser Phe Ser Ala Ser Ala Leu Ser Gly Asp Lys
        35                  40                  45

Leu Val Ser Lys Thr Val Thr Ser Ser Arg Gln Met Lys Arg Thr Pro
50                  55                  60

Phe Ile Val Ser Pro Lys Ala Val Ser Asp Ser Gln Asn Ser Gln Thr
65                  70                  75                  80

Cys Leu Asp Pro Asp Ala Ser Arg Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Val Ser Lys Ile Tyr Val Leu Thr Gln
        130                 135                 140

Phe Asn Ser Ala Ser Leu Asn Arg His Leu Ser Arg Ala Tyr Ala Ser
145                 150                 155                 160
```

```
Asn Met Gly Gly Tyr Lys Asn Glu Gly Phe Val Glu Val Leu Ala Ala
            165                 170                 175
Gln Gln Ser Pro Glu Asn Pro Asn Trp Phe Gln Gly Thr Ala Asp Ala
        180                 185                 190
Val Arg Gln Tyr Leu Trp Leu Phe Glu Glu His Asn Val Leu Glu Phe
    195                 200                 205
Leu Val Leu Ala Gly Asp His Leu Tyr Arg Met Asp Tyr Glu Lys Phe
210                 215                 220
Ile Gln Ala His Arg Glu Thr Asp Ala Asp Ile Thr Val Ala Ala Leu
225                 230                 235                 240
Pro Met Asp Glu Lys Arg Ala Thr Ala Phe Gly Leu Met Lys Ile Asp
                245                 250                 255
Glu Glu Gly Arg Ile Ile Glu Phe Ala Glu Lys Pro Lys Gly Asp Gln
            260                 265                 270
Leu Lys Ala Met Lys Val Asp Thr Thr Ile Leu Gly Leu Asp Asp Val
        275                 280                 285
Arg Ala Lys Glu Met Pro Tyr Ile Ala Ser Met Gly Ile Tyr Val Val
    290                 295                 300
Ser Lys Asn Val Met Leu Asp Leu Leu Arg Glu Lys Phe Pro Gly Ala
305                 310                 315                 320
Asn Asp Phe Gly Ser Glu Val Ile Pro Gly Ala Thr Ser Ile Gly Met
                325                 330                 335
Arg Val Gln Ala Tyr Leu Tyr Asp Gly Tyr Trp Glu Asp Ile Gly Thr
            340                 345                 350
Ile Glu Ala Phe Tyr Asn Ala Asn Leu Gly Ile Thr Lys Lys Pro Val
        355                 360                 365
Pro Asp Phe Ser Phe Tyr Asp Arg Ser Ser Pro Ile Tyr Thr Gln Pro
    370                 375                 380
Arg Tyr Leu Pro Pro Ser Lys Met Leu Asp Ala Asp Val Thr Asp Ser
385                 390                 395                 400
Val Ile Gly Glu Gly Cys Val Ile Lys Asn Cys Lys Ile His His Ser
                405                 410                 415
Val Val Gly Leu Arg Ser Cys Ile Ser Glu Gly Ala Ile Ile Glu Asp
            420                 425                 430
Thr Leu Leu Met Gly Ala Asp Tyr Tyr Glu Thr Asp Ala Asp Arg Arg
        435                 440                 445
Phe Leu Ala Ala Lys Gly Ser Val Pro Ile Gly Ile Gly Lys Asn Ser
    450                 455                 460
His Ile Lys Arg Ala Ile Ile Asp Lys Asn Ala Arg Ile Gly Asp Asn
465                 470                 475                 480
Val Lys Ile Ile Asn Ser Asp Asn Val Gln Glu Ala Ala Arg Glu Thr
                485                 490                 495
Asp Gly Tyr Phe Ile Lys Ser Gly Ile Val Thr Val Leu Lys Asp Ala
            500                 505                 510
Leu Ile Pro Ser Gly Thr Val Ile
        515                 520

<210> SEQ ID NO 71
<211> LENGTH: 578
<212> TYPE: PRT
<213> ORGANISM: Citrus clementina
<220> FEATURE:
<221> NAME/KEY: MISC_FEATURE
<222> LOCATION: (1)..(578)
<223> OTHER INFORMATION: ADP-glucose pyrophosphorylase small subunit
```

<400> SEQUENCE: 71

```
Met Thr Lys Leu Phe Ile Tyr His Asp His Asp Arg Asp His Thr Glu
1               5                   10                  15
Thr Trp Leu His Ile Arg Ser Ser Ala Phe Phe Ser Leu Gln Leu
            20                  25                  30
Thr Leu Ser Leu Ala His Thr His Ser Gly Ser Ala Arg Leu Thr Ile
        35                  40                  45
Thr Val Asn Val Asn Arg Leu Tyr Arg Leu Met Ala Ser Met Ala Ser
50                  55                  60
Ile Gly Ser Leu Lys Val Pro Ser Ser Pro Ser Thr Ala Ala Thr Ser
65                  70                  75                  80
Ser Asn Ser Asn Asn His Ser Arg Arg Ser Val Val Lys Arg Leu Ala
                85                  90                  95
Phe Ser Ser Gln Leu Ser Gly Asp Lys Ile Phe Ser Lys Ala Val
            100                 105                 110
Thr Gly Asp Arg Arg Arg Glu Arg Arg Pro Ile Val Val Ser Pro Gln
        115                 120                 125
Ala Val Ser Asp Ser Lys Asn Ser Gln Thr Cys Leu Asp Pro Glu Ala
130                 135                 140
Ser Arg Ser Val Leu Gly Ile Ile Leu Gly Gly Gly Ala Gly Thr Arg
145                 150                 155                 160
Leu Tyr Pro Leu Thr Lys Lys Arg Ala Lys Pro Ala Val Pro Leu Gly
                165                 170                 175
Ala Asn Tyr Arg Leu Ile Asp Ile Pro Val Ser Asn Cys Leu Asn Ser
            180                 185                 190
Asn Ile Ser Lys Ile Tyr Val Leu Thr Gln Phe Asn Ser Ala Ser Leu
        195                 200                 205
Asn Arg His Leu Ser Arg Ala Tyr Ala Ser Asn Met Gly Gly Tyr Lys
210                 215                 220
Asn Glu Gly Phe Val Glu Val Leu Ala Ala Gln Gln Ser Pro Glu Asn
225                 230                 235                 240
Pro Asn Trp Phe Gln Gly Thr Ala Asp Ala Val Arg Gln Tyr Leu Trp
                245                 250                 255
Leu Phe Glu Glu His Asn Val Leu Glu Phe Leu Val Leu Ala Gly Asp
            260                 265                 270
His Leu Tyr Arg Met Asp Tyr Glu Arg Phe Ile Gln Ala His Arg Glu
        275                 280                 285
Thr Asp Ala Asp Ile Thr Val Ala Ala Leu Pro Met Asp Glu Lys Arg
290                 295                 300
Ala Thr Ala Phe Gly Leu Met Lys Ile Asp Glu Gly Arg Ile Ile
305                 310                 315                 320
Glu Phe Ser Glu Lys Pro Lys Gly Glu Gln Leu Lys Ala Met Lys Val
                325                 330                 335
Asp Thr Thr Ile Leu Gly Leu Asp Asp Glu Arg Ala Lys Glu Met Pro
            340                 345                 350
Tyr Ile Ala Ser Met Gly Ile Tyr Val Ile Ser Lys Asp Val Met Leu
        355                 360                 365
Asn Leu Leu Arg Asp Lys Phe Pro Gly Ala Asn Asp Phe Gly Ser Glu
370                 375                 380
Val Ile Pro Gly Ala Thr Ser Ile Gly Met Arg Val Gln Ala Tyr Leu
385                 390                 395                 400
Tyr Asp Gly Tyr Trp Glu Asp Ile Gly Thr Ile Glu Ala Phe Tyr Asn
                405                 410                 415
```

```
Ala Asn Leu Gly Ile Thr Lys Pro Ile Pro Asp Phe Ser Phe Tyr
            420                 425                 430

Asp Arg Ser Ala Pro Ile Tyr Thr Gln Pro Arg Tyr Leu Pro Pro Ser
            435                 440                 445

Lys Met Leu Asp Ala Asp Val Thr Asp Ser Val Ile Gly Glu Gly Cys
            450                 455                 460

Val Ile Lys Asn Cys Lys Ile His His Ser Val Val Gly Leu Arg Ser
465                 470                 475                 480

Cys Ile Ser Glu Gly Ala Ile Ile Glu Asp Thr Leu Leu Met Gly Ala
                485                 490                 495

Asp Tyr Tyr Glu Thr Asp Ala Asp Arg Arg Phe Leu Ala Ala Lys Gly
                500                 505                 510

Ser Val Pro Ile Gly Ile Gly Lys Asn Ser His Ile Lys Arg Ala Ile
            515                 520                 525

Ile Asp Lys Asn Ala Arg Ile Gly Asp Asn Val Lys Ile Val Asn Ser
530                 535                 540

Asp Ser Val Gln Glu Ala Ala Arg Glu Thr Asp Gly Tyr Phe Ile Lys
545                 550                 555                 560

Ser Gly Ile Val Thr Ile Ile Lys Asp Ala Leu Ile Pro Ser Gly Thr
                565                 570                 575

Ile Ile

<210> SEQ ID NO 72
<211> LENGTH: 514
<212> TYPE: PRT
<213> ORGANISM: Daucus carota
<220> FEATURE:
<221> NAME/KEY: MISC_FEATURE
<222> LOCATION: (1)..(514)
<223> OTHER INFORMATION: ADP-glucose pyrophosphorylase small subunit

<400> SEQUENCE: 72

Met Ala Ala Ile Gly Thr Leu Lys Pro Pro Gln Ser Ser Ser Ala Gly
1               5                   10                  15

Thr Cys Ser Ser Pro Ala Arg Asp Phe Arg Arg Thr Thr Ser Leu Arg
            20                  25                  30

Lys Leu Ser Phe Ser Ser Gln Val Ser Gly Ala Lys Ile Ser His Ser
        35                  40                  45

Val Gln Arg Arg Arg Ser Arg Gly Ala Ala Val Val Ser Pro Lys
    50                  55                  60

Ala Val Ser Asp Ser Gln Asn Ser Gln Thr Cys Leu Asp Pro Asp Ala
65                  70                  75                  80

Ser Arg Ser Val Leu Gly Ile Ile Leu Gly Gly Gly Ala Gly Thr Arg
                85                  90                  95

Leu Tyr Pro Leu Thr Lys Lys Arg Ala Lys Pro Ala Val Pro Leu Gly
            100                 105                 110

Ala Asn Tyr Arg Leu Ile Asp Ile Pro Val Ser Asn Cys Leu Asn Ser
        115                 120                 125

Asn Ile Ser Lys Ile Tyr Val Leu Thr Gln Phe Asn Ser Ala Ser Leu
130                 135                 140

Asn Arg His Leu Ser Arg Ala Tyr Ala Ser Asn Met Gly Gly Tyr Lys
145                 150                 155                 160

Asn Glu Gly Phe Val Glu Val Leu Ala Ala Gln Gln Ser Pro Glu Asn
                165                 170                 175

Pro Asn Trp Phe Gln Gly Thr Ala Asp Ala Val Arg Gln Tyr Leu Trp
```

```
                    180                 185                 190
Leu Phe Glu Glu His Asn Val Leu Glu Tyr Leu Val Leu Ala Gly Asp
            195                 200                 205
His Leu Tyr Arg Met Asp Tyr Glu Lys Phe Ile Gln Ala His Arg Glu
        210                 215                 220
Thr Asp Ala Asp Ile Thr Val Ala Ala Leu Pro Met Asp Glu Lys Arg
225                 230                 235                 240
Ala Thr Ala Phe Gly Leu Met Lys Ile Asp Glu Glu Gly Arg Ile Ile
            245                 250                 255
Glu Phe Ala Glu Lys Pro Gln Gly Gln Leu Lys Ala Met Lys Val
        260                 265                 270
Asp Thr Thr Ile Leu Gly Leu Asp Asp Val Arg Ala Lys Glu Met Pro
        275                 280                 285
Tyr Ile Ala Ser Met Gly Ile Tyr Val Val Ser Lys Asp Val Met Met
        290                 295                 300
Ser Leu Leu Arg Asp Lys Phe Pro Gly Ala Asn Asp Phe Gly Ser Glu
305                 310                 315                 320
Val Ile Pro Gly Ala Thr Ser Leu Gly Leu Arg Val Gln Ala Tyr Leu
                325                 330                 335
Tyr Asp Gly Tyr Trp Glu Asp Ile Gly Thr Ile Glu Ala Phe Tyr Asn
            340                 345                 350
Ala Asn Leu Gly Ile Thr Lys Lys Pro Val Pro Asp Phe Ser Phe Tyr
        355                 360                 365
Asp Arg Ser Ser Pro Ile Tyr Thr Gln Pro Arg Tyr Leu Pro Pro Ser
    370                 375                 380
Lys Met Leu Asp Ala Asp Val Thr Asp Ser Val Ile Gly Glu Gly Cys
385                 390                 395                 400
Val Ile Lys Asn Cys Lys Ile His His Ser Val Val Gly Leu Arg Ser
                405                 410                 415
Cys Ile Ser Glu Gly Ala Ile Ile Glu Asp Thr Leu Leu Met Gly Ala
            420                 425                 430
Asp Tyr Tyr Glu Thr Asp Ala Asp Arg Arg Ser Leu Ala Ala Lys Gly
        435                 440                 445
Gly Val Pro Ile Gly Ile Gly Lys Asn Ser His Ile Lys Arg Ala Ile
    450                 455                 460
Ile Asp Lys Asn Ala Arg Ile Gly Asp Asn Val Lys Ile Ile Asn Ser
465                 470                 475                 480
Asp Asn Val Gln Glu Ala Ala Arg Glu Thr Asp Gly Tyr Phe Ile Lys
                485                 490                 495
Ser Gly Ile Val Thr Val Ile Lys Asp Ala Leu Ile Pro Ser Gly Thr
            500                 505                 510
Val Ile

<210> SEQ ID NO 73
<211> LENGTH: 520
<212> TYPE: PRT
<213> ORGANISM: Gossypium raimondii
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 73

Met Ala Ala Thr Ala Ala Leu Arg Leu Ile Thr Thr Thr Lys Ser Ser
1               5                   10                  15
```

```
Ser Ser Ser Asn Ala Ala Ser Ile Ser Pro Ser Ser Gly Ile Phe Leu
            20                  25                  30

Ala Pro Arg Thr Leu Ser Phe Ser Ala Ser Ala Leu Ser Gly Asp Lys
            35                  40                  45

Leu Val Ser Lys Thr Val Thr Ser Ser Arg Gln Met Lys Arg Thr Pro
 50                  55                  60

Phe Ile Ile Ser Pro Lys Ala Val Ser Asp Ser Gln Asn Ser Gln Thr
 65                  70                  75                  80

Cys Leu Asp Pro Asp Ala Ser Arg Ser Val Leu Gly Ile Ile Leu Gly
             85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
            115                 120                 125

Ser Asn Cys Leu Asn Ser Asn Val Ser Lys Ile Tyr Val Leu Thr Gln
            130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Phe
            195                 200                 205

Leu Val Leu Ala Gly Asp His Leu Tyr Arg Met Asp Tyr Glu Lys Phe
210                 215                 220

Ile Gln Ala His Arg Glu Thr Asp Ala Asp Ile Thr Val Ala Ala Leu
225                 230                 235                 240

Pro Met Asp Glu Lys Arg Ala Thr Ala Phe Gly Leu Met Lys Ile Asp
            245                 250                 255

Glu Glu Gly Arg Ile Ile Glu Phe Ala Glu Lys Pro Lys Gly Asp Gln
            260                 265                 270

Leu Lys Ala Met Lys Val Asp Thr Thr Ile Leu Gly Leu Asp Asp Glu
            275                 280                 285

Arg Ala Lys Glu Met Pro Tyr Ile Ala Ser Met Gly Ile Tyr Val Val
            290                 295                 300

Ser Lys Asn Val Met Leu Asp Leu Leu Arg Glu Lys Phe Pro Gly Ala
305                 310                 315                 320

Asn Asp Phe Gly Ser Glu Val Ile Pro Gly Ala Thr Ser Ile Gly Met
            325                 330                 335

Arg Val Gln Ala Tyr Leu Tyr Asp Gly Tyr Trp Glu Asp Ile Gly Thr
            340                 345                 350

Ile Glu Ala Phe Tyr Asn Ala Asn Leu Gly Ile Thr Lys Lys Pro Val
            355                 360                 365

Pro Asp Phe Ser Phe Tyr Asp Arg Ser Ser Pro Ile Tyr Thr Gln Pro
            370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
            405                 410                 415

Val Val Gly Leu Arg Ser Cys Ile Ser Glu Gly Ala Ile Ile Glu Asp
            420                 425                 430

Thr Leu Leu Met Gly Ala Asp Tyr Tyr Glu Thr Asp Ala Asp Arg Arg
```

```
                435                 440                 445
Phe Leu Ala Ala Lys Gly Ser Val Pro Ile Gly Ile Gly Lys Asn Ser
450                 455                 460

His Ile Lys Arg Ala Ile Ile Asp Lys Asn Ala Arg Ile Gly Asp Asn
465                 470                 475                 480

Val Lys Ile Ile Asn Ser Asp Asn Val Gln Glu Thr Ala Arg Glu Thr
                485                 490                 495

Asp Gly Tyr Phe Ile Lys Ser Gly Ile Val Thr Val Ile Lys Asp Ala
            500                 505                 510

Leu Ile Pro Ser Gly Thr Val Ile
        515                 520

<210> SEQ ID NO 74
<211> LENGTH: 524
<212> TYPE: PRT
<213> ORGANISM: Tarenaya hassleriana
<220> FEATURE:
<221> NAME/KEY: MISC_FEATURE
<222> LOCATION: (1)..(524)
<223> OTHER INFORMATION: ADP-glucose pyrophosphorylase small subunit

<400> SEQUENCE: 74

Met Ala Thr Met Ala Ala Ile Gly Ala Leu Lys Ile Pro Ala Ser Ser
1               5                   10                  15

Thr Ser Ser Phe Ser Ser Asn Leu Asn Arg Arg Ala Gly Cys Arg Arg
            20                  25                  30

Asn Leu Ser Phe Ser Ser Ser Leu Ala Gly Glu Lys Leu Ala Ser
        35                  40                  45

Pro Glu Ile Met Val Ser Ser Gly Arg Thr Glu Thr Asn Ser Cys Gly
50                  55                  60

Lys Arg Thr Pro Thr Ile Val Ser Pro Lys Ala Val Ser Asp Ser Gln
65                  70                  75                  80

Asn Ser Gln Thr Cys Leu Asp Pro Asp Ala Ser Arg Ser Val Leu Gly
            85                  90                  95

Ile Ile Leu Gly Gly Gly Ala Gly Thr Arg Leu Tyr Pro Leu Thr Lys
        100                 105                 110

Lys Arg Ala Lys Pro Ala Val Pro Leu Gly Ala Asn Tyr Arg Leu Ile
        115                 120                 125

Asp Ile Pro Val Ser Asn Cys Leu Asn Ser Asn Ile Ser Lys Ile Tyr
        130                 135                 140

Val Leu Thr Gln Phe Asn Ser Ala Ser Leu Asn Arg His Leu Ser Arg
145                 150                 155                 160

Ala Tyr Ala Ser Asn Met Gly Gly Tyr Lys Asn Glu Gly Phe Val Glu
                165                 170                 175

Val Leu Ala Ala Gln Gln Ser Pro Glu Asn Pro Asn Trp Phe Gln Gly
            180                 185                 190

Thr Ala Asp Ala Val Arg Gln Tyr Leu Trp Leu Phe Glu Glu His Asn
        195                 200                 205

Val Leu Glu Phe Leu Val Leu Ala Gly Asp His Leu Tyr Arg Met Asp
    210                 215                 220

Tyr Glu Arg Phe Ile Gln Ala His Arg Glu Thr Asp Ala Asp Ile Thr
225                 230                 235                 240

Val Ala Ala Leu Pro Met Asp Glu Lys Arg Ala Thr Ala Phe Gly Leu
                245                 250                 255

Met Lys Ile Asp Glu Glu Gly Arg Ile Ile Glu Phe Ala Glu Lys Pro
            260                 265                 270
```

Lys Gly Glu Gln Leu Lys Ala Met Lys Val Asp Thr Thr Ile Leu Gly
            275                 280                 285

Leu Asp Asp Glu Arg Ala Lys Glu Met Pro Tyr Ile Ala Ser Met Gly
        290                 295                 300

Ile Tyr Val Val Ser Lys His Val Met Leu Asp Leu Leu Arg Glu Lys
305                 310                 315                 320

Phe Pro Gly Ala Asn Asp Phe Gly Ser Glu Val Ile Pro Gly Ala Thr
                325                 330                 335

Ser Leu Gly Leu Arg Val Gln Ala Tyr Leu Tyr Asp Gly Tyr Trp Glu
            340                 345                 350

Asp Ile Gly Thr Ile Glu Ala Phe Tyr Asn Ala Asn Leu Gly Ile Thr
        355                 360                 365

Lys Lys Pro Ile Pro Asp Phe Ser Phe Tyr Asp Arg Ser Ala Pro Ile
370                 375                 380

Tyr Thr Gln Pro Arg Tyr Leu Pro Pro Ser Lys Met Leu Asp Ala Asp
385                 390                 395                 400

Val Thr Asp Ser Val Ile Gly Glu Gly Cys Val Ile Lys Asn Cys Lys
                405                 410                 415

Ile His His Ser Val Ile Gly Leu Arg Ser Cys Ile Ser Glu Gly Ala
            420                 425                 430

Ile Ile Glu Asp Thr Leu Leu Met Gly Ala Asp Tyr Tyr Glu Thr Asp
        435                 440                 445

Ala Asp Arg Arg Phe Leu Ala Ala Lys Gly Ser Val Pro Ile Gly Ile
    450                 455                 460

Gly Arg Asp Ser His Ile Lys Arg Ala Ile Ile Asp Lys Asn Ala Arg
465                 470                 475                 480

Ile Gly Asp Asn Val Lys Ile Ile Asn Thr Asp Asn Val Gln Glu Ala
                485                 490                 495

Ala Arg Glu Thr Asp Gly Tyr Phe Ile Lys Ser Gly Ile Val Thr Val
            500                 505                 510

Ile Lys Asp Ala Leu Ile Pro Ser Gly Thr Val Ile
        515                 520

<210> SEQ ID NO 75
<211> LENGTH: 521
<212> TYPE: PRT
<213> ORGANISM: Ziziphus jujuba
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 75

Met Ala Ser Met Ala Ala Ser Gly Ala Leu Arg Val Pro Ser Ser Ser
1               5                   10                  15

Leu Ser Ser Ser Ser Ser Ser Gly Ser Tyr Leu Ser Pro Lys Thr
            20                  25                  30

Ser Ser Lys Ser Leu Ser Phe Ala His Ser His Leu Ser Gly Glu Lys
        35                  40                  45

Ile Ser Ser Ile Ala Asn Phe Arg Arg Thr Pro Ser Thr Asp Arg Ser
50                  55                  60

Pro Lys Ile Val Ser Pro Lys Ala Val Ser Asp Ser Lys Asn Ser Gln
65                  70                  75                  80

Thr Cys Leu Asp Pro Asp Ala Ser Arg Ser Val Leu Gly Ile Ile Leu
            85                  90                  95

```
Gly Gly Gly Ala Gly Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
        115                 120                 125

Val Ser Asn Cys Leu Asn Ser Asn Ile Ser Lys Ile Tyr Val Leu Thr
    130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
            165                 170                 175

Ala Gln Gln Ser Pro Glu Asn Pro Asn Trp Phe Gln Gly Thr Ala Asp
        180                 185                 190

Ala Val Arg Gln Tyr Leu Trp Leu Phe Glu Glu His Asn Val Leu Glu
    195                 200                 205

Phe Leu Val Leu Ala Gly Asp His Leu Tyr Arg Met Asp Tyr Glu Arg
210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
            245                 250                 255

Asp Glu Glu Gly Arg Ile Ile Glu Phe Ala Glu Lys Pro Lys Gly Glu
        260                 265                 270

Gln Leu Lys Ala Met Lys Val Asp Thr Thr Ile Leu Gly Leu Asp Asp
    275                 280                 285

Val Arg Ala Lys Glu Met Pro Tyr Ile Ala Ser Met Gly Ile Tyr Val
290                 295                 300

Val Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Ile Gly
            325                 330                 335

Leu Arg Val Gln Ala Tyr Leu Tyr Asp Gly Tyr Trp Glu Asp Ile Gly
        340                 345                 350

Thr Ile Glu Ala Phe Tyr Asn Ala Asn Leu Gly Ile Thr Lys Lys Pro
    355                 360                 365

Val Pro Asp Phe Ser Phe Tyr Asp Arg Ser Ser Pro Ile Tyr Thr Gln
370                 375                 380

Pro Arg Tyr Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
            405                 410                 415

Ser Val Val Gly Leu Arg Ser Cys Ile Ser Glu Gly Ala Ile Ile Glu
        420                 425                 430

Asp Thr Leu Leu Met Gly Ala Asp Tyr Tyr Glu Thr Asp Ala Asp Arg
    435                 440                 445

Arg Phe Leu Ala Ala Lys Gly Ser Val Pro Ile Gly Ile Gly Lys Ser
450                 455                 460

Ser His Ile Lys Arg Ala Ile Ile Asp Lys Asn Ala Arg Ile Gly Glu
465                 470                 475                 480

Asn Val Lys Ile Ile Asn Gly Asp Asn Val Gln Glu Ala Ala Arg Glu
            485                 490                 495

Thr Asp Gly Tyr Phe Ile Lys Ser Gly Ile Val Thr Val Ile Lys Asp
        500                 505                 510

Ala Leu Ile Pro Ser Gly Thr Val Ile
```

```
            515                 520

<210> SEQ ID NO 76
<211> LENGTH: 520
<212> TYPE: PRT
<213> ORGANISM: Gossypium arboreum
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 76

Met Ala Ser Thr Ala Ala Leu Arg Leu Ile Thr Thr Lys Ser Ser
1               5                   10                  15

Ser Ser Ser Asn Ala Ala Ser Val Ser Pro Ser Ser Gly Ile Phe Leu
                20                  25                  30

Ala Pro Arg Thr Leu Ser Phe Ser Ala Ser Ala Leu Ser Gly Asp Lys
            35                  40                  45

Leu Val Ser Lys Thr Val Thr Ser Ser Arg Gln Met Lys Arg Thr Pro
        50                  55                  60

Phe Ile Val Ser Pro Lys Ala Val Ser Asp Ser Gln Asn Ser Gln Thr
65                  70                  75                  80

Cys Leu Asp Pro Asp Ala Ser Arg Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Val Ser Lys Ile Tyr Val Leu Thr Gln
    130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Phe
        195                 200                 205

Leu Val Leu Ala Gly Asp His Leu Tyr Arg Met Asp Tyr Glu Lys Phe
    210                 215                 220

Ile Gln Ala His Arg Glu Thr Asp Ala Asp Ile Thr Val Ala Ala Leu
225                 230                 235                 240

Pro Met Asp Glu Lys Arg Ala Thr Ala Phe Gly Leu Met Lys Ile Asp
                245                 250                 255

Glu Glu Gly Arg Ile Ile Glu Phe Ala Glu Lys Pro Lys Gly Asp Gln
            260                 265                 270

Leu Lys Ala Met Lys Val Asp Thr Thr Ile Leu Gly Leu Asp Asp Val
        275                 280                 285

Arg Ala Lys Glu Met Pro Tyr Ile Ala Ser Met Gly Ile Tyr Val Val
    290                 295                 300

Ser Lys Asn Val Met Leu Asp Leu Leu Arg Glu Lys Phe Pro Gly Ala
305                 310                 315                 320

Asn Asp Phe Gly Ser Glu Val Ile Pro Gly Ala Thr Ser Ile Gly Met
                325                 330                 335

Arg Val Gln Ala Tyr Leu Tyr Asp Gly Tyr Trp Glu Asp Ile Gly Thr
            340                 345                 350
```

```
Ile Glu Ala Phe Tyr Asn Ala Asn Leu Gly Ile Thr Lys Lys Pro Val
            355                 360                 365

Pro Asp Phe Ser Phe Tyr Asp Arg Ser Ser Pro Ile Tyr Thr Gln Pro
370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
            405                 410                 415

Val Val Gly Leu Arg Ser Cys Ile Ser Glu Gly Ala Ile Ile Glu Asp
            420                 425                 430

Thr Leu Leu Met Gly Ala Asp Tyr Tyr Glu Thr Asp Ala Asp Arg Arg
            435                 440                 445

Phe Leu Ala Ala Lys Gly Ser Val Pro Ile Gly Ile Gly Lys Asn Ser
            450                 455                 460

His Ile Lys Arg Ala Ile Ile Asp Lys Asn Ala Arg Ile Gly Asp Asn
465                 470                 475                 480

Val Lys Ile Ile Asn Ser Asp Asn Val Gln Glu Ala Ser Arg Glu Thr
            485                 490                 495

Asp Gly Tyr Phe Ile Lys Ser Gly Ile Val Thr Val Ile Lys Asp Ala
            500                 505                 510

Leu Ile Pro Ser Gly Thr Val Ile
            515                 520

<210> SEQ ID NO 77
<211> LENGTH: 521
<212> TYPE: PRT
<213> ORGANISM: Fragaria x ananassa
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 77

Met Ala Ser Ser Ser Met Ala Ala Asn Gly Val Pro Thr Leu Arg Leu
1               5                   10                  15

Ser Thr Ser Asn Ile Ala Thr Asn Gln Thr Gln Lys Thr Asn Arg Gly
            20                  25                  30

Leu Ser Phe Ser Gly Ser His Leu Ser Gly Thr Lys Ile Pro Thr Pro
        35                  40                  45

Ala Thr Cys Leu Arg Thr Cys Ser Pro Ser Pro Ser Thr Arg Arg Ala
    50                  55                  60

Pro Leu Val Val Ser Pro Lys Ala Val Ser Asp Ser Lys Asn Ser Glu
65                  70                  75                  80

Thr Cys Leu Asp Pro Asp Ala Ser Arg Ser Val Leu Gly Ile Ile Leu
                85                  90                  95

Gly Gly Asp Gly Arg Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
        115                 120                 125

Val Ser Asn Cys Leu Asn Ser Asn Val Ser Lys Ile Tyr Val Leu Thr
    130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175
```

Ala Gln Gln Ser Pro Glu Asn Pro Asn Trp Phe Gln Gly Thr Ala Asp
            180                 185                 190

Ala Val Arg Gln Cys Leu Trp Leu Phe Glu Glu His Asn Val Leu Glu
        195                 200                 205

Phe Leu Val Leu Ala Gly Asp His Leu Tyr Arg Met Asp Tyr Glu Lys
    210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Asp Glu Gly Arg Ile Ile Glu Phe Ala Glu Lys Pro Lys Gly Glu
            260                 265                 270

Gln Leu Lys Ala Met Lys Val Asp Thr Thr Ile Leu Gly Leu Asp Asp
        275                 280                 285

Glu Arg Ala Lys Glu Met Pro Tyr Ile Ala Ser Met Gly Ile Tyr Val
    290                 295                 300

Val Ser Lys Asn Val Met Leu Asp Leu Arg Glu Lys Phe Pro Gly
305                 310                 315                 320

Ala Asn Asp Phe Gly Ser Glu Val Ile Pro Gly Ala Thr Ser Ile Gly
                325                 330                 335

Leu Arg Val Gln Ala Tyr Leu Tyr Asp Gly Tyr Trp Glu Asp Ile Gly
            340                 345                 350

Thr Ile Glu Ala Phe Tyr Asn Ala Asn Leu Gly Ile Thr Lys Lys Pro
        355                 360                 365

Ile Pro Asp Phe Ser Phe Tyr Asp Ser Ser Pro Ile Tyr Thr Gln
    370                 375                 380

Pro Arg Tyr Leu Pro Pro Ser Lys Met Leu Asp Ala Asp Ile Thr Asp
385                 390                 395                 400

Ser Val Ile Gly Glu Gly Cys Val Ile Lys Asn Cys Lys Ile His His
                405                 410                 415

Ser Val Ile Gly Leu Arg Ser Cys Ile Ser Glu Gly Ala Val Ile Glu
            420                 425                 430

Asp Thr Leu Leu Met Gly Ala Asp Tyr Tyr Glu Thr Asp Val Asp Arg
        435                 440                 445

Arg Leu Met Ala Lys Lys Gly Ser Val Pro Ile Gly Ile Gly Lys Asn
    450                 455                 460

Ser His Ile Lys Arg Ala Ile Ile Asp Lys Asn Ala Arg Ile Gly Asp
465                 470                 475                 480

Asn Val Lys Ile Ile Lys Ser Asp Asn Val Gln Glu Thr Ala Arg Glu
                485                 490                 495

Thr Asp Gly Tyr Phe Ile Lys Ser Gly Ile Val Thr Val Ile Lys Asp
            500                 505                 510

Ala Trp Ile Pro Ser Gly Thr Val Ile
        515                 520

<210> SEQ ID NO 78
<211> LENGTH: 520
<212> TYPE: PRT
<213> ORGANISM: Brassica napus
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 78

Met Ala Thr Met Ala Ala Ile Gly Ser Leu Lys Val Pro Ser Ser Ser

-continued

```
1               5                   10                  15
Ser Asn His Thr Arg Arg Leu Ser Ser Ser Gln Arg Lys Thr Leu
                20                  25                  30
Ser Phe Ser Ser Ser Leu Thr Gly Glu Lys Leu Asn Pro Thr Gln
                35                  40                  45
Glu Ile Ile Ile Ser Asn Leu Pro Arg Gly Asn Glu Arg Thr Pro
                50                  55                  60
Ser Ile Val Ser Pro Lys Ala Val Ser Asp Ser Gln Asn Ser Gln Thr
65                      70                  75                  80
Cys Leu Asp Pro Asp Ala Ser Arg Ser Val Leu Gly Ile Ile Leu Gly
                    85                  90                  95
Gly Gly Ala Gly Thr Arg Leu Tyr Pro Leu Thr Lys Lys Arg Ala Lys
                    100                 105                 110
Pro Ala Val Pro Leu Gly Ala Asn Tyr Arg Leu Ile Asp Ile Pro Val
                    115                 120                 125
Ser Asn Cys Leu Asn Ser Asn Ile Ser Lys Ile Tyr Val Leu Thr Gln
                    130                 135                 140
Phe Asn Ser Ala Ser Leu Asn Arg His Leu Ser Arg Ala Tyr Ala Ser
145                     150                 155                 160
Asn Met Gly Gly Tyr Lys Asn Glu Gly Phe Val Glu Val Leu Ala Ala
                    165                 170                 175
Gln Gln Ser Pro Glu Asn Pro Asn Trp Phe Gln Gly Thr Ala Asp Ala
                    180                 185                 190
Val Arg Gln Tyr Leu Trp Leu Phe Glu Glu His Asn Val Leu Glu Phe
                    195                 200                 205
Leu Val Leu Ala Gly Asp His Leu Tyr Arg Met Asp Tyr Glu Lys Phe
                    210                 215                 220
Ile Gln Ala His Arg Glu Thr Asp Ala Asp Ile Thr Val Ala Ala Leu
225                     230                 235                 240
Pro Met Asp Glu Lys Arg Ala Thr Ala Phe Gly Leu Met Lys Ile Asp
                    245                 250                 255
Asp Glu Gly Arg Ile Ile Glu Phe Ala Glu Lys Pro Lys Gly Glu Gln
                    260                 265                 270
Leu Lys Ala Met Lys Val Asp Thr Thr Ile Leu Gly Leu Asp Asp Glu
                    275                 280                 285
Arg Ala Lys Glu Met Pro Phe Ile Ala Ser Met Gly Ile Tyr Val Val
                    290                 295                 300
Ser Lys Asn Val Met Leu Asp Leu Leu Arg Asp Gln Phe Pro Gly Ala
305                     310                 315                 320
Asn Asp Phe Gly Ser Glu Val Ile Pro Gly Ala Thr Asp Leu Gly Leu
                    325                 330                 335
Arg Val Gln Ala Tyr Leu Tyr Asp Gly Tyr Trp Glu Asp Ile Gly Thr
                    340                 345                 350
Ile Glu Ala Phe Tyr Asn Ala Asn Leu Gly Ile Thr Lys Lys Pro Val
                    355                 360                 365
Pro Asp Phe Ser Phe Tyr Asp Arg Ser Ala Pro Ile Tyr Thr Gln Pro
                    370                 375                 380
Arg Tyr Leu Pro Pro Ser Lys Met Leu Asp Ala Asp Val Thr Asp Ser
385                     390                 395                 400
Val Ile Gly Glu Gly Cys Val Ile Lys Asn Cys Lys Ile His His Ser
                    405                 410                 415
Val Ile Gly Leu Arg Ser Cys Ile Ser Glu Gly Ala Ile Ile Glu Asp
                    420                 425                 430
```

```
Thr Leu Leu Met Gly Ala Asp Tyr Tyr Glu Thr Asp Ala Asp Arg Thr
            435                 440                 445

Leu Leu Ala Ala Lys Gly Ser Ile Pro Ile Gly Ile Gly Arg Asp Ser
            450                 455                 460

His Ile Lys Arg Ala Ile Ile Asp Lys Asn Ala Arg Ile Gly Asp Asn
465                 470                 475                 480

Val Lys Ile Ile Asn Thr Asp Asn Val Gln Glu Ala Ala Arg Glu Thr
                485                 490                 495

Asp Gly Tyr Phe Ile Lys Ser Gly Ile Val Thr Val Ile Lys Asp Ala
            500                 505                 510

Leu Ile Pro Ser Gly Thr Val Ile
            515                 520

<210> SEQ ID NO 79
<211> LENGTH: 514
<212> TYPE: PRT
<213> ORGANISM: Medicago truncatula
<220> FEATURE:
<221> NAME/KEY: MISC_FEATURE
<222> LOCATION: (1)..(514)
<223> OTHER INFORMATION: ADP-glucose pyrophosphorylase small subunit

<400> SEQUENCE: 79

Met Ala Ser Met Ala Ser Ile Gly Val Leu Lys Val Pro Ser Ser Ser
1               5                   10                  15

Ser Ser Ser Ser Ser Ser Ser Ser Lys Ala Ile Ala Arg Asn Leu
                20                  25                  30

Ser Phe Thr Ser Ser Gln Leu Cys Gly Asp Lys Ile Thr Thr Val Ser
            35                  40                  45

Thr Arg Arg Ser Tyr Gly Cys Ser Lys Pro Phe Ile Val Ser Pro Lys
50                  55                  60

Ala Val Ser Asp Ser Lys Asn Ser Gln Thr Cys Leu Asp Pro Asp Ala
65                  70                  75                  80

Ser Arg Ser Val Leu Gly Ile Ile Leu Gly Gly Gly Ala Gly Thr Arg
                85                  90                  95

Leu Tyr Pro Leu Thr Lys Lys Arg Ala Lys Pro Ala Val Pro Leu Gly
            100                 105                 110

Ala Asn Tyr Arg Leu Ile Asp Ile Pro Val Ser Asn Cys Leu Asn Ser
            115                 120                 125

Asn Ile Ser Lys Ile Tyr Val Leu Thr Gln Phe Asn Ser Ala Ser Leu
130                 135                 140

Asn Arg His Leu Ser Arg Ala Tyr Ala Ser Asn Met Gly Gly Tyr Lys
145                 150                 155                 160

Asn Glu Gly Phe Val Glu Val Leu Ala Ala Gln Gln Ser Pro Glu Asn
                165                 170                 175

Pro Asn Trp Phe Gln Gly Thr Ala Asp Ala Val Arg Gln Tyr Leu Trp
            180                 185                 190

Leu Phe Glu Glu His Asn Val Leu Glu Tyr Leu Val Leu Ala Gly Asp
            195                 200                 205

His Leu Tyr Arg Met Asp Tyr Glu Arg Phe Ile Gln Ala His Arg Glu
            210                 215                 220

Ser Asp Ala Asp Ile Thr Val Ala Ala Leu Pro Met Asp Glu Ala Arg
225                 230                 235                 240

Ala Thr Ala Phe Gly Leu Met Lys Ile Asp Glu Glu Gly Arg Ile Ile
                245                 250                 255
```

```
Glu Phe Ala Glu Lys Pro Lys Gly Glu Gln Leu Lys Ala Met Lys Val
                260                 265                 270

Asp Thr Thr Ile Leu Gly Leu Asp Asp Glu Arg Ala Lys Glu Met Pro
            275                 280                 285

Tyr Ile Ala Ser Met Gly Ile Tyr Val Val Ser Lys His Val Met Leu
        290                 295                 300

Asp Leu Leu Arg Asp Lys Phe Pro Gly Ala Asn Asp Phe Gly Ser Glu
305                 310                 315                 320

Val Ile Pro Gly Ala Thr Glu Leu Gly Met Arg Val Gln Ala Tyr Leu
                325                 330                 335

Tyr Asp Gly Tyr Trp Glu Asp Ile Gly Thr Ile Glu Ala Phe Tyr Asn
            340                 345                 350

Ala Asn Leu Gly Ile Thr Lys Lys Pro Val Pro Asp Phe Ser Phe Tyr
        355                 360                 365

Asp Arg Ser Ser Pro Ile Tyr Thr Gln Pro Arg Tyr Leu Pro Pro Ser
370                 375                 380

Lys Met Leu Asp Ala Asp Ile Thr Asp Ser Val Ile Gly Glu Gly Cys
385                 390                 395                 400

Val Ile Lys Asn Cys Lys Ile His His Ser Val Val Gly Leu Arg Ser
                405                 410                 415

Cys Ile Ser Glu Gly Ala Ile Ile Glu Asp Thr Leu Leu Met Gly Ala
            420                 425                 430

Asp Tyr Tyr Glu Thr Asp Ala Asp Arg Arg Phe Leu Ala Ala Lys Gly
        435                 440                 445

Ser Val Pro Ile Gly Ile Gly Lys Asn Ser His Ile Lys Arg Ala Ile
    450                 455                 460

Ile Asp Lys Asn Ala Arg Ile Gly Asp Asp Val Lys Ile Ile Asn Ser
465                 470                 475                 480

Asp Asn Val Gln Glu Ala Ala Arg Glu Thr Glu Gly Tyr Phe Ile Lys
                485                 490                 495

Ser Gly Ile Val Thr Val Ile Lys Asp Ala Leu Ile Pro Ser Gly Thr
            500                 505                 510

Val Ile

<210> SEQ ID NO 80
<211> LENGTH: 520
<212> TYPE: PRT
<213> ORGANISM: Citrus sinensis
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 80

Met Ala Ser Met Ala Ser Ile Gly Ser Leu Lys Val Pro Ser Ser Pro
1               5                   10                  15

Ser Thr Ala Thr Thr Ser Ser Asn Ser Asn Asn His Ser Arg Arg Ser
            20                  25                  30

Val Val Lys Arg Leu Ala Phe Ser Ser Gln Leu Ser Gly Asp Lys
        35                  40                  45

Ile Phe Ser Lys Ala Val Thr Gly Asp Arg Arg Ser Glu Arg Arg Pro
    50                  55                  60

Ile Val Val Ser Pro Gln Ala Val Ser Asp Ser Lys Asn Ser Gln Thr
65                  70                  75                  80

Cys Leu Asp Pro Glu Ala Ser Arg Ser Val Leu Gly Ile Ile Leu Gly
                85                  90                  95
```

-continued

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
            115                 120                 125

Ser Asn Cys Leu Asn Ser Asn Ile Ser Lys Ile Tyr Val Leu Thr Gln
            130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Phe
            195                 200                 205

Leu Val Leu Ala Gly Asp His Leu Tyr Arg Met Asp Tyr Glu Arg Phe
            210                 215                 220

Ile Gln Ala His Arg Glu Thr Asp Ala Asp Ile Thr Val Ala Ala Leu
225                 230                 235                 240

Pro Met Asp Glu Lys Arg Ala Thr Ala Phe Gly Leu Met Lys Ile Asp
                245                 250                 255

Glu Glu Gly Arg Ile Ile Glu Phe Ser Glu Lys Pro Lys Gly Glu Gln
            260                 265                 270

Leu Lys Ala Met Lys Val Asp Thr Thr Ile Leu Gly Leu Asp Asp Glu
            275                 280                 285

Arg Ala Lys Glu Met Pro Tyr Ile Ala Ser Met Gly Ile Tyr Val Ile
290                 295                 300

Ser Lys Asp Val Met Leu Asn Leu Leu Arg Asp Lys Phe Pro Gly Ala
305                 310                 315                 320

Asn Asp Phe Gly Ser Glu Val Ile Pro Gly Ala Thr Ser Ile Gly Met
                325                 330                 335

Arg Val Gln Ala Tyr Leu Tyr Asp Gly Tyr Trp Glu Asp Ile Gly Thr
            340                 345                 350

Ile Glu Ala Phe Tyr Asn Ala Asn Leu Gly Ile Thr Lys Lys Pro Ile
            355                 360                 365

Pro Asp Phe Ser Phe Tyr Asp Arg Ser Ala Pro Ile Tyr Thr Gln Pro
370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
                405                 410                 415

Val Val Gly Leu Arg Ser Cys Ile Ser Glu Gly Ala Ile Ile Glu Asp
            420                 425                 430

Thr Leu Leu Met Gly Ala Asp Tyr Tyr Glu Thr Asp Ala Asp Arg Arg
            435                 440                 445

Phe Leu Ala Ala Lys Gly Ser Val Pro Ile Gly Ile Gly Lys Asn Ser
            450                 455                 460

His Ile Lys Arg Ala Ile Ile Asp Lys Asn Ala Arg Ile Gly Asp Asn
465                 470                 475                 480

Val Lys Ile Val Asn Ser Asp Ser Val Gln Glu Ala Ala Arg Glu Thr
                485                 490                 495

Asp Gly Tyr Phe Ile Lys Ser Gly Ile Val Thr Ile Ile Lys Asp Ala
            500                 505                 510

```
Leu Ile Pro Ser Gly Thr Ile Ile
        515                 520
```

<210> SEQ ID NO 81
<211> LENGTH: 520
<212> TYPE: PRT
<213> ORGANISM: Gossypium hirsutum
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 81

```
Met Ala Ala Thr Ala Ala Leu Arg Leu Ile Thr Thr Thr Lys Ser Ser
1               5                   10                  15

Ser Ser Ser Asn Ala Ala Ser Ile Ser Pro Ser Ser Gly Ile Phe Leu
            20                  25                  30

Ala Pro Arg Thr Leu Ser Phe Ser Ala Ser Ala Leu Ser Gly Asp Lys
        35                  40                  45

Leu Val Ser Lys Thr Val Thr Ser Ser Arg Gln Met Lys Arg Thr Pro
    50                  55                  60

Phe Ile Ile Ser Pro Lys Ala Val Ser Asp Ser Gln Asn Ser Gln Thr
65                  70                  75                  80

Cys Leu Asp Pro Asp Ala Ser Arg Ser Val Leu Gly Ile Ile Leu Gly
                85                  90                  95

Gly Gly Ala Gly Ala Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Val Ser Lys Ile Tyr Val Leu Thr Gln
    130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Phe
        195                 200                 205

Leu Val Leu Ala Gly Asp His Leu Tyr Arg Met Asp Tyr Glu Lys Phe
    210                 215                 220

Ile Gln Ala His Arg Glu Thr Asp Ala Asp Ile Thr Val Ala Ala Leu
225                 230                 235                 240

Pro Met Asp Glu Lys Arg Ala Thr Ala Phe Gly Leu Met Lys Ile Asp
                245                 250                 255

Glu Glu Gly Arg Ile Ile Glu Phe Ala Glu Lys Pro Lys Gly Asp Gln
            260                 265                 270

Leu Lys Ala Met Lys Val Asp Thr Thr Ile Leu Gly Leu Asp Asp Glu
        275                 280                 285

Arg Ala Lys Lys Met Pro Tyr Ile Ala Ser Met Gly Ile Tyr Val Val
    290                 295                 300

Ser Lys Asn Val Met Leu Asp Leu Leu Arg Glu Lys Phe Pro Gly Ala
305                 310                 315                 320

Asn Asp Phe Gly Ser Glu Val Ile Pro Gly Ala Thr Ser Ile Gly Met
                325                 330                 335

Arg Val Gln Ala Tyr Leu Tyr Asp Gly Tyr Trp Glu Asp Ile Gly Thr
```

```
              340                 345                 350
Ile Glu Ala Phe Tyr Asn Ala Asn Leu Gly Ile Thr Lys Lys Pro Val
            355                 360                 365

Pro Asp Phe Ser Phe Tyr Asp Arg Ser Ser Pro Ile Tyr Thr Gln Pro
        370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
                405                 410                 415

Val Val Gly Leu Arg Ser Cys Ile Ser Glu Gly Ala Ile Ile Glu Asp
            420                 425                 430

Thr Leu Leu Met Gly Ala Asp Tyr Tyr Glu Thr Asp Ala Asp Arg Arg
        435                 440                 445

Phe Leu Ala Ala Lys Gly Ser Val Pro Ile Gly Ile Gly Lys Asn Ser
    450                 455                 460

His Ile Lys Arg Ala Ile Ile Asp Lys Asn Ala Arg Ile Gly Asp Asn
465                 470                 475                 480

Val Lys Ile Ile Asn Ser Asp Asn Val Gln Glu Thr Ala Arg Glu Thr
                485                 490                 495

Asp Gly Tyr Phe Ile Lys Ser Gly Ile Val Thr Val Ile Lys Asp Ala
            500                 505                 510

Leu Ile Pro Ser Gly Thr Val Ile
        515                 520

<210> SEQ ID NO 82
<211> LENGTH: 507
<212> TYPE: PRT
<213> ORGANISM: Spinacia oleracea
<220> FEATURE:
<221> NAME/KEY: MISC_FEATURE
<222> LOCATION: (1)..(507)
<223> OTHER INFORMATION: ADP-glucose pyrophosphorylase small subunit

<400> SEQUENCE: 82

Met Ala Ala Ala Gly Met Ala Val Ile Gly Ala Ile Thr Ile Pro Ser
1               5                   10                  15

Lys Asn Ile Gln His Gly Leu Ala Phe Ser Thr Ser Ser Leu Ser Gly
            20                  25                  30

Asp Lys Phe Leu Pro Thr Leu Ser Arg Arg Asn Ile Arg Ile Ser Ser
        35                  40                  45

Asp Val Glu Arg Ala Pro Val Ile Lys Ala Val Ser Asp Ser Gln Asn
    50                  55                  60

Ser Gln Thr Cys Leu Asp Pro Glu Ala Ser Arg Ser Val Leu Gly Ile
65                  70                  75                  80

Ile Leu Gly Gly Gly Ala Gly Thr Arg Leu Tyr Pro Leu Thr Lys Lys
                85                  90                  95

Arg Ala Lys Pro Ala Val Pro Leu Gly Ala Asn Tyr Arg Leu Ile Asp
            100                 105                 110

Ile Pro Val Ser Asn Cys Leu Asn Ser Asn Ile Ser Lys Ile Tyr Val
        115                 120                 125

Leu Thr Gln Phe Asn Ser Ala Ser Leu Asn Arg His Leu Ser Arg Ala
    130                 135                 140

Tyr Ala Ser Asn Leu Gly Gly Tyr Lys Asn Glu Gly Phe Val Glu Val
145                 150                 155                 160

Leu Ala Ala Gln Gln Ser Pro Glu Asn Pro Asp Trp Phe Gln Gly Thr
                165                 170                 175
```

Ala Asp Ala Val Arg Gln Tyr Leu Trp Leu Phe Glu His Asn Val
            180                 185                 190

Met Glu Phe Leu Ile Leu Ala Gly Asp His Leu Tyr Arg Met Asp Tyr
        195                 200                 205

Glu Arg Phe Ile Gln Ala His Arg Glu Thr Asp Ala Asp Ile Thr Val
    210                 215                 220

Ala Ala Leu Pro Met Asp Glu Lys Arg Ala Thr Ala Phe Gly Leu Met
225                 230                 235                 240

Lys Ile Asp Glu Glu Gly Arg Ile Ile Glu Phe Ala Glu Lys Pro Lys
            245                 250                 255

Gly Glu Gln Leu Gln Ala Met Lys Val Asp Thr Ile Leu Gly Leu
        260                 265                 270

Asp Asp Glu Arg Ala Lys Glu Met Pro Tyr Ile Ala Ser Met Gly Ile
    275                 280                 285

Tyr Val Ile Ser Lys Asp Val Met Leu Asn Leu Leu Arg Asp Lys Phe
290                 295                 300

Pro Gly Ala Asn Asp Phe Gly Ser Glu Val Ile Pro Gly Ala Thr Ser
305                 310                 315                 320

Ile Gly Leu Arg Val Gln Ala Tyr Leu Tyr Asp Gly Tyr Trp Glu Asp
            325                 330                 335

Ile Gly Thr Ile Glu Ala Phe Tyr Asn Ala Asn Leu Gly Ile Thr Lys
        340                 345                 350

Lys Pro Val Pro Asp Phe Ser Phe Tyr Asp Arg Ser Ser Pro Ile Tyr
    355                 360                 365

Thr Gln Pro Arg Tyr Leu Pro Pro Ser Lys Met Leu Asp Ala Asp Ile
370                 375                 380

Thr Asp Ser Val Ile Gly Glu Gly Cys Val Ile Lys Asn Cys Lys Ile
385                 390                 395                 400

His His Ser Val Ile Gly Leu Arg Ser Cys Ile Ser Glu Gly Ala Ile
            405                 410                 415

Ile Glu Asp Thr Leu Leu Met Gly Ala Asp Tyr Tyr Glu Thr Asp Ala
        420                 425                 430

Asp Arg Lys Leu Leu Ala Ala Lys Gly Ser Val Ala Ile Gly Ile Gly
    435                 440                 445

Gln Asn Ser His Ile Lys Arg Ala Ile Ile Asp Lys Asn Ala Arg Ile
450                 455                 460

Gly Asp Asn Val Lys Ile Ile Asn Ser Asp Asn Val Gln Glu Ala Ala
465                 470                 475                 480

Arg Glu Thr Asp Gly Tyr Phe Ile Lys Ser Gly Ile Val Thr Val Ile
            485                 490                 495

Lys Asp Ala Leu Ile Pro Ser Gly Thr Val Ile
        500                 505

<210> SEQ ID NO 83
<211> LENGTH: 519
<212> TYPE: PRT
<213> ORGANISM: Cicer arietinum
<220> FEATURE:
<221> NAME/KEY: MISC_FEATURE
<222> LOCATION: (1)..(519)
<223> OTHER INFORMATION: ADP-glucose pyrophosphorylase small subunit

<400> SEQUENCE: 83

Met Ala Ser Ser Met Ala Ala Ile Gly Val Val Lys Val Pro His Ser
1               5                   10                  15

```
Ser Ser Ser Ser Ser Ser Ser Asn Val Ala Asn Lys Ala Ile Gln
            20                  25                  30

Gln Ser Asn Leu Ser Phe Ser Ser His Leu Ser Gly Asp Lys Ile
        35                  40                  45

Val Thr Leu Ser Gly Ala Gly Arg Gly Arg Cys Thr Arg Lys His Val
50                      55                  60

Ile Val Thr Pro Lys Ala Val Ser Asp Ser Gln Asn Ser Gln Thr Cys
65                  70                  75                  80

Leu Asp Pro Asp Ala Ser Arg Ser Val Leu Gly Ile Ile Leu Gly Gly
                85                  90                  95

Gly Ala Gly Thr Arg Leu Tyr Pro Leu Thr Lys Lys Arg Ala Lys Pro
            100                 105                 110

Ala Val Pro Leu Gly Ala Asn Tyr Arg Leu Ile Asp Ile Pro Val Ser
            115                 120                 125

Asn Cys Leu Asn Ser Asn Ile Ser Lys Ile Tyr Val Leu Thr Gln Phe
        130                 135                 140

Asn Ser Ala Ser Leu Asn Arg His Leu Ser Arg Ala Tyr Ala Ser Asn
145                 150                 155                 160

Leu Gly Gly Tyr Lys Asn Glu Gly Phe Val Glu Val Leu Ala Ala Gln
            165                 170                 175

Gln Ser Pro Glu Asn Pro Asn Trp Phe Gln Gly Thr Ala Asp Ala Val
            180                 185                 190

Arg Gln Tyr Leu Trp Leu Phe Glu His Asn Val Leu Glu Phe Leu
        195                 200                 205

Ile Leu Ala Gly Asp His Leu Tyr Arg Met Asp Tyr Glu Lys Phe Ile
210                 215                 220

Gln Ala His Arg Glu Thr Asp Ala Asp Ile Thr Val Ala Ala Leu Pro
225                 230                 235                 240

Met Asp Glu Lys Arg Ala Thr Ala Phe Gly Leu Met Lys Ile Asp Glu
            245                 250                 255

Glu Gly Arg Ile Ile Glu Phe Ala Glu Lys Pro Lys Gly Asp Gln Leu
            260                 265                 270

Asn Ala Met Lys Val Asp Thr Thr Ile Leu Gly Leu Asp Asp Glu Arg
        275                 280                 285

Ala Lys Glu Met Pro Phe Ile Ala Ser Met Gly Ile Tyr Val Ile Ser
        290                 295                 300

Lys Asn Val Met Leu Asp Leu Leu Ser Asp Lys Phe Pro Gly Ala Asn
305                 310                 315                 320

Asp Phe Gly Ser Glu Val Ile Pro Gly Ala Thr Ser Ile Gly Met Arg
            325                 330                 335

Val Gln Ala Tyr Leu Tyr Asp Gly Tyr Trp Glu Asp Ile Gly Thr Ile
            340                 345                 350

Glu Ala Phe Tyr Asn Ala Asn Leu Gly Ile Thr Lys Lys Pro Val Pro
        355                 360                 365

Asp Phe Ser Phe Tyr Asp Arg Ser Ser Pro Ile Tyr Thr Gln Pro Arg
        370                 375                 380

Tyr Leu Pro Pro Ser Lys Met Leu Asp Ala Asp Ile Thr Asp Ser Val
385                 390                 395                 400

Ile Gly Glu Gly Cys Val Ile Lys Asn Cys Lys Ile Phe His Ser Val
            405                 410                 415

Ile Gly Leu Arg Ser Cys Ile Ser Glu Gly Ala Ile Ile Glu Asp Thr
        420                 425                 430

Leu Leu Met Gly Ala Asp Tyr Tyr Glu Thr Asp Ala Asp Lys Arg Phe
```

```
                435                 440                 445
Leu Ala Ala Lys Gly Ser Val Pro Ile Gly Ile Gly Arg Asn Ser His
            450                 455                 460
Ile Lys Arg Ala Ile Val Asp Lys Asn Ala Arg Ile Gly Glu Asn Val
465                 470                 475                 480
Lys Ile Ile Asn Ser Asp Asn Val Gln Glu Ala Ala Arg Glu Thr Asp
                485                 490                 495
Gly Tyr Phe Ile Lys Ser Gly Ile Val Thr Val Ile Lys Asp Ala Leu
            500                 505                 510
Ile Pro Ser Gly Thr Val Ile
        515

<210> SEQ ID NO 84
<211> LENGTH: 524
<212> TYPE: PRT
<213> ORGANISM: Prunus persica
<220> FEATURE:
<221> NAME/KEY: MISC_FEATURE
<222> LOCATION: (1)..(524)
<223> OTHER INFORMATION: ADP-glucose pyrophosphorylase small subunit

<400> SEQUENCE: 84

Met Ala Ser Ser Ser Met Ala Ala Ser Gly Val Leu Arg Pro Arg Ser
1               5                   10                  15
Ser Ser Met Phe Pro Asn Ala Leu Lys Gln Thr Gln Asn Ala Ser Leu
            20                  25                  30
Cys Arg Ser Ser Arg Gly Leu Ser Phe Ser Gly Ser His Leu Ser Gly
        35                  40                  45
Thr Lys Ile Pro Thr Ala Ser Thr Cys Leu Arg Lys Cys Pro Thr His
    50                  55                  60
Arg Ala Pro Pro Leu Val Val Ser Pro Lys Ala Val Ser Asp Ser Lys
65                  70                  75                  80
Asn Ser Gln Thr Cys Leu Asp Pro Asp Ala Ser Arg Ser Val Leu Gly
                85                  90                  95
Ile Ile Leu Gly Gly Gly Ala Gly Thr Arg Leu Tyr Pro Leu Thr Lys
            100                 105                 110
Lys Arg Ala Lys Pro Ala Val Pro Leu Gly Ala Asn Tyr Arg Leu Ile
        115                 120                 125
Asp Ile Pro Val Ser Asn Cys Leu Asn Ser Asn Val Ser Lys Ile Tyr
    130                 135                 140
Val Leu Thr Gln Phe Asn Ser Ala Ser Leu Asn Arg His Leu Ser Arg
145                 150                 155                 160
Ala Tyr Ala Ser Asn Met Gly Gly Tyr Lys Asn Glu Gly Phe Val Glu
                165                 170                 175
Val Leu Ala Ala Gln Gln Ser Pro Glu Asn Pro Asn Trp Phe Gln Gly
            180                 185                 190
Thr Ala Asp Ala Val Arg Gln Tyr Leu Trp Leu Phe Glu Glu His Asn
        195                 200                 205
Val Leu Glu Phe Leu Val Leu Ala Gly Asp His Leu Tyr Arg Met Asp
    210                 215                 220
Tyr Glu Arg Phe Ile Gln Ala His Arg Glu Thr Asp Ala Asp Ile Thr
225                 230                 235                 240
Val Ala Ala Leu Pro Met Asp Glu Lys Arg Ala Thr Ala Phe Gly Leu
                245                 250                 255
Met Lys Ile Asp Asp Glu Gly Arg Ile Ile Glu Phe Ala Glu Lys Pro
            260                 265                 270
```

```
Lys Gly Glu Gln Leu Lys Ala Met Gln Val Asp Thr Thr Ile Leu Gly
            275                 280                 285

Leu Asp Asp Gln Arg Ala Lys Glu Met Pro Tyr Ile Ala Ser Met Gly
    290                 295                 300

Ile Tyr Val Val Ser Lys Asn Val Met Leu Asp Leu Leu Arg Asp Lys
305                 310                 315                 320

Phe Pro Gly Ala Asn Asp Phe Gly Ser Glu Val Ile Pro Gly Ala Thr
                325                 330                 335

Ser Met Gly Leu Arg Val Gln Ala Tyr Leu Tyr Asp Gly Tyr Trp Glu
            340                 345                 350

Asp Ile Gly Thr Ile Glu Ala Phe Tyr Asn Ala Asn Leu Gly Ile Thr
            355                 360                 365

Lys Lys Pro Val Pro Asp Phe Ser Phe Tyr Asp Arg Ser Ser Pro Ile
    370                 375                 380

Tyr Thr Gln Pro Arg Tyr Leu Pro Pro Ser Lys Met Leu Asp Ala Asp
385                 390                 395                 400

Val Thr Asp Ser Val Ile Gly Glu Gly Cys Val Ile Lys Asn Cys Lys
                405                 410                 415

Ile His His Ser Val Val Gly Leu Arg Ser Cys Ile Ser Glu Gly Ala
            420                 425                 430

Val Ile Glu Asp Thr Leu Leu Met Gly Ala Asp Tyr Tyr Glu Thr Asp
            435                 440                 445

Ala Asp Arg Arg Phe Leu Ala Ala Lys Gly Ser Val Pro Ile Gly Ile
    450                 455                 460

Gly Lys Ser Ser His Ile Lys Arg Ala Ile Ile Asp Lys Asn Ala Arg
465                 470                 475                 480

Ile Gly Asp Asn Val Lys Ile Ile Asn Ser Asp Asn Val Gln Glu Ala
                485                 490                 495

Ala Arg Glu Thr Asp Gly Tyr Phe Ile Lys Ser Gly Ile Val Thr Val
            500                 505                 510

Ile Lys Asp Ala Leu Ile Pro Ser Gly Thr Val Ile
            515                 520
```

<210> SEQ ID NO 85
<211> LENGTH: 524
<212> TYPE: PRT
<213> ORGANISM: Prunus mume
<220> FEATURE:
<221> NAME/KEY: MISC_FEATURE
<222> LOCATION: (1)..(524)
<223> OTHER INFORMATION: ADP-glucose pyrophosphorylase small subunit

<400> SEQUENCE: 85

```
Met Ala Ser Ser Met Ala Ala Ser Gly Val Leu Arg Pro Arg Ser
1               5                   10                  15

Ser Ser Met Ser Pro Asn Ala Ser Lys Gln Thr Gln Asn Ala Ser Leu
            20                  25                  30

Cys Arg Ser Ser Arg Gly Leu Ser Phe Ser Gly Ser His Leu Ala Gly
        35                  40                  45

Thr Lys Ile Pro Thr Ala Ser Thr Cys Leu Arg Lys Cys Pro Thr His
    50                  55                  60

Arg Ala Pro Pro Leu Val Val Ser Pro Lys Ala Val Ser Asp Ser Lys
65                  70                  75                  80

Asn Ser Gln Thr Cys Leu Asp Pro Asp Ala Ser Arg Ser Val Leu Gly
                85                  90                  95
```

```
Ile Ile Leu Gly Gly Ala Gly Thr Arg Leu Tyr Pro Leu Thr Lys
            100             105             110

Lys Arg Ala Lys Pro Ala Val Pro Leu Gly Ala Asn Tyr Arg Leu Ile
        115             120             125

Asp Ile Pro Val Ser Asn Cys Leu Asn Ser Asn Val Ser Lys Ile Tyr
        130             135             140

Val Leu Thr Gln Phe Asn Ser Ala Ser Leu Asn Arg His Leu Ser Arg
145             150             155             160

Ala Tyr Ala Ser Asn Met Gly Gly Tyr Lys Asn Glu Gly Phe Val Glu
                165             170             175

Val Leu Ala Ala Gln Gln Ser Pro Glu Asn Pro Asn Trp Phe Gln Gly
            180             185             190

Thr Ala Asp Ala Val Arg Gln Tyr Leu Trp Leu Phe Glu Glu His Asn
            195             200             205

Val Leu Glu Phe Leu Val Leu Ala Gly Asp His Leu Tyr Arg Met Asp
            210             215             220

Tyr Glu Arg Phe Ile Gln Ala His Arg Glu Thr Asp Ala Asp Ile Thr
225             230             235             240

Val Ala Ala Leu Pro Met Asp Glu Lys Arg Ala Thr Ala Phe Gly Leu
                245             250             255

Met Lys Ile Asp Asp Glu Gly Arg Ile Ile Glu Phe Ala Glu Lys Pro
            260             265             270

Lys Gly Glu Gln Leu Lys Ala Met Gln Val Asp Thr Thr Ile Leu Gly
            275             280             285

Leu Asp Asp Gln Arg Ala Lys Glu Met Pro Tyr Ile Ala Ser Met Gly
            290             295             300

Ile Tyr Val Val Ser Lys Asn Val Met Leu Asp Leu Leu Arg Asp Lys
305             310             315             320

Phe Pro Gly Ala Asn Asp Phe Gly Ser Glu Val Ile Pro Gly Ala Thr
                325             330             335

Ser Met Gly Leu Arg Val Gln Ala Tyr Leu Tyr Asp Gly Tyr Trp Glu
            340             345             350

Asp Ile Gly Thr Ile Glu Ala Phe Tyr Asn Ala Asn Leu Gly Ile Thr
            355             360             365

Lys Lys Pro Val Pro Asp Phe Ser Phe Tyr Asp Arg Ser Ser Pro Ile
        370             375             380

Tyr Thr Gln Pro Arg Tyr Leu Pro Pro Ser Lys Met Leu Asp Ala Asp
385             390             395             400

Val Thr Asp Ser Val Ile Gly Glu Gly Cys Val Ile Lys Asn Cys Lys
                405             410             415

Ile His His Ser Val Val Gly Leu Arg Ser Cys Ile Ser Glu Gly Ala
            420             425             430

Val Ile Glu Asp Thr Leu Leu Met Gly Ala Asp Tyr Tyr Glu Thr Asp
            435             440             445

Ala Asp Arg Arg Phe Leu Ala Ala Lys Gly Ser Val Pro Ile Gly Ile
        450             455             460

Gly Lys Ser Ser His Ile Lys Arg Ala Ile Ile Asp Lys Asn Ala Arg
465             470             475             480

Ile Gly Glu Asn Val Lys Ile Ile Asn Ser Asp Asn Val Gln Glu Ala
                485             490             495

Ala Arg Glu Thr Asp Gly Tyr Phe Ile Lys Ser Gly Ile Val Thr Val
            500             505             510

Ile Lys Asp Ala Leu Ile Pro Ser Gly Thr Val Ile
```

<210> SEQ ID NO 86
<211> LENGTH: 524
<212> TYPE: PRT
<213> ORGANISM: Brassica oleracea
<220> FEATURE:
<221> NAME/KEY: MISC_FEATURE
<222> LOCATION: (1)..(524)
<223> OTHER INFORMATION: ADP-glucose pyrophosphorylase small subunit

<400> SEQUENCE: 86

Met Ala Thr Met Ala Met Ala Ile Gly Ser Ser Lys Phe Pro Ser
1               5                   10                  15

Ser Ser Ser Thr Ser Ser Ser Asn His Ser Arg Arg Ala Ser Ser
                20                  25                  30

Leu Arg Lys Thr Leu Ser Phe Ser Ser Ser Leu Thr Gly Glu Lys
                35                  40                  45

Leu Asn Pro Thr Gln Glu Ile Ile Ser Ser Leu Pro Arg Ser Asn Glu
            50                  55                  60

Arg Arg Thr Pro Ser Ile Ile Ser Pro Lys Ala Val Ser Asp Ser Gln
65                  70                  75                  80

Asn Ser Gln Thr Cys Leu Asp Pro Asp Ala Ser Arg Ser Val Leu Gly
                85                  90                  95

Ile Ile Leu Gly Gly Gly Ala Gly Thr Arg Leu Tyr Pro Leu Thr Lys
                100                 105                 110

Lys Arg Ala Lys Pro Ala Val Pro Leu Gly Ala Asn Tyr Arg Leu Ile
                115                 120                 125

Asp Ile Pro Val Ser Asn Cys Leu Asn Ser Asn Ile Ser Lys Ile Tyr
            130                 135                 140

Val Leu Thr Gln Phe Asn Ser Ala Ser Leu Asn Arg His Leu Ser Arg
145                 150                 155                 160

Ala Tyr Ala Ser Asn Met Gly Gly Tyr Lys Asn Glu Gly Phe Val Glu
                165                 170                 175

Val Leu Ala Ala Gln Gln Ser Pro Glu Asn Pro Asn Trp Phe Gln Gly
                180                 185                 190

Thr Ala Asp Ala Val Arg Gln Tyr Leu Trp Leu Phe Glu Glu His Asn
                195                 200                 205

Val Leu Glu Phe Leu Val Leu Ala Gly Asp His Leu Tyr Arg Met Asp
            210                 215                 220

Tyr Glu Lys Phe Ile Gln Ala His Arg Glu Thr Asp Ala Asp Ile Thr
225                 230                 235                 240

Val Ala Ala Leu Pro Met Asp Glu Lys Arg Ala Thr Ala Phe Gly Leu
                245                 250                 255

Met Lys Ile Asp Asp Glu Gly Arg Ile Ile Glu Phe Ala Glu Lys Pro
                260                 265                 270

Lys Gly Glu Gln Leu Lys Ala Met Lys Val Asp Thr Thr Ile Leu Gly
                275                 280                 285

Leu Asp Asp Glu Arg Ala Lys Glu Met Pro Phe Ile Ala Ser Met Gly
            290                 295                 300

Ile Tyr Val Val Ser Lys Asn Val Met Leu Asp Leu Leu Arg Asp Gln
305                 310                 315                 320

Phe Pro Gly Ala Asn Asp Phe Gly Ser Glu Val Ile Pro Gly Ala Thr
                325                 330                 335

Asp Leu Gly Leu Arg Val Gln Ala Tyr Leu Tyr Asp Gly Tyr Trp Glu
                340                 345                 350

```
Asp Ile Gly Thr Ile Glu Ala Phe Tyr Asn Ala Asn Leu Gly Ile Thr
            355                 360                 365

Lys Lys Pro Val Pro Asp Phe Ser Phe Tyr Asp Arg Ser Ala Pro Ile
    370                 375                 380

Tyr Thr Gln Pro Arg Tyr Leu Pro Pro Ser Lys Met Leu Asp Ala Asp
385                 390                 395                 400

Val Thr Asp Ser Val Ile Gly Glu Gly Cys Val Ile Lys Asn Cys Lys
                405                 410                 415

Ile His His Ser Val Ile Gly Leu Arg Ser Cys Ile Ser Glu Gly Ala
            420                 425                 430

Ile Ile Glu Asp Thr Leu Leu Met Gly Ala Asp Tyr Tyr Glu Thr Asp
        435                 440                 445

Ala Asp Arg Thr Leu Leu Ala Ala Lys Gly Ser Ile Pro Ile Gly Ile
    450                 455                 460

Gly Arg Asp Ser His Ile Lys Arg Ala Ile Ile Asp Lys Asn Ala Arg
465                 470                 475                 480

Ile Gly Asp Asn Val Lys Ile Ile Asn Thr Asp Asn Val Gln Glu Ala
                485                 490                 495

Ala Arg Glu Thr Asp Gly Tyr Phe Ile Lys Ser Gly Ile Val Thr Val
            500                 505                 510

Ile Lys Asp Ala Leu Ile Pro Ser Gly Thr Val Ile
        515                 520

<210> SEQ ID NO 87
<211> LENGTH: 520
<212> TYPE: PRT
<213> ORGANISM: Lotus japonicus
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 87

Met Ala Cys Met Ala Ala Ile Gly Val Leu Lys Val Pro Cys Ser Ser
1               5                   10                  15

Ser Ser Ser Ser Thr Ser Ser Asn Val Gly Arg Lys Pro Thr Ser Arg
            20                  25                  30

Ser Leu Leu Ser Phe Ser Ala Ser Gln Leu Ser Gly Asp Lys Val Ser
        35                  40                  45

Gly Ala Val Val Ala Pro Gly Arg Gly Ser Ser Asn Arg Arg Ser Pro
    50                  55                  60

Val Ile Val Ser Pro Lys Ala Val Ser Asp Ser Gln Asn Ser Gln Thr
65                  70                  75                  80

Cys Leu Asp Pro Asp Ala Ser Arg Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Val Ser Lys Ile Tyr Val Leu Thr Gln
    130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175
```

```
Gln Gln Ser Pro Glu Asn Pro Asn Trp Phe Gln Gly Thr Ala Asp Ala
            180                 185                 190
Val Arg Gln Tyr Leu Trp Leu Phe Glu Glu His Asn Val Leu Glu Phe
        195                 200                 205
Leu Val Leu Ala Gly Asp His Leu Tyr Arg Met Asp Tyr Glu Lys Phe
    210                 215                 220
Ile Gln Ala His Arg Glu Thr Asp Ala Asp Ile Thr Val Ala Ala Leu
225                 230                 235                 240
Pro Met Asp Glu Gln Arg Ala Thr Ala Phe Gly Leu Met Lys Ile Asp
                245                 250                 255
Glu Glu Gly Arg Ile Ile Glu Phe Ala Glu Lys Pro Lys Gly Glu Gln
            260                 265                 270
Leu Lys Ala Met Lys Val Asp Thr Thr Ile Leu Gly Leu Asp Asp Glu
        275                 280                 285
Arg Ala Lys Glu Met Pro Phe Ile Ala Ser Met Gly Ile Tyr Val Val
    290                 295                 300
Ser Lys Asn Val Met Leu Asp Leu Leu Arg Glu Lys Phe Pro Gly Ala
305                 310                 315                 320
Asn Asp Phe Gly Ser Glu Val Ile Pro Gly Ala Thr Ser Ile Gly Met
                325                 330                 335
Arg Val Gln Ala Tyr Leu Tyr Asp Gly Tyr Trp Glu Asp Ile Gly Thr
            340                 345                 350
Ile Glu Ala Phe Tyr Asn Ala Asn Leu Gly Ile Thr Lys Lys Pro Val
        355                 360                 365
Pro Asp Phe Ser Phe Tyr Asp Arg Ser Ser Pro Ile Tyr Thr Gln Pro
    370                 375                 380
Arg Tyr Leu Pro Pro Ser Lys Met Leu Asp Ala Asp Ile Thr Asp Ser
385                 390                 395                 400
Val Ile Gly Glu Gly Cys Val Ile Lys Asn Cys Lys Ile His His Ser
                405                 410                 415
Val Val Gly Leu Arg Ser Cys Val Ser Glu Gly Ala Ile Ile Glu Asp
            420                 425                 430
Thr Leu Leu Met Gly Ala Asp Tyr Tyr Glu Thr Asp Ala Asp Lys Arg
        435                 440                 445
Phe Leu Ala Ala Lys Gly Ser Val Pro Ile Gly Ile Gly Arg Asn Ser
    450                 455                 460
His Ile Lys Arg Ala Ile Ile Asp Lys Asn Ala Arg Ile Gly Glu Asn
465                 470                 475                 480
Val Lys Ile Ile Asn Thr Asp Asn Val Gln Glu Ala Ala Arg Glu Thr
                485                 490                 495
Glu Gly Tyr Phe Ile Lys Ser Gly Ile Val Thr Val Ile Lys Asp Ala
            500                 505                 510
Leu Ile Pro Ser Gly Thr Val Ile
        515                 520

<210> SEQ ID NO 88
<211> LENGTH: 509
<212> TYPE: PRT
<213> ORGANISM: Vitis vinifera
<220> FEATURE:
<221> NAME/KEY: MISC_FEATURE
<222> LOCATION: (1)..(509)
<223> OTHER INFORMATION: ADP-glucose pyrophosphorylase small subunit

<400> SEQUENCE: 88

Met Ala Ser Leu Ser Ala Leu Gly Val Thr Gly Val Val Pro Thr Ser
```

```
1               5                   10                  15
Ser Lys Ser Arg Asp Leu Pro Ser Ser His Arg Thr Leu Ser Phe Ser
                20                  25                  30
Ser Arg Ile Ser Gly Asn Lys Ile Thr Trp Lys Ala Ser Leu Gly Ser
                35                  40                  45
His Arg Arg Ala Pro Val Ile Val Ser Pro Lys Ala Val Ser Asp Ser
        50                  55                  60
Arg Asn Ser Gln Thr Cys Leu Asp Pro Asp Ala Ser Arg Ser Val Leu
65                  70                  75                  80
Gly Ile Ile Leu Gly Gly Ala Gly Thr Arg Leu Tyr Pro Leu Thr
                    85                  90                  95
Lys Lys Arg Ala Lys Pro Ala Val Pro Leu Gly Ala Asn Tyr Arg Leu
                100                 105                 110
Ile Asp Ile Pro Val Ser Asn Cys Leu Asn Ser Asn Ile Ser Lys Ile
                115                 120                 125
Tyr Val Leu Thr Gln Phe Asn Ser Ala Ser Leu Asn Arg His Leu Ser
            130                 135                 140
Arg Ala Tyr Ala Ser Asn Met Gly Gly Tyr Lys Asn Glu Gly Phe Val
145                 150                 155                 160
Glu Val Leu Ala Ala Gln Gln Ser Pro Glu Asn Pro Asn Trp Phe Gln
                    165                 170                 175
Gly Thr Ala Asp Ala Val Arg Gln Tyr Leu Trp Leu Phe Glu Glu His
                180                 185                 190
Asn Val Leu Glu Phe Leu Val Leu Ala Gly Asp His Leu Tyr Arg Met
            195                 200                 205
Asp Tyr Glu Arg Phe Ile Gln Ala His Arg Glu Thr Asp Ala Asp Ile
            210                 215                 220
Thr Val Ala Ala Leu Pro Met Asp Glu Lys Arg Ala Thr Ala Phe Gly
225                 230                 235                 240
Leu Met Lys Ile Asp Glu Glu Gly Arg Ile Ile Glu Phe Ala Glu Lys
                    245                 250                 255
Pro Lys Gly Glu Gln Leu Lys Ala Met Lys Val Asp Thr Thr Ile Leu
                260                 265                 270
Gly Leu Asp Asp Glu Arg Ala Lys Glu Met Pro Tyr Ile Ala Ser Met
            275                 280                 285
Gly Ile Tyr Val Val Ser Lys Asp Val Met Leu Asp Leu Leu Arg Asp
            290                 295                 300
Gln Phe Pro Gly Ala Asn Asp Phe Gly Ser Glu Val Ile Pro Gly Ala
305                 310                 315                 320
Thr Ser Leu Gly Leu Arg Val Gln Ala Tyr Leu Tyr Asp Gly Tyr Trp
                    325                 330                 335
Glu Asp Ile Gly Thr Ile Glu Ala Phe Tyr Asn Ala Asn Leu Gly Ile
                340                 345                 350
Thr Lys Lys Pro Val Pro Asp Phe Ser Phe Tyr Asp Arg Ser Ser Pro
            355                 360                 365
Ile Tyr Thr Gln Pro Arg Tyr Leu Pro Pro Ser Lys Met Leu Asp Ala
        370                 375                 380
Asp Val Thr Asp Ser Val Ile Gly Glu Gly Cys Val Ile Lys Asn Cys
385                 390                 395                 400
Lys Ile His His Ser Val Val Gly Leu Arg Ser Cys Ile Ser Glu Gly
                    405                 410                 415
Ala Ile Ile Glu Asp Thr Leu Leu Met Gly Ala Asp Tyr Tyr Glu Thr
                420                 425                 430
```

```
Asp Ala Asp Arg Arg Phe Leu Met Ala Lys Gly Ser Val Pro Ile Gly
            435                 440                 445

Ile Gly Lys Asn Ser His Ile Lys Arg Ala Ile Ile Asp Lys Asn Ala
        450                 455                 460

Arg Ile Gly Asp Asn Val Lys Ile Ile Asn Ser Asp Asn Val Gln Glu
465                 470                 475                 480

Ala Ala Arg Glu Thr Asp Gly Tyr Phe Ile Lys Ser Gly Ile Val Thr
            485                 490                 495

Val Ile Lys Asp Ala Leu Leu Pro Ser Gly Thr Ile Ile
        500                 505

<210> SEQ ID NO 89
<211> LENGTH: 522
<212> TYPE: PRT
<213> ORGANISM: Morus notabilis
<220> FEATURE:
<221> NAME/KEY: MISC_FEATURE
<222> LOCATION: (1)..(522)
<223> OTHER INFORMATION: ADP-glucose pyrophosphorylase small subunit

<400> SEQUENCE: 89

Met Ala Ser Met Ala Ala Val Gly Ala Leu Arg Leu Pro Ser Ser Ser
1               5                   10                  15

Ser Ser Phe Ser His Ser Ser Asn Ala Ser Ser Leu Val Pro Arg Thr
            20                  25                  30

Gly Leu Arg Ser Leu Ser Phe Ala Asn Ser His Leu Ser Gly Asp Lys
        35                  40                  45

Ile Thr Ser Phe Ala Ile Ser Gly Cys Arg Ala Ala Ser Thr Asp Arg
    50                  55                  60

Ile Pro Arg Ile Val Ser Pro Lys Ala Val Ser Asp Ser Lys Asn Ser
65                  70                  75                  80

Gln Thr Cys Leu Asp Pro Asp Ala Ser Arg Ser Val Leu Gly Ile Ile
            85                  90                  95

Leu Gly Gly Gly Ala Gly Thr Arg Leu Tyr Pro Leu Thr Lys Lys Arg
        100                 105                 110

Ala Lys Pro Ala Val Pro Leu Gly Ala Asn Tyr Arg Leu Ile Asp Ile
        115                 120                 125

Pro Val Ser Asn Cys Leu Asn Ser Asn Ile Ser Lys Ile Tyr Val Leu
    130                 135                 140

Thr Gln Phe Asn Ser Ala Ser Leu Asn Arg His Leu Ser Arg Ala Tyr
145                 150                 155                 160

Ala Ser Asn Met Gly Gly Tyr Lys Asn Glu Gly Phe Val Glu Val Leu
            165                 170                 175

Ala Ala Gln Gln Ser Pro Glu Asn Pro Asn Trp Phe Gln Gly Thr Ala
        180                 185                 190

Asp Ala Val Arg Gln Tyr Leu Trp Leu Phe Glu Glu His Asn Val Leu
        195                 200                 205

Glu Phe Leu Val Leu Ala Gly Asp His Leu Tyr Arg Met Asp Tyr Glu
    210                 215                 220

Arg Phe Ile Gln Ala His Arg Glu Thr Asp Ala Asp Ile Thr Val Ala
225                 230                 235                 240

Ala Leu Pro Met Asp Glu Lys Arg Ala Thr Ala Phe Gly Leu Met Lys
            245                 250                 255

Ile Asp Glu Glu Gly Arg Ile Val Glu Phe Ala Glu Lys Pro Lys Gly
        260                 265                 270
```

```
Glu Gln Leu Lys Ala Met Lys Val Asp Thr Thr Ile Leu Gly Leu Asp
        275                 280                 285

Asp Glu Arg Ala Lys Glu Met Pro Tyr Ile Ala Ser Met Gly Ile Tyr
290                 295                 300

Val Val Ser Lys Asp Ala Met Leu Asn Leu Leu Arg Asp Lys Phe Pro
305                 310                 315                 320

Gly Ala Asn Asp Phe Gly Ser Glu Val Ile Pro Gly Ala Thr Ser Thr
                325                 330                 335

Gly Met Arg Val Gln Ala Tyr Leu Tyr Asp Gly Tyr Trp Glu Asp Ile
            340                 345                 350

Gly Thr Ile Glu Ala Phe Tyr Asn Ala Asn Leu Gly Ile Thr Lys Lys
        355                 360                 365

Pro Val Pro Asp Phe Ser Phe Tyr Asp Arg Ser Ser Pro Ile Tyr Thr
    370                 375                 380

Gln Pro Arg Tyr Leu Pro Pro Ser Lys Met Leu Asp Ala Asp Val Thr
385                 390                 395                 400

Asp Ser Val Ile Gly Glu Gly Cys Val Ile Lys Asn Cys Lys Ile His
                405                 410                 415

His Ser Val Val Gly Leu Arg Ser Cys Ile Ser Glu Gly Ala Ile Ile
            420                 425                 430

Glu Asp Ser Leu Leu Met Gly Ala Asp Tyr Tyr Glu Thr Ala Ala Asp
        435                 440                 445

Arg Arg Phe Leu Ala Ala Lys Gly Ser Val Pro Ile Gly Ile Gly Lys
    450                 455                 460

Ser Ser His Ile Lys Arg Ala Ile Ile Asp Lys Asn Ala Arg Ile Gly
465                 470                 475                 480

Asp Asn Val Lys Ile Ile Asn Ser Asp Gly Val Gln Glu Ala Ala Arg
                485                 490                 495

Glu Thr Asp Gly Tyr Phe Ile Lys Ser Gly Ile Val Thr Val Ile Lys
            500                 505                 510

Asp Ala Leu Ile Pro Ser Gly Thr Val Ile
        515                 520

<210> SEQ ID NO 90
<211> LENGTH: 515
<212> TYPE: PRT
<213> ORGANISM: Glycine max
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 90

Met Ala Ser Met Ala Ala Ile Gly Ser Leu Asn Val Pro Arg Ser Ala
1               5                   10                  15

Ser Ser Arg Ser Ser Phe Val Gly Arg Lys Ser Val Pro Arg Ser Leu
            20                  25                  30

Ser Phe Ser Ala Ser Gln Leu Cys Gly Asp Lys Ile Pro Thr Asp Ser
        35                  40                  45

Val Leu Leu Ala Pro Lys Ile Gly Arg Ser Pro Val Ile Val Thr Pro
    50                  55                  60

Lys Ala Val Ser Asp Ser Gln Asn Ser Gln Thr Cys Leu Asp Pro Asp
65                  70                  75                  80

Ala Ser Arg Ser Val Leu Gly Ile Ile Leu Gly Gly Gly Ala Gly Thr
                85                  90                  95

Arg Leu Tyr Pro Leu Thr Lys Lys Arg Ala Lys Pro Ala Val Pro Leu
```

```
            100                 105                 110
Gly Ala Asn Tyr Arg Leu Ile Asp Ile Pro Val Ser Asn Cys Leu Asn
            115                 120                 125

Ser Asn Val Ser Lys Ile Tyr Val Leu Thr Gln Phe Asn Ser Ala Ser
        130                 135             140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Phe Leu Val Leu Ala Gly
        195                 200                 205

Asp His Leu Tyr Arg Met Asp Tyr Glu Lys Phe Ile Gln Ala His Arg
        210                 215                 220

Glu Thr Asp Ala Asp Ile Thr Val Ala Ala Leu Pro Met Asp Glu Ala
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
                260                 265                 270

Val Asp Thr Thr Ile Leu Gly Leu Asp Asp Glu Arg Ala Lys Glu Met
            275                 280                 285

Pro Tyr Ile Ala Ser Met Gly Ile Tyr Val Val Ser Lys Asn Val Met
        290                 295                 300

Leu Asp Leu Leu Arg Glu Lys Phe Pro Gly Ala Asn Asp Phe Gly Ser
305                 310                 315                 320

Glu Val Ile Pro Gly Ala Thr Ser Ile Gly Met Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
        355                 360                 365

Tyr Asp Arg Ser Ser Pro Ile Tyr Thr Gln Pro Arg Tyr Leu Pro Pro
        370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Thr Leu Leu Met Gly
            420                 425                 430

Ala Asp Tyr Tyr Glu Thr Glu Ala Asp Lys Arg Phe Leu Ala Ala Lys
        435                 440                 445

Gly Ser Val Pro Ile Gly Ile Gly Arg Asn Ser His Ile Lys Arg Ala
        450                 455                 460

Ile Ile Asp Lys Asn Ala Arg Ile Gly Glu Asn Val Lys Ile Ile Asn
465                 470                 475                 480

Ser Asp Asn Val Gln Glu Ala Ala Arg Glu Thr Asp Gly Tyr Phe Ile
                485                 490                 495

Lys Ser Gly Ile Val Thr Val Ile Lys Asp Ala Leu Ile Pro Ser Gly
            500                 505                 510

Thr Val Ile
        515
```

<210> SEQ ID NO 91
<211> LENGTH: 515
<212> TYPE: PRT
<213> ORGANISM: Glycine max
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 91

```
Met Ala Ser Met Ala Ala Ile Gly Ser Leu Asn Val Pro Cys Ser Ala
1               5                   10                  15

Ser Ser Arg Ser Ser Asn Val Gly Arg Lys Ser Phe Pro Arg Ser Leu
            20                  25                  30

Ser Phe Ser Ala Ser Gln Leu Cys Gly Asp Lys Ile His Thr Asp Ser
        35                  40                  45

Val Ser Phe Ala Pro Lys Ile Gly Arg Asn Pro Val Ile Val Thr Pro
    50                  55                  60

Lys Ala Val Ser Asp Ser Gln Asn Ser Gln Thr Cys Leu Asp Pro Asp
65                  70                  75                  80

Ala Ser Arg Ser Val Leu Gly Ile Ile Leu Gly Gly Gly Ala Gly Thr
                85                  90                  95

Arg Leu Tyr Pro Leu Thr Lys Lys Arg Ala Lys Pro Ala Val Pro Leu
            100                 105                 110

Gly Ala Asn Tyr Arg Leu Ile Asp Ile Pro Val Ser Asn Cys Leu Asn
        115                 120                 125

Ser Asn Val Ser Lys Ile Tyr Val Leu Thr Gln Phe Asn Ser Ala Ser
    130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Phe Leu Val Leu Ala Gly
        195                 200                 205

Asp His Leu Tyr Arg Met Asp Tyr Glu Lys Phe Ile Gln Ala His Arg
    210                 215                 220

Glu Thr Asp Ala Asp Ile Thr Val Ala Ala Leu Pro Met Asp Glu Lys
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
            260                 265                 270

Val Asp Thr Thr Ile Leu Gly Leu Asp Asp Glu Arg Ala Lys Glu Leu
        275                 280                 285

Pro Tyr Ile Ala Ser Met Gly Ile Tyr Val Val Ser Lys Asn Val Met
    290                 295                 300

Leu Asp Leu Leu Arg Glu Lys Phe Pro Gly Ala Asn Asp Phe Gly Ser
305                 310                 315                 320

Glu Val Ile Pro Gly Ala Thr Ser Ile Gly Met Arg Val Gln Ala Tyr
                325                 330                 335

Leu Tyr Asp Gly Tyr Trp Glu Asp Ile Gly Thr Ile Glu Ala Phe Tyr
            340                 345                 350
```

Asn Ala Asn Leu Gly Ile Thr Lys Lys Pro Val Pro Asp Phe Ser Phe
            355                 360                 365

Tyr Asp Arg Ser Ser Pro Ile Tyr Thr Gln Pro Arg Tyr Leu Pro Pro
    370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Thr Leu Leu Met Gly
            420                 425                 430

Ala Asp Tyr Tyr Glu Thr Glu Ala Asp Lys Arg Phe Leu Ala Ala Lys
            435                 440                 445

Gly Ser Val Pro Ile Gly Ile Gly Arg Asn Ser His Ile Lys Arg Ala
        450                 455                 460

Ile Ile Asp Lys Asn Ala Arg Ile Gly Glu Asn Val Lys Ile Ile Asn
465                 470                 475                 480

Ser Asp Asn Val Gln Glu Ala Ala Arg Glu Thr Asp Gly Tyr Phe Ile
                485                 490                 495

Lys Ser Gly Ile Val Thr Val Ile Lys Asp Ala Leu Ile Pro Ser Gly
            500                 505                 510

Thr Val Ile
        515

<210> SEQ ID NO 92
<211> LENGTH: 523
<212> TYPE: PRT
<213> ORGANISM: Eutrema salsugineum
<220> FEATURE:
<221> NAME/KEY: MISC_FEATURE
<222> LOCATION: (1)..(523)
<223> OTHER INFORMATION: ADP-glucose pyrophosphorylase small subunit

<400> SEQUENCE: 92

Met Ala Ser Met Ala Ala Ile Gly Ala Leu Lys Val Pro Ala Ala Ser
1               5                   10                  15

Cys Ser Asp Ser Thr Arg Ile Val Thr Glu Ala Val Pro Ala Arg Thr
            20                  25                  30

Leu Ser Phe Ser Ser Ser Val Gly Leu Ser Asp Glu Lys Leu Ser Leu
        35                  40                  45

Arg Ala Thr Val Ser Arg Arg Glu Ser Val Ala Arg Gly Arg Val
    50                  55                  60

Arg Asn Pro Met Ile Val Ser Pro Lys Ala Val Ser Asp Ser Gln Asn
65                  70                  75                  80

Ser Gln Thr Cys Leu Asp Pro Asp Ala Ser Arg Ser Val Leu Gly Ile
                85                  90                  95

Ile Leu Gly Gly Gly Ala Gly Thr Arg Leu Tyr Pro Leu Thr Lys Lys
            100                 105                 110

Arg Ala Lys Pro Ala Val Pro Leu Gly Ala Asn Tyr Arg Leu Ile Asp
        115                 120                 125

Ile Pro Val Ser Asn Cys Leu Asn Ser Asn Ile Asn Lys Ile Tyr Val
    130                 135                 140

Leu Thr Gln Phe Asn Ser Ala Ser Leu Asn His Leu Ser Arg Ala
145                 150                 155                 160

Tyr Ala Thr Asn Met Gly Gly Tyr Lys Asn Glu Gly Phe Val Glu Val
                165                 170                 175

Leu Ala Ala Gln Gln Ser Pro Glu Asn Pro Asn Trp Phe Gln Gly Thr

```
            180                 185                 190
Ala Asp Ala Val Arg Gln Tyr Leu Trp Leu Phe Glu Glu His Asn Val
        195                 200                 205

Leu Glu Tyr Leu Ile Leu Ala Gly Asp His Leu Tyr Arg Met Asp Tyr
    210                 215                 220

Glu Lys Phe Ile Gln Ala His Arg Glu Thr Asp Ala Asp Ile Thr Val
225                 230                 235                 240

Ala Ala Leu Pro Met Asp Glu Arg Ala Thr Ala Phe Gly Leu Met
            245                 250                 255

Lys Ile Asp Glu Glu Gly Arg Ile Val Glu Phe Ala Glu Lys Pro Lys
        260                 265                 270

Gly Glu Gln Leu Lys Ala Met Lys Val Asp Thr Thr Ile Leu Gly Leu
    275                 280                 285

Asp Asp Lys Arg Ala Lys Glu Met Pro Tyr Ile Ala Ser Met Gly Ile
290                 295                 300

Tyr Val Val Ser Lys Asp Val Met Leu Glu Leu Leu Arg Asn Thr Phe
305                 310                 315                 320

Pro Gly Ala Asn Asp Phe Gly Ser Glu Val Ile Pro Gly Ala Thr Ser
            325                 330                 335

Leu Gly Leu Arg Val Gln Ala Tyr Leu Tyr Asp Gly Tyr Trp Glu Asp
        340                 345                 350

Ile Gly Thr Ile Glu Ala Phe Tyr Asn Ala Asn Leu Gly Ile Thr Lys
    355                 360                 365

Lys Pro Val Pro Asp Phe Ser Phe Tyr Asp Arg Ser Ala Pro Ile Tyr
    370                 375                 380

Thr Gln Pro Arg Tyr Leu Pro Pro Ser Lys Met Leu Asp Ala Asp Val
385                 390                 395                 400

Thr Asp Ser Val Ile Gly Glu Gly Cys Val Ile Lys Asn Cys Lys Ile
            405                 410                 415

His His Ser Val Val Gly Leu Arg Ser Cys Ile Ser Glu Gly Ala Ile
        420                 425                 430

Ile Glu Asp Ser Leu Leu Met Gly Ala Asp Tyr Tyr Glu Thr Ala Ser
    435                 440                 445

Glu Lys Ser Leu Leu Thr Ala Lys Gly Ser Val Pro Ile Gly Ile Gly
    450                 455                 460

Lys Ser Ser His Ile Lys Arg Ala Ile Ile Asp Lys Asn Ala Arg Ile
465                 470                 475                 480

Gly Asp Asn Val Lys Ile Ile Asn Ser Asp Asn Val Gln Glu Ala Ala
            485                 490                 495

Arg Glu Thr Glu Gly Tyr Phe Ile Lys Ser Gly Ile Val Thr Val Ile
        500                 505                 510

Lys Asp Ala Leu Ile Pro Thr Gly Thr Leu Ile
        515                 520

<210> SEQ ID NO 93
<211> LENGTH: 515
<212> TYPE: PRT
<213> ORGANISM: Glycine soja
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 93

Met Ala Ser Met Ala Ala Ile Gly Ser Leu Asn Val Pro Arg Ser Ala
1               5                   10                  15
```

```
Ser Ser Arg Ser Ser Phe Val Gly Arg Lys Ser Val Pro Arg Ser Leu
            20                  25                  30

Ser Phe Ser Ala Ser Gln Leu Cys Gly Asp Lys Ile Pro Thr Asp Ser
        35                  40                  45

Val Leu Leu Ala Pro Lys Ile Gly Arg Ser Pro Val Ile Val Thr Pro
 50                  55                  60

Lys Ala Val Ser Asp Ser Gln Asn Ser Gln Thr Cys Leu Asp Pro Asp
 65                  70                  75                  80

Ala Ser Arg Ser Val Leu Gly Ile Ile Leu Gly Gly Ala Gly Thr
                85                  90                  95

Arg Leu Tyr Pro Leu Thr Lys Lys Arg Ala Lys Pro Ala Val Pro Leu
            100                 105                 110

Gly Ala Asn Tyr Arg Leu Ile Asp Ile Pro Val Ser Asn Cys Leu Asn
            115                 120                 125

Ser Asn Val Ser Lys Ile Tyr Val Leu Thr Gln Phe Asn Ser Ala Ser
        130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Phe Leu Val Leu Ala Gly
        195                 200                 205

Asp His Leu Tyr Arg Met Asp Tyr Glu Lys Phe Ile Gln Ala His Arg
        210                 215                 220

Glu Thr Asp Ala Asp Ile Thr Val Ala Ala Leu Pro Met Asp Glu Ala
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
            260                 265                 270

Val Asp Thr Thr Ile Leu Gly Leu Asp Asp Glu Arg Ala Lys Glu Met
        275                 280                 285

Pro Tyr Ile Ala Ser Met Gly Ile Tyr Val Val Ser Lys Asn Val Met
        290                 295                 300

Leu Asp Leu Leu Arg Glu Lys Phe Pro Gly Ala Asn Asp Phe Gly Ser
305                 310                 315                 320

Glu Val Ile Pro Gly Ala Thr Ser Ile Gly Met Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
        355                 360                 365

Tyr Asp Arg Ser Ser Pro Ile Tyr Thr Gln Pro Arg Tyr Leu Pro Pro
        370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Ala Leu Leu Met Gly
            420                 425                 430
```

```
Ala Asp Tyr Tyr Glu Thr Glu Ala Asp Lys Arg Phe Leu Ala Ala Lys
        435                 440                 445

Gly Ser Val Pro Ile Gly Ile Gly Arg Asn Ser His Ile Lys Arg Ala
    450                 455                 460

Ile Ile Asp Lys Asn Ala Arg Ile Gly Glu Asn Val Lys Ile Ile Asn
465                 470                 475                 480

Ser Asp Asn Val Gln Glu Ala Ala Arg Glu Thr Asp Gly Tyr Phe Ile
                485                 490                 495

Lys Ser Gly Ile Val Thr Val Ile Lys Asp Ala Leu Ile Pro Ser Gly
                500                 505                 510

Thr Val Ile
        515

<210> SEQ ID NO 94
<211> LENGTH: 521
<212> TYPE: PRT
<213> ORGANISM: Ricinus communis
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 94

Met Ala Ser Met Ala Ala Ile Gly Val Leu Lys Val Pro Ser Ala Ser
1               5                   10                  15

Ser Ser Ser Phe Ser Asn Ser Ser Asn Cys Ser Arg Arg Leu Gly Asn
                20                  25                  30

Leu Ser Phe Ser Ser Val Asn Val Ser Gly Asp Lys Ile Tyr Cys
            35                  40                  45

Ser Lys Ser Ser Ser Phe Ser Gly His Tyr Asn Tyr Asn Gly Arg Thr
    50                  55                  60

Pro Met Ile Val Ser Pro Lys Ala Val Ser Asp Ser Arg Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala
                100                 105                 110

Lys Pro Ala Val Pro Leu Gly Ala Asn Tyr Arg Leu Ile Asp Ile Pro
            115                 120                 125

Val Ser Asn Cys Leu Asn Ser Asn Ile Ser Lys Ile Tyr Val Leu Thr
    130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175

Ala Gln Gln Ser Pro Glu Asn Pro Asn Trp Phe Gln Gly Thr Ala Asp
                180                 185                 190

Ala Val Arg Gln Tyr Leu Trp Leu Phe Glu Glu His Asn Val Leu Glu
            195                 200                 205

Phe Leu Ile Leu Ala Gly Asp His Leu Tyr Arg Met Asp Tyr Glu Arg
    210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Glu Glu Gly Arg Ile Ile Glu Phe Ala Glu Lys Pro Lys Gly Glu
```

```
                260                 265                 270
Gln Leu Lys Ala Met Lys Val Asp Thr Thr Ile Leu Gly Leu Asp Asp
        275                 280                 285

Glu Arg Ala Lys Glu Met Pro Tyr Ile Ala Ser Met Gly Ile Tyr Val
        290                 295                 300

Val Ser Lys Asn Val Met Leu Asp Leu Leu Arg Asp Lys Phe Pro Gly
305                 310                 315                 320

Ala Asn Asp Phe Gly Ser Glu Val Ile Pro Gly Ala Thr Ser Ile Gly
                325                 330                 335

Leu Arg Val Gln Ala Tyr Leu Tyr Asp Gly Tyr Trp Glu Asp Ile Gly
            340                 345                 350

Thr Ile Glu Ala Phe Tyr Asn Ala Asn Leu Gly Ile Thr Lys Lys Pro
        355                 360                 365

Ile Pro Asp Phe Ser Phe Tyr Asp Arg Ser Ser Pro Ile Tyr Thr Gln
            370                 375                 380

Pro Arg Tyr Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
                405                 410                 415

Ser Val Val Gly Leu Arg Ser Cys Ile Ser Glu Gly Ala Ile Ile Glu
            420                 425                 430

Asp Thr Leu Leu Met Gly Ala Asp Tyr Tyr Glu Thr Asp Ala Asp Arg
        435                 440                 445

Arg Phe Leu Ala Ala Lys Gly Ser Val Pro Ile Gly Ile Gly Arg Asn
        450                 455                 460

Ser His Ile Lys Arg Ala Ile Ile Asp Lys Asn Ala Arg Ile Gly Asp
465                 470                 475                 480

Asn Val Lys Ile Ile Asn Ser Asp Asn Val Gln Glu Ala Ala Arg Glu
                485                 490                 495

Thr Asp Gly Tyr Phe Ile Lys Ser Gly Ile Val Thr Val Ile Lys Asp
            500                 505                 510

Ala Leu Ile Pro Ser Gly Thr Val Ile
        515                 520

<210> SEQ ID NO 95
<211> LENGTH: 524
<212> TYPE: PRT
<213> ORGANISM: Arabidopsis lyrata
<220> FEATURE:
<221> NAME/KEY: MISC_FEATURE
<222> LOCATION: (1)..(524)
<223> OTHER INFORMATION: ADP-glucose pyrophosphorylase small subunit

<400> SEQUENCE: 95

Met Ala Thr Met Ala Ala Ile Gly Ala Leu Lys Phe Pro Ser Ser Ser
1               5                   10                  15

Thr Ser Ser Ser Ser Ser Asn Leu Thr Arg Arg Ser Ser Ser Ser Leu
            20                  25                  30

Arg Lys Pro Leu Ser Phe Ser Ser Ser Leu Thr Gly Glu Lys Leu
        35                  40                  45

Ser Thr Pro Glu Lys Thr Ile Ser Asn His His Arg Arg Arg Gln Ser
    50                  55                  60

Lys Arg Thr Pro Ser Ile Ile Ser Pro Lys Ala Val Ser Asp Ser Gln
65                  70                  75                  80

Asn Ser Gln Thr Cys Leu Asp Pro Asp Ala Ser Arg Ser Val Leu Gly
                85                  90                  95
```

```
Ile Ile Leu Gly Gly Gly Ala Gly Thr Arg Leu Tyr Pro Leu Thr Lys
            100                 105                 110

Lys Arg Ala Lys Pro Ala Val Pro Leu Gly Ala Asn Tyr Arg Leu Ile
            115                 120                 125

Asp Ile Pro Val Ser Asn Cys Leu Asn Ser Asn Ile Ser Lys Ile Tyr
130                 135                 140

Val Leu Thr Gln Phe Asn Ser Ala Ser Leu Asn Arg His Leu Ser Arg
145                 150                 155                 160

Ala Tyr Ala Ser Asn Met Gly Gly Tyr Lys Asn Glu Gly Phe Val Glu
                165                 170                 175

Val Leu Ala Ala Gln Gln Ser Pro Glu Asn Pro Asn Trp Phe Gln Gly
            180                 185                 190

Thr Ala Asp Ala Val Arg Gln Tyr Leu Trp Leu Phe Glu Glu His Asn
            195                 200                 205

Val Leu Glu Phe Leu Val Leu Ala Gly Asp His Leu Tyr Arg Met Asp
            210                 215                 220

Tyr Glu Lys Phe Ile Gln Ala His Arg Glu Thr Asp Ala Asp Ile Thr
225                 230                 235                 240

Val Ala Ala Leu Pro Met Asp Glu Lys Arg Ala Thr Ala Phe Gly Leu
            245                 250                 255

Met Lys Ile Asp Asp Glu Gly Arg Ile Thr Glu Phe Ala Glu Lys Pro
            260                 265                 270

Gln Gly Glu Gln Leu Lys Ala Met Lys Val Asp Thr Thr Ile Leu Gly
            275                 280                 285

Leu Asp Asp Glu Arg Ala Lys Glu Met Pro Phe Ile Ala Ser Met Gly
            290                 295                 300

Ile Tyr Val Val Ser Lys Asn Val Met Leu Asp Leu Leu Arg Glu Gln
305                 310                 315                 320

Phe Pro Gly Ala Asn Asp Phe Gly Ser Glu Val Ile Pro Gly Ala Thr
            325                 330                 335

Ala Leu Gly Leu Arg Val Gln Ala Tyr Leu Tyr Asp Gly Tyr Trp Glu
            340                 345                 350

Asp Ile Gly Thr Ile Glu Ala Phe Tyr Asn Ala Asn Leu Gly Ile Thr
            355                 360                 365

Lys Lys Pro Val Pro Asp Phe Ser Phe Tyr Asp Arg Ser Ala Pro Ile
370                 375                 380

Tyr Thr Gln Pro Arg Tyr Leu Pro Pro Ser Lys Met Leu Asp Ala Asp
385                 390                 395                 400

Val Thr Asp Ser Val Ile Gly Glu Gly Cys Val Ile Lys Asn Cys Lys
            405                 410                 415

Ile His His Ser Val Ile Gly Leu Arg Ser Leu Ile Ser Glu Gly Ala
            420                 425                 430

Ile Ile Glu Asp Thr Leu Leu Met Gly Ala Asp Tyr Tyr Glu Thr Asp
            435                 440                 445

Ala Asp Arg Thr Leu Leu Ala Ala Lys Gly Ser Ile Pro Ile Gly Ile
            450                 455                 460

Gly Arg Asp Ser His Ile Lys Arg Ala Ile Ile Asp Lys Asn Ala Arg
465                 470                 475                 480

Ile Gly Asp Asn Val Lys Ile Ile Asn Thr Asp Asn Val Gln Glu Ala
                485                 490                 495

Ala Arg Glu Thr Asp Gly Tyr Phe Ile Lys Ser Gly Ile Val Thr Val
            500                 505                 510
```

```
Ile Lys Asp Ala Leu Ile Pro Ser Gly Thr Val Ile
        515                 520
```

<210> SEQ ID NO 96
<211> LENGTH: 521
<212> TYPE: PRT
<213> ORGANISM: Cucumis sativus
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 96

```
Met Ala Ser Ser Met Ala Ala Val Gly Val Leu Arg Leu Pro Thr Ser
1               5                   10                  15

Ser Ser Ser Ser Asn Gly Ser Asn Arg Ala Arg Arg Thr Ser Phe Arg
            20                  25                  30

Ser Leu Ser Phe Gly Ala Ser His Ile Ser Gly Asp Lys Val Asp Leu
        35                  40                  45

Arg Gly Ser Gly Leu Gly Ser Arg Arg Val Ser Gly Cys Arg Val Ala
    50                  55                  60

Pro Ser Ile Val Ser Pro Lys Ala Val Ser Asp Ser Lys Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala
            100                 105                 110

Lys Pro Ala Val Pro Leu Gly Ala Asn Tyr Arg Leu Ile Asp Ile Pro
        115                 120                 125

Val Ser Asn Cys Leu Asn Ser Asn Ile Ser Lys Ile Tyr Val Leu Thr
    130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175

Ala Gln Gln Ser Pro Glu Asn Pro Asn Trp Phe Gln Gly Thr Ala Asp
            180                 185                 190

Ala Val Arg Gln Tyr Leu Trp Leu Phe Glu Glu Gln Asn Val Leu Glu
        195                 200                 205

Phe Leu Val Leu Ala Gly Asp His Leu Tyr Arg Met Asp Tyr Glu Arg
    210                 215                 220

Phe Ile Gln Ala His Arg Glu Thr Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

Asp Glu Glu Gly Arg Ile Ile Glu Phe Ala Glu Lys Pro Lys Gly Glu
            260                 265                 270

Gln Leu Lys Ala Met Lys Val Asp Thr Thr Ile Leu Gly Leu Asp Asp
        275                 280                 285

Glu Arg Ala Lys Glu Met Pro Tyr Ile Ala Ser Met Gly Ile Tyr Val
    290                 295                 300

Ile Ser Lys Asp Val Met Leu Asn Leu Leu Arg Asp Arg Phe Pro Gly
305                 310                 315                 320

Ala Asn Asp Phe Gly Ser Glu Val Ile Pro Gly Ala Thr Ser Ile Gly
                325                 330                 335

Met Arg Val Gln Ala Tyr Leu Tyr Asp Gly Tyr Trp Glu Asp Ile Gly
```

```
                 340                 345                 350
Thr Ile Glu Ala Phe Tyr Asn Ala Asn Leu Gly Ile Thr Lys Lys Pro
            355                 360                 365

Val Pro Asp Phe Ser Phe Tyr Asp Arg Ser Ser Pro Ile Tyr Thr Gln
        370                 375                 380

Pro Arg Tyr Leu Pro Pro Ser Lys Met Leu Asp Ala Asp Ile Thr Asp
385                 390                 395                 400

Ser Val Ile Gly Glu Gly Cys Val Ile Lys Asn Cys Lys Ile His His
                405                 410                 415

Ser Val Val Gly Ile Arg Thr Cys Ile Ser Glu Gly Ala Ile Ile Glu
            420                 425                 430

Asp Thr Leu Leu Met Gly Ala Asp Tyr Tyr Glu Thr Asp Ala Asp Arg
        435                 440                 445

Arg Leu Leu Ala Ala Lys Gly Ser Val Pro Ile Gly Ile Gly Arg Asn
450                 455                 460

Ser His Ile Lys Arg Ala Ile Ile Asp Lys Asn Ala Arg Ile Gly Glu
465                 470                 475                 480

Asn Val Lys Ile Val Asn Gly Asp Asn Val Gln Glu Ala Ala Arg Glu
                485                 490                 495

Thr Asp Gly Tyr Phe Ile Lys Ser Gly Ile Val Thr Val Ile Lys Asp
            500                 505                 510

Ala Leu Ile Pro Ser Gly Thr Ile Ile
            515                 520

<210> SEQ ID NO 97
<211> LENGTH: 520
<212> TYPE: PRT
<213> ORGANISM: Arabidopsis thaliana
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 97

Met Ala Ser Val Ser Ala Ile Gly Val Leu Lys Val Pro Pro Ala Ser
1               5                   10                  15

Thr Ser Asn Ser Thr Gly Lys Ala Thr Glu Ala Val Pro Thr Arg Thr
            20                  25                  30

Leu Ser Phe Ser Ser Val Thr Ser Ser Asp Lys Ile Ser Leu
        35                  40                  45

Lys Ser Thr Val Ser Arg Leu Cys Lys Ser Val Arg Arg Asn Pro
    50                  55                  60

Ile Ile Val Ser Pro Lys Ala Val Ser Asp Ser Gln Asn Ser Gln Thr
65                  70                  75                  80

Cys Leu Asp Pro Asp Ala Ser Ser Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Ile Ser Lys Ile Tyr Val Leu Thr Gln
    130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175
```

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Tyr
        195                 200                 205

Leu Ile Leu Ala Gly Asp His Leu Tyr Arg Met Asp Tyr Glu Lys Phe
    210                 215                 220

Ile Gln Ala His Arg Glu Thr Asp Ala Asp Ile Thr Val Ala Ala Leu
225                 230                 235                 240

Pro Met Asp Glu Gln Arg Ala Thr Ala Phe Gly Leu Met Lys Ile Asp
                245                 250                 255

Glu Glu Gly Arg Ile Ile Glu Phe Ala Glu Lys Pro Lys Gly Glu His
            260                 265                 270

Leu Lys Ala Met Lys Val Asp Thr Thr Ile Leu Gly Leu Asp Asp Gln
        275                 280                 285

Arg Ala Lys Glu Met Pro Phe Ile Ala Ser Met Gly Ile Tyr Val Val
    290                 295                 300

Ser Arg Asp Val Met Leu Asp Leu Leu Arg Asn Gln Phe Pro Gly Ala
305                 310                 315                 320

Asn Asp Phe Gly Ser Glu Val Ile Pro Gly Ala Thr Ser Leu Gly Leu
                325                 330                 335

Arg Val Gln Ala Tyr Leu Tyr Asp Gly Tyr Trp Glu Asp Ile Gly Thr
            340                 345                 350

Ile Glu Ala Phe Tyr Asn Ala Asn Leu Gly Ile Thr Lys Lys Pro Val
        355                 360                 365

Pro Asp Phe Ser Phe Tyr Asp Arg Ser Ala Pro Ile Tyr Thr Gln Pro
    370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
                405                 410                 415

Val Val Gly Leu Arg Ser Cys Ile Ser Glu Gly Ala Ile Ile Glu Asp
            420                 425                 430

Ser Leu Leu Met Gly Ala Asp Tyr Tyr Glu Thr Ala Thr Glu Lys Ser
        435                 440                 445

Leu Leu Ser Ala Lys Gly Ser Val Pro Ile Gly Ile Gly Lys Asn Ser
    450                 455                 460

His Ile Lys Arg Ala Ile Ile Asp Lys Asn Ala Arg Ile Gly Asp Asn
465                 470                 475                 480

Val Lys Ile Ile Asn Ser Asp Asn Val Gln Glu Ala Ala Arg Glu Thr
                485                 490                 495

Asp Gly Tyr Phe Ile Lys Ser Gly Ile Val Thr Val Ile Lys Asp Ala
            500                 505                 510

Leu Ile Pro Thr Gly Thr Val Ile
        515                 520

<210> SEQ ID NO 98
<211> LENGTH: 509
<212> TYPE: PRT
<213> ORGANISM: Vitis labrusca x Vitis vinifera
<220> FEATURE:
<221> NAME/KEY: MISC_FEATURE
<222> LOCATION: (1)..(509)
<223> OTHER INFORMATION: ADP-glucose pyrophosphorylase small subunit

<400> SEQUENCE: 98

```
Met Ala Ser Leu Ser Ala Leu Gly Val Thr Gly Val Pro Thr Ser
1               5                   10                  15

Ser Lys Ser Arg Asp Leu Pro Ser Ser His Arg Thr Leu Ser Phe Ser
        20                  25                  30

Ser Arg Ile Ser Gly Asn Lys Ile Thr Trp Lys Ala Ser Leu Gly Ser
            35                  40                  45

His Arg Arg Ala Pro Val Ile Val Ser Pro Lys Ala Val Ser Asp Ser
    50                  55                  60

Arg Asn Ser Gln Thr Cys Leu Asp Pro Asp Ala Ser Arg Ser Val Leu
65                  70                  75                  80

Gly Ile Ile Leu Gly Gly Ala Gly Thr Arg Leu Tyr Pro Leu Thr
                85                  90                  95

Lys Lys Arg Ala Lys Pro Ala Val Pro Leu Gly Ala Asn Tyr Arg Leu
            100                 105                 110

Ile Asp Ile Pro Val Ser Asn Cys Leu Asn Ser Asn Ile Ser Lys Ile
            115                 120                 125

Tyr Val Leu Thr Gln Phe Asn Ser Ala Ser Leu Asn Arg His Leu Ser
    130                 135                 140

Arg Ala Tyr Ala Ser Asn Met Gly Gly Tyr Lys Asn Glu Gly Phe Val
145                 150                 155                 160

Glu Val Leu Ala Ala Gln Gln Ser Pro Glu Asn Pro Asn Trp Phe Gln
                165                 170                 175

Gly Thr Ala Asp Ala Val Arg Gln Tyr Leu Trp Leu Phe Glu His
                180                 185                 190

Asn Val Leu Glu Phe Leu Val Leu Ala Gly Asp His Leu Tyr Arg Met
        195                 200                 205

Asp Tyr Glu Arg Phe Ile Gln Ala His Arg Glu Thr Asp Ala Asp Ile
    210                 215                 220

Thr Val Ala Ala Leu Pro Met Asp Glu Lys Arg Ala Thr Ala Phe Gly
225                 230                 235                 240

Leu Met Lys Ile Asp Glu Glu Gly Arg Ile Ile Glu Phe Ala Glu Lys
                245                 250                 255

Pro Lys Gly Glu Gln Leu Lys Ala Met Lys Val Asp Thr Thr Ile Leu
            260                 265                 270

Gly Leu Asp Asp Glu Arg Ala Lys Glu Met Pro Tyr Ile Ala Ser Met
            275                 280                 285

Gly Ile Tyr Val Val Ser Lys Asp Val Met Leu Asp Leu Leu Arg Asp
    290                 295                 300

Gln Phe Pro Gly Ala Asn Asp Phe Gly Ser Glu Val Ile Pro Gly Ala
305                 310                 315                 320

Thr Ser Leu Gly Leu Arg Val Gln Ala Tyr Leu Tyr Asp Gly Tyr Trp
                325                 330                 335

Glu Asp Ile Gly Thr Ile Glu Ala Phe Tyr Asn Ala Asn Leu Gly Ile
            340                 345                 350

Thr Lys Lys Pro Val Pro Asp Phe Ser Phe Tyr Asp Arg Ser Ser Pro
            355                 360                 365

Ile Tyr Thr Gln Pro Arg Tyr Leu Pro Pro Ser Lys Met Leu Asp Ala
    370                 375                 380

Asp Val Thr Asp Ser Val Ile Gly Glu Gly Cys Val Ile Lys Asn Cys
385                 390                 395                 400

Lys Ile His His Ser Val Val Gly Leu Arg Ser Cys Ile Ser Glu Gly
                405                 410                 415

Ala Ile Ile Glu Asp Thr Leu Leu Met Gly Ala Asp Tyr Tyr Glu Thr
```

```
                420              425              430
Asp Ala Asp Arg Arg Phe Leu Met Ala Lys Gly Ser Val Pro Ile Gly
            435              440              445

Ile Gly Lys Asn Ser His Ile Lys Arg Ala Ile Ile Asp Lys Asn Ala
450              455              460

Arg Ile Gly Asp Asn Val Lys Ile Ile Asn Gly Asp Asn Val Gln Glu
465              470              475              480

Ala Ala Arg Glu Thr Asp Gly Tyr Phe Ile Arg Ser Gly Ile Val Thr
            485              490              495

Val Ile Lys Asp Ala Leu Leu Pro Ser Gly Thr Ile Ile
            500              505
```

<210> SEQ ID NO 99
<211> LENGTH: 522
<212> TYPE: PRT
<213> ORGANISM: Populus euphratica
<220> FEATURE:
<221> NAME/KEY: MISC_FEATURE
<222> LOCATION: (1)..(522)
<223> OTHER INFORMATION: ADP-glucose pyrophosphorylase small subunit

<400> SEQUENCE: 99

```
Met Ala Ser Met Ala Ala Ile Gly Val Met Arg Pro Pro Ser Ser Ser
1               5                   10                  15

Ser Leu Ser Ser Ser Ser Ser Ser Leu Ser Arg Arg Thr Ala Phe
            20                  25                  30

Arg Ser Leu Ser Phe Ser Ala Ser Ser Asn Leu Ser Gly Glu Lys Val
            35                  40                  45

Cys Ser Thr Ala Phe Ser Val Arg Arg Asp Thr Gly Arg Asn Glu Arg
    50                  55                  60

Thr Pro Met Ile Val Ser Pro Lys Ala Val Ser Asp Ser Arg Asn Ser
65                  70                  75                  80

Gln Thr Cys Leu Asp Pro Asp Ala Ser Arg Ser Val Leu Gly Ile Ile
                85                  90                  95

Leu Gly Gly Gly Ala Gly Thr Arg Leu Tyr Pro Leu Thr Lys Lys Arg
            100                 105                 110

Ala Lys Pro Ala Val Pro Leu Gly Ala Asn Tyr Arg Leu Ile Asp Ile
            115                 120                 125

Pro Val Ser Asn Cys Leu Asn Ser Asn Ile Ser Lys Ile Tyr Val Leu
        130                 135                 140

Thr Gln Phe Asn Ser Ala Ser Leu Asn Arg His Leu Ser Arg Ala Tyr
145                 150                 155                 160

Ala Ser Asn Met Gly Gly Tyr Lys Asn Glu Gly Phe Val Glu Val Leu
                165                 170                 175

Ala Ala Gln Gln Ser Pro Glu Asn Pro Asn Trp Phe Gln Gly Thr Ala
            180                 185                 190

Asp Ala Val Arg Gln Tyr Leu Trp Leu Phe Glu Glu His Asn Val Leu
            195                 200                 205

Glu Phe Leu Val Leu Ala Gly Asp His Leu Tyr Arg Met Asp Tyr Glu
    210                 215                 220

Arg Phe Ile Gln Ala His Arg Glu Thr Asp Ala Asp Ile Thr Val Ala
225                 230                 235                 240

Ala Leu Pro Met Asp Glu Lys Arg Ala Thr Ala Phe Gly Leu Met Lys
                245                 250                 255

Ile Asp Glu Glu Gly Arg Ile Ile Glu Phe Ala Glu Lys Pro Lys Gly
            260                 265                 270
```

Glu Gln Leu Lys Ala Met Lys Val Asp Thr Thr Ile Leu Gly Leu Asp
            275                 280                 285

Asp Glu Arg Ala Lys Glu Met Pro Tyr Ile Ala Ser Met Gly Ile Tyr
290                 295                 300

Val Val Ser Lys Asn Val Met Met Asp Leu Leu Arg Glu Lys Phe Pro
305                 310                 315                 320

Gly Ala Asn Asp Phe Gly Ser Glu Val Ile Pro Gly Ala Thr Ser Ile
                325                 330                 335

Gly Met Arg Val Gln Ala Tyr Leu Tyr Asp Gly Tyr Trp Glu Asp Ile
            340                 345                 350

Gly Thr Ile Glu Ala Phe Tyr Asn Ala Asn Leu Gly Ile Thr Lys Lys
            355                 360                 365

Pro Val Pro Asp Phe Ser Phe Tyr Asp Arg Ser Ser Pro Ile Tyr Thr
            370                 375                 380

Gln Pro Arg Tyr Leu Pro Pro Ser Lys Met Leu Asp Ala Asp Val Thr
385                 390                 395                 400

Asp Ser Val Ile Gly Glu Gly Cys Val Ile Lys Asn Cys Lys Ile His
                405                 410                 415

His Ser Val Ile Gly Leu Arg Ser Cys Ile Ser Glu Gly Ala Ile Val
            420                 425                 430

Glu Asp Thr Leu Leu Met Gly Ala Asp Tyr Tyr Glu Thr Asp Ala Asp
            435                 440                 445

Arg Arg Phe Leu Ala Ala Lys Gly Ser Val Pro Ile Gly Ile Gly Lys
450                 455                 460

Asn Ser His Val Lys Arg Ala Ile Ile Asp Lys Asn Ala Arg Ile Gly
465                 470                 475                 480

Asp Asn Val Lys Ile Ile Asn Gly Asp Asn Val Gln Glu Ala Ala Arg
                485                 490                 495

Glu Thr Asp Gly Tyr Phe Ile Lys Ser Gly Ile Val Thr Val Ile Lys
            500                 505                 510

Asp Ala Leu Ile Pro Ser Gly Thr Val Ile
            515                 520

<210> SEQ ID NO 100
<211> LENGTH: 505
<212> TYPE: PRT
<213> ORGANISM: Actinidia chinensis
<220> FEATURE:
<221> NAME/KEY: MISC_FEATURE
<222> LOCATION: (1)..(505)
<223> OTHER INFORMATION: ADP-glucose pyrophosphorylase small subunit

<400> SEQUENCE: 100

Met Ala Ala Ile Gly Val Leu Lys Val Pro His Arg Thr Ala Asn Val
1               5                   10                  15

Thr Gly Glu Arg Ala Thr Leu Arg Ser Thr Pro Phe Arg Arg Leu Ser
            20                  25                  30

Leu Ala Gly Gly Lys Ile Ser Pro Lys Leu Ala Ser Pro Arg Arg Arg
        35                  40                  45

Ser Ala Thr Phe Ser Pro Lys Ala Val Ser Asp Ser Gln Asn Ser Gln
    50                  55                  60

Thr Cys Leu Asp Pro Asp Ala Ser Arg Ser Val Leu Gly Ile Ile Leu
65                  70                  75                  80

Gly Gly Gly Ala Gly Thr Arg Leu Tyr Pro Leu Thr Lys Lys Arg Ala
                85                  90                  95

```
Lys Pro Ala Val Pro Leu Gly Ala Asn Tyr Arg Leu Ile Asp Ile Pro
            100                 105                 110

Val Ser Asn Cys Leu Asn Ser Asn Ile Ser Lys Ile Tyr Val Leu Thr
            115                 120                 125

Gln Phe Asn Ser Ala Ser Leu Asn Arg His Leu Ser Arg Ala Tyr Ala
            130                 135                 140

Ser Asn Met Gly Gly Tyr Lys Asn Glu Gly Phe Val Glu Val Leu Ala
145                 150                 155                 160

Ala Gln Gln Ser Pro Glu Asn Pro Asn Trp Phe Gln Gly Thr Ala Asp
                165                 170                 175

Ala Val Arg Gln Tyr Leu Trp Leu Phe Glu Glu His Asn Val Leu Glu
            180                 185                 190

Phe Leu Val Leu Ala Gly Asp His Leu Tyr Arg Met Asp Tyr Glu Arg
            195                 200                 205

Phe Ile Gln Ala His Arg Glu Thr Asp Ala Asp Ile Thr Val Ala Ala
            210                 215                 220

Leu Pro Met Asp Glu Lys Arg Ala Thr Ala Phe Gly Leu Met Lys Ile
225                 230                 235                 240

Asp Glu Glu Gly Arg Ile Ile Glu Phe Ala Glu Lys Pro Lys Gly Glu
                245                 250                 255

Gln Leu Lys Ala Met Lys Val Asp Thr Thr Ile Leu Gly Leu Asp Asp
            260                 265                 270

Glu Arg Ala Lys Glu Met Pro Tyr Ile Ala Ser Met Gly Ile Tyr Val
            275                 280                 285

Val Ser Lys Asp Val Met Leu Asn Leu Leu Arg Asp Lys Phe Pro Gly
290                 295                 300

Ala Asn Asp Phe Gly Ser Glu Val Ile Pro Gly Ala Thr Ser Ile Gly
305                 310                 315                 320

Met Arg Val Gln Ala Tyr Leu Tyr Asp Gly Tyr Trp Glu Asp Ile Gly
            325                 330                 335

Thr Ile Glu Ala Phe Tyr Asn Ala Asn Leu Gly Ile Thr Lys Lys Pro
            340                 345                 350

Val Pro Asp Phe Ser Phe Tyr Asp Arg Ser Ala Pro Ile Tyr Thr Gln
            355                 360                 365

Pro Arg Tyr Leu Pro Pro Ser Lys Met Leu Asp Ala Asp Val Thr Asp
370                 375                 380

Ser Val Ile Gly Glu Gly Cys Val Ile Lys Asn Cys Lys Ile His His
385                 390                 395                 400

Ser Val Val Gly Leu Arg Ser Cys Ile Ser Glu Gly Ala Ile Ile Glu
            405                 410                 415

Asp Ser Leu Leu Met Gly Ala Asp Tyr Tyr Glu Thr Asp Ala Asp Arg
            420                 425                 430

Arg Phe Leu Ala Ala Lys Gly Ser Val Pro Ile Gly Ile Gly Lys Asn
            435                 440                 445

Ser His Ile Lys Arg Ala Ile Ile Asp Lys Asn Ala Arg Ile Gly Asp
            450                 455                 460

Asp Val Lys Ile Ile Asn Ser Asp Asn Ile Gln Glu Ala Ala Arg Glu
465                 470                 475                 480

Thr Asp Gly Tyr Phe Ile Lys Ser Gly Ile Val Thr Val Ile Lys Asp
                485                 490                 495

Ala Leu Ile Pro Ser Gly Thr Val Ile
            500                 505
```

```
<210> SEQ ID NO 101
<211> LENGTH: 526
<212> TYPE: PRT
<213> ORGANISM: Cucumis melo
<220> FEATURE:
<221> NAME/KEY: MISC_FEATURE
<222> LOCATION: (1)..(526)
<223> OTHER INFORMATION: ADP-glucose pyrophosphorylase small subunit

<400> SEQUENCE: 101
```

| Met | Ala | Ser | Ser | Met | Ala | Ala | Val | Gly | Val | Leu | Arg | Leu | Pro | Thr | Ser |
|---|---|---|---|---|---|---|---|---|---|---|---|---|---|---|---|
| 1 | | | | 5 | | | | | 10 | | | | | 15 | |

Ser Ser Ser Ser Ser Ser Ser Asn Gly Gly Ser Asn Arg Ala Arg
            20                  25                  30

Arg Thr Ser Leu Arg Ser Leu Ser Phe Gly Ala Ser Gln Ile Ser Gly
            35                  40                  45

Asp Lys Ile Asp Phe Arg Gly Phe Gly Leu Gly Ser Arg Arg Val Ser
 50                  55                  60

Gly Gly Arg Val Ala Pro Ser Ile Val Ser Pro Lys Ala Val Ser Asp
 65                  70                  75                  80

Ser Lys Asn Ser Gln Thr Cys Leu Asp Pro Asp Ala Ser Arg Ser Val
                85                  90                  95

Leu Gly Ile Ile Leu Gly Gly Gly Ala Gly Thr Arg Leu Tyr Pro Leu
            100                 105                 110

Thr Lys Lys Arg Ala Lys Pro Ala Val Pro Leu Gly Ala Asn Tyr Arg
            115                 120                 125

Leu Ile Asp Ile Pro Val Ser Asn Cys Leu Asn Ser Asn Ile Ser Lys
    130                 135                 140

Ile Tyr Val Leu Thr Gln Phe Asn Ser Ala Ser Leu Asn Arg His Leu
145                 150                 155                 160

Ser Arg Ala Tyr Ala Ser Asn Met Gly Gly Tyr Lys Asn Glu Gly Phe
                165                 170                 175

Val Glu Val Leu Ala Ala Gln Gln Ser Pro Glu Asn Pro Asn Trp Phe
            180                 185                 190

Gln Gly Thr Ala Asp Ala Val Arg Gln Tyr Leu Trp Leu Phe Glu Glu
            195                 200                 205

Gln Asn Val Leu Glu Tyr Leu Val Leu Ala Gly Asp His Leu Tyr Arg
    210                 215                 220

Met Asp Tyr Glu Arg Phe Ile Gln Ala His Arg Glu Thr Asp Ala Asp
225                 230                 235                 240

Ile Thr Val Ala Ala Leu Pro Met Asp Glu Lys Arg Ala Thr Ala Phe
                245                 250                 255

Gly Leu Met Lys Ile Asp Glu Glu Gly Arg Ile Ile Glu Phe Ala Glu
            260                 265                 270

Lys Pro Lys Gly Glu Gln Leu Lys Ala Met Lys Val Asp Thr Thr Ile
            275                 280                 285

Leu Gly Leu Asp Asp Glu Arg Ala Lys Glu Met Pro Tyr Ile Ala Ser
    290                 295                 300

Met Gly Ile Tyr Val Ile Ser Lys Asp Val Met Leu Asn Leu Leu Arg
305                 310                 315                 320

Asp Lys Phe Pro Gly Ala Asn Asp Phe Gly Ser Glu Val Ile Pro Gly
                325                 330                 335

Ala Thr Ser Ile Gly Met Arg Val Gln Ala Tyr Leu Tyr Asp Gly Tyr
            340                 345                 350

Trp Glu Asp Ile Gly Thr Ile Glu Ala Phe Tyr Asn Ala Asn Leu Gly
            355                 360                 365

```
Ile Thr Lys Lys Pro Val Pro Asp Phe Ser Phe Tyr Asp Arg Ser Ser
    370                 375                 380

Pro Ile Tyr Thr Gln Pro Arg Tyr Leu Pro Pro Ser Lys Met Leu Asp
385                 390                 395                 400

Ala Asp Ile Thr Asp Ser Val Ile Gly Glu Gly Cys Val Ile Lys Asn
                405                 410                 415

Cys Lys Ile His His Ser Val Val Gly Ile Arg Thr Cys Ile Ser Glu
            420                 425                 430

Gly Ala Ile Ile Glu Asp Thr Leu Leu Met Gly Ala Asp Tyr Tyr Glu
        435                 440                 445

Thr Asp Ala Asp Arg Arg Leu Leu Ala Ala Lys Gly Ser Val Pro Ile
    450                 455                 460

Gly Ile Gly Arg Asn Ser His Ile Lys Arg Ala Ile Ile Asp Lys Asn
465                 470                 475                 480

Ala Arg Ile Gly Glu Asn Val Lys Ile Val Asn Gly Asp Asn Val Gln
                485                 490                 495

Glu Ala Ala Arg Glu Thr Asp Gly Tyr Phe Ile Lys Ser Gly Ile Val
            500                 505                 510

Thr Val Ile Lys Asp Ala Leu Ile Pro Ser Gly Thr Ile Ile
        515                 520                 525

<210> SEQ ID NO 102
<211> LENGTH: 515
<212> TYPE: PRT
<213> ORGANISM: Cajanus cajan
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 102

Met Ala Ser Met Ala Ala Ile Gly Ser Leu Asn Val Pro Cys Ser Ala
1               5                   10                  15

Ser Ser Cys Ser Ser Asn Val Gly Arg Lys Ser Val Pro Arg Ser Leu
            20                  25                  30

Ser Phe Ser Ala Ser Gln Leu Ser Gly Asp Lys Ile Ser Thr Asp Ser
        35                  40                  45

Leu Ser Leu Pro Pro Lys Arg Val Arg Asn Pro Val Ile Val Ser Pro
    50                  55                  60

Lys Ala Val Ser Asp Ser Gln Asn Ser Gln Thr Cys Leu Asp Pro Asp
65                  70                  75                  80

Ala Ser Arg Ser Val Leu Gly Ile Ile Leu Gly Gly Gly Ala Gly Thr
                85                  90                  95

Arg Leu Tyr Pro Leu Thr Lys Lys Arg Ala Lys Pro Ala Val Pro Leu
            100                 105                 110

Gly Ala Asn Tyr Arg Leu Ile Asp Ile Pro Val Ser Asn Cys Leu Asn
        115                 120                 125

Ser Asn Val Ser Lys Ile Tyr Val Leu Thr Gln Phe Asn Ser Ala Ser
    130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
            180                 185                 190
```

```
Trp Leu Phe Glu Glu His Asn Val Leu Glu Phe Leu Val Leu Ala Gly
            195                 200                 205

Asp His Leu Tyr Arg Met Asp Tyr Glu Lys Phe Ile Gln Ala His Arg
        210                 215                 220

Glu Thr Asp Ala Asp Ile Thr Val Ala Ala Leu Pro Met Asp Glu Lys
225                 230                 235                 240

Arg Ala Thr Ala Phe Gly Leu Met Lys Ile Asp Glu Glu Gly Arg Ile
                245                 250                 255

Ile Gln Phe Ala Glu Lys Pro Lys Gly Asp Gln Leu Lys Ala Met Lys
            260                 265                 270

Val Asp Thr Thr Ile Leu Gly Leu Asp Asp Glu Arg Ala Lys Glu Met
        275                 280                 285

Pro Phe Ile Ala Ser Met Gly Ile Tyr Val Val Ser Lys Ser Val Met
290                 295                 300

Leu Asp Leu Leu Arg Glu Lys Phe Pro Gly Ala Asn Asp Phe Gly Ser
305                 310                 315                 320

Glu Val Ile Pro Gly Ala Thr Ser Leu Gly Leu Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
        355                 360                 365

Tyr Asp Arg Ser Ser Pro Ile Tyr Thr Gln Pro Arg Tyr Leu Pro Pro
    370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Glu Thr Leu Leu Met Gly
            420                 425                 430

Ala Asp Tyr Tyr Glu Thr Asp Ala Asp Lys Arg Phe Leu Ala Ala Lys
        435                 440                 445

Gly Ser Val Pro Ile Gly Ile Gly Arg Asn Ser His Ile Arg Arg Ala
450                 455                 460

Ile Ile Asp Lys Asn Ala Arg Ile Gly Glu Asn Val Lys Ile Leu Asn
465                 470                 475                 480

Ser Asp Asn Val Gln Glu Ala Ser Arg Glu Thr Asp Gly Tyr Phe Ile
                485                 490                 495

Lys Ser Gly Ile Val Thr Val Leu Lys Asp Ala Leu Ile Pro Ser Gly
            500                 505                 510

Thr Val Ile
        515

<210> SEQ ID NO 103
<211> LENGTH: 516
<212> TYPE: PRT
<213> ORGANISM: Pisum sativum
<220> FEATURE:
<221> NAME/KEY: MISC_FEATURE
<222> LOCATION: (1)..(516)
<223> OTHER INFORMATION: ADP-glucose pyrophosphorylase small subunit

<400> SEQUENCE: 103

Met Ala Ser Met Ala Ala Ile Gly Val Leu Lys Val Pro Pro Ser Ser
1               5                   10                  15

Ser Ser Ser Ser Ser Ser Ser Ser Ser Ser Lys Ala Ile Ala Arg
```

```
                  20                  25                  30
Asn Leu Ser Phe Thr Ser Ser Gln Leu Cys Gly Asp Lys Ile Phe Thr
             35                  40                  45

Val Ser Gly Thr Arg Arg Ser Ser Gly Arg Asn Pro Phe Ile Val Ser
         50                  55                  60

Pro Lys Ala Val Ser Asp Ser Lys Asn Ser Gln Thr Cys Leu Asp Pro
 65                  70                  75                  80

Asp Ala Ser Arg Ser Val Leu Gly Ile Ile Leu Gly Gly Gly Ala Gly
                 85                  90                  95

Thr Arg Leu Tyr Pro Leu Thr Lys Lys Arg Ala Lys Pro Ala Val Pro
             100                 105                 110

Leu Gly Ala Asn Tyr Arg Leu Ile Asp Ile Pro Val Ser Asn Cys Leu
         115                 120                 125

Asn Ser Asn Ile Ser Lys Ile Tyr Val Leu Thr Gln Phe Asn Ser Ala
130                 135                 140

Ser Leu Asn Arg His Leu Ser Arg Ala Tyr Ala Ser Asn Leu Gly Gly
145                 150                 155                 160

Tyr Lys Asn Glu Gly Phe Val Glu Val Leu Ala Ala Gln Gln Ser Pro
                 165                 170                 175

Glu Asn Pro Asn Trp Phe Gln Gly Thr Ala Asp Ala Val Arg Gln Tyr
             180                 185                 190

Leu Trp Leu Phe Glu Glu His Asn Val Leu Glu Tyr Leu Val Leu Ala
         195                 200                 205

Gly Asp His Leu Tyr Arg Met Asp Tyr Glu Arg Phe Ile Gln Ala His
         210                 215                 220

Arg Glu Ser Asp Ala Asp Ile Thr Val Ala Ser Leu Pro Met Asp Glu
225                 230                 235                 240

Ala Arg Ala Thr Ala Phe Gly Leu Met Lys Ile Asp Glu Glu Gly Arg
                 245                 250                 255

Ile Val Glu Phe Ser Glu Lys Pro Lys Gly Glu Gln Leu Lys Ala Met
             260                 265                 270

Lys Val Asp Thr Thr Ile Leu Gly Leu Asp Asp Glu Arg Ala Lys Glu
         275                 280                 285

Met Pro Tyr Ile Ala Ser Met Gly Ile Tyr Val Val Ser Lys His Val
         290                 295                 300

Met Leu Asp Leu Leu Arg Asp Lys Phe Pro Gly Ala Asn Asp Phe Gly
305                 310                 315                 320

Ser Glu Val Ile Pro Gly Ala Thr Glu Leu Gly Leu Arg Val Gln Ala
                 325                 330                 335

Tyr Leu Tyr Asp Gly Tyr Trp Glu Asp Ile Gly Thr Ile Glu Ala Phe
             340                 345                 350

Tyr Asn Ala Asn Leu Gly Ile Thr Lys Lys Pro Val Pro Asp Phe Ser
         355                 360                 365

Phe Tyr Asp Arg Ser Ser Pro Ile Tyr Thr Gln Pro Arg Tyr Leu Pro
         370                 375                 380

Pro Ser Lys Met Leu Asp Ala Asp Ile Thr Asp Ser Val Ile Gly Glu
385                 390                 395                 400

Gly Cys Val Ile Lys Asn Cys Lys Ile His His Ser Val Val Gly Leu
                 405                 410                 415

Arg Ser Cys Ile Ser Glu Gly Ala Ile Ile Glu Asp Thr Leu Leu Met
             420                 425                 430

Gly Ala Asp Tyr Tyr Glu Thr Asp Ala Asp Arg Arg Phe Leu Ala Ala
         435                 440                 445
```

```
Lys Gly Gly Val Pro Ile Gly Ile Gly Lys Asn Ser His Ile Lys Arg
            450                 455                 460

Ala Ile Ile Asp Lys Asn Ala Arg Ile Gly Asp Asp Val Lys Ile Ile
465                 470                 475                 480

Asn Ser Asp Asn Val Gln Glu Ala Ala Arg Glu Thr Glu Gly Tyr Phe
                485                 490                 495

Ile Lys Ser Gly Ile Val Thr Val Ile Lys Asp Ala Leu Ile Pro Ser
            500                 505                 510

Gly Thr Val Ile
            515

<210> SEQ ID NO 104
<211> LENGTH: 517
<212> TYPE: PRT
<213> ORGANISM: Coffea canephora
<220> FEATURE:
<221> NAME/KEY: MISC_FEATURE
<222> LOCATION: (1)..(517)
<223> OTHER INFORMATION: ADP-glucose pyrophosphorylase small subunit

<400> SEQUENCE: 104

Met Ala Ala Val Gly Ser Ser Val Arg Ile Ser Pro Tyr Tyr Asn His
1               5                   10                  15

Lys Asn Cys Asn Ala Gly Thr Asp Gly Asp Phe Ser Arg Arg Leu Ser
            20                  25                  30

Phe Ser Ser Val Ser Ser Asn Ala Phe Gly Glu Lys Leu Ile Ala Ser
        35                  40                  45

Val Ala Gln Gly Arg Arg Arg Pro Glu Ser Arg Lys Pro Leu Ile Val
    50                  55                  60

Ser Pro Lys Ala Val Ser Asp Ser Gln Asn Ser Gln Thr Cys Leu Asp
65                  70                  75                  80

Pro Asp Ala Ser Arg Ser Val Leu Gly Ile Ile Leu Gly Gly Gly Ala
                85                  90                  95

Gly Thr Arg Leu Tyr Pro Leu Thr Lys Lys Arg Ala Lys Pro Ala Val
            100                 105                 110

Pro Leu Gly Ala Asn Tyr Arg Leu Ile Asp Ile Pro Val Ser Asn Cys
        115                 120                 125

Leu Asn Ser Asn Ile Ser Lys Ile Tyr Val Leu Thr Gln Phe Asn Ser
    130                 135                 140

Ala Ser Leu Asn Arg His Leu Ser Arg Ala Tyr Ala Ser Asn Met Gly
145                 150                 155                 160

Gly Tyr Lys Asn Glu Gly Phe Val Glu Val Leu Ala Ala Gln Gln Ser
                165                 170                 175

Pro Glu Asn Pro Asn Trp Phe Gln Gly Thr Ala Asp Ala Val Arg Gln
            180                 185                 190

Tyr Leu Trp Leu Phe Glu Glu His Asn Val Leu Glu Phe Leu Val Leu
        195                 200                 205

Ala Gly Asp His Leu Tyr Arg Met Asp Tyr Glu Arg Phe Ile Gln Ala
    210                 215                 220

His Arg Glu Thr Asp Ala Asp Ile Thr Val Ala Ala Leu Pro Met Asp
225                 230                 235                 240

Glu Lys Arg Ala Thr Ala Phe Gly Leu Met Lys Ile Asp Glu Glu Gly
                245                 250                 255

Arg Ile Ile Glu Phe Ala Glu Lys Pro Lys Gly Glu Gln Leu Lys Ala
            260                 265                 270
```

```
Met Met Val Asp Thr Thr Ile Leu Gly Leu Asp Asp Glu Arg Ala Lys
            275                 280                 285

Glu Met Pro Tyr Ile Ala Ser Met Gly Ile Tyr Val Ile Ser Lys Asp
        290                 295                 300

Val Met Ile Ser Leu Leu Arg Glu Thr Phe Pro Gly Ala Asn Asp Phe
305                 310                 315                 320

Gly Ser Glu Val Ile Pro Gly Ala Thr Thr Leu Gly Leu Arg Val Gln
                325                 330                 335

Ala Tyr Leu Tyr Asp Gly Tyr Trp Glu Asp Ile Gly Thr Ile Glu Ala
            340                 345                 350

Phe Tyr Asn Ala Asn Leu Gly Ile Thr Lys Lys Pro Val Pro Asp Phe
        355                 360                 365

Ser Phe Tyr Asp Arg Ser Ala Pro Ile Tyr Thr Gln Pro Arg Tyr Leu
    370                 375                 380

Pro Pro Ser Lys Met Leu Asp Ala Asp Val Thr Asp Ser Val Ile Gly
385                 390                 395                 400

Glu Gly Cys Val Ile Lys Asn Cys Lys Ile His His Ser Val Val Gly
                405                 410                 415

Leu Arg Ser Cys Ile Ser Glu Gly Ala Ile Ile Glu Asp Ser Leu Leu
            420                 425                 430

Met Gly Ala Asp Tyr Tyr Glu Thr Asp Ala Asp Arg Arg Phe Leu Ala
        435                 440                 445

Ala Lys Gly Ser Val Pro Ile Gly Ile Gly Lys His Ser His Ile Lys
    450                 455                 460

Arg Ala Ile Ile Asp Lys Asn Ala Arg Ile Gly Asp Asp Val Lys Ile
465                 470                 475                 480

Ile Asn Gly Asp Asn Val Gln Glu Ala Ala Arg Glu Thr Asp Gly Tyr
                485                 490                 495

Phe Ile Lys Ser Gly Ile Val Thr Val Val Lys Asp Ala Leu Ile Pro
            500                 505                 510

Ser Gly Thr Val Ile
        515

<210> SEQ ID NO 105
<211> LENGTH: 525
<212> TYPE: PRT
<213> ORGANISM: Erythranthe guttata
<220> FEATURE:
<221> NAME/KEY: MISC_FEATURE
<222> LOCATION: (1)..(525)
<223> OTHER INFORMATION: ADP-glucose pyrophosphorylase small subunit

<400> SEQUENCE: 105

Met Ala Ala Thr Ser Val Met Lys Leu Ser Pro Ser Ala Thr Ala Val
1               5                   10                  15

Ala Asn Tyr Lys Ser Ala Glu Asp Ser Asn Ser Thr Thr Phe Thr Arg
            20                  25                  30

Leu Ser Phe Ala Ala Ser Asn Val Ser Gly Glu Ser Ile Thr Ala Ala
        35                  40                  45

Ser Pro Arg Gln Leu Arg Ile Arg Arg Arg Ser Gly Asp Glu Leu
    50                  55                  60

Glu Arg Arg Ser Pro Val Ile Val Ser Pro Lys Ala Val Ser Asp Ser
65                  70                  75                  80

Gln Asn Ser Gln Thr Cys Leu Asp Pro Asp Ala Ser Arg Ser Val Leu
                85                  90                  95

Gly Ile Ile Leu Gly Gly Gly Ala Gly Thr Arg Leu Tyr Pro Leu Thr
```

```
            100                 105                 110
Lys Lys Arg Ala Lys Pro Ala Val Pro Leu Gly Ala Asn Tyr Arg Leu
            115                 120                 125

Ile Asp Ile Pro Val Ser Asn Cys Leu Asn Ser Asn Ile Ser Lys Ile
    130                 135                 140

Tyr Val Leu Thr Gln Phe Asn Ser Ala Ser Leu Asn Arg His Leu Ser
145                 150                 155                 160

Arg Ala Tyr Ala Ser Asn Met Gly Gly Tyr Lys Asn Glu Gly Phe Val
                165                 170                 175

Glu Val Leu Ala Ala Gln Gln Ser Pro Glu Asn Pro Asn Trp Phe Gln
        180                 185                 190

Gly Thr Ala Asp Ala Val Arg Gln Tyr Leu Trp Leu Phe Glu Glu His
            195                 200                 205

Asn Ile Leu Glu Phe Leu Ile Leu Ala Gly Asp His Leu Tyr Arg Met
210                 215                 220

Asp Tyr Glu Arg Phe Ile Gln Ala His Arg Glu Thr Asp Ala Asp Ile
225                 230                 235                 240

Thr Val Ala Ala Leu Pro Met Asp Glu Lys Arg Ala Glu Ser Phe Gly
                245                 250                 255

Leu Met Lys Ile Asp Glu Glu Gly Arg Ile Val Glu Phe Ala Glu Lys
            260                 265                 270

Pro Lys Gly Glu Lys Leu Lys Ser Met Lys Val Asp Thr Thr Ile Leu
        275                 280                 285

Gly Leu Asp Asp Glu Arg Ala Lys Glu Met Pro Tyr Ile Ala Ser Met
    290                 295                 300

Gly Ile Tyr Val Val Ser Lys Asp Val Met Ile Asn Leu Leu Arg Asp
305                 310                 315                 320

Lys Phe Pro Ser Ala Asn Asp Phe Gly Ser Glu Val Ile Pro Gly Ala
                325                 330                 335

Thr Ala Met Gly Leu Arg Val Gln Ala Tyr Leu Phe Glu Gly Tyr Trp
            340                 345                 350

Glu Asp Ile Gly Thr Ile Glu Ala Phe Tyr Asn Ala Asn Leu Gly Ile
        355                 360                 365

Thr Lys Lys Pro Val Pro Asp Phe Ser Phe Tyr Asp Arg Ser Ala Pro
    370                 375                 380

Ile Tyr Thr Gln Pro Arg Tyr Leu Pro Pro Ser Lys Met Leu Asp Ala
385                 390                 395                 400

Asp Val Thr Asp Ser Val Ile Gly Glu Gly Cys Val Ile Lys Asn Cys
                405                 410                 415

Lys Ile His His Ser Val Val Gly Leu Arg Ser Cys Ile Ser Glu Gly
            420                 425                 430

Ala Val Ile Glu Asp Thr Leu Leu Met Gly Ala Asp Tyr Tyr Glu Thr
        435                 440                 445

Asp Ala Asp Arg Arg Leu Leu Ala Ala Lys Gly Ser Val Pro Ile Gly
    450                 455                 460

Ile Gly Lys Asn Thr His Ile Lys Arg Ala Ile Ile Asp Lys Asn Ala
465                 470                 475                 480

Arg Ile Gly Glu Asn Val Lys Ile Ile Asn Ser Asp Asn Val Gln Glu
                485                 490                 495

Ala Ala Arg Glu Ala Glu Gly Tyr Phe Ile Lys Ser Gly Ile Val Thr
            500                 505                 510

Val Ile Lys Asp Ala Leu Ile Pro Ser Gly Ile Val Ile
        515                 520                 525
```

<210> SEQ ID NO 106
<211> LENGTH: 523
<212> TYPE: PRT
<213> ORGANISM: Sesamum indicum
<220> FEATURE:
<221> NAME/KEY: MISC_FEATURE
<222> LOCATION: (1)..(523)
<223> OTHER INFORMATION: ADP-glucose pyrophosphorylase small subunit

<400> SEQUENCE: 106

```
Met Ala Ala Thr Ala Val Leu Arg Leu Val Pro Asn Ala Thr Val Val
1               5                   10                  15

Val Asn His Arg Gly Val Glu Asp Val Asn Ser Ala Ser Phe Thr Arg
            20                  25                  30

Leu Ser Phe Ala Ala Ser Asn Val Ala Gly Glu Ser Leu Lys Ser Ser
        35                  40                  45

Arg Gln Val Arg Val Arg Gln Arg Ser Gly Gly Asp Leu Glu Ser
    50                  55                  60

Arg Gly Pro Met Ile Val Ser Pro Lys Ala Val Ser Asp Ser Gln Asn
65                  70                  75                  80

Ser Gln Thr Cys Leu Asp Pro Asp Ala Ser Arg Ser Val Leu Gly Ile
                85                  90                  95

Ile Leu Gly Gly Gly Ala Gly Thr Arg Leu Tyr Pro Leu Thr Lys Lys
            100                 105                 110

Arg Ala Lys Pro Ala Val Pro Leu Gly Ala Asn Tyr Arg Leu Ile Asp
        115                 120                 125

Ile Pro Val Ser Asn Cys Leu Asn Ser Asn Ile Ser Lys Ile Tyr Val
    130                 135                 140

Leu Thr Gln Phe Asn Ser Ala Ser Leu Asn Arg His Leu Ser Arg Ala
145                 150                 155                 160

Tyr Ala Ser Asn Met Ala Gly Tyr Lys Asn Glu Gly Phe Val Glu Val
                165                 170                 175

Leu Ala Ala Gln Gln Ser Pro Glu Asn Pro Asn Trp Phe Gln Gly Thr
            180                 185                 190

Ala Asp Ala Val Arg Gln Tyr Leu Trp Leu Phe Glu Glu His Asn Ile
        195                 200                 205

Leu Glu Phe Leu Val Leu Ala Gly Asp His Leu Tyr Arg Met Asp Tyr
    210                 215                 220

Glu Arg Phe Ile Gln Ala His Arg Glu Thr Asp Ala Asp Ile Ser Val
225                 230                 235                 240

Ala Ala Leu Pro Met Asp Glu Lys Arg Ala Thr Ala Phe Gly Leu Met
                245                 250                 255

Lys Ile Asp Glu Glu Gly Arg Ile Ile Glu Phe Ala Glu Lys Pro Lys
            260                 265                 270

Gly Glu Gln Leu Lys Ala Met Lys Val Asp Thr Thr Ile Leu Gly Leu
        275                 280                 285

Asp Asp Lys Arg Ala Lys Glu Met Pro Tyr Ile Ala Ser Met Gly Ile
    290                 295                 300

Tyr Val Val Ser Lys Asp Val Met Ile Ser Leu Leu Arg Asp Lys Phe
305                 310                 315                 320

Pro Ala Ala Asn Asp Phe Gly Ser Glu Val Ile Pro Gly Ala Thr Ser
                325                 330                 335

Met Gly Leu Arg Val Gln Ala Tyr Leu Phe Asp Gly Tyr Trp Glu Asp
            340                 345                 350
```

```
Ile Gly Thr Ile Glu Ala Phe Tyr Asn Ala Asn Leu Gly Ile Thr Lys
            355                 360                 365

Lys Pro Val Pro Asp Phe Ser Phe Tyr Asp Arg Ser Ala Pro Ile Tyr
370                 375                 380

Thr Gln Pro Arg Tyr Leu Pro Pro Ser Lys Met Leu Asp Ala Asp Val
385                 390                 395                 400

Thr Asp Ser Val Ile Gly Glu Gly Cys Val Ile Lys Asn Cys Lys Ile
                405                 410                 415

His His Ser Val Val Gly Leu Arg Ser Cys Ile Ser Glu Gly Ala Val
                420                 425                 430

Ile Glu Asp Ser Leu Leu Met Gly Ala Asp Tyr Tyr Glu Thr Asp Ala
            435                 440                 445

Asp Arg Arg Phe Leu Ala Ala Lys Gly Gly Val Pro Ile Gly Ile Gly
450                 455                 460

Lys Asn Thr His Ile Lys Arg Ala Ile Ile Asp Lys Asn Ala Arg Ile
465                 470                 475                 480

Gly Glu Asp Val Lys Ile Ile Asn Thr Asp Asn Val Gln Glu Ala Ala
                485                 490                 495

Arg Glu Thr Asp Gly Tyr Phe Ile Lys Ser Gly Ile Val Thr Val Val
                500                 505                 510

Lys Asp Ala Leu Ile Pro Ser Gly Thr Val Ile
            515                 520
```

<210> SEQ ID NO 107
<211> LENGTH: 515
<212> TYPE: PRT
<213> ORGANISM: Vigna angularis
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 107

```
Met Ala Ser Met Ala Ala Ile Gly Ser Leu Asn Val Pro Cys Ala Ala
1               5                   10                  15

Ser Ala Ser Ser Ser Gly Gly Arg Lys Thr Val Pro Arg Ser Leu
                20                  25                  30

Ser Phe Ser Ala Ser Gln Leu Ser Gly Asp Lys Ile Ser Thr Asp Ser
            35                  40                  45

Val Ser Val Ala Pro Arg Arg Val Arg Asn Pro Val Ile Val Ser Pro
50                  55                  60

Lys Ala Val Ser Asp Ser Gln Asn Ser Gln Thr Cys Leu Asp Pro Asp
65                  70                  75                  80

Ala Ser Arg Ser Val Leu Gly Ile Ile Leu Gly Gly Ala Gly Thr
                85                  90                  95

Arg Leu Tyr Pro Leu Thr Lys Lys Arg Ala Lys Pro Ala Val Pro Leu
                100                 105                 110

Gly Gly Asn Tyr Arg Leu Ile Asp Ile Pro Val Ser Asn Cys Leu Asn
            115                 120                 125

Ser Asn Val Ser Lys Ile Tyr Val Leu Thr Gln Phe Asn Ser Ala Ser
130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
```

```
            180                 185                 190
Trp Leu Phe Glu Glu His Asn Val Leu Glu Phe Leu Val Leu Ala Gly
        195                 200                 205

Asp His Leu Tyr Arg Met Asp Tyr Glu Lys Phe Ile Gln Ala His Arg
    210                 215                 220

Glu Ser Asp Ala Asp Ile Thr Val Ala Ala Leu Pro Met Asp Glu Lys
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
            260                 265                 270

Val Asp Thr Thr Ile Leu Gly Leu Asp Asp Glu Arg Ala Lys Glu Met
        275                 280                 285

Pro Phe Ile Ala Ser Met Gly Ile Tyr Val Val Ser Lys Asn Val Met
    290                 295                 300

Leu Asp Leu Leu Arg Glu Lys Phe Pro Gly Ala Asn Asp Phe Gly Ser
305                 310                 315                 320

Glu Val Ile Pro Gly Ala Thr Ser Ile Gly Leu Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
        355                 360                 365

Tyr Asp Arg Ser Ser Pro Ile Tyr Thr Gln Pro Arg Tyr Leu Pro Pro
    370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Glu Thr Leu Leu Met Gly
            420                 425                 430

Ala Asp Tyr Tyr Glu Thr Asp Ala Asp Lys Arg Phe Leu Ala Ala Lys
        435                 440                 445

Gly Ser Val Pro Ile Gly Ile Gly Lys Asn Thr His Ile Arg Lys Ala
    450                 455                 460

Ile Ile Asp Lys Asn Ala Arg Ile Gly Asp Asn Val Lys Ile Leu Asn
465                 470                 475                 480

Ala Asp Asn Ile Gln Glu Ala Ala Arg Glu Thr Asp Gly Tyr Phe Ile
                485                 490                 495

Lys Ser Gly Ile Val Thr Val Ile Lys Asp Ala Leu Ile Pro Ser Gly
            500                 505                 510

Thr Val Ile
        515

<210> SEQ ID NO 108
<211> LENGTH: 505
<212> TYPE: PRT
<213> ORGANISM: Actinidia eriantha
<220> FEATURE:
<221> NAME/KEY: MISC_FEATURE
<222> LOCATION: (1)..(505)
<223> OTHER INFORMATION: ADP-glucose pyrophosphorylase small subunit

<400> SEQUENCE: 108

Met Ala Ala Ile Gly Val Leu Lys Val Pro His Arg Thr Ala Asn Val
1               5                   10                  15
```

```
Thr Gly Glu Arg Ala Thr Leu Arg Ser Thr Pro Phe Arg Arg Leu Ser
            20                  25                  30

Leu Ala Gly Gly Lys Ile Ser Pro Lys Leu Ala Ser Pro Arg Arg Arg
        35                  40                  45

Ser Ala Thr Phe Ser Pro Lys Ala Val Ser Asp Ser Gln Asn Ser Gln
    50                  55                  60

Thr Cys Leu Asp Pro Asp Ala Ser Arg Ser Val Leu Gly Ile Ile Leu
65                  70                  75                  80

Gly Gly Gly Ala Gly Thr Arg Leu Tyr Pro Leu Thr Lys Lys Arg Ala
                85                  90                  95

Lys Pro Ala Val Pro Leu Gly Ala Asn Tyr Arg Leu Ile Asp Ile Pro
                100                 105                 110

Val Ser Asn Cys Leu Asn Ser Asn Ile Ser Lys Ile Tyr Val Leu Thr
                115                 120                 125

Gln Phe Asn Ser Ala Ser Leu Asn Arg His Leu Ser Arg Ala Tyr Ala
            130                 135                 140

Ser Asn Met Gly Gly Tyr Lys Asn Glu Gly Phe Val Glu Val Leu Ala
145                 150                 155                 160

Ala Gln Gln Ser Pro Glu Asn Pro Asn Trp Phe Gln Gly Thr Ala Asp
                165                 170                 175

Ala Val Arg Gln Tyr Leu Trp Leu Phe Glu Glu His Asn Val Leu Glu
                180                 185                 190

Phe Leu Val Leu Ala Gly Asp His Leu Tyr Arg Met Asp Tyr Glu Arg
            195                 200                 205

Phe Ile Gln Ala His Arg Glu Thr Asp Ala Asp Ile Thr Val Ala Ala
            210                 215                 220

Leu Pro Met Asp Glu Lys Arg Ala Thr Ala Phe Gly Leu Met Lys Ile
225                 230                 235                 240

Asp Glu Glu Gly Arg Ile Ile Glu Phe Ala Glu Lys Pro Lys Gly Glu
                245                 250                 255

Gln Leu Lys Ala Met Lys Val Asp Thr Thr Ile Leu Gly Leu Asp Asp
            260                 265                 270

Glu Arg Ala Lys Glu Met Pro Tyr Ile Ala Ser Met Gly Ile Tyr Val
            275                 280                 285

Val Ser Lys Asp Val Met Leu Ser Leu Leu His Asp Lys Phe Pro Gly
            290                 295                 300

Ala Asn Asp Phe Gly Ser Glu Val Ile Pro Gly Ala Thr Ser Ile Gly
305                 310                 315                 320

Met Arg Val Gln Ala Tyr Leu Tyr Asp Gly Tyr Trp Glu Asp Ile Gly
                325                 330                 335

Thr Ile Glu Ala Phe Tyr Asn Ala Asn Leu Gly Ile Thr Lys Lys Pro
            340                 345                 350

Val Pro Asp Phe Ser Phe Tyr Asp Arg Ser Ala Pro Ile Tyr Thr Gln
            355                 360                 365

Pro Arg Tyr Leu Pro Pro Ser Lys Met Leu Asp Ala Asp Val Thr Asp
            370                 375                 380

Ser Val Ile Gly Glu Gly Cys Val Ile Lys Asn Cys Lys Ile His His
385                 390                 395                 400

Ser Val Val Gly Leu Arg Ser Cys Ile Ser Glu Gly Ala Ile Ile Glu
                405                 410                 415

Asp Ser Leu Leu Met Gly Ala Asp Tyr Tyr Glu Thr Asp Ala Asp Arg
            420                 425                 430
```

```
Arg Phe Leu Ala Ala Lys Gly Ser Val Pro Ile Gly Ile Gly Lys Asn
                435                 440                 445
Ser His Ile Lys Arg Ala Ile Ile Asp Lys Asn Ala Arg Ile Gly Asp
    450                 455                 460
Asn Val Lys Ile Ile Asn Ser Asp Asn Val Gln Glu Ala Ala Arg Glu
465                 470                 475                 480
Thr Asp Gly Tyr Phe Ile Lys Ser Gly Ile Val Thr Val Ile Lys Asp
                485                 490                 495
Ala Leu Ile Pro Ser Gly Thr Val Ile
                500                 505

<210> SEQ ID NO 109
<211> LENGTH: 516
<212> TYPE: PRT
<213> ORGANISM: Malus domestica
<220> FEATURE:
<221> NAME/KEY: MISC_FEATURE
<222> LOCATION: (1)..(516)
<223> OTHER INFORMATION: ADP-glucose pyrophosphorylase small subunit

<400> SEQUENCE: 109

Met Ala Ser Ser Met Ala Ala Asn Gly Val Leu Thr Pro Arg Ser
1               5                   10                  15
Ser Val Leu Pro Asn Ser Lys Gln Thr Gln Asn Ile Ser Arg Leu Ser
                20                  25                  30
Phe Ser Gly Ser His Leu Ser Gly Thr Lys Ile Pro Ala Pro Ser Thr
            35                  40                  45
Cys Met Arg Lys Cys Pro Thr His Arg Val Pro Pro Leu Val Val Ser
50                  55                  60
Pro Lys Ala Val Ser Asp Ser Lys Asn Ser Gln Thr Cys Leu Asp Pro
65                  70                  75                  80
Asp Ala Ser Arg Ser Val Leu Gly Ile Ile Leu Gly Gly Gly Ala Gly
                85                  90                  95
Thr Arg Leu Tyr Pro Leu Thr Lys Lys Arg Ala Lys Pro Ala Val Pro
                100                 105                 110
Leu Gly Ala Asn Tyr Arg Leu Ile Asp Ile Pro Val Ser Asn Cys Leu
            115                 120                 125
Asn Ser Asn Val Ser Lys Ile Tyr Val Leu Thr Gln Phe Asn Ser Ala
130                 135                 140
Ser Leu Asn Arg His Leu Ser Arg Ala Tyr Ala Ser Asn Met Gly Gly
145                 150                 155                 160
Tyr Lys Asn Glu Gly Phe Val Glu Val Leu Ala Ala Gln Gln Ser Pro
                165                 170                 175
Glu Asn Pro Asn Trp Phe Gln Gly Thr Ala Asp Ala Val Arg Gln Tyr
            180                 185                 190
Leu Trp Leu Phe Glu Glu His Asn Val Leu Glu Phe Leu Val Leu Ala
        195                 200                 205
Gly Asp His Leu Tyr Arg Met Asp Tyr Glu Lys Phe Ile Gln Ala His
    210                 215                 220
Arg Glu Thr Asp Ala Asp Ile Thr Val Ala Ala Leu Pro Met Asp Glu
225                 230                 235                 240
Lys Arg Ala Thr Ala Phe Gly Leu Met Lys Ile Asp Glu Glu Gly Arg
                245                 250                 255
Ile Ile Glu Phe Ala Glu Lys Pro Lys Gly Glu Gln Leu Lys Ala Met
            260                 265                 270
Lys Val Asp Thr Thr Ile Leu Gly Leu Asp Asp Glu Arg Ala Lys Glu
```

```
            275                 280                 285
Met Pro Tyr Ile Ala Ser Met Gly Ile Tyr Val Val Ser Lys Asn Val
            290                 295                 300

Met Leu Asp Leu Leu Arg Asp Lys Phe Pro Gly Ala Asn Asp Phe Gly
305                 310                 315                 320

Ser Glu Val Ile Pro Gly Ala Thr Ser Ile Gly Leu Arg Val Gln Ala
                325                 330                 335

Tyr Leu Tyr Asp Gly Tyr Trp Glu Asp Ile Gly Thr Ile Glu Ala Phe
            340                 345                 350

Tyr Asn Ala Asn Leu Gly Ile Thr Lys Lys Pro Val Pro Asp Phe Ser
        355                 360                 365

Phe Tyr Asp Arg Ser Ser Pro Ile Tyr Thr Gln Pro Arg Tyr Leu Pro
370                 375                 380

Pro Ser Lys Met Leu Asp Ala Asp Val Thr Asp Ser Val Ile Gly Glu
385                 390                 395                 400

Gly Cys Val Ile Lys Asn Cys Lys Ile His His Ser Val Val Gly Leu
                405                 410                 415

Arg Ser Cys Ile Ala Glu Gly Ala Val Ile Glu Asp Thr Leu Leu Met
            420                 425                 430

Gly Ala Asp Tyr Tyr Glu Thr Asp Ala Asp Arg Arg Phe Leu Ala Ala
        435                 440                 445

Lys Gly Ser Val Pro Ile Gly Ile Gly Lys Asn Ser His Ile Arg Arg
450                 455                 460

Ala Ile Ile Asp Lys Asn Ala Arg Ile Gly Glu Asn Val Lys Ile Ile
465                 470                 475                 480

Asn Ile Asp Asn Val Gln Glu Ala Ala Arg Glu Thr Asp Gly Tyr Phe
                485                 490                 495

Ile Lys Ser Gly Ile Val Thr Val Ile Lys Asp Ala Leu Ile Pro Ser
            500                 505                 510

Gly Thr Val Ile
        515

<210> SEQ ID NO 110
<211> LENGTH: 526
<212> TYPE: PRT
<213> ORGANISM: Gladiolus hybrid cultivar
<220> FEATURE:
<221> NAME/KEY: MISC_FEATURE
<222> LOCATION: (1)..(526)
<223> OTHER INFORMATION: ADP-glucose pyrophosphorylase small subunit

<400> SEQUENCE: 110

Met Ala Met Ala Ser Ile Gly Ile Ser Lys Phe Pro Thr Ser Lys Thr
1               5                   10                  15

Leu Asn Ser Ser Ser Gln Thr Lys Asn Ser Arg Ser Pro Thr Thr Ser
            20                  25                  30

Phe Arg Phe Ala Asp Ser Asn Leu Ser Ser Gly Ser Ser Arg Phe Ser
        35                  40                  45

Gly Glu Arg Leu Val Ser Lys Ala Ile Phe Gln Arg Lys Asn Gly
    50                  55                  60

Phe Glu Arg Arg Thr Pro Val Val Ser Pro Lys Ala Val Ser Asp
65                  70                  75                  80

Ser Arg Asn Ser Gln Thr Cys Leu Asp Pro Asp Ala Ser Gln Ser Val
                85                  90                  95

Leu Gly Ile Ile Leu Gly Gly Gly Ala Gly Thr Arg Leu Tyr Pro Leu
            100                 105                 110
```

```
Thr Lys Lys Arg Ala Lys Pro Ala Val Pro Leu Gly Ala Asn Tyr Arg
    115                 120                 125

Leu Ile Asp Ile Pro Val Ser Asn Cys Leu Asn Ser Asn Ile Ser Lys
130                 135                 140

Ile Tyr Val Leu Thr Gln Phe Asn Ser Ala Ser Leu Asn Arg His Leu
145                 150                 155                 160

Ser Arg Ala Tyr Gly Ser Asn Met Gly Gly Tyr Lys Asn Glu Gly Phe
                165                 170                 175

Val Glu Val Leu Ala Ala Gln Gln Ser Pro Glu Asn Pro Asn Trp Phe
            180                 185                 190

Gln Gly Thr Ala Asp Ala Val Arg Gln Tyr Leu Trp Leu Phe Glu Glu
        195                 200                 205

His Asn Val Met Glu Tyr Leu Val Leu Ala Gly Asp His Leu Tyr Arg
    210                 215                 220

Met Asp Tyr Glu Arg Phe Val Gln Ala His Arg Glu Thr Asp Ala Asp
225                 230                 235                 240

Ile Thr Val Ala Ala Leu Pro Met Asp Glu Lys Arg Ala Thr Ala Phe
                245                 250                 255

Gly Leu Met Lys Ile Asp Glu Glu Gly Arg Ile Val Glu Phe Ala Glu
            260                 265                 270

Lys Pro Lys Gly Asp Gln Leu Lys Ala Met Lys Val Asp Thr Thr Ile
        275                 280                 285

Leu Gly Leu Asp Asp Glu Arg Ala Lys Glu Met Pro Tyr Ile Ala Ser
    290                 295                 300

Met Gly Ile Tyr Val Ile Ser Lys Asp Val Met Leu Gln Leu Leu Arg
305                 310                 315                 320

Asp Lys Phe Pro Gly Ala Asn Asp Phe Gly Ser Glu Val Ile Pro Gly
                325                 330                 335

Ala Thr Asn Ile Gly Met Arg Val Gln Ala Tyr Leu Tyr Asp Gly Tyr
            340                 345                 350

Trp Glu Asp Ile Gly Thr Ile Glu Ala Phe Tyr Asn Ala Asn Leu Gly
        355                 360                 365

Ile Thr Lys Lys Pro Ile Pro Asp Phe Ser Phe Tyr Asp Arg Ser Ser
    370                 375                 380

Pro Ile Tyr Thr Gln Pro Arg Tyr Leu Pro Pro Ser Lys Met Leu Asp
385                 390                 395                 400

Ala Asp Val Thr Asp Ser Val Ile Gly Glu Gly Cys Val Ile Lys Asn
                405                 410                 415

Cys Lys Ile His His Ser Val Val Gly Leu Arg Ser Cys Ile Ser Glu
            420                 425                 430

Gly Ala Ile Ile Glu Asp Thr Leu Leu Met Gly Ala Asp Tyr Tyr Glu
        435                 440                 445

Thr Asp Ala Asp Lys Arg Phe Leu Ala Ala Lys Gly Ser Ile Pro Ile
450                 455                 460

Gly Ile Gly Lys Asn Thr His Ile Lys Arg Ala Ile Ile Asp Lys Asn
465                 470                 475                 480

Ala Arg Ile Gly Asp Asp Val Lys Ile Ile Asn Asn Asp Asn Val Gln
                485                 490                 495

Glu Ala Ala Arg Glu Thr Asp Gly Tyr Phe Ile Lys Ser Gly Ile Val
            500                 505                 510

Thr Ile Ile Lys Asp Ala Leu Val Pro Ser Gly Thr Val Ile
    515                 520                 525
```

<210> SEQ ID NO 111
<211> LENGTH: 524
<212> TYPE: PRT
<213> ORGANISM: Nelumbo nucifera
<220> FEATURE:
<221> NAME/KEY: MISC_FEATURE
<222> LOCATION: (1)..(524)
<223> OTHER INFORMATION: ADP-glucose pyrophosphorylase small subunit

<400> SEQUENCE: 111

Met Ala Met Ala Ala Val Gly Gly Val Thr Arg Ile Pro Ser Ser Asn
1               5                   10                  15

Leu Ile Thr Gln Lys Thr Ser Thr Arg Pro Thr Ser Pro Phe Leu Lys
            20                  25                  30

Pro Ile Asn Gln Ser Leu Ser Ser Ser Ser Asp Leu Ser Gly Asp
        35                  40                  45

Lys Ile Pro Leu Lys Ser Val Leu Arg Ser Leu Lys Ala Ser Phe Asn
    50                  55                  60

Ala Arg Ile Pro Ile Leu Val Ser Pro Lys Ala Val Ser Asp Ser Gln
65                  70                  75                  80

Gly Ser Gln Thr Cys Leu Asp Pro Asp Ala Ser Arg Ser Val Leu Gly
                85                  90                  95

Ile Ile Leu Gly Gly Gly Ala Gly Thr Arg Leu Tyr Pro Leu Thr Lys
            100                 105                 110

Lys Arg Ala Lys Pro Ala Val Pro Leu Gly Ala Asn Tyr Arg Leu Ile
        115                 120                 125

Asp Ile Pro Val Ser Asn Cys Leu Asn Ser Asn Ile Ser Lys Ile Tyr
130                 135                 140

Val Leu Thr Gln Phe Asn Ser Ala Ser Leu Asn Arg His Leu Ser Arg
145                 150                 155                 160

Ala Tyr Ala Ser Asn Met Gly Gly Tyr Lys Asn Glu Gly Phe Val Glu
                165                 170                 175

Val Leu Ala Ala Gln Gln Ser Pro Glu Asn Pro Asn Trp Phe Gln Gly
            180                 185                 190

Thr Ala Asp Ala Val Arg Gln Tyr Leu Trp Leu Phe Glu Glu His Asn
        195                 200                 205

Val Met Glu Phe Leu Val Leu Ala Gly Asp His Leu Tyr Arg Met Asp
210                 215                 220

Tyr Glu Lys Phe Ile Gln Ala His Arg Glu Thr Asp Ala Asp Ile Thr
225                 230                 235                 240

Val Ala Ala Leu Pro Met Asp Glu Lys Arg Ala Thr Ala Phe Gly Leu
                245                 250                 255

Met Lys Ile Asp Glu Glu Gly Arg Ile Ile Glu Phe Ala Glu Lys Pro
            260                 265                 270

Lys Gly Glu Gln Leu Lys Ala Met Lys Val Asp Thr Thr Ile Leu Gly
        275                 280                 285

Leu Asp Asp Glu Arg Ala Lys Glu Met Pro Tyr Ile Ala Ser Met Gly
290                 295                 300

Ile Tyr Val Val Ser Lys Asp Val Met Leu Gln Leu Leu Arg Glu Lys
305                 310                 315                 320

Phe Pro Gly Ala Asn Asp Phe Gly Ser Glu Val Ile Pro Gly Ala Thr
                325                 330                 335

Ser Ile Gly Met Arg Val Gln Ala Tyr Leu Tyr Asp Gly Tyr Trp Glu
            340                 345                 350

Asp Ile Gly Thr Ile Glu Ala Phe Tyr Asn Ala Asn Leu Gly Ile Thr

```
                355                 360                 365
Lys Lys Pro Ile Pro Asp Phe Ser Phe Tyr Asp Arg Ser Ser Pro Ile
            370                 375                 380

Tyr Thr Gln Pro Arg Tyr Leu Pro Pro Ser Lys Met Leu Asp Ala Asp
385                 390                 395                 400

Val Thr Asp Ser Val Ile Gly Glu Gly Cys Val Ile Lys Asn Cys Lys
                405                 410                 415

Ile His His Ser Val Val Gly Leu Arg Ser Cys Ile Ser Glu Gly Ala
            420                 425                 430

Ile Ile Glu Asp Thr Leu Leu Met Gly Ala Asp Tyr Tyr Glu Thr Asp
            435                 440                 445

Ala Asp Arg Arg Phe Leu Ala Ala Lys Gly Ser Val Pro Ile Gly Ile
        450                 455                 460

Gly Arg Asn Thr His Ile Lys Arg Ala Ile Ile Asp Lys Asn Ala Arg
465                 470                 475                 480

Ile Gly Asp Asp Val Lys Ile Ile Asn Ser Asp Asn Val Leu Glu Ala
                485                 490                 495

Ala Arg Glu Thr Asp Gly Tyr Phe Ile Lys Ser Gly Ile Val Thr Val
            500                 505                 510

Ile Lys Asp Ala Leu Ile Pro Ser Gly Thr Ile Ile
            515                 520

<210> SEQ ID NO 112
<211> LENGTH: 526
<212> TYPE: PRT
<213> ORGANISM: Citrullus lanatus
<220> FEATURE:
<221> NAME/KEY: MISC_FEATURE
<222> LOCATION: (1)..(526)
<223> OTHER INFORMATION: ADP-glucose pyrophosphorylase small subunit

<400> SEQUENCE: 112

Met Ala Ser Ser Met Ala Ala Val Gly Val Leu Arg Leu Pro Thr Thr
1               5                   10                  15

Ser Ala Ser Ser Ser Ser Ser Asn Gly Gly Ser Asn Arg Ala Arg
            20                  25                  30

Arg His Ser Leu Arg Ser Leu Ser Phe Gly Ala Ser His Ile Ser Gly
        35                  40                  45

Asp Lys Ile Asp Phe Arg Ala Ser Ala Leu Gly Ser Arg Arg Val Ser
    50                  55                  60

Gly Gly Arg Ala Val Pro Ser Ile Val Ser Pro Lys Ala Val Ser Asp
65                  70                  75                  80

Ser Lys Asn Thr Gln Thr Cys Leu Asp Pro Asp Ala Ser Arg Ser Val
                85                  90                  95

Leu Gly Ile Ile Leu Gly Gly Gly Ala Gly Thr Arg Leu Tyr Pro Leu
            100                 105                 110

Thr Lys Lys Arg Ala Lys Pro Ala Val Pro Leu Gly Ala Asn Tyr Arg
        115                 120                 125

Leu Ile Asp Ile Pro Val Ser Asn Cys Leu Asn Ser Asn Ile Ser Lys
    130                 135                 140

Ile Tyr Val Leu Thr Gln Phe Asn Ser Ala Ser Leu Asn Arg His Leu
145                 150                 155                 160

Ser Arg Ala Tyr Ala Ser Asn Met Gly Gly Tyr Lys Asn Glu Gly Phe
                165                 170                 175

Val Glu Val Leu Ala Ala Gln Gln Ser Pro Glu Asn Pro Asn Trp Phe
            180                 185                 190
```

-continued

```
Gln Gly Thr Ala Asp Ala Val Arg Gln Tyr Leu Trp Leu Phe Glu Glu
            195                 200                 205

Gln Asn Val Leu Glu Tyr Leu Val Leu Ala Gly Asp His Leu Tyr Arg
        210                 215                 220

Met Asp Tyr Glu Arg Phe Ile Gln Ala His Arg Glu Thr Asp Ala Asp
225                 230                 235                 240

Ile Thr Val Ala Ala Leu Pro Met Asp Glu Lys Arg Ala Thr Ala Phe
                245                 250                 255

Gly Leu Met Lys Ile Asp Glu Glu Gly Arg Ile Ile Glu Phe Ala Glu
            260                 265                 270

Lys Pro Lys Gly Glu Gln Leu Lys Thr Met Lys Val Asp Thr Thr Ile
        275                 280                 285

Leu Gly Leu Asp Asp Ala Arg Gly Lys Glu Met Pro Phe Ile Ala Ser
        290                 295                 300

Met Gly Ile Tyr Val Ile Ser Lys Asp Val Met Leu Ser Leu Leu Arg
305                 310                 315                 320

Asp Lys Phe Pro Gly Ala Asn Asp Phe Gly Ser Glu Val Ile Pro Gly
                325                 330                 335

Ala Thr Ser Ile Gly Met Arg Val Gln Ala Tyr Leu Tyr Asp Gly Tyr
            340                 345                 350

Trp Glu Asp Ile Gly Thr Ile Glu Ala Phe Tyr Asn Ala Asn Leu Gly
        355                 360                 365

Ile Thr Lys Lys Pro Val Pro Asp Phe Ser Phe Tyr Asp Arg Ser Ser
        370                 375                 380

Pro Ile Tyr Thr Gln Pro Arg Tyr Leu Pro Pro Ser Lys Met Leu Asp
385                 390                 395                 400

Ala Asp Ile Thr Asp Ser Val Ile Gly Glu Gly Cys Val Ile Lys Asn
                405                 410                 415

Cys Lys Ile His His Ser Val Val Gly Ile Arg Thr Cys Ile Ser Glu
            420                 425                 430

Gly Ala Ile Ile Glu Asp Thr Leu Leu Met Gly Ala Asp Tyr Tyr Glu
        435                 440                 445

Thr Asp Ala Asp Arg Arg Leu Leu Ala Ala Lys Gly Ser Val Pro Ile
450                 455                 460

Gly Ile Gly Arg Asn Ser His Ile Lys Arg Ala Ile Ile Asp Lys Asn
465                 470                 475                 480

Ala Arg Ile Gly Glu Asp Val Lys Ile Val Asn Gly Asp Asn Val Gln
                485                 490                 495

Glu Ala Ala Arg Glu Thr Asp Gly Tyr Phe Ile Lys Ser Gly Ile Val
            500                 505                 510

Thr Val Ile Lys Asp Ala Leu Ile Pro Ser Gly Thr Val Ile
        515                 520                 525
```

<210> SEQ ID NO 113
<211> LENGTH: 515
<212> TYPE: PRT
<213> ORGANISM: Vigna radiata
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 113

```
Met Ala Ser Met Ala Ala Ile Gly Ser Leu Asn Val Pro Cys Ala Ala
1               5                   10                  15
```

Ser Ala Ser Ser Ser Gly Gly Arg Lys Ser Leu Pro Arg Ser Leu
        20                  25                  30

Ser Phe Ser Ala Ser Gln Leu Ser Gly Asp Lys Ile Ser Thr Asp Ser
    35                  40                  45

Val Ser Val Ala Pro Arg Arg Val Arg Asn Pro Val Ile Val Ser Pro
 50                  55                  60

Lys Ala Val Ser Asp Ser Gln Asn Ser Gln Thr Cys Leu Asp Pro Asp
 65                  70                  75                  80

Ala Ser Arg Ser Val Leu Gly Ile Ile Leu Gly Gly Ala Gly Thr
            85                  90                  95

Arg Leu Tyr Pro Leu Thr Lys Lys Arg Ala Lys Pro Ala Val Pro Leu
             100                 105                 110

Gly Gly Asn Tyr Arg Leu Ile Asp Ile Pro Val Ser Asn Cys Leu Asn
             115                 120                 125

Ser Asn Val Ser Lys Ile Tyr Val Leu Thr Gln Phe Asn Ser Ala Ser
     130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Gln Ser Pro Glu
                 165                 170                 175

Asn Pro Asn Trp Phe Gln Gly Thr Ala Asp Ala Val Arg Gln Tyr Leu
             180                 185                 190

Trp Leu Phe Glu Glu His Asn Val Leu Glu Phe Leu Val Leu Ala Gly
         195                 200                 205

Asp His Leu Tyr Arg Met Asp Tyr Glu Lys Phe Ile Gln Ala His Arg
 210                 215                 220

Glu Ser Asp Ala Asp Ile Thr Val Ala Ala Leu Pro Met Asp Glu Lys
225                 230                 235                 240

Arg Ala Thr Ala Phe Gly Leu Met Lys Ile Asp Glu Glu Gly Arg Ile
                 245                 250                 255

Ile Glu Phe Ala Glu Lys Pro Lys Gly Glu Gln Leu Lys Ala Met Lys
                 260                 265                 270

Val Asp Thr Thr Ile Leu Gly Leu Asp Asp Glu Arg Ala Lys Glu Met
         275                 280                 285

Pro Phe Ile Ala Ser Met Gly Ile Tyr Val Val Ser Lys Asn Val Met
 290                 295                 300

Leu Asp Leu Leu Arg Glu Lys Phe Pro Gly Ala Asn Asp Phe Gly Ser
305                 310                 315                 320

Glu Val Ile Pro Gly Ala Thr Ser Ile Gly Leu Arg Val Gln Ala Tyr
                 325                 330                 335

Leu Tyr Asp Gly Tyr Trp Glu Asp Ile Gly Thr Ile Glu Ala Phe Tyr
                 340                 345                 350

Asn Ala Asn Leu Gly Ile Thr Lys Lys Pro Val Pro Asp Phe Ser Phe
         355                 360                 365

Tyr Asp Arg Ser Ser Pro Ile Tyr Thr Gln Pro Arg Tyr Leu Pro Pro
 370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                 405                 410                 415

Ser Cys Ile Ser Glu Gly Ala Ile Ile Glu Glu Thr Leu Leu Met Gly
                 420                 425                 430

Ala Asp Tyr Tyr Glu Thr Glu Ala Asp Lys Arg Phe Leu Ala Ala Lys

```
                435                 440                 445
Gly Ser Val Pro Ile Gly Ile Gly Lys Asn Thr His Ile Arg Lys Ala
        450                 455                 460

Ile Ile Asp Lys Asn Ala Arg Ile Gly Asp Asn Val Lys Ile Leu Asn
465                 470                 475                 480

Ala Asp Asn Ile Gln Glu Ala Ala Arg Glu Thr Asp Gly Tyr Phe Ile
                    485                 490                 495

Lys Ser Gly Ile Val Thr Val Ile Lys Asp Ala Leu Ile Pro Ser Gly
                500                 505                 510

Thr Val Ile
        515

<210> SEQ ID NO 114
<211> LENGTH: 510
<212> TYPE: PRT
<213> ORGANISM: Beta vulgaris
<220> FEATURE:
<221> NAME/KEY: MISC_FEATURE
<222> LOCATION: (1)..(510)
<223> OTHER INFORMATION: ADP-glucose pyrophosphorylase small subunit

<400> SEQUENCE: 114

Met Ala Gly Met Ala Val Ile Gly Gly Ile Thr Val Pro Ser Thr Ser
1               5                   10                  15

Ser Lys Asn Leu Gln Asn Ser Leu Ala Phe Ser Ser Ser Ser Leu Ser
            20                  25                  30

Gly Asp Lys Ile Gln Thr Thr Ser Phe Leu Asn Arg Arg Tyr Cys Arg
        35                  40                  45

Ile Ser Ser Arg Ala Pro Ile Val Ser Pro Lys Ala Val Ser Asp
50                  55                  60

Ser Lys Asn Ser Gln Thr Cys Leu Asp Pro Ala Ser Arg Ser Val
65                  70                  75                  80

Leu Gly Ile Ile Leu Gly Gly Ala Gly Thr Arg Leu Tyr Pro Leu
                    85                  90                  95

Thr Lys Lys Arg Ala Lys Pro Ala Val Pro Leu Gly Ala Asn Tyr Arg
                100                 105                 110

Leu Ile Asp Ile Pro Val Ser Asn Cys Leu Asn Ser Asn Ile Ser Lys
            115                 120                 125

Ile Tyr Val Leu Thr Gln Phe Asn Ser Ala Ser Leu Asn Arg His Leu
        130                 135                 140

Ser Arg Ala Tyr Ala Ser Asn Met Gly Gly Tyr Lys Asn Glu Gly Phe
145                 150                 155                 160

Val Glu Val Leu Ala Ala Gln Gln Ser Pro Glu Asn Pro Asn Trp Phe
                165                 170                 175

Gln Gly Thr Ala Asp Ala Val Arg Gln Tyr Leu Trp Leu Phe Glu Glu
                180                 185                 190

His Asn Val Leu Glu Tyr Leu Ile Leu Ala Gly Asp His Leu Tyr Arg
            195                 200                 205

Met Asp Tyr Glu Arg Phe Val Gln Ala His Arg Glu Thr Asp Ala Asp
        210                 215                 220

Ile Thr Val Ala Ala Leu Pro Met Asp Glu Lys Arg Ala Thr Ala Phe
225                 230                 235                 240

Gly Leu Met Lys Ile Asp Glu Glu Gly Arg Ile Ile Glu Phe Ala Glu
                245                 250                 255

Lys Pro Lys Gly Glu Gln Leu Lys Ala Met Lys Val Asp Thr Thr Ile
                260                 265                 270
```

```
Leu Gly Leu Asp Asp Glu Arg Ala Lys Glu Met Pro Phe Ile Ala Ser
            275                 280                 285

Met Gly Ile Tyr Val Ile Ser Lys Asp Val Met Leu Asn Leu Leu Arg
            290                 295                 300

Glu Gln Phe Pro Gly Ala Asn Asp Phe Gly Ser Glu Val Ile Pro Gly
305                 310                 315                 320

Ala Thr Ser Ile Gly Leu Arg Val Gln Ala Tyr Leu Tyr Asp Gly Tyr
                325                 330                 335

Trp Glu Asp Ile Gly Thr Ile Glu Ala Phe Tyr Asn Ala Asn Leu Gly
                340                 345                 350

Ile Thr Lys Lys Pro Val Pro Asp Phe Ser Phe Tyr Asp Arg Ser Ser
                355                 360                 365

Pro Ile Tyr Thr Gln Pro Arg Tyr Leu Pro Pro Ser Lys Met Leu Asp
            370                 375                 380

Ala Asp Ile Thr Asp Ser Val Ile Gly Glu Gly Cys Val Ile Lys Asn
385                 390                 395                 400

Cys Lys Ile His His Ser Val Ile Gly Leu Arg Ser Cys Ile Ser Glu
                405                 410                 415

Gly Ala Ile Ile Glu Asp Thr Leu Leu Met Gly Ala Asp Tyr Tyr Glu
                420                 425                 430

Thr Asp Ala Asp Arg Lys Phe Leu Ala Ala Lys Gly Ser Val Pro Ile
            435                 440                 445

Gly Ile Gly Lys Asn Ala His Ile Lys Arg Ala Ile Ile Asp Lys Asn
            450                 455                 460

Ala Arg Ile Gly Asp Asp Val Lys Ile Ile Asn Ser Asp Asn Val Gln
465                 470                 475                 480

Glu Ala Ala Arg Glu Thr Asp Gly Tyr Phe Ile Lys Ser Gly Ile Val
                485                 490                 495

Thr Ile Ile Lys Asp Ala Leu Ile Pro Ser Gly Thr Val Ile
            500                 505                 510

<210> SEQ ID NO 115
<211> LENGTH: 515
<212> TYPE: PRT
<213> ORGANISM: Phaseolus vulgaris
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 115

Met Ala Ser Met Ala Ser Ile Gly Ser Leu Asn Val Pro Cys Ser Ser
1               5                   10                  15

Ser Ser Ser Ser Ser Asn Gly Gly Arg Lys Ile Leu Pro Arg Ala Leu
            20                  25                  30

Ser Phe Ser Ala Ser Gln Leu Tyr Gly Asp Lys Ile Ser Thr Asp Ser
            35                  40                  45

Val Ser Val Ala Pro Lys Arg Val Arg Asn Pro Val Val Ser Pro
        50                  55                  60

Lys Ala Val Ser Asp Ser Gln Asn Ser Gln Thr Cys Leu Asp Pro Asp
65                  70                  75                  80

Ala Ser Lys Ser Val Leu Gly Ile Ile Leu Gly Gly Gly Ala Gly Thr
                85                  90                  95

Arg Leu Tyr Pro Leu Thr Lys Lys Arg Ala Lys Pro Ala Val Pro Leu
            100                 105                 110
```

```
Gly Ala Asn Tyr Arg Leu Ile Asp Ile Pro Val Ser Asn Cys Leu Asn
            115                 120                 125

Ser Asn Val Ser Lys Ile Tyr Val Leu Thr Gln Phe Asn Ser Ala Ser
130                 135                 140

Leu Asn Arg His Leu Ser Arg Ala Tyr Ala Ser Asn Met Gly Gly Tyr
145                 150                 155                 160

Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Tyr Leu Val Leu Ala Gly
        195                 200                 205

Asp His Leu Tyr Arg Met Asp Tyr Glu Lys Phe Ile Gln Val His Arg
    210                 215                 220

Glu Ser Asp Ala Asp Ile Thr Val Ala Ala Leu Pro Met Asp Glu Asn
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Glu Gln Leu Lys Ala Met Lys
            260                 265                 270

Val Asp Thr Thr Ile Leu Gly Leu Asp Asp Glu Arg Ala Lys Glu Met
        275                 280                 285

Pro Tyr Ile Ala Ser Met Gly Ile Tyr Val Val Ser Lys Asn Val Met
    290                 295                 300

Leu Asn Leu Leu Arg Glu Lys Phe Pro Ala Ala Asn Asp Phe Gly Ser
305                 310                 315                 320

Glu Val Ile Pro Gly Ala Thr Ser Ile Gly Leu Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
        355                 360                 365

Tyr Asp Arg Ser Ser Pro Ile Tyr Thr Gln Pro Arg Tyr Leu Pro Pro
    370                 375                 380

Ser Lys Met Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Thr Leu Leu Met Gly
            420                 425                 430

Ala Asp Tyr Tyr Glu Thr Asp Ala Asp Lys Arg Phe Leu Ala Ala Lys
        435                 440                 445

Gly Ser Val Pro Ile Gly Ile Gly Arg Asn Ser His Val Lys Arg Ala
    450                 455                 460

Ile Ile Asp Lys Asn Ala Arg Ile Gly Glu Asn Val Lys Ile Leu Asn
465                 470                 475                 480

Ser Asp Asn Val Gln Glu Ala Ala Arg Glu Thr Asp Gly Tyr Phe Ile
                485                 490                 495

Lys Ser Gly Ile Val Thr Val Ile Lys Asp Ala Leu Ile Pro Ser Gly
            500                 505                 510

Thr Val Ile
        515
```

```
<210> SEQ ID NO 116
<211> LENGTH: 524
<212> TYPE: PRT
<213> ORGANISM: Fragaria vesca
<220> FEATURE:
<221> NAME/KEY: MISC_FEATURE
<222> LOCATION: (1)..(524)
<223> OTHER INFORMATION: ADP-glucose pyrophosphorylase small subunit

<400> SEQUENCE: 116
```

| Met | Ala | Ser | Ser | Met | Ala | Ala | Asn | Gly | Val | Pro | Thr | Leu | Arg | Leu |
|-----|-----|-----|-----|-----|-----|-----|-----|-----|-----|-----|-----|-----|-----|-----|
| 1   |     |     |     | 5   |     |     |     |     | 10  |     |     |     |     | 15  |

Ser Thr Ser Asn Ile Ala Thr Asn Gln Thr Gln Lys Thr Asn Pro Ser
            20                  25                  30

Leu Thr Arg Gly Leu Ser Phe Ser Gly Ser Gly Leu Ser Gly Thr Lys
        35                  40                  45

Ile Pro Thr Pro Ala Thr Cys Leu Arg Thr Ser Thr Pro Pro Asn Thr
    50                  55                  60

Thr Arg Ala Pro Leu Val Val Ser Pro Lys Ala Val Ser Asp Ser Lys
65                  70                  75                  80

Asn Ser Gln Thr Cys Leu Asp Pro Asp Ala Ser Arg Ser Val Leu Gly
                85                  90                  95

Ile Ile Leu Gly Gly Gly Ala Gly Thr Arg Leu Tyr Pro Leu Thr Lys
            100                 105                 110

Lys Arg Ala Lys Pro Ala Val Pro Leu Gly Ala Asn Tyr Arg Leu Ile
        115                 120                 125

Asp Ile Pro Val Ser Asn Cys Leu Asn Ser Asn Val Ser Lys Ile Tyr
    130                 135                 140

Val Leu Thr Gln Phe Asn Ser Ala Ser Leu Asn Arg His Leu Ser Arg
145                 150                 155                 160

Ala Tyr Ala Ser Asn Met Gly Gly Tyr Lys Asn Glu Gly Phe Val Glu
                165                 170                 175

Val Leu Ala Ala Gln Gln Ser Pro Glu Asn Pro Asn Trp Phe Gln Gly
            180                 185                 190

Thr Ala Asp Ala Val Arg Gln Tyr Leu Trp Leu Phe Glu Glu His Asn
        195                 200                 205

Val Leu Glu Phe Leu Val Leu Ala Gly Asp His Leu Tyr Arg Met Asp
    210                 215                 220

Tyr Glu Lys Phe Ile Gln Ala His Arg Glu Thr Asp Ala Asp Ile Thr
225                 230                 235                 240

Val Ala Ala Leu Pro Met Asp Glu Lys Arg Ala Thr Ala Phe Gly Leu
                245                 250                 255

Met Lys Ile Asp Asp Glu Gly Arg Ile Ile Glu Phe Ala Glu Lys Pro
            260                 265                 270

Lys Gly Glu Gln Leu Lys Ala Met Lys Val Asp Thr Thr Ile Leu Gly
        275                 280                 285

Leu Asp Asp Glu Arg Ala Lys Glu Met Pro Tyr Ile Ala Ser Met Gly
    290                 295                 300

Ile Tyr Val Val Ser Lys Asn Val Met Leu Asp Leu Leu Arg Glu Lys
305                 310                 315                 320

Phe Pro Gly Ala Asn Asp Phe Gly Ser Glu Val Ile Pro Gly Ala Thr
                325                 330                 335

Ser Ile Gly Leu Arg Val Gln Ala Tyr Leu Tyr Asp Gly Tyr Trp Glu
            340                 345                 350

Asp Ile Gly Thr Ile Glu Ala Phe Tyr Asn Ala Asn Leu Gly Ile Thr
        355                 360                 365

```
Lys Lys Pro Ile Pro Asp Phe Ser Phe Tyr Asp Arg Ser Ser Pro Ile
        370                 375                 380

Tyr Thr Gln Pro Arg Tyr Leu Pro Pro Ser Lys Met Leu Asp Ala Asp
385                 390                 395                 400

Ile Thr Asp Ser Val Ile Gly Glu Gly Cys Val Ile Lys Asn Cys Lys
                405                 410                 415

Ile His His Ser Val Ile Gly Leu Arg Ser Cys Ile Ser Glu Gly Ala
                420                 425                 430

Val Ile Glu Asp Thr Leu Leu Met Gly Ala Asp Tyr Tyr Glu Thr Asp
                435                 440                 445

Val Asp Arg Arg Leu Met Ala Lys Lys Gly Ser Val Pro Ile Gly Ile
450                 455                 460

Gly Lys Asn Ser His Ile Lys Arg Ala Ile Ile Asp Lys Asn Ala Arg
465                 470                 475                 480

Ile Gly Asp Asn Val Lys Ile Ile Asn Ser Asp Asn Val Gln Glu Thr
                485                 490                 495

Ala Arg Glu Thr Asp Gly Tyr Phe Ile Lys Ser Gly Ile Val Thr Val
                500                 505                 510

Ile Lys Asp Ala Trp Ile Pro Cys Gly Thr Val Ile
                515                 520
```

<210> SEQ ID NO 117
<211> LENGTH: 536
<212> TYPE: PRT
<213> ORGANISM: Eucalyptus grandis
<220> FEATURE:
<221> NAME/KEY: MISC_FEATURE
<222> LOCATION: (1)..(536)
<223> OTHER INFORMATION: ADP-glucose pyrophosphorylase small subunit

<400> SEQUENCE: 117

```
Met Ala Ser Met Ala Ala Val Gly Ala Ile Arg Val Pro Thr Ser Ser
1               5                   10                  15

Ser Ser Ser Ser Ser Ser Ser Ser Ser Phe Pro Ala Ala Ser Ser Glu
                20                  25                  30

Ser Arg His Gln Arg Arg Trp Cys Asn Gly His Gly Arg Ser Ser Ser
            35                  40                  45

Ala Leu Ser Phe Ala Ser Ser Gln Val Ala Gly Asp Lys Ile Ala Ser
        50                  55                  60

Ser Ala Ala Ala Ser Ala Ala Phe Lys Ser Val Arg Arg Ala Pro
65                  70                  75                  80

Ala Val Val Ser Pro Arg Ala Val Ser Asp Ser Arg Asn Ser Gln Thr
                85                  90                  95

Cys Leu Asp Pro Asp Ala Ser Arg Ser Val Leu Gly Ile Ile Leu Gly
                100                 105                 110

Gly Gly Ala Gly Thr Arg Leu Tyr Pro Leu Thr Lys Lys Arg Ala Lys
            115                 120                 125

Pro Ala Val Pro Leu Gly Ala Asn Tyr Arg Leu Ile Asp Ile Pro Val
        130                 135                 140

Ser Asn Cys Leu Asn Ser Asn Val Ser Lys Ile Tyr Val Leu Thr Gln
145                 150                 155                 160

Phe Asn Ser Ala Ser Leu Asn Arg His Leu Ser Arg Ala Tyr Ala Ser
                165                 170                 175

Asn Met Gly Gly Tyr Lys Asn Glu Gly Phe Val Glu Val Leu Ala Ala
                180                 185                 190
```

```
Gln Gln Ser Pro Glu Asn Pro Asn Trp Phe Gln Gly Thr Ala Asp Ala
        195                 200                 205

Val Arg Gln Tyr Leu Trp Leu Phe Glu Glu His Asp Val Leu Glu Phe
    210                 215                 220

Leu Ile Leu Ala Gly Asp His Leu Tyr Arg Met Asp Tyr Glu Arg Phe
225                 230                 235                 240

Ile Gln Ala His Arg Glu Thr Asp Ala Asp Ile Thr Val Ala Ala Leu
                245                 250                 255

Pro Met Asp Glu Lys Arg Ala Thr Ala Phe Gly Leu Met Lys Ile Asp
            260                 265                 270

Glu Glu Gly Arg Ile Ile Glu Phe Ala Glu Lys Pro Lys Gly Glu Gln
        275                 280                 285

Leu Lys Ala Met Lys Val Asp Thr Thr Ile Leu Gly Leu Asp Asp Glu
    290                 295                 300

Arg Ala Lys Glu Met Pro Tyr Ile Ala Ser Met Gly Ile Tyr Val Ile
305                 310                 315                 320

Ser Lys Asp Val Met Leu Asn Leu Leu Arg Asp Lys Phe Pro Gly Ala
                325                 330                 335

Asn Asp Phe Gly Ser Glu Val Ile Pro Gly Ala Thr Ser Val Gly Met
            340                 345                 350

Arg Val Gln Ala Tyr Leu Tyr Asp Gly Tyr Trp Glu Asp Ile Gly Thr
        355                 360                 365

Ile Glu Ala Phe Tyr Asn Ala Asn Leu Gly Ile Thr Lys Lys Pro Val
    370                 375                 380

Pro Asp Phe Ser Phe Tyr Asp Arg Ser Ser Pro Ile Tyr Thr Gln Pro
385                 390                 395                 400

Arg Tyr Leu Pro Pro Ser Lys Met Leu Asp Ala Asp Val Thr Asp Ser
                405                 410                 415

Val Ile Gly Glu Gly Cys Val Ile Lys Asn Cys Lys Ile His His Ser
            420                 425                 430

Val Ile Gly Leu Arg Ser Cys Ile Ser Glu Gly Ala Ile Ile Glu Asp
        435                 440                 445

Thr Leu Leu Met Gly Ala Asp Tyr Tyr Glu Thr Asp Ala Asp Arg Arg
    450                 455                 460

Phe Leu Ala Ala Lys Gly Ser Val Pro Ile Gly Ile Gly Lys Asn Ser
465                 470                 475                 480

His Ile Lys Arg Ala Ile Ile Asp Lys Asn Ala Arg Ile Gly Glu Asn
                485                 490                 495

Val Lys Ile Ile Asn Ser Asp Asp Val Gln Glu Ala Ala Arg Glu Thr
            500                 505                 510

Asp Gly Tyr Phe Ile Lys Ser Gly Ile Val Thr Val Ile Lys Asp Ala
        515                 520                 525

Leu Leu Pro Ser Gly Thr Val Ile
    530                 535

<210> SEQ ID NO 118
<211> LENGTH: 515
<212> TYPE: PRT
<213> ORGANISM: Lens culinaris
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 118

Met Ala Ser Met Ala Ala Ile Gly Val Leu Lys Val Pro Pro Ser Ser
```

```
1               5                   10                  15
Ser Ser Ser Leu Ser Ser Ser Ser Lys Ala Ile Ala Arg Asn Leu
            20                  25                  30

Ser Phe Thr Ser Ser Gln Leu Ser Gly Asp Lys Ile Phe Thr Val Ser
            35                  40                  45

Gly Thr Arg Thr Arg Ser Ser Gly Arg Asn Pro Phe Ile Val Ser Pro
50                      55                  60

Glu Ala Val Ser Asp Ser Lys Asn Ser Gln Thr Cys Leu Asp Pro Asp
65                  70                  75                  80

Ala Ser Arg Ser Val Leu Gly Ile Ile Leu Gly Gly Ala Gly Thr
                85                  90                  95

Arg Leu Tyr Pro Leu Thr Lys Lys Arg Ala Lys Pro Ala Val Pro Leu
            100                 105                 110

Gly Ala Asn Tyr Arg Leu Ile Asp Ile Pro Val Ser Asn Cys Leu Asn
            115                 120                 125

Ser Asn Ile Ser Lys Ile Tyr Val Leu Thr Gln Phe Asn Ser Ala Ser
130                 135                 140

Leu Asn Arg His Leu Ser Arg Ala Tyr Ala Ser Asn Leu Gly Gly Tyr
145                 150                 155                 160

Lys Asn Glu Gly Phe Val Glu Val Leu Ala Ala Gln Gln Ser Pro Glu
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Leu Glu Tyr Leu Val Leu Ala Gly
            195                 200                 205

Asp His Leu Tyr Arg Met Asp Tyr Glu Arg Phe Ile Gln Ala His Arg
            210                 215                 220

Glu Ser Asp Ala Asp Ile Thr Val Ala Ala Leu Pro Met Asp Glu Ala
225                 230                 235                 240

Arg Ala Thr Ala Phe Gly Leu Met Lys Ile Asp Glu Glu Gly Arg Ile
                245                 250                 255

Ile Glu Phe Ser Glu Lys Pro Lys Gly Gly Gln Leu Lys Ala Met Lys
            260                 265                 270

Val Asp Thr Thr Ile Leu Gly Leu Asp Asp Glu Arg Ala Lys Glu Met
            275                 280                 285

Pro Tyr Ile Ala Ser Met Gly Ile Tyr Val Val Ser Lys His Val Met
            290                 295                 300

Leu Asp Leu Leu Arg Asp Lys Phe Pro Gly Ala Asn Asp Phe Gly Ser
305                 310                 315                 320

Glu Val Ile Pro Gly Ala Thr Asp Leu Gly Met Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Val Pro Asp Phe Ser Phe
            355                 360                 365

Tyr Asp Arg Ser Ser Pro Ile Tyr Thr Gln Pro Arg Tyr Leu Pro Pro
370                 375                 380

Ser Lys Met Leu Asp Ala Asp Ile Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Thr Leu Leu Met Gly
            420                 425                 430
```

Ala Asp Tyr Tyr Glu Thr Asp Ala Asp Arg Arg Phe Leu Ala Ala Lys
        435                 440                 445

Gly Gly Val Pro Ile Gly Ile Gly Lys Asn Ser His Ile Lys Arg Ala
    450                 455                 460

Ile Ile Asp Lys Asn Ala Arg Ile Gly Asp Asp Val Lys Ile Ile Asn
465                 470                 475                 480

Ser Asp Asn Val Gln Glu Ala Ala Arg Glu Thr Glu Gly Tyr Phe Ile
                485                 490                 495

Lys Ser Gly Ile Val Thr Val Ile Asn Glu Ala Phe Ile Pro Ser Gly
                500                 505                 510

Thr Val Ile
        515

<210> SEQ ID NO 119
<211> LENGTH: 521
<212> TYPE: PRT
<213> ORGANISM: Arachis duranensis
<220> FEATURE:
<221> NAME/KEY: MISC_FEATURE
<222> LOCATION: (1)..(521)
<223> OTHER INFORMATION: ADP-glucose pyrophosphorylase small subunit

<400> SEQUENCE: 119

Met Ala Ser Met Ser Ala Ile Gly Val Leu Lys Leu Pro Ser Ser Ser
1               5                   10                  15

Ser Ser Ser Pro Ser Ala Ser Asn Asn Ala Ala Leu Arg Lys Cys Ile
                20                  25                  30

Pro Arg Ser Leu Ser Phe Ser Ser Gln Leu Ser Gly Asp Lys Ile
            35                  40                  45

Ser Ser Leu Pro Thr Ala Ser Ser Arg Thr Ser Thr Cys Thr Arg Asn
    50                  55                  60

Pro Leu Ile Val Thr Pro Lys Ala Val Ser Asp Ser Gln Asn Ser Gln
65                  70                  75                  80

Thr Cys Leu Asp Pro Asp Ala Ser Arg Ser Val Leu Gly Ile Ile Leu
                85                  90                  95

Gly Gly Gly Ala Gly Thr Arg Leu Tyr Pro Leu Thr Lys Lys Arg Ala
                100                 105                 110

Lys Pro Ala Val Pro Leu Gly Ala Asn Tyr Arg Leu Ile Asp Ile Pro
            115                 120                 125

Val Ser Asn Cys Leu Asn Ser Asn Val Ser Lys Ile Tyr Val Leu Thr
130                 135                 140

Gln Phe Asn Ser Ala Ser Leu Asn Arg His Leu Ser Arg Ala Tyr Ala
145                 150                 155                 160

Ser Asn Met Gly Gly Tyr Lys Asn Glu Gly Phe Val Glu Val Leu Ala
                165                 170                 175

Ala Gln Gln Ser Pro Glu Asn Pro Asn Trp Phe Gln Gly Thr Ala Asp
            180                 185                 190

Ala Val Arg Gln Tyr Leu Trp Leu Phe Glu Glu His Asn Val Leu Glu
        195                 200                 205

Phe Leu Val Leu Ala Gly Asp His Leu Tyr Arg Met Asp Tyr Glu Lys
    210                 215                 220

Phe Ile Gln Ala His Arg Glu Ser Asp Ala Asp Ile Thr Val Ala Ala
225                 230                 235                 240

Leu Pro Met Asp Glu Lys Arg Ala Thr Ala Phe Gly Leu Met Lys Ile
                245                 250                 255

```
Asp Glu Glu Gly Arg Ile Ile Glu Phe Ala Glu Lys Pro Lys Gly Glu
                260                 265                 270

Gln Leu Arg Ala Met Lys Val Asp Thr Thr Ile Leu Gly Leu Asp Asp
            275                 280                 285

Ala Arg Ala Lys Glu Met Pro Tyr Ile Ala Ser Met Gly Ile Tyr Val
        290                 295                 300

Val Ser Lys Asp Val Met Leu Asn Leu Leu Arg Asp Lys Phe Pro Gly
305                 310                 315                 320

Ala Asn Asp Phe Gly Ser Glu Val Ile Pro Gly Ala Thr Ser Ile Gly
                325                 330                 335

Met Arg Val Gln Ala Tyr Leu Tyr Asp Gly Tyr Trp Glu Asp Ile Gly
            340                 345                 350

Thr Ile Glu Ala Phe Tyr Asn Ala Asn Leu Gly Ile Thr Lys Lys Pro
        355                 360                 365

Val Pro Asp Phe Ser Phe Tyr Asp Arg Ser Ser Pro Ile Tyr Thr Gln
370                 375                 380

Pro Arg Tyr Leu Pro Pro Ser Lys Met Leu Asp Ala Asp Val Thr Asp
385                 390                 395                 400

Ser Val Ile Gly Glu Gly Cys Val Ile Lys Asn Cys Lys Ile His His
                405                 410                 415

Ser Val Val Gly Leu Arg Ser Cys Ile Ser Glu Gly Ala Ile Ile Glu
            420                 425                 430

Asp Thr Leu Met Gly Ala Asp Tyr Tyr Glu Thr Glu Ala Asp Lys
        435                 440                 445

Arg Phe Leu Ala Ala Lys Gly Ser Val Pro Ile Gly Ile Gly Lys Asn
450                 455                 460

Ser His Ile Lys Arg Ala Ile Ile Asp Lys Asn Ala Arg Ile Gly Glu
465                 470                 475                 480

Asn Val Lys Ile Val Asn Gly Asp Asn Val Gln Glu Ala Ala Arg Glu
                485                 490                 495

Thr Asp Gly Tyr Phe Ile Lys Ser Gly Ile Val Thr Ile Lys Asp
            500                 505                 510

Ala Leu Ile Pro Ser Gly Thr Val Ile
        515                 520

<210> SEQ ID NO 120
<211> LENGTH: 512
<212> TYPE: PRT
<213> ORGANISM: Brassica rapa
<220> FEATURE:
<221> NAME/KEY: MISC_FEATURE
<222> LOCATION: (1)..(512)
<223> OTHER INFORMATION: ADP-glucose pyrophosphorylase small subunit

<400> SEQUENCE: 120

Met Ala Ser Ile Ala Ala Thr Gly Val Leu Lys Val Pro Pro Pro Ala
1               5                   10                  15

Ala Ala Ser Cys Glu Ala Val Pro Thr Met Thr Leu Ser Phe Ser Ser
            20                  25                  30

Ser Val Ser Leu Arg Ala Thr Val Ser His Arg Arg Gly Ser Val Leu
        35                  40                  45

Ser Arg Asn Arg Val Arg Asn Pro Met Ile Val Ser Pro Lys Ala Val
    50                  55                  60

Ser Asp Ser Gln Asn Ser Gln Thr Cys Leu Asp Pro Asp Ala Ser Arg
65                  70                  75                  80

Ser Val Leu Gly Ile Ile Leu Gly Gly Gly Ala Gly Thr Arg Leu Tyr
```

```
                    85                  90                  95
Pro Leu Thr Lys Lys Arg Ala Lys Pro Ala Val Pro Leu Gly Ala Asn
                100                 105                 110

Tyr Arg Leu Ile Asp Ile Pro Val Ser Asn Cys Leu Asn Ser Asn Ile
                115                 120                 125

Asn Lys Ile Tyr Val Leu Thr Gln Phe Asn Ser Ala Ser Leu Asn Arg
            130                 135                 140

His Leu Ser Arg Ala Tyr Ala Thr Asn Met Gly Gly Tyr Lys Asn Glu
145                 150                 155                 160

Gly Phe Val Glu Val Leu Ala Ala Gln Gln Ser Pro Glu Asn Pro Asn
                165                 170                 175

Trp Phe Gln Gly Thr Ala Asp Ala Val Arg Gln Tyr Leu Trp Leu Phe
                180                 185                 190

Glu Glu His Asn Val Leu Glu Tyr Leu Ile Leu Ala Gly Asp His Leu
            195                 200                 205

Tyr Arg Met Asp Tyr Glu Lys Phe Ile Gln Ala His Arg Glu Thr Asp
        210                 215                 220

Ala Asp Ile Thr Val Ala Ala Leu Pro Met Asp Glu Glu Arg Ala Thr
225                 230                 235                 240

Ala Phe Gly Leu Met Lys Ile Asp Glu Glu Gly Arg Ile Val Glu Phe
                245                 250                 255

Ala Glu Lys Pro Lys Gly Glu Gln Leu Lys Gly Met Lys Val Asp Thr
                260                 265                 270

Thr Ile Leu Gly Leu Asp Asp Lys Arg Ala Lys Glu Met Pro Tyr Ile
            275                 280                 285

Ala Ser Met Gly Ile Tyr Val Val Ser Lys Asp Val Met Leu Glu Leu
        290                 295                 300

Leu Arg Asn Lys Phe Pro Gly Ala Asn Asp Phe Gly Ser Glu Val Ile
305                 310                 315                 320

Pro Gly Ala Thr Ser Leu Gly Leu Arg Val Gln Ala Tyr Leu Tyr Asp
                325                 330                 335

Gly Tyr Trp Glu Asp Ile Gly Thr Ile Glu Ala Phe Tyr Asn Ala Asn
                340                 345                 350

Leu Gly Ile Thr Lys Lys Pro Val Pro Asp Phe Ser Phe Tyr Asp Arg
            355                 360                 365

Ser Ala Pro Ile Tyr Thr Gln Pro Arg Tyr Leu Pro Pro Ser Lys Met
370                 375                 380

Leu Asp Ala Asp Val Thr Asp Ser Val Ile Gly Glu Gly Cys Val Ile
                385                 390                 395             400

Lys Asn Cys Lys Ile His His Ser Val Val Gly Leu Arg Ser Cys Ile
                405                 410                 415

Ser Glu Gly Ala Ile Ile Glu Asp Ser Leu Leu Met Gly Ala Asp Tyr
            420                 425                 430

Tyr Glu Thr Ala Ser Glu Lys Ser Leu Leu Thr Ala Lys Gly Ser Val
        435                 440                 445

Pro Ile Gly Ile Gly Lys Asn Ser His Ile Lys Arg Ala Ile Ile Asp
450                 455                 460

Lys Asn Ala Arg Ile Gly Asp Asn Val Lys Ile Ile Asn Ser Asp Asn
465                 470                 475                 480

Val Gln Glu Ala Ala Arg Glu Thr Glu Gly Tyr Phe Ile Lys Ser Gly
                485                 490                 495

Ile Val Thr Val Ile Lys Asp Ala Leu Ile Pro Thr Gly Thr Leu Ile
            500                 505                 510
```

<210> SEQ ID NO 121
<211> LENGTH: 522
<212> TYPE: PRT
<213> ORGANISM: Jatropha curcas
<220> FEATURE:
<221> NAME/KEY: MISC_FEATURE
<222> LOCATION: (1)..(522)
<223> OTHER INFORMATION: ADP-glucose pyrophosphorylase small subunit

<400> SEQUENCE: 121

```
Met Ala Ser Ala Ala Ile Gly Ala Leu Lys Val Pro Leu Pro Ala
1               5                   10                  15

Ser Ser Ser Thr Asn Ser Ser Lys Leu Asn Arg Lys Thr Ser Pro Leu
                20                  25                  30

Val Gln Ser Leu Ser Phe Ser Ser Asn Leu Ser Gly Asp Lys Ile
                35                  40                  45

Tyr Tyr Lys Ala Phe Ser Gly Arg Pro Gly Asn Gly Ser Asn Glu Arg
50                  55                  60

Thr Pro Met Val Val Ser Pro Lys Ala Val Ser Asp Ser Lys Asn Ser
65                  70                  75                  80

Gln Thr Cys Leu Asp Pro Asp Ala Ser Arg Ser Val Leu Gly Ile Ile
                85                  90                  95

Leu Gly Gly Gly Ala Gly Thr Arg Leu Tyr Pro Leu Thr Lys Lys Arg
                100                 105                 110

Ala Lys Pro Ala Val Pro Leu Gly Ala Asn Tyr Arg Leu Ile Asp Ile
                115                 120                 125

Pro Val Ser Asn Cys Leu Asn Ser Asn Ile Ser Lys Ile Tyr Val Leu
130                 135                 140

Thr Gln Phe Asn Ser Ala Ser Leu Asn Arg His Leu Ser Arg Ala Tyr
145                 150                 155                 160

Ala Ser Asn Met Gly Gly Tyr Lys Asn Glu Gly Phe Val Glu Val Leu
                165                 170                 175

Ala Ala Gln Gln Ser Pro Glu Asn Pro Asn Trp Phe Gln Gly Thr Ala
                180                 185                 190

Asp Ala Val Arg Gln Tyr Leu Trp Leu Phe Glu Glu His Asn Val Leu
                195                 200                 205

Glu Phe Leu Ile Leu Ala Gly Asp His Leu Tyr Arg Met Asp Tyr Glu
210                 215                 220

Arg Phe Ile Gln Ala His Arg Glu Thr Asp Ala Asp Ile Thr Val Ala
225                 230                 235                 240

Ala Leu Pro Met Asp Glu Ala Arg Ala Thr Ala Phe Gly Leu Met Lys
                245                 250                 255

Ile Asp Glu Glu Gly Arg Ile Val Glu Phe Ala Glu Lys Pro Lys Gly
                260                 265                 270

Glu Gln Leu Lys Ala Met Lys Val Asp Thr Thr Ile Leu Gly Leu Asp
                275                 280                 285

Asp Glu Arg Ala Lys Glu Met Pro Tyr Ile Ala Ser Met Gly Ile Tyr
                290                 295                 300

Val Val Ser Lys Asn Ala Met Leu Asp Leu Leu Arg Asp Arg Phe Pro
305                 310                 315                 320

Gly Ala Asn Asp Phe Gly Ser Glu Val Ile Pro Gly Ala Thr Ser Ile
                325                 330                 335

Gly Met Arg Val Gln Ala Tyr Leu Tyr Asp Gly Tyr Trp Glu Asp Ile
                340                 345                 350
```

```
Gly Thr Ile Glu Ala Phe Tyr Asn Ala Asn Leu Gly Ile Thr Lys Lys
            355                 360                 365

Pro Ile Pro Asp Phe Ser Phe Tyr Asp Arg Ser Ser Pro Ile Tyr Thr
    370                 375                 380

Gln Pro Arg Tyr Leu Pro Pro Ser Lys Met Leu Asp Ala Asp Val Thr
385                 390                 395                 400

Asp Ser Val Ile Gly Glu Gly Cys Val Ile Lys Asn Cys Lys Ile His
                405                 410                 415

His Ser Val Val Gly Leu Arg Ser Cys Ile Ser Glu Gly Ala Ile Ile
            420                 425                 430

Glu Asp Thr Leu Leu Met Gly Ala Asp Tyr Tyr Glu Thr Asp Ala Asp
        435                 440                 445

Arg Arg Phe Leu Ala Ala Lys Gly Ser Val Pro Ile Gly Ile Gly Lys
    450                 455                 460

Asn Ser His Ile Lys Arg Ala Ile Ile Asp Lys Asn Ala Arg Ile Gly
465                 470                 475                 480

Asp Asn Val Lys Ile Ile Asn Ser Asp Asn Val Gln Glu Ala Ala Arg
                485                 490                 495

Glu Thr Asp Gly Tyr Phe Ile Lys Ser Gly Ile Val Thr Val Ile Lys
            500                 505                 510

Asp Ala Leu Ile Pro Ser Gly Thr Val Ile
        515                 520

<210> SEQ ID NO 122
<211> LENGTH: 516
<212> TYPE: PRT
<213> ORGANISM: Cicer arietinum
<220> FEATURE:
<221> NAME/KEY: MISC_FEATURE
<222> LOCATION: (1)..(516)
<223> OTHER INFORMATION: ADP-glucose pyrophosphorylase small subunit

<400> SEQUENCE: 122

Met Ala Ser Met Ala Ala Ile Gly Val Leu Lys Val Pro Pro Ser Ser
1               5                   10                  15

Ser Ser Ser Ser Ser Ser Ser Ser Lys Ala Ile Ile Ala Arg Asn
            20                  25                  30

Leu Ser Phe Thr Ser Ser Gln Val Cys Gly Asp Lys Ile Gly Thr Phe
        35                  40                  45

Ser Arg Arg Gly Arg Gly Ser Tyr Val Gly Asn Pro Ile Ile Val Ser
    50                  55                  60

Pro Lys Ala Val Ser Asp Ser Lys Asn Ala Gln Thr Cys Leu Asp Pro
65                  70                  75                  80

Asp Ala Ser Arg Ser Val Leu Gly Ile Ile Leu Gly Gly Gly Ala Gly
                85                  90                  95

Thr Arg Leu Tyr Pro Leu Thr Lys Lys Arg Ala Lys Pro Ala Val Pro
            100                 105                 110

Leu Gly Ala Asn Tyr Arg Leu Ile Asp Ile Pro Val Ser Asn Cys Leu
        115                 120                 125

Asn Ser Asn Val Ser Lys Ile Tyr Val Leu Thr Gln Phe Asn Ser Ala
    130                 135                 140

Ser Leu Asn Arg His Leu Ser Arg Ala Tyr Ala Ser Asn Met Gly Gly
145                 150                 155                 160

Tyr Lys Asn Glu Gly Phe Val Glu Gly Leu Ala Ala Gln Gln Ser Pro
                165                 170                 175

Glu Asn Pro Asn Trp Phe Gln Gly Thr Ala Asp Ala Val Arg Gln Tyr
```

```
                180                 185                 190
Leu Trp Leu Phe Glu Glu His Asn Val Leu Glu Tyr Leu Val Leu Ala
        195                 200                 205

Gly Asp His Leu Tyr Arg Met Asp Tyr Glu Arg Phe Ile Gln Ala His
    210                 215                 220

Arg Glu Ser Asp Ala Asp Ile Thr Val Ala Ala Leu Pro Met Asp Glu
225                 230                 235                 240

Leu Arg Ala Thr Ala Phe Gly Leu Met Lys Ile Asp Glu Glu Gly Arg
                245                 250                 255

Ile Ile Glu Phe Ala Glu Lys Pro Lys Gly Glu Gln Leu Lys Ala Met
            260                 265                 270

Lys Val Asp Thr Thr Ile Leu Gly Leu Asp Glu Glu Arg Ala Lys Glu
        275                 280                 285

Met Pro Tyr Ile Ala Ser Met Gly Ile Tyr Val Val Ser Lys His Val
    290                 295                 300

Met Leu Asp Leu Leu Arg Glu Lys Phe Pro Gly Ala Asn Asp Phe Gly
305                 310                 315                 320

Ser Glu Val Ile Pro Gly Ala Thr Asn Ile Gly Met Arg Val Gln Ala
                325                 330                 335

Tyr Leu Tyr Asp Gly Tyr Trp Glu Asp Ile Gly Thr Ile Glu Ala Phe
            340                 345                 350

Tyr Asn Ala Asn Leu Gly Ile Thr Lys Lys Pro Val Pro Asp Phe Ser
        355                 360                 365

Phe Tyr Asp Arg Ser Ser Pro Ile Tyr Thr Gln Pro Arg Tyr Leu Pro
    370                 375                 380

Pro Ser Lys Met Leu Asp Ala Asp Ile Thr Asp Ser Val Ile Gly Glu
385                 390                 395                 400

Gly Cys Val Ile Lys Asn Cys Lys Ile His His Ser Val Val Gly Leu
                405                 410                 415

Arg Ser Cys Ile Ser Glu Gly Ala Ile Ile Glu Asp Thr Leu Leu Met
            420                 425                 430

Gly Ala Asp Tyr Tyr Glu Thr Asp Ala Asp Arg Arg Phe Leu Ala Ala
        435                 440                 445

Lys Gly Ser Val Pro Ile Gly Ile Gly Lys Asn Ser His Ile Arg Arg
    450                 455                 460

Ala Ile Ile Asp Lys Asn Ala Arg Ile Gly Asp Asn Val Lys Ile Ile
465                 470                 475                 480

Asn Ser Asp Asn Val Gln Glu Ala Ala Arg Glu Thr Glu Gly Tyr Phe
                485                 490                 495

Ile Lys Ser Gly Ile Val Thr Val Ile Lys Asp Ala Leu Ile Pro Ser
            500                 505                 510

Gly Thr Val Ile
        515

<210> SEQ ID NO 123
<211> LENGTH: 523
<212> TYPE: PRT
<213> ORGANISM: Camelina sativa
<220> FEATURE:
<221> NAME/KEY: MISC_FEATURE
<222> LOCATION: (1)..(523)
<223> OTHER INFORMATION: ADP-glucose pyrophosphorylase small subunit

<400> SEQUENCE: 123

Met Ala Tyr Val Ala Val Thr Gly Val Leu Lys Val Pro Ser Ala Ser
1               5                   10                  15
```

```
Ala Ser Ser Phe His Ser Thr Gly Thr Lys Ser Ser Thr Glu Ala Val
         20                  25                  30

Pro Thr Arg Ser Thr Leu Ser Phe Ser Ser Val Asp Glu Asn Asp
         35                  40              45

Ser Leu Arg Ala Ile Val Ser Arg Arg Phe Cys Val Gly Arg Glu Ser
50                       55                  60

Arg Asn Pro Met Ile Val Ser Pro Lys Ala Val Ser Asp Ser Gln Asn
65              70                  75                      80

Ser Gln Thr Cys Leu Asp Pro Asp Ala Ser Ser Ser Val Leu Gly Ile
                85              90                  95

Ile Leu Gly Gly Gly Ala Gly Thr Arg Leu Tyr Pro Leu Thr Lys Lys
            100                 105                 110

Arg Ala Lys Pro Ala Val Pro Leu Gly Ala Asn Tyr Arg Leu Ile Asp
            115                 120                 125

Ile Pro Val Ser Asn Cys Leu Asn Ser Asn Ile Ser Lys Ile Tyr Val
            130                 135                 140

Leu Thr Gln Phe Asn Ser Ala Ser Leu Asn Arg His Leu Ser Arg Ala
145                 150                 155                 160

Tyr Ala Ser Asn Met Gly Gly Tyr Lys Asn Glu Gly Phe Val Glu Val
                165                 170                 175

Leu Ala Ala Gln Gln Ser Pro Glu Asn Pro Asn Trp Phe Gln Gly Thr
            180                 185                 190

Ala Asp Ala Val Arg Gln Tyr Leu Trp Leu Phe Glu Glu His Asn Val
            195                 200                 205

Leu Glu Tyr Leu Ile Leu Ala Gly Asp His Leu Tyr Arg Met Asp Tyr
            210                 215                 220

Glu Lys Phe Ile Gln Ala His Arg Glu Thr Asp Ala Asp Ile Thr Val
225                 230                 235                 240

Ala Ala Leu Pro Met Asp Glu Gln Arg Ala Thr Ala Phe Gly Leu Met
                245                 250                 255

Lys Ile Asp Glu Glu Gly Arg Ile Val Glu Phe Ser Glu Lys Pro Lys
                260                 265                 270

Gly Glu Gln Leu Lys Ala Met Lys Val Asp Thr Thr Ile Leu Gly Leu
            275                 280                 285

Asp Asp Lys Arg Ala Lys Glu Met Pro Tyr Ile Ala Ser Met Gly Ile
            290                 295                 300

Tyr Val Val Ser Arg Asp Val Met Leu Glu Leu Leu Arg Asn Lys Phe
305                 310                 315                 320

Pro Gly Ala Asn Asp Phe Gly Ser Glu Val Ile Pro Gly Ala Thr Asp
                325                 330                 335

Leu Gly Leu Arg Val Gln Ala Tyr Leu Tyr Asp Gly Tyr Trp Glu Asp
            340                 345                 350

Ile Gly Thr Ile Glu Ala Phe Tyr Asn Ala Asn Leu Gly Ile Thr Lys
            355                 360                 365

Lys Pro Val Pro Asp Phe Ser Phe Tyr Asp Arg Ser Ala Pro Ile Tyr
            370                 375                 380

Thr Gln Pro Arg Tyr Leu Pro Pro Ser Lys Met Leu Asp Ala Asp Val
385                 390                 395                 400

Thr Asp Ser Val Ile Gly Glu Gly Cys Val Ile Lys Asn Cys Lys Ile
                405                 410                 415

His His Ser Val Ile Gly Leu Arg Ser Cys Ile Ser Glu Gly Ala Ile
            420                 425                 430
```

```
Ile Glu Asp Thr Leu Leu Met Gly Ala Asp Tyr Tyr Glu Thr Ala Ser
            435                 440                 445

Glu Lys Ser Leu Leu Ser Ala Lys Gly Ser Val Pro Ile Gly Ile Gly
    450                 455                 460

Lys Asn Ala His Ile Lys Arg Ala Ile Ile Asp Lys Asn Ala Arg Ile
465                 470                 475                 480

Gly Asp Asn Val Lys Ile Ile Asn Ser Asp Asn Val Gln Glu Ser Ala
                485                 490                 495

Arg Glu Thr Glu Gly Tyr Phe Ile Lys Ser Gly Ile Val Thr Val Met
            500                 505                 510

Lys Asp Ala Leu Ile Pro Ala Gly Thr Val Ile
            515                 520
```

<210> SEQ ID NO 124
<211> LENGTH: 520
<212> TYPE: PRT
<213> ORGANISM: Capsella rubella
<220> FEATURE:
<221> NAME/KEY: MISC_FEATURE
<222> LOCATION: (1)..(520)
<223> OTHER INFORMATION: ADP-glucose pyrophosphorylase small subunit

<400> SEQUENCE: 124

```
Met Ala Tyr Leu Ala Ala Thr Gly Val Leu Lys Val Pro Ala Ser Ser
1               5                   10                  15

Ser Phe Thr Gly Cys Lys Ser Thr Asp Ser Val Pro Thr Pro Thr Arg
            20                  25                  30

Ser Thr Leu Ser Phe Ser Ser Val Glu Asp Asn Val Ser Ser Ser Leu
        35                  40                  45

Arg Ala Ala Val Ser Ser Arg Cys Ala Gly Arg Glu Thr Arg Thr Pro
    50                  55                  60

Thr Ile Val Ser Pro Lys Ala Val Ser Asp Ser Gln Asn Ser Gln Thr
65                  70                  75                  80

Cys Leu Asp Pro Asp Ala Ser Ser Val Leu Gly Ile Ile Leu Gly
                85                  90                  95

Gly Gly Ala Gly Thr Arg Leu Tyr Pro Leu Thr Lys Lys Arg Ala Lys
            100                 105                 110

Pro Ala Val Pro Leu Gly Ala Asn Tyr Arg Leu Ile Asp Ile Pro Val
        115                 120                 125

Ser Asn Cys Leu Asn Ser Asn Ile Ser Lys Ile Tyr Val Leu Thr Gln
    130                 135                 140

Phe Asn Ser Ala Ser Leu Asn Arg His Leu Ser Arg Ala Tyr Ala Ser
145                 150                 155                 160

Asn Met Gly Gly Tyr Lys Asn Glu Gly Phe Val Glu Val Leu Ala Ala
                165                 170                 175

Gln Gln Ser Pro Glu Asn Pro Asn Trp Phe Gln Gly Thr Ala Asp Ala
            180                 185                 190

Val Arg Gln Tyr Leu Trp Leu Phe Glu Glu His Asn Val Leu Glu Tyr
        195                 200                 205

Leu Ile Leu Ala Gly Asp His Leu Tyr Arg Met Asp Tyr Glu Lys Phe
    210                 215                 220

Ile Gln Ala His Arg Glu Thr Asp Ala Asp Ile Thr Val Ala Ala Leu
225                 230                 235                 240

Pro Met Asp Glu Ala Arg Ala Thr Ala Phe Gly Leu Met Lys Ile Asp
                245                 250                 255

Glu Glu Gly Arg Ile Val Glu Phe Ala Glu Lys Pro Lys Gly Glu Gln
```

```
              260                 265                 270
Leu Lys Ala Met Lys Val Asp Thr Thr Ile Leu Gly Leu Asp Asp Glu
            275                 280                 285

Arg Ala Lys Glu Met Pro Tyr Ile Ala Ser Met Gly Ile Tyr Val Val
            290                 295                 300

Ser Arg Asp Val Met Leu Glu Leu Leu Arg Asn Lys Phe Pro Gly Ala
305                 310                 315                 320

Asn Asp Phe Gly Ser Glu Val Ile Pro Gly Ala Thr Ser Leu Gly Leu
                325                 330                 335

Arg Val Gln Ala Tyr Leu Tyr Asp Gly Tyr Trp Glu Asp Ile Gly Thr
            340                 345                 350

Ile Glu Ala Phe Tyr Asn Ala Asn Leu Gly Ile Thr Lys Lys Pro Val
            355                 360                 365

Pro Asp Phe Ser Phe Tyr Asp Arg Ser Ala Pro Ile Tyr Thr Gln Pro
        370                 375                 380

Arg Tyr Leu Pro Pro Ser Lys Met Leu Asp Ala Asp Val Thr Asp Ser
385                 390                 395                 400

Val Ile Gly Glu Gly Cys Val Ile Lys Asn Cys Lys Ile His His Ser
                405                 410                 415

Val Val Gly Leu Arg Ser Cys Ile Ser Glu Gly Ala Ile Ile Glu Asp
                420                 425                 430

Ser Leu Leu Met Gly Ala Asp Tyr Tyr Glu Thr Ala Ser Glu Lys Ser
            435                 440                 445

Ile Leu Ser Ala Lys Gly Ser Val Pro Ile Gly Ile Gly Lys Asn Ser
        450                 455                 460

His Ile Lys Arg Ala Ile Ile Asp Lys Asn Ala Arg Ile Gly Asp Asn
465                 470                 475                 480

Val Lys Ile Ile Asn Ser Asp Asn Val Gln Glu Ala Ala Arg Glu Thr
                485                 490                 495

Glu Gly Tyr Phe Ile Lys Ser Gly Ile Val Thr Val Ile Lys Asp Ala
            500                 505                 510

Leu Ile Pro Ala Gly Thr Val Ile
        515                 520

<210> SEQ ID NO 125
<211> LENGTH: 522
<212> TYPE: PRT
<213> ORGANISM: Populus trichocarpa
<220> FEATURE:
<221> NAME/KEY: MISC_FEATURE
<222> LOCATION: (1)..(522)
<223> OTHER INFORMATION: ADP-glucose pyrophosphorylase small subunit

<400> SEQUENCE: 125

Met Ala Ser Met Ala Ala Ile Gly Val Met Arg Pro Pro Ser Ser Ser
1               5                   10                  15

Ser Leu Ser Ser Ser Ser Ser Ser Asn Leu Ser Arg Arg Thr Ala Phe
            20                  25                  30

Arg Ser Leu Ser Phe Ser Ser Ser Asn Leu Ser Gly Gly Lys Val
        35                  40                  45

Cys Ser Thr Ala Phe Ser Val Arg Arg Asp Thr Gly Arg Asn Glu Arg
    50                  55                  60

Thr Pro Met Ile Val Ser Pro Lys Ala Val Ser Asp Ser Arg Asn Ser
65                  70                  75                  80

Gln Thr Cys Leu Asp Pro Asp Ala Ser Arg Ser Val Leu Gly Ile Ile
                85                  90                  95
```

```
Leu Gly Gly Gly Ala Gly Thr Arg Leu Tyr Pro Leu Thr Lys Lys Arg
            100                 105                 110

Ala Lys Pro Ala Val Pro Leu Gly Ala Asn Tyr Arg Leu Ile Asp Ile
        115                 120                 125

Pro Val Ser Asn Cys Leu Asn Ser Asn Ile Ser Lys Ile Tyr Val Leu
    130                 135                 140

Thr Gln Phe Asn Ser Ala Ser Leu Asn Arg His Leu Ser Arg Ala Tyr
145                 150                 155                 160

Ala Ser Asn Met Gly Gly Tyr Lys Asn Glu Gly Phe Val Glu Val Leu
                165                 170                 175

Ala Ala Gln Gln Ser Pro Glu Asn Pro Asn Trp Phe Gln Gly Thr Ala
            180                 185                 190

Asp Ala Val Arg Gln Tyr Leu Trp Leu Phe Glu Glu His Asn Val Leu
        195                 200                 205

Glu Phe Leu Val Leu Ala Gly Asp His Leu Tyr Arg Met Asp Tyr Glu
    210                 215                 220

Arg Phe Ile Gln Ala His Arg Glu Thr Asp Ala Asp Ile Thr Val Ala
225                 230                 235                 240

Ala Leu Pro Met Asp Glu Lys Arg Ala Thr Ala Phe Gly Leu Met Lys
                245                 250                 255

Ile Asp Glu Glu Gly Arg Ile Ile Glu Phe Ala Glu Lys Pro Lys Gly
            260                 265                 270

Glu Gln Leu Lys Ala Met Lys Val Asp Thr Thr Ile Leu Gly Leu Asp
        275                 280                 285

Asp Glu Arg Ala Lys Glu Met Pro Tyr Ile Ala Ser Met Gly Ile Tyr
    290                 295                 300

Val Val Ser Lys Asn Val Met Leu Asp Leu Leu Arg Glu Lys Phe Pro
305                 310                 315                 320

Gly Ala Asn Asp Phe Gly Ser Glu Val Ile Pro Gly Ala Thr Ser Ile
                325                 330                 335

Gly Met Arg Val Gln Ala Tyr Leu Tyr Asp Gly Tyr Trp Glu Asp Ile
            340                 345                 350

Gly Thr Ile Glu Ala Phe Tyr Asn Ala Asn Leu Gly Ile Thr Lys Lys
        355                 360                 365

Pro Val Pro Asp Phe Ser Phe Tyr Asp Arg Ser Ser Pro Ile Tyr Thr
    370                 375                 380

Gln Pro Arg Tyr Leu Pro Pro Ser Lys Met Leu Asp Ala Asp Val Thr
385                 390                 395                 400

Asp Ser Val Ile Gly Glu Gly Cys Val Ile Lys Asn Cys Lys Ile His
                405                 410                 415

His Ser Val Ile Gly Leu Arg Ser Cys Ile Ser Glu Gly Ala Ile Ile
            420                 425                 430

Glu Asp Thr Leu Leu Met Gly Ala Asp Tyr Tyr Glu Thr Asp Ala Asp
        435                 440                 445

Arg Arg Phe Leu Ala Ala Lys Gly Ser Val Pro Ile Gly Ile Gly Lys
    450                 455                 460

Asn Ser His Ile Lys Arg Ala Ile Ile Asp Lys Asn Ala Arg Ile Gly
465                 470                 475                 480

Asp Asn Val Lys Ile Ile Asn Gly Asp Asn Val Gln Glu Ala Ala Arg
                485                 490                 495

Glu Thr Asp Gly Tyr Phe Ile Lys Ser Gly Ile Val Thr Val Ile Lys
            500                 505                 510
```

```
Asp Ala Leu Ile Pro Ser Gly Thr Val Ile
        515                 520
```

<210> SEQ ID NO 126
<211> LENGTH: 517
<212> TYPE: PRT
<213> ORGANISM: Zea mays
<220> FEATURE:
<221> NAME/KEY: MISC_FEATURE
<222> LOCATION: (1)..(517)
<223> OTHER INFORMATION: ADP-glucose pyrophosphorylase small subunit

<400> SEQUENCE: 126

```
Met Ala Met Ala Ala Ile Ala Ser Pro Ser Ser Arg Thr Leu Ile Pro
1               5                   10                  15

Pro Arg His His Gly Ala Ala Pro Ser Pro Ser Thr Ser Gly Asp Ser
            20                  25                  30

Ser Leu Arg Leu Leu Cys Ala His Pro Arg His Gly Arg Arg Gly Arg
        35                  40                  45

Ala Met Ser Val Ser Thr Pro Ala Ala Arg Ser Arg Pro Phe Val Phe
    50                  55                  60

Ser Pro Arg Ala Val Ser Asp Ser Lys Ser Ser Gln Thr Cys Leu Asp
65                  70                  75                  80

Pro Asp Ala Ser Thr Ser Val Leu Gly Ile Ile Leu Gly Gly Gly Ala
                85                  90                  95

Gly Thr Arg Leu Tyr Pro Leu Thr Lys Lys Arg Ala Lys Pro Ala Val
            100                 105                 110

Pro Leu Gly Ala Asn Tyr Arg Leu Ile Asp Ile Pro Val Ser Asn Cys
        115                 120                 125

Leu Asn Ser Asn Ile Ser Lys Ile Tyr Val Leu Thr Gln Phe Asn Ser
    130                 135                 140

Ala Ser Leu Asn Arg His Leu Ser Arg Ala Tyr Gly Asn Asn Ile Gly
145                 150                 155                 160

Gly Tyr Lys Asn Asp Gly Phe Val Glu Val Leu Ala Ala Gln Gln Ser
                165                 170                 175

Pro Asp Asn Pro Asn Trp Phe Gln Gly Thr Ala Asp Ala Val Arg Gln
            180                 185                 190

Tyr Leu Trp Leu Phe Glu Glu His Asn Val Met Glu Phe Leu Ile Leu
        195                 200                 205

Ala Gly Asp His Leu Tyr Arg Met Asp Tyr Glu Lys Phe Ile Gln Ala
    210                 215                 220

His Arg Glu Thr Asp Ala Asp Ile Thr Val Ala Ala Leu Pro Met Asp
225                 230                 235                 240

Glu Lys Arg Ala Thr Ala Phe Gly Leu Met Lys Ile Asp Glu Glu Gly
                245                 250                 255

Arg Ile Ile Glu Phe Ala Glu Lys Pro Lys Gly Asp Gln Leu Lys Ala
            260                 265                 270

Met Met Val Asp Thr Thr Ile Leu Gly Leu Asp Asp Glu Arg Ala Lys
        275                 280                 285

Glu Met Pro Tyr Ile Ala Ser Met Gly Ile Tyr Val Phe Ser Lys Asp
    290                 295                 300

Val Met Leu Gln Leu Leu Arg Glu Gln Phe Pro Gly Ala Asn Asp Phe
305                 310                 315                 320

Gly Ser Glu Val Ile Pro Gly Ala Thr Ser Ile Gly Lys Arg Val Gln
                325                 330                 335

Ala Tyr Leu Tyr Asp Gly Tyr Trp Glu Asp Ile Gly Thr Ile Glu Ala
```

```
                340             345             350
Phe Tyr Asn Ala Asn Leu Gly Ile Thr Lys Pro Ile Pro Asp Phe
            355                 360             365

Ser Phe Tyr Asp Arg Ser Ala Pro Ile Tyr Thr Gln Pro Arg His Leu
    370                 375                 380

Pro Pro Ser Lys Val Leu Asp Ala Asp Val Thr Asp Ser Val Ile Gly
385                 390                 395                 400

Glu Gly Cys Val Ile Lys Asn Cys Lys Ile His His Ser Val Val Gly
                405                 410                 415

Leu Arg Ser Cys Ile Ser Glu Gly Ala Ile Ile Glu Asp Thr Leu Leu
            420                 425                 430

Met Gly Ala Asp Tyr Tyr Glu Thr Glu Ala Asp Lys Lys Leu Leu Ala
            435                 440                 445

Glu Asn Gly Gly Ile Pro Ile Gly Ile Gly Lys Asn Ser His Ile Arg
            450                 455                 460

Lys Ala Ile Ile Asp Lys Asn Ala Arg Ile Gly Asp Asn Val Lys Ile
465                 470                 475                 480

Leu Asn Ala Asp Asn Val Gln Glu Ala Ala Arg Glu Thr Asp Gly Tyr
                485                 490                 495

Phe Ile Lys Gly Gly Ile Val Thr Val Ile Lys Asp Ala Leu Leu Pro
            500                 505                 510

Ser Gly Thr Val Ile
            515

<210> SEQ ID NO 127
<211> LENGTH: 517
<212> TYPE: PRT
<213> ORGANISM: Sorghum bicolor
<220> FEATURE:
<221> NAME/KEY: MISC_FEATURE
<222> LOCATION: (1)..(517)
<223> OTHER INFORMATION: ADP-glucose pyrophosphorylase small subunit

<400> SEQUENCE: 127

Met Ala Met Thr Ala Ile Ala Ser Pro Ser Ser Arg Thr Leu Ile Pro
1               5                   10                  15

Pro Arg His His Gly Ala Ala Pro Pro Ser Thr Ser Gly Asp Ser
            20                  25                  30

Ser Leu Arg Leu Leu Arg Ala His Pro Arg His Gly Arg Arg Ser Arg
        35                  40                  45

Gly Val Ser Val Ser Thr Pro Ala Ala Arg Ser Arg Pro Phe Val Phe
    50                  55                  60

Ser Ser Arg Ala Val Ser Asp Ser Lys Ser Ser Gln Thr Cys Leu Asp
65                  70                  75                  80

Pro Asp Ala Ser Thr Ser Val Leu Gly Ile Ile Leu Gly Gly Gly Ala
                85                  90                  95

Gly Thr Arg Leu Tyr Pro Leu Thr Lys Lys Arg Ala Lys Pro Ala Val
            100                 105                 110

Pro Leu Gly Ala Asn Tyr Arg Leu Ile Asp Ile Pro Val Ser Asn Cys
        115                 120                 125

Leu Asn Ser Asn Ile Ser Lys Ile Tyr Val Leu Thr Gln Phe Asn Ser
    130                 135                 140

Ala Ser Leu Asn Arg His Leu Ser Arg Ala Tyr Gly Ser Asn Ile Gly
145                 150                 155                 160

Gly Tyr Lys Asn Glu Gly Phe Val Glu Val Leu Ala Ala Gln Gln Ser
                165                 170                 175
```

```
Pro Asp Asn Pro Asn Trp Phe Gln Gly Thr Ala Asp Ala Val Arg Gln
            180                 185                 190

Tyr Leu Trp Leu Phe Glu Glu His Asn Val Met Glu Phe Leu Ile Leu
        195                 200                 205

Ala Gly Asp His Leu Tyr Arg Met Asp Tyr Glu Lys Phe Ile Gln Ala
    210                 215                 220

His Arg Glu Thr Asp Ala Asp Ile Thr Val Ala Ala Leu Pro Met Asp
225                 230                 235                 240

Glu Ala Arg Ala Thr Ala Phe Gly Leu Met Lys Ile Asp Glu Glu Gly
                245                 250                 255

Arg Ile Ile Glu Phe Ala Glu Lys Pro Lys Gly Glu Gln Leu Lys Ala
                260                 265                 270

Met Met Val Asp Thr Thr Ile Leu Gly Leu Asp Asp Val Arg Ala Lys
            275                 280                 285

Glu Met Pro Tyr Ile Ala Ser Met Gly Ile Tyr Val Phe Ser Lys Asp
    290                 295                 300

Val Met Leu Gln Leu Leu Arg Glu Gln Phe Pro Gly Ala Asn Asp Phe
305                 310                 315                 320

Gly Ser Glu Val Ile Pro Gly Ala Thr Thr Ile Gly Lys Arg Val Gln
                325                 330                 335

Ala Tyr Leu Tyr Asp Gly Tyr Trp Glu Asp Ile Gly Thr Ile Thr Ala
            340                 345                 350

Phe Tyr Asn Ala Asn Leu Gly Ile Thr Lys Lys Pro Val Pro Asp Phe
    355                 360                 365

Ser Phe Tyr Asp Arg Ser Ala Pro Ile Tyr Thr Gln Pro Arg His Leu
370                 375                 380

Pro Pro Ser Lys Val Leu Asp Ala Asp Val Thr Asp Ser Val Ile Gly
385                 390                 395                 400

Glu Gly Cys Val Ile Lys Asn Cys Lys Ile His His Ser Val Val Gly
                405                 410                 415

Leu Arg Ser Cys Ile Ser Glu Gly Ala Ile Ile Glu Asp Thr Leu Leu
            420                 425                 430

Met Gly Ala Asp Tyr Tyr Glu Thr Glu Ala Asp Lys Lys Leu Leu Ala
    435                 440                 445

Glu Asn Gly Gly Ile Pro Ile Gly Ile Gly Lys Asn Ser His Ile Arg
450                 455                 460

Arg Ala Ile Ile Asp Lys Asn Ala Arg Ile Gly Asp Asn Val Lys Ile
465                 470                 475                 480

Leu Asn Ala Asp Asn Val Gln Glu Ala Ala Arg Glu Thr Asp Gly Tyr
                485                 490                 495

Phe Ile Lys Gly Gly Ile Val Thr Val Ile Lys Asp Ala Leu Leu Pro
            500                 505                 510

Ser Gly Thr Val Ile
            515

<210> SEQ ID NO 128
<211> LENGTH: 515
<212> TYPE: PRT
<213> ORGANISM: Setaria italica
<220> FEATURE:
<221> NAME/KEY: MISC_FEATURE
<222> LOCATION: (1)..(515)
<223> OTHER INFORMATION: ADP-glucose pyrophosphorylase small subunit

<400> SEQUENCE: 128
```

-continued

```
Met Ala Met Ala Ala Met Ala Ser Pro Ser Met Thr Leu Ile Pro
1               5                   10                  15

Ala Arg His His Gly Ala Ala Pro Ser Thr Ser Gly Asp Ser Ser Leu
         20                  25                  30

Arg Leu Leu Ser Ala Gln Pro Arg His Gly Arg Arg Gly Arg Gly Val
             35                  40                  45

Pro Val Ser Thr Ala Pro Ala Arg Arg Arg Pro Phe Val Phe Thr Pro
        50                  55                  60

Arg Ala Val Ser Asp Ser Lys Ser Ser Gln Thr Cys Leu Asp Pro Asp
65                  70                  75                  80

Ala Ser Thr Ser Val Leu Gly Ile Ile Leu Gly Gly Gly Ala Gly Thr
                85                  90                  95

Arg Leu Tyr Pro Leu Thr Lys Lys Arg Ala Lys Pro Ala Val Pro Leu
                100                 105                 110

Gly Ala Asn Tyr Arg Leu Ile Asp Ile Pro Val Ser Asn Cys Leu Asn
            115                 120                 125

Ser Asn Ile Ser Lys Ile Tyr Val Leu Thr Gln Phe Asn Ser Ala Ser
        130                 135                 140

Leu Asn Arg His Leu Ser Arg Ala Tyr Gly Ser Asn Ile Gly Gly Tyr
145                 150                 155                 160

Lys Asn Glu Gly Phe Val Glu Val Leu Ala Ala Gln Gln Ser Pro Asp
                165                 170                 175

Asn Pro Asn Trp Phe Gln Gly Thr Ala Asp Ala Val Arg Gln Tyr Leu
            180                 185                 190

Trp Leu Phe Glu Glu His Asn Val Met Glu Phe Ile Ile Leu Ala Gly
        195                 200                 205

Asp His Leu Tyr Arg Met Asp Tyr Glu Lys Phe Ile Gln Ala His Arg
    210                 215                 220

Glu Thr Asp Ala Asp Ile Thr Val Ala Ala Leu Pro Met Asp Glu Lys
225                 230                 235                 240

Arg Ala Thr Ala Phe Gly Leu Met Lys Ile Asp Glu Glu Gly Arg Ile
                245                 250                 255

Ile Glu Phe Ala Glu Lys Pro Lys Gly Asp Gln Leu Lys Ala Met Met
            260                 265                 270

Val Asp Thr Thr Ile Leu Gly Leu Asp Asp Val Arg Ala Lys Glu Met
        275                 280                 285

Pro Tyr Ile Ala Ser Met Gly Ile Tyr Val Phe Ser Lys Asp Val Met
    290                 295                 300

Leu Gln Leu Leu Arg Glu Gln Phe Pro Gly Ala Asn Asp Phe Gly Ser
305                 310                 315                 320

Glu Val Ile Pro Gly Ala Thr Ser Ile Gly Lys Arg Val Gln Ala Tyr
                325                 330                 335

Leu Tyr Asp Gly Tyr Trp Glu Asp Ile Gly Thr Ile Glu Ala Phe Tyr
            340                 345                 350

Asn Ala Asn Leu Gly Ile Thr Lys Lys Pro Ile Pro Asp Phe Ser Phe
        355                 360                 365

Tyr Asp Arg Ser Ala Pro Ile Tyr Thr Gln Pro Arg His Leu Pro Pro
    370                 375                 380

Ser Lys Ile Leu Asp Ala Asp Val Thr Asp Ser Val Ile Gly Glu Gly
385                 390                 395                 400

Cys Val Ile Lys Asn Cys Lys Ile His His Ser Val Val Gly Leu Arg
                405                 410                 415

Ser Cys Ile Ser Glu Gly Ala Ile Ile Glu Asp Thr Leu Leu Met Gly
```

```
            420             425             430
Ala Asp Tyr Tyr Glu Thr Glu Ala Asp Lys Lys Leu Leu Ala Glu Asn
                435                 440                 445

Gly Gly Ile Pro Ile Gly Ile Gly Lys Asn Ser His Ile Arg Arg Ala
            450                 455                 460

Ile Ile Asp Lys Asn Ala Arg Ile Gly Asp Asn Val Lys Ile Ile Asn
465                 470                 475                 480

Ala Asp Asn Val Gln Glu Ala Ala Arg Glu Thr Asp Gly Tyr Phe Ile
                485                 490                 495

Lys Gly Gly Ile Val Thr Val Ile Lys Asp Ala Leu Leu Pro Ser Gly
                500                 505                 510

Thr Val Ile
        515

<210> SEQ ID NO 129
<211> LENGTH: 517
<212> TYPE: PRT
<213> ORGANISM: Brachypodium distachyon
<220> FEATURE:
<221> NAME/KEY: MISC_FEATURE
<222> LOCATION: (1)..(517)
<223> OTHER INFORMATION: ADP-glucose pyrophosphorylase small subunit

<400> SEQUENCE: 129

Met Ala Met Ala Ala Ala Gly Ser Pro Ser Lys Thr Leu Ile Pro Pro
1               5                   10                  15

His Arg Ala Ser Ala Ala Pro Ala Ser Thr Ser Cys Asp Ser Leu Arg
                20                  25                  30

Leu Leu Leu His Arg Ala Pro Arg Gly Ser Ser Arg Arg Thr Pro Leu
            35                  40                  45

Gly Val Ala Ser Ser Ser Pro Ala Pro Ala Arg Arg Pro Phe Val Phe
        50                  55                  60

Ser Pro Arg Ala Val Ser Asp Ser Lys Ser Ser Gln Thr Cys Leu Asp
65                  70                  75                  80

Pro Asp Ala Ser Thr Ser Val Leu Gly Ile Ile Leu Gly Gly Gly Ala
                85                  90                  95

Gly Thr Arg Leu Tyr Pro Leu Thr Lys Lys Arg Ala Lys Pro Ala Val
                100                 105                 110

Pro Leu Gly Ala Asn Tyr Arg Leu Ile Asp Ile Pro Val Ser Asn Cys
            115                 120                 125

Leu Asn Ser Asn Ile Ser Lys Ile Tyr Val Leu Thr Gln Phe Asn Ser
        130                 135                 140

Ala Ser Leu Asn Arg His Leu Ser Arg Ala Tyr Gly Ser Asn Ile Gly
145                 150                 155                 160

Gly Tyr Lys Asn Glu Gly Phe Val Glu Val Leu Ala Ala Gln Gln Ser
                165                 170                 175

Pro Asp Asn Pro Asn Trp Phe Gln Gly Thr Ala Asp Ala Val Arg Gln
            180                 185                 190

Tyr Leu Trp Leu Phe Glu Glu His Asn Val Met Glu Tyr Leu Ile Leu
        195                 200                 205

Ala Gly Asp His Leu Tyr Arg Met Asp Tyr Glu Lys Phe Ile Gln Ala
    210                 215                 220

His Arg Glu Thr Asp Ala Asp Ile Thr Val Ala Ala Leu Pro Met Asp
225                 230                 235                 240

Glu Glu Arg Ala Thr Ala Phe Gly Leu Met Lys Ile Asp Glu Glu Gly
                245                 250                 255
```

```
Arg Ile Ile Glu Phe Ala Glu Lys Pro Lys Gly Glu Gln Leu Lys Ala
              260                 265                 270

Met Met Val Asp Thr Thr Ile Leu Gly Leu Asp Asp Val Arg Ala Lys
        275                 280                 285

Glu Met Pro Tyr Ile Ala Ser Met Gly Ile Tyr Val Ile Ser Lys His
    290                 295                 300

Val Met Leu Gln Leu Leu Arg Glu Gln Phe Pro Gly Ala Asn Asp Phe
305                 310                 315                 320

Gly Ser Glu Val Ile Pro Gly Ala Thr Ser Thr Gly Met Arg Val Gln
                325                 330                 335

Ala Tyr Leu Tyr Asp Gly Tyr Trp Glu Asp Ile Gly Thr Ile Glu Ala
            340                 345                 350

Phe Tyr Asn Ala Asn Leu Gly Ile Thr Lys Lys Pro Ile Pro Asp Phe
        355                 360                 365

Ser Phe Tyr Asp Arg Ser Ala Pro Ile Tyr Thr Gln Pro Arg His Leu
    370                 375                 380

Pro Pro Ser Lys Val Leu Asp Ala Asp Val Thr Asp Ser Val Ile Gly
385                 390                 395                 400

Glu Gly Cys Val Ile Lys Asn Cys Lys Ile His His Ser Val Val Gly
                405                 410                 415

Leu Arg Ser Cys Ile Ser Glu Gly Ala Ile Ile Glu Asp Thr Leu Leu
            420                 425                 430

Met Gly Ala Asp Tyr Tyr Glu Thr Glu Ala Asp Lys Gln Leu Leu Ala
        435                 440                 445

Glu Lys Gly Gly Ile Pro Ile Gly Ile Gly Lys Asn Ser His Ile Lys
    450                 455                 460

Arg Ala Ile Ile Asp Lys Asn Ala Arg Ile Gly Asp Asn Val Lys Ile
465                 470                 475                 480

Ile Asn Val Asp Asn Val Gln Glu Ala Ala Arg Glu Thr Asp Gly Tyr
                485                 490                 495

Phe Ile Lys Ser Gly Ile Val Thr Val Ile Lys Asp Ala Leu Leu Pro
            500                 505                 510

Ser Gly Thr Val Ile
        515

<210> SEQ ID NO 130
<211> LENGTH: 513
<212> TYPE: PRT
<213> ORGANISM: Hordeum vulgare
<220> FEATURE:
<221> NAME/KEY: MISC_FEATURE
<222> LOCATION: (1)..(513)
<223> OTHER INFORMATION: ADP-glucose pyrophosphorylase small subunit

<400> SEQUENCE: 130

Met Ala Met Ala Ala Ala Ala Ser Pro Ser Lys Ile Leu Ile Pro Pro
1               5                   10                  15

His Arg Ala Ser Ala Val Thr Ala Ala Ser Thr Ser Cys Asp Ser
            20                  25                  30

Leu Arg Leu Leu Cys Ala Pro Arg Gly Arg Pro Gly Pro Arg Gly Leu
        35                  40                  45

Val Ala Arg Pro Val Pro Arg Arg Pro Phe Phe Ser Pro Arg Ala
    50                  55                  60

Val Ser Asp Ser Lys Ser Ser Gln Thr Cys Leu Asp Pro Asp Ala Ser
65                  70                  75                  80
```

```
Thr Ser Val Leu Gly Ile Ile Leu Gly Gly Gly Ala Gly Thr Arg Leu
            85                  90                  95
Tyr Pro Leu Thr Lys Lys Arg Ala Lys Pro Ala Val Pro Leu Gly Ala
       100                 105                 110
Asn Tyr Arg Leu Ile Asp Ile Pro Val Ser Asn Cys Leu Asn Ser Asn
        115                 120                 125
Ile Ser Lys Ile Tyr Val Leu Thr Gln Phe Asn Ser Ala Ser Leu Asn
    130                 135                 140
Arg His Leu Ser Arg Ala Tyr Gly Ser Asn Ile Gly Gly Tyr Lys Asn
145                 150                 155                 160
Glu Gly Phe Val Glu Val Leu Ala Ala Gln Gln Ser Pro Asp Asn Pro
                165                 170                 175
Asp Trp Phe Gln Gly Thr Ala Asp Ala Val Arg Gln Tyr Leu Trp Leu
            180                 185                 190
Phe Glu Glu His Asn Val Met Glu Tyr Leu Ile Leu Ala Gly Asp His
        195                 200                 205
Leu Tyr Arg Met Asp Tyr Glu Lys Phe Ile Gln Ala His Arg Glu Thr
    210                 215                 220
Asp Ala Asp Ile Thr Val Ala Ala Leu Pro Met Asp Glu Glu Arg Ala
225                 230                 235                 240
Thr Ala Phe Gly Leu Met Lys Ile Asp Glu Glu Gly Arg Ile Ile Glu
                245                 250                 255
Phe Ala Glu Lys Pro Lys Gly Glu Gln Leu Lys Ala Met Met Val Asp
            260                 265                 270
Thr Thr Ile Leu Gly Leu Glu Asp Ala Arg Ala Lys Glu Met Pro Tyr
        275                 280                 285
Ile Ala Ser Met Gly Ile Tyr Val Ile Ser Lys His Val Met Leu Gln
    290                 295                 300
Leu Leu Arg Glu Gln Phe Pro Gly Ala Asn Asp Phe Gly Ser Glu Val
305                 310                 315                 320
Ile Pro Gly Ala Thr Ser Thr Gly Met Arg Val Gln Ala Tyr Leu Tyr
                325                 330                 335
Asp Gly Tyr Trp Glu Asp Ile Gly Thr Ile Glu Ala Phe Tyr Asn Ala
            340                 345                 350
Asn Leu Gly Ile Thr Lys Lys Pro Ile Pro Asp Phe Ser Phe Tyr Asp
        355                 360                 365
Arg Ser Ala Pro Ile Tyr Thr Gln Pro Arg His Leu Pro Pro Ser Lys
    370                 375                 380
Val Leu Asp Ala Asp Val Thr Asp Ser Val Ile Gly Glu Gly Cys Val
385                 390                 395                 400
Ile Lys Asn Cys Lys Ile His His Ser Val Gly Leu Arg Ser Cys
                405                 410                 415
Ile Ser Glu Gly Ala Ile Ile Glu Asp Thr Leu Leu Met Gly Ala Asp
            420                 425                 430
Tyr Tyr Glu Thr Glu Ala Asp Lys Lys Leu Leu Ala Lys Gly Gly
        435                 440                 445
Ile Pro Ile Gly Ile Gly Lys Asn Ser His Ile Lys Arg Ala Ile Ile
    450                 455                 460
Asp Lys Asn Ala Arg Ile Gly Asp Asn Val Met Ile Ile Asn Val Asp
465                 470                 475                 480
Asn Val Gln Glu Ala Ala Arg Glu Thr Asp Gly Tyr Phe Ile Lys Ser
                485                 490                 495
Gly Ile Val Thr Val Ile Lys Asp Ala Leu Leu Pro Ser Gly Thr Val
```

Ile

<210> SEQ ID NO 131
<211> LENGTH: 514
<212> TYPE: PRT
<213> ORGANISM: Oryza sativa
<220> FEATURE:
<221> NAME/KEY: MISC_FEATURE
<222> LOCATION: (1)..(514)
<223> OTHER INFORMATION: ADP-glucose pyrophosphorylase small subunit

<400> SEQUENCE: 131

Met Ala Met Ala Ala Met Gly Val Ala Ser Pro Tyr His Ala Ala
1               5                   10                  15

His Ala Ala Ser Thr Ser Cys Asp Ser Leu Arg Leu Leu Val Ala
            20                  25                  30

Glu Gly Arg Pro Arg Pro Arg Gly Val Ala Ser Ser Ser Ser Ser
        35                  40                  45

Ser Ser Ser Ala Gly Arg Arg Arg Pro Leu Val Phe Ser Pro Arg
    50                  55                  60

Ala Val Ser Asp Ser Lys Ser Ser Gln Thr Cys Leu Asp Pro Asp Ala
65                  70                  75                  80

Ser Thr Ser Val Leu Gly Ile Ile Leu Gly Gly Ala Gly Thr Arg
                85                  90                  95

Leu Tyr Pro Leu Thr Lys Lys Arg Ala Lys Pro Ala Val Pro Leu Gly
                100                 105                 110

Ala Asn Tyr Arg Leu Ile Asp Ile Pro Val Ser Asn Cys Leu Asn Ser
                115                 120                 125

Asn Ile Ser Lys Ile Tyr Val Leu Thr Gln Phe Asn Ser Ala Ser Leu
130                 135                 140

Asn Arg His Leu Ser Arg Ala Tyr Gly Asn Asn Ile Gly Gly Tyr Lys
145                 150                 155                 160

Asn Glu Gly Phe Val Glu Val Leu Ala Ala Gln Gln Ser Pro Asp Asn
                165                 170                 175

Pro Asn Trp Phe Gln Gly Thr Ala Asp Ala Val Arg Gln Tyr Leu Trp
                180                 185                 190

Leu Phe Glu Glu His Asn Val Met Glu Phe Leu Ile Leu Ala Gly Asp
                195                 200                 205

His Leu Tyr Arg Met Asp Tyr Glu Lys Phe Ile Gln Ala His Arg Glu
                210                 215                 220

Thr Asp Ser Asp Ile Thr Val Ala Ala Leu Pro Met Asp Glu Lys Arg
225                 230                 235                 240

Ala Thr Ala Phe Gly Leu Met Lys Ile Asp Glu Glu Gly Arg Ile Val
                245                 250                 255

Glu Phe Ala Glu Lys Pro Lys Gly Glu Gln Leu Lys Ala Met Met Val
                260                 265                 270

Asp Thr Thr Ile Leu Gly Leu Asp Asp Val Arg Ala Lys Glu Met Pro
                275                 280                 285

Tyr Ile Ala Ser Met Gly Ile Tyr Val Ile Ser Lys Asn Val Met Leu
                290                 295                 300

Gln Leu Leu Arg Glu Gln Phe Pro Gly Ala Asn Asp Phe Gly Ser Glu
305                 310                 315                 320

Val Ile Pro Gly Ala Thr Asn Ile Gly Met Arg Val Gln Ala Tyr Leu
                325                 330                 335

```
Tyr Asp Gly Tyr Trp Glu Asp Ile Gly Thr Ile Glu Ala Phe Tyr Asn
            340                 345                 350

Ala Asn Leu Gly Ile Thr Lys Lys Pro Val Pro Asp Phe Ser Phe Tyr
        355                 360                 365

Asp Arg Ser Ala Pro Ile Tyr Thr Gln Pro Arg His Leu Pro Pro Ser
    370                 375                 380

Lys Val Leu Asp Ala Asp Val Thr Asp Ser Val Ile Gly Glu Gly Cys
385                 390                 395                 400

Val Ile Lys Asn Cys Lys Ile His His Ser Val Val Gly Leu Arg Ser
            405                 410                 415

Cys Ile Ser Glu Gly Ala Ile Ile Glu Asp Ser Leu Leu Met Gly Ala
        420                 425                 430

Asp Tyr Tyr Glu Thr Glu Ala Asp Lys Lys Leu Leu Gly Glu Lys Gly
    435                 440                 445

Gly Ile Pro Ile Gly Ile Gly Lys Asn Cys His Ile Arg Arg Ala Ile
450                 455                 460

Ile Asp Lys Asn Ala Arg Ile Gly Asp Asn Val Lys Ile Ile Asn Val
465                 470                 475                 480

Asp Asn Val Gln Glu Ala Ala Arg Glu Thr Asp Gly Tyr Phe Ile Lys
            485                 490                 495

Ser Gly Ile Val Thr Val Ile Lys Asp Ala Leu Leu Pro Ser Gly Thr
        500                 505                 510

Val Ile

<210> SEQ ID NO 132
<211> LENGTH: 514
<212> TYPE: PRT
<213> ORGANISM: Triticum aestivum
<220> FEATURE:
<221> NAME/KEY: MISC_FEATURE
<222> LOCATION: (1)..(514)
<223> OTHER INFORMATION: ADP-glucose pyrophosphorylase small subunit

<400> SEQUENCE: 132

Met Ala Met Ala Ala Ala Ala Ser Pro Ser Lys Ile Leu Ile Pro Pro
1               5                   10                  15

His Arg Ala Ser Ala Ala Thr Ala Ala Ala Ser Thr Ser Cys Asp Ser
            20                  25                  30

Phe Arg Leu Leu Cys Ala Pro Arg Gly Arg Arg Gln Arg Pro Arg Gly
        35                  40                  45

Leu Val Ala Arg Ser Ala Pro Arg Arg Pro Phe Phe Phe Ser Pro Arg
    50                  55                  60

Ala Val Ser Asp Ser Lys Ser Ser Gln Thr Cys Leu Asp Pro Asp Ala
65                  70                  75                  80

Ser Thr Ser Val Leu Gly Ile Ile Leu Gly Gly Gly Ala Gly Thr Arg
            85                  90                  95

Leu Tyr Pro Leu Thr Lys Lys Arg Ala Lys Pro Ala Val Pro Leu Gly
        100                 105                 110

Ala Asn Tyr Arg Leu Ile Asp Ile Pro Val Ser Asn Cys Leu Asn Ser
    115                 120                 125

Asn Ile Ser Lys Ile Tyr Val Leu Thr Gln Phe Asn Ser Ala Ser Leu
130                 135                 140

Asn Arg His Leu Ser Arg Ala Tyr Gly Ser Asn Ile Gly Gly Tyr Lys
145                 150                 155                 160

Asn Glu Gly Phe Val Glu Val Leu Ala Ala Gln Gln Ser Pro Asp Asn
            165                 170                 175
```

```
Pro Asp Trp Phe Gln Gly Thr Ala Asp Ala Val Arg Gln Tyr Leu Trp
                180                 185                 190

Leu Phe Glu Glu His Asn Val Met Glu Tyr Leu Ile Leu Ala Gly Asp
        195                 200                 205

His Leu Tyr Arg Met Asp Tyr Glu Lys Phe Ile Gln Ala His Arg Glu
210                 215                 220

Thr Asp Ala Asp Ile Thr Val Ala Ala Leu Pro Met Asp Glu Glu Arg
225                 230                 235                 240

Ala Thr Ala Phe Gly Leu Met Lys Ile Asp Glu Gly Arg Ile Ile
                245                 250                 255

Glu Phe Ala Glu Lys Pro Lys Gly Glu Gln Leu Lys Ala Met Met Val
                260                 265                 270

Asp Thr Thr Ile Leu Gly Leu Asp Asp Ala Arg Ala Lys Glu Met Pro
            275                 280                 285

Tyr Ile Ala Ser Met Gly Ile Tyr Val Ile Ser Lys His Val Met Leu
        290                 295                 300

Gln Leu Leu Arg Glu Gln Phe Pro Gly Ala Asn Asp Phe Gly Ser Glu
305                 310                 315                 320

Val Ile Pro Gly Ala Thr Ser Thr Gly Met Arg Val Gln Ala Tyr Leu
                325                 330                 335

Tyr Asp Gly Tyr Trp Glu Asp Ile Gly Thr Ile Glu Ala Phe Tyr Asn
                340                 345                 350

Ala Asn Leu Gly Ile Thr Lys Lys Pro Ile Pro Asp Phe Ser Phe Tyr
            355                 360                 365

Asp Arg Ser Ala Pro Ile Tyr Thr Gln Pro Arg His Leu Pro Pro Ser
370                 375                 380

Lys Val Leu Asp Ala Asp Val Thr Asp Ser Val Ile Gly Glu Gly Cys
385                 390                 395                 400

Val Ile Lys Asn Cys Lys Ile His His Ser Val Val Gly Leu Arg Ser
                405                 410                 415

Cys Ile Ser Glu Gly Ala Ile Ile Glu Asp Thr Leu Leu Met Gly Ala
                420                 425                 430

Asp Tyr Tyr Glu Thr Glu Ala Asp Lys Lys Leu Leu Ala Glu Lys Gly
            435                 440                 445

Gly Ile Pro Ile Gly Ile Gly Lys Asn Ser His Ile Lys Arg Ala Ile
        450                 455                 460

Ile Asp Lys Asn Ala Arg Ile Gly Asp Asn Val Met Ile Ile Asn Val
465                 470                 475                 480

Asp Asn Val Gln Glu Ala Ala Arg Glu Thr Asp Gly Tyr Phe Ile Lys
                485                 490                 495

Ser Gly Ile Val Thr Val Ile Lys Asp Ala Leu Leu Pro Ser Gly Thr
            500                 505                 510

Val Ile

<210> SEQ ID NO 133
<211> LENGTH: 1814
<212> TYPE: DNA
<213> ORGANISM: Zea mays
<220> FEATURE:
<221> NAME/KEY: promoter
<222> LOCATION: (1)..(1814)
<223> OTHER INFORMATION: ZmCA1 5'mod promoter

<400> SEQUENCE: 133
ccccgcccat gtcagcaggc ctccgaggct tttggttgcc caaccagccc atgggctgaa    60
```

```
ttcataacag tgttggcaca cagtttcctc ttcactcgga agcttattat tatcgatcct    120
gaaccagaga ctagcagagc tagcatttcg acgacgcgtc tcaactctca acctccaagt   180
ccacctcgtg tacgtgctgc cttgccagtt gccactgggc actgctggcc cagtgaccaa   240
ccatgcgtta gatctgacag caccaccgaa ccatcctccc cggtgatcaa caaacgacgg   300
cagccacatc ttgcacccaa cgtgatgatg aatgatgcct agaacttttg acaacaaaac   360
gcagcacagg tagcaggttt aattcaacaa gactttctac tatatagagc cacaccatag   420
agataactaa tctgtgcgca aagccaaagt gctgacggca actgtggtgc agccttttca   480
tctccgtttt taagttttt gcccctcctt ttgttttctg tttttctggg aactcttaa    540 accgccgtgg cgccgtgtaa actttgctgt agccttttcg cgtgcaatgg cagagcgccc   600
tgttcttttc ctgctaaaga aaaaaaaaaa ggagcacctg atcgctggca ggcccacggc   660
ccacccaact gtgtctgtaa cgctcggcgt ccctgcattg catgccaagt gccaaccacc   720
agtccatagc agggtcaggg agaccgcaga tgaggccggg gcaacggtga tgccgcaaag   780
aggattcaga atcctttttc ttttcttttc ttttaccacc gggctggcat cacagattac   840
acgcgcagta gagtaagcac gtctctctcg tagccaagaa caacagtcta cacagctcgc   900
tttctccgcc cttgtctggg cgttacggca ggcaagcccc ctcgttttct tctgctcgcg   960
ttctccttcc atgtccacat ctcctgtgcc accgcacgca aggtgccaac gctccctcgc  1020
cgcagtagca tcgcgtccac acaaactgca cctccactag atacggcggt gatccggcga  1080
gagagcgcga cacgcacagg ccagctagcg tttctccgac gccgcgcgtt tcatcatttc  1140
ccgcttcccc tgcccccggc cgcgcgcgcg cgcccgtgtg gtccagacca ggacgcgcgc  1200
ggatgtgcat ccggcgcgcg cccgtcggcc acacggtgcc gccgcgcgtt atcccgagcc  1260
ctgtcctgtc ctgtcctgtt ccatctcgcg cgcgaggggg ggaggggagg gcagcgagtg  1320
gcgcgctggc ggatgaggcg ccgagtggcc cgcatccacc ggcgcaggcg agccgcacga  1380
cgccgccgcg ctcgcggaac gccgccgcca cacatgcgca cccccggccc gcggggctgt  1440
aacggccttg tcgccacgcg tgcgccccgt gtgtataagg aggcagcgcg tacaggggc   1500 gacaacgata agcggcactc gcacgatcaa tctacacatt gcccgtccgc gccaccacat  1560
ccagcatcgt cgccagcctc gccacccccg cgccgtcctc ctcctccggc tccggctccg  1620
gccgccccag gccaggctc atccggaacg ccccgtctt cgccgccccc gccaccgtcg   1680
tgtaaacggg acggcgggca gctgaggagt caaacgagag agatcgagag aaagaaaggg  1740
agggcatcca ccagccgccg gcgataagag gggaggagag agaggccaga gaagaggagg  1800
agaagaagaa gaaa                                                    1814
```

<210> SEQ ID NO 134
<211> LENGTH: 1086
<212> TYPE: DNA
<213> ORGANISM: Zea mays
<220> FEATURE:
<221> NAME/KEY: misc_feature
<222> LOCATION: (1)..(1086)
<223> OTHER INFORMATION: transcription factor

<400> SEQUENCE: 134

```
atgggctcca acgatccaaa cacaccgtcc aaggcctcca aggcgagcga gcaggatcag    60
ccaccggcga caaccacctc cagcgggacc gccagcgtgt acccagagtg gccgtcccttt  120 caagcgtatt ccgccattcc accgcacgcc ttttccccac cgaccgtcgc ggccaacccg   180
```

```
caggcgcatc cgtacatgtg gggcgcccaa ccaatcgtcc cgccatatgg accccacca     240 ccgccgccat atgtcatgta cccgccgggg accgtctatg cgcacccgtc cacaccacca    300
gcgatgcacc catttgggca ctatccgatg ccgacaaatg gccatgccga acacacggg     360 gccgccccga gcgcgccaga aatgaacggc aaatccgagc caggccgcac aagcgcccca    420
agcgcgaacg gcattaccag ccactccgaa tccggcagcg aaagcgaatc cgaaggctcc    480
gatgacaatt cccaaaatga ttcccactcc aaggataacg acgggaagga agacgggaat    540
tcccaaaacg ggatgagcta ttccggctcc caggggtcg tgaatcagac catggcgatg     600
ctcccgatgc agccaggggc gatggtcggg ggggtgccga gctccacagc cgccaatctg    660
aatatcgggg tggactactg gccgcgccg gggtccgccg cggtcccggc ggcgcacggg     720
aaggccccag cggggagcgc gaggggcgac cagtgggatg agcgcgagct caaaaaacag    780
aaaaggaaac aatccaatcg cgaaagcgcg cgcaggtccc gcctcaggaa gcaggccgag    840
tgtgaggaac tggggcagcg cgccgaagcg ctgcgcagcg aaaactccag cctgcgcgcc    900
gagctcgagc gcatcaggaa agaatacgag cagctcctct cccagaatgc gtccctcaaa    960
gagaagctgg gggcggcgag ctccgacagc ctgccagaca tgaatgaaca aaatgatggc   1020
gacggcgatg ggggctacag gaaacaaccg gattccgacg ccaccaacc gggcagcgaa   1080 tcctga                                                             1086
```

<210> SEQ ID NO 135
<211> LENGTH: 361
<212> TYPE: PRT
<213> ORGANISM: Zea mays
<220> FEATURE:
<221> NAME/KEY: MISC_FEATURE
<222> LOCATION: (1)..(361)
<223> OTHER INFORMATION: transcription factor

<400> SEQUENCE: 135

Met Gly Ser Asn Asp Pro Asn Thr Pro Ser Lys Ala Ser Lys Ala Ser
1               5                   10                  15

Glu Gln Asp Gln Pro Pro Ala Thr Thr Thr Ser Ser Gly Thr Ala Ser
            20                  25                  30

Val Tyr Pro Glu Trp Pro Ser Phe Gln Ala Tyr Ser Ala Ile Pro Pro
        35                  40                  45

His Ala Phe Phe Pro Pro Thr Val Ala Ala Asn Pro Gln Ala His Pro
    50                  55                  60

Tyr Met Trp Gly Ala Gln Pro Ile Val Pro Pro Tyr Gly Thr Pro Pro
65                  70                  75                  80

Pro Pro Pro Tyr Val Met Tyr Pro Pro Gly Thr Val Tyr Ala His Pro
                85                  90                  95

Ser Thr Pro Pro Ala Met His Pro Phe Gly His Tyr Pro Met Pro Thr
            100                 105                 110

Asn Gly His Ala Glu Thr His Gly Ala Ala Pro Ser Ala Pro Glu Met
        115                 120                 125

Asn Gly Lys Ser Glu Pro Gly Arg Thr Ser Ala Pro Ser Ala Asn Gly
    130                 135                 140

Ile Thr Ser His Ser Glu Ser Gly Ser Glu Ser Glu Ser Glu Gly Ser
145                 150                 155                 160

Asp Asp Asn Ser Gln Asn Asp Ser His Ser Lys Asp Asn Asp Gly Lys
                165                 170                 175

Glu Asp Gly Asn Ser Gln Asn Gly Met Ser Tyr Ser Gly Ser Gln Gly
            180                 185                 190

```
Val Val Asn Gln Thr Met Ala Met Leu Pro Met Gln Pro Gly Ala Met
    195                 200                 205
Val Gly Gly Val Pro Ser Ser Thr Ala Ala Asn Leu Asn Ile Gly Val
    210                 215                 220
Asp Tyr Trp Ala Ala Pro Gly Ser Ala Ala Val Pro Ala Ala His Gly
225                 230                 235                 240
Lys Ala Pro Ala Gly Ser Ala Arg Gly Asp Gln Trp Asp Glu Arg Glu
                245                 250                 255
Leu Lys Lys Gln Lys Arg Lys Gln Ser Asn Arg Glu Ser Ala Arg Arg
                260                 265                 270
Ser Arg Leu Arg Lys Gln Ala Glu Cys Glu Glu Leu Gly Gln Arg Ala
            275                 280                 285
Glu Ala Leu Arg Ser Glu Asn Ser Ser Leu Arg Ala Glu Leu Glu Arg
        290                 295                 300
Ile Arg Lys Glu Tyr Glu Gln Leu Leu Ser Gln Asn Ala Ser Leu Lys
305                 310                 315                 320
Glu Lys Leu Gly Ala Ala Ser Ser Asp Ser Leu Pro Asp Met Asn Glu
                325                 330                 335
Gln Asn Asp Gly Asp Gly Asp Gly Gly Tyr Arg Lys Gln Pro Asp Ser
                340                 345                 350
Asp Gly His Gln Pro Gly Ser Glu Ser
            355                 360
```